United States Patent
Gelin et al.

(10) Patent No.: US 11,447,503 B2
(45) Date of Patent: Sep. 20, 2022

(54) PYRIDINE CARBAMATES AND THEIR USE AS GLUN2B RECEPTOR MODULATORS

(71) Applicant: JANSSEN PHARMACEUTICA NV, Beerse (BE)

(72) Inventors: Christine Gelin, San Diego, CA (US); Heather Coate, San Diego, CA (US); Brice Stenne, La Jolla, CA (US); Curt Dvorak, Poway, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 159 days.

(21) Appl. No.: 16/899,809

(22) Filed: Jun. 12, 2020

(65) Prior Publication Data

US 2020/0392154 A1    Dec. 17, 2020

Related U.S. Application Data

(60) Provisional application No. 62/861,634, filed on Jun. 14, 2019.

(51) Int. Cl.
| | |
|---|---|
| *C07D 498/10* | (2006.01) |
| *A61P 25/18* | (2006.01) |
| *A61P 25/24* | (2006.01) |
| *A61P 25/08* | (2006.01) |
| *C07D 413/06* | (2006.01) |
| *C07D 413/14* | (2006.01) |

(52) U.S. Cl.
CPC ............ *C07D 498/10* (2013.01); *A61P 25/08* (2018.01); *A61P 25/18* (2018.01); *A61P 25/24* (2018.01); *C07D 413/06* (2013.01); *C07D 413/14* (2013.01)

(58) Field of Classification Search
CPC .. C07D 498/10; C07D 413/06; C07D 413/14; A61P 25/08; A61P 25/18; A61P 25/24; A61P 25/00; A61K 31/4439; A61K 31/5355
See application file for complete search history.

(56) References Cited

U.S. PATENT DOCUMENTS

| | | |
|---|---|---|
| 7,622,486 B2 | 11/2009 | Pal et al. |
| 8,765,784 B2 | 7/2014 | Arrington et al. |
| 8,785,438 B2 | 7/2014 | Ohtsuka et al. |
| 8,877,772 B2 | 11/2014 | Gelbard et al. |
| 8,987,473 B2 | 3/2015 | Nagai et al. |
| 9,174,993 B2 | 11/2015 | Nazare et al. |
| 9,434,743 B2 | 9/2016 | Cheruvallath et al. |
| 9,963,447 B2 | 5/2018 | Chrovian et al. |
| 9,981,950 B2 | 5/2018 | Schindler et al. |
| 10,071,988 B2 | 9/2018 | Chen et al. |
| 10,155,727 B2 | 12/2018 | Schindler et al. |
| 10,233,173 B2 | 3/2019 | Chen et al. |
| 10,323,021 B2 | 6/2019 | Schindler et al. |
| 10,377,753 B2 | 8/2019 | Chrovian et al. |
| 10,617,676 B2 | 4/2020 | Chrovian et al. |
| 2007/0275965 A1 | 11/2007 | Thomas et al. |
| 2008/0300239 A1 | 12/2008 | Adams et al. |
| 2011/0130384 A1 | 6/2011 | Setoh |
| 2014/0275011 A1 | 9/2014 | Mastracchio et al. |
| 2015/0210681 A1 | 7/2015 | Bourque et al. |
| 2016/0024087 A1 | 1/2016 | Gelbard et al. |
| 2018/0125826 A1 | 5/2018 | Chrovian et al. |
| 2018/0208595 A1 | 7/2018 | Chrovian et al. |
| 2018/0282305 A1 | 10/2018 | Schindler et al. |
| 2018/0334451 A1 | 11/2018 | Chen et al. |
| 2019/0135791 A1 | 5/2019 | Chen et al. |
| 2019/0308950 A1 | 10/2019 | Ziff et al. |
| 2020/0392113 A1 | 12/2020 | Dvorak et al. |
| 2020/0392130 A1 | 12/2020 | Hiscox et al. |
| 2020/0392155 A1 | 12/2020 | Gelin |
| 2021/0017168 A1 | 1/2021 | Hiscox et al. |
| 2021/0017169 A1 | 1/2021 | Hiscox et al. |

FOREIGN PATENT DOCUMENTS

| | | |
|---|---|---|
| CN | 110294756 A | 10/2019 |
| EP | 928789 A1 | 7/1999 |
| EP | 2194045 A1 | 6/2010 |
| JP | 2004-501901 A1 | 1/2004 |
| JP | 2012-188363 A | 4/2012 |
| WO | 1995028400 A1 | 10/1995 |
| WO | 2002060877 A1 | 8/2002 |
| WO | 2003082868 A1 | 10/2003 |
| WO | 2003097637 A1 | 11/2003 |
| WO | 2003/101968 A1 | 12/2003 |
| WO | 2005080379 A1 | 9/2005 |
| WO | 2008145616 A1 | 12/2008 |
| WO | 2009004430 A1 | 1/2009 |
| WO | 2009058261 A1 | 5/2009 |
| WO | 2009118187 A1 | 10/2009 |

(Continued)

OTHER PUBLICATIONS

International Search Report and Written Opinion of the International Searching Authority for International Application No. PCT/EP2020/066396, dated Jul. 29, 2020.

International Search Report and Written Opinion of the International Searching Authority for International Application No. PCT/EP2020/066392, dated Sep. 21, 2020.

International Search Report and Written Opinion of the International Searching Authority for International Application No. PCT/EP2020/066384, dated Jul. 28, 2020.

(Continued)

*Primary Examiner* — Robert H Havlin

(74) *Attorney, Agent, or Firm* — Biospark Intellectual Property Law

(57) ABSTRACT

Pyridine carbamates, pharmaceutical compositions containing pyridine carbamates, and uses of the pyridine carbamates and pharmaceutical compositions for modulating GluN2B receptors and for treating diseases, disorders, and medical conditions mediated by GluN2B receptor activity.

33 Claims, No Drawings

(56) References Cited

FOREIGN PATENT DOCUMENTS

| | | |
|---|---|---|
| WO | 2009/157196 A1 | 12/2009 |
| WO | 2010043396 A1 | 4/2010 |
| WO | 2010108187 A1 | 9/2010 |
| WO | 2011/022348 A1 | 2/2011 |
| WO | 2011140202 A2 | 11/2011 |
| WO | 2013060029 A1 | 5/2013 |
| WO | 2013130855 A1 | 9/2013 |
| WO | 2014124651 A1 | 8/2014 |
| WO | 2014145051 A1 | 9/2014 |
| WO | 2015002754 A2 | 1/2015 |
| WO | 2015017502 A1 | 2/2015 |
| WO | 2016025917 A1 | 2/2016 |
| WO | 2016081649 A1 | 5/2016 |
| WO | 2016/150971 A1 | 9/2016 |
| WO | 2017/007938 | 1/2017 |
| WO | 2018/067786 | 4/2018 |
| WO | 2018/231745 A1 | 12/2018 |
| WO | 2020/249785 A1 | 12/2020 |
| WO | 2020/249791 A1 | 12/2020 |
| WO | 2020/249792 A1 | 12/2020 |
| WO | 2020/249796 A1 | 12/2020 |
| WO | 2020/249799 A1 | 12/2020 |
| WO | 2020/249802 A1 | 12/2020 |

OTHER PUBLICATIONS

International Search Report and Written Opinion of the International Searching Authority for International Application No. PCT/EP2020/066391, dated Jul. 29, 2020.

International Search Report and Written Opinion of the International Searching Authority for International Application No. PCT/EP2020/066405, dated Jul. 29, 2020.

First Examination Report issued Nov. 30, 2020 in connection with European application No. 17859165.7.

Iadarola et al., 2015 Therapeutic Advances in Chronic Disease, vol. 6 (3), p. 97-114.

Machado-Vieira et al., 2017, "New Targets for Rapid Antidepressant Action" Prog. Neurobiol. 152-21-37.

Sun et al., 2020 "Synthesis and preliminary evaluation of novel C-labled GluN2B-selective NMDA receptor negative allosteric modulators" Acta Pharmacologica Sinica, pp. 1-8.

Davies et al., 2012, "A novel series of benzimidazole NR2B-selective NMDA receptor antagonists," Bioorganic & Medicinal Chemistry Letters 22:2620-2623.

Layton et al., 2006, "Recent Advances in the Development of NR2B Subtype-Selective NMDA Receptor Antagonist," Current Topics in Medicinal Chemistry 6:697-709.

Mao et al., 2014, "Phosphorylation and regulation of glutamate receptors by CaMKII," Acta Physiologica Sinica 66(3):365-372.

Pratap et al., 2007, "Guanidine and amidine mediated synthesis of bridgehead triazaphenalenes, pyrimidines and pyridines through domino reactions," Tetrahedron Letters 48:5845-5849.

Vippagunta et al., 2001, "Crystalline Solids" Advanced Drug Delivery Reviews 48:3-26.

International Search Report and Written Opinion of the International Searching Authority for International Application No. PCT/EP2020/066400, dated Jul. 28, 2020.

International Search Report and Written Opinion of the International Searching Authority for International Application No. PCT/US2015/045412, dated Nov. 10, 2015.

International Search Report and Written Opinion of the International Searching Authority for International Application No. PCT/US2015/045413, dated Nov. 27, 2015.

International Search Report and Written Opinion of the International Searching Authority for International Application No. PCT/US2016/041339 dated Sep. 27, 2016.

International Search Report and Written Opinion of the International Searching Authority for International Application No. PCT/US2017/017093, dated Apr. 7, 2017.

International Search Report and Written Opinion of the International Searching Authority issued in connection with PCT/US2017/055278, dated Mar. 9, 2018.

International Search Report and Written Opinion of the International Searching Authority for International Application No. PCT/IB2019/052731, dated Nov. 1, 2019.

Addy, et al., Single-Dc3e Administration of MK-0657, an N112B-Selective NMDA Antagonist, Does Not Result in Clinically Meaningful Improvement in Motor Function in Patients 127ith Moderate Parkinson's Disease, Journal of Clinical Pharmacology, 2009, pp. 856-864, vol. 49.

Andreas Straube., Pharmacology of vertigo/nystagmus/oscillopsia, Current Opinion in Neurology, 2005, pp. 11-14, vol. 18 Issue 1.

Arnold, et al., Glutamate receptor gene (GRIN2B) associated with reduced anterior cingulate glutamatergic concentration in pediatric obsessive-compulsive disorder, Psychiatry Research: Neuroimaging, Feb. 19, 2009, pp. 136-139, vol. 172 Issue 2.

Bagshawe, Kenneth D., 1995, "Antibody-Directed Enzyme prodrug Therapy : A Review," Drug Development Research, 34:220-230.

Berberich, et al., The role of NMDAR subtypes and charge transfer during hippocampal LTP induction, Neuropharmacology, 2007, pp. 77-86, vol. 52 Issue 1.

Berge, et al., Pharmaceutical Salts, Journal of Pharmaceutical Sciences, 1977, pp. 1-19, vol. 66, No. 1.

Bertolini, et al., A New Rational Hypothesis for the Pharmacophore of the Active Metabolite of Leflunomide, a Potent Immunosuppressive Drug, Journal of Medicinal Chemistry, Jan. 17, 1997, pp. 2011-2016, vol. 40 Issue 13.

Bodor, Nicholas, 1984, "Novel Approaches to the Design of Safer Drugs: Soft Drugs and Site-Specific Chemical Delivery Systems," Advances in Drug Research, 13:256-331.

Bullock, et al., An Open-Label Study of CP-101,606 in Subjects with a Severe Traumatic Head Injury or Spontaneous Intracerebral Hemorrhage, Annals New York Academy of Sciences, 1999, pp. 51-58, vol. 890.

Buonarati, et al., Role of sulfation and acetylation in the activation of 2-hydroxyamino- 1 -methyl-6-phenylimidazo[4,5-b]pyridine to intermediates which bind DNA, Mutation Research, Jun. 21, 1990, pp. 185-190, vol. 245.

Chattopadhyay, et al., Fused Tetrazoles as Azide Surrogates in Click Reaction: Efficient Synthesis of N-Heterocycle-Substituted 1,2,3-Triazoles, Organic Letters, Mar. 30, 2010, pp. 2166-2169, vol. 12 Issue 9.

Chrovian, et al., "1H-Pyrrolo[3,2-b]pyridine GluN2B-Selective Negative Allosteric Modulators", ACS Med. Chem. Lett, 2019, vol. 10, pp. 261-266.

Chemical Abstract Service (CAS), Database Registry [Online], Database Registry [Online], STN Sep. 18, 2012, pp. 1-1, Database Accession No. 1394745_67_5.

Collingridge, et al., "A nomenclature for ligand-gated ion channels" Neuropharmacology, 2009, vol. 56, pp. 2-5.

Cull-Candy, et al., NMDA receptor subunits: diversity, development and disease, Current Opinion in Neurobiology, 2001, pp. 327-335, vol. 11 Issue 3.

Dalmau, et al., Anti-NMDA-receptor encephalitis: case series and analysis of the eff ects of antibodies, Lancet Neurol, Dec. 2008, pp. 1091-1098, vol. 7 Issue 12.

Dorval, et al., Association of the glutamate receptor subunit gene GRIN2B with attention-deficit/hyperactivity disorder, Genes, Brain and Behavior, 2007, pp. 444-452, vol. 6 Issue 5.

Duty, Susan, 2012, "Targeting Glutamate Receptors to Tackle the Pathogenesis, Clinical Symptoms and Levodopa-Induced Dyskinesia Associated with Parkinson's Disease," CNS Drugs, 26(12):1017-1032.

Farjam, et al., Inhibition of NR2B-Containing N-methyl-D-Aspartate Receptors (NMDARs) in Experimental Autoimmune Encephalomyelitis, a Model of Multiple Sclerosis, Iranian Journal of Pharmaceutical Research, 2014, pp. 695-705, vol. 13 Issue 2.

Fleisher, et al., Improved oral drug delivery: solubility limitations overcome by the use of prodrugs, Advanced Drug Delivery Reviews, 1996, pp. 115-130, vol. 19.

Fuller, et al., Differential expression of the NMDA NR2B receptor subunit in motoneuron populations susceptible and resistant to

(56) References Cited

OTHER PUBLICATIONS amyotrophic lateral sclerosis, Neuroscience Letters, Jan. 26, 2006, pp. 157-161, vol. 399 Issue (1-2).
Glenn D. Considine, Van Nostrand's Encyclopedia of Chemistry,, Encyclopedia of Chemistry, 2005, pp. 261, Chapter 5.
Grasselli, et al., Abnormal NMDA receptor function exacerbates experimental autoimmune encephalomyelitis, British Journal of Pharmacology, 2013, pp. 502-517, vol. 168 Issue 2.
Grimwood, et al., NR2B-containing NMDA receptors are upregulated in temporal cortex in schizophrenia, NeuroReport, Feb. 25, 1999, pp. 461-465, vol. 10 Issue 3.
Guitton, et al., Blockade of Cochlear NMDA Receptors Prevents Long-Term Tinnitus during a Brief Consolidation Window after Acoustic Trauma, Neural Plasticity, Dec. 12, 2007, pp. 1-11, Article ID 80904.
Haller, et al., NR2B subunit-specific NMDA antagonist Ro25-6981 inhibits the expression of conditioned fear: a comparison with the NMDA antagonist MK-801 and fluoxetine, Behavioural Pharmacology, 2011, pp. 113-121, vol. 22 Issue 2.
Hanson, et al., Altered GluN2B NMDA receptor function and synaptic plasticity during early pathology in the PS2APP mouse model of Alzheimer's disease, Neurobiology of Disease, 2015, pp. 254-262, vol. 74.
Hu, et al., Expression of immediate-early genes in the dorsal cochlear nucleus in salicylate-induced tinnitus, Eur Arch Otorhinolaryngol, 2016, pp. 325-332, vol. 273 Issue 2.
Houston, et al., "Methods for Predicting In Vivo Pharmacokinetics Using Data from In Vitro Assays" Current Drug Metabolism, 2008, vol. 9, pp. 940-951.
Ito, et al., A Medium-term rat liver bioassay for rapid in vivo detection of carcinogenic potential of chemicals, Cancer Sei, 2003, pp. 3-8, vol. 94 Issue 1.
Jozsef Nagy, The NR2B Subtype of NMDA Receptor: A Potential Target for the Treatment of Alcohol Dependence, Current Drug Targets—CNS & Neurological Disorders, 2004, pp. 169-179, vol. 3 Issue 3.
Jun Wu, et al., Targeting the NMDA Receptor Subunit NR2B for the Treatment of Neuropathic Pain, Neurotherapeutics:, 2009, pp. 693-702, vol. 6 Issue 4.
Kamalesh B. Ruppa et al., Chapter 7: NMDA Antagonists of GluN2B Subtype and Modulators of GluN2A, GluN2C, and GluN2D Subtypes-Recent Results and Developments, Annual Reports in Medicinal Chemistry, Jan. 1, 2012, pp. 89-103, vol. 47.
Kolb, et al., Click Chemistry: Diverse Chemical Function from a Few Good Reactions, Angew. Chem. Int. Ed, 2001, pp. 2004-2021, vol. 40.
Kowal, et al., Human lupus autoantibodies against NMDA receptors mediate cognitive impairment, PNAS, Dec. 26, 2006, pp. 19854-19859, vol. 103 Issue 52.
Layton, et al., Discovery of 5-aryl-1,3-dihydro-2H-imidazo[4,5-b]pyridin-2-ones as positive allosteric modulators of metabotropic glutamate subtype-2(mGlu2) receptors with efficacy in a preclinical model of psychosis, Bioorganic & Medicinal Chemistry Letters, Feb. 15, 2016, pp. 1260-1264, vol. 26.
Leaderbrand, et al., Co-activation of NR2A and NR2B subunits induces resistance to fear extinction, Neurobiol Learn Mem, 2013, pp. 35-40, vol. 113.
Leaver, et al., Neuroprotective Effects of a Selective N-METHYL-d-ASPARTATE NR2B Receptor Antagonist in the 6-HYDROXYDOPAMINE Rat Model of Parkinson'S Disease, Clinical and Experimental Pharmacology and Physiology, May 27, 2008, pp. 1388-1394, vol. 35 Issue 11.
Leyva, et al., Photochemistry of Fluorinated Aryl Azides in Toluene Solution and in Frozen Polycrystals, J. Org. Chem, May 8, 1989, pp. 5938-5945, vol. 54 Issue 25, American Chemical Society.
Li, et al., Enhanced Striatal NR2B-Containing N-Methyl-D-Aspartate Receptor-Mediated Synaptic Currents in a Mouse Model of Huntington Disease, J Neurophysiol, Jun. 3, 2004, pp. 2738-2746, vol. 92 Issue 5.
Li, et al., Glutamate N-methyl-D-aspartate Receptor Antagonists Rapidly Reverse Behavioral and Synaptic Deficits Caused by Chronic Stress Exposure, Biol Psychiatry, 2011, pp. 754-761, vol. 69 Issue 8.
Li, et al., Soluble Ab Oligomers Inhibit Long-Term Potentiation through a Mechanism Involving Excessive Activation of Extrasynaptic NR2B-Containing NMDA Receptors, The Journal of Neuroscience, May 4, 2011, pp. 6627-6638, vol. 31 Issue 18.
Lima-Ojeda, et al., Pharmacological blockade of GluN2B-containing NMDA receptors induces antidepressant-like effects lacking psychotomimetic action and neurotoxicity in the perinatal and adult rodent brain, Progress in Neuro-Psychopharmacology & Biological Psychiatry, Apr. 30, 2013, pp. 28-33, vol. 45.
Martucci, et al., N-methyl-d-aspartate receptor NR2B subunit gene GRIN2B in schizophrenia and bipolar disorder: Polymorphisms and mRNA levels, Schizophrenia Research, Mar. 20, 2006, pp. 214-221, vol. 84 Issue (2-3).
Massey, et al., Differential Roles of NR2A and NR2B-Containing NMDA Receptors in Cortical Long-Term Potentiation and Long-Term Depression, The Journal of Neuroscience, Sep. 8, 2004, pp. 7821-7828, vol. 24 Issue 36.
Miller, et al., GluN2B-containing NMDA receptors regulate depression-like behavior and are critical for the rapid antidepressant actions of ketamine, eLife, Oct. 23, 2014, pp. 1-22, vol. 3.
Morissette, et al., Prevention of Levodopa-Induced Dyskinesias by a Selective NR1A/2B N-Methyl-D-aspartate Receptor Antagonist in Parkinsonian Monkeys: Implication of Preproenkephalin, Movement Disorders, 2006, pp. 9-17, vol. 21 Issue 1.
Naskar, et al., Saving the Nerve from Glaucoma: Memantine to Caspaces, Seminars in Ophthalmology, Sep. 1999, pp. 152-158, vol. 14 Issue 3.
Naspolini, et al., Traxoprodil decreases pentylenetetrazol-induced seizures, Epilepsy Research, Jan. 24, 2012, pp. 12-19, vol. 100 Issue (1-2).
Nutt, et al., Effects of a NR2B Selective NMDA Glutamate Antagonist, CP-101,606, on Dyskinesia and Parkinsonism, Movement Disorders, Aug. 29, 2008, pp. 1860-1866, vol. 23 Issue 13.
Orgogozo, et al., Efficacy and Safety of Memantine in Patients With Mild to Moderate Vascular Dementia A Randomized, Placebo-Controlled Trial (MMM 300), Stroke, 2002, pp. 1834-1839, vol. 33.
Paoletti, et al., NMDA receptor subunit diversity: impact on receptor properties, synaptic plasticity and disease, Nature Reviews | NEUROSCIENCE, 2013, pp. 383-400, vol. 14 Issue 6.
Park et al. "Metabolism of Fluorine-containing drugs", Annu. Rev. Pharmacol. Toxicol. 2001. vol. 41, pp. 443-470, entire document.
Paulekuhn, et al., Trends in Active Pharmaceutical Ingredient Salt Selection based on Analysis of the Orange Book Database, Journal of Medicinal Chemistry, Aug. 20, 2007, pp. 6665-6672, vol. 50 Issue 26.
Peeters, et al., Effects of Pan- and Subtype-Selective N-Methyl-D-aspartate Receptor Antagonists on Cortical Spreading Depression in the Rat: Therapeutic Potential for Migraine, The Journal of Pharmacology and Experimental Therapeutics, Jan. 24, 2007, pp. 564-572, vol. 321 Issue 2.
Porsolt, et al., Behavioural Despair in Mice: A Primary Screening Test for Antidepressants, Arch int Pharmacodyn, 1977, pp. 327-336, vol. 229.
Preskorn, et al., An Innovative Design to Establish Proof of Concept of the Antidepressant Effects of the NR2B Subunit Selective N-Methyl-D-Aspartate Antagonist, CP-101,606, in Patients With Treatment-Refractory Major Depressive Disorder, Journal of Clinical Psychopharmacology, Dec. 2008, pp. 631-637, vol. 28 Issue 6.
PubChem-CID-90046926, Create Date: Feb. 13, 2015 (Feb. 13, 2015), entire document.
Remington, Remington Pharmaceutical Sciences., Pharmaceutical Sciences., 1985, pp. 1418, vol. 76.
Robinson, et al., Discovery of the Hemifumarate and (r-L-Alanyloxy)methyl Ether as Prodrugs of an Antirheumatic Oxindole: Prodrugs for the Enolic OH Group, Journal of Medicinal Chemistry, 1996, pp. 10-18, vol. 39 Issue 1.
Shan, et al., Prodrug Strategies Based on Intramolecular Cyclization Reactions, Journal of Pharmaceutical Sciences, Jul. 1997, pp. 765-767, vol. 86 Issue 7.

(56) References Cited

OTHER PUBLICATIONS

Shen, et al., Heroin relapse requires long-term potentiation-like plasticity mediated by NMDA2b-containing receptors, PNAS, Nov. 29, 2011, pp. 19407-19412, vol. 108 Issue 48.

Starck, et al., Drug therapy for acquired pendular nystagmus in multiple sclerosis, J Neurol, 1997, pp. 9-16, vol. 244 Issue 1.

Steece-Collier, et al., Antiparkinsonian Actions of CP-101,606, an Antagonist of NR2B Subunit-Containing N-Methyl-D-Aspartate Receptors, Experimental Neurology, Feb. 4, 2000, pp. 239-243, vol. 163 Issue 1.

STN Registry database entry for CAS RN 1394745-67-5, entered STN Sep. 18, 2012, Accessed Sep. 8, 2017.

STN Registry database entry for CAS RN 1493474-46-6, 1491341-24-2, 1479235-62-5, and 1477636-42-2, Accessed Apr. 10, 2019.

Tang, et al., 2005, "Disturbed Ca2+ signaling and apoptosis of medium spiny neurons in Huntington's disease," PNAS, 102(7):2602-2607.

Tang, et al., Genetic enhancement of learning and memory in mice, NATURE, Sep. 2, 1999, pp. 63-69, vol. 401 Issue 6748.

Traynelis, et al., Glutamate Receptor Ion Channels: Structure, Regulation, and Function, Pharmacol Rev, 2010, pp. 405-496, vol. 62 Issue 3.

Wang, et al., Targeting the NMDA receptor subunit NR2B for treating or preventing age-related memory decline, Expert Opin. Ther. Targets, 2014, pp. 1121-1130, vol. 18 Issue 10.

Watanabe, et al., Distinct Distributions of Five N-Methyl-D-Aspartate Receptor Channel Subunit mRNAs in the Forebrain, The Journal of Comparative Neurology, Jul. 30, 1993, pp. 377-390, vol. 338 Issue 3.

Weickert, et al., Molecular evidence of N-methyl-D-aspartate receptor hypofunction in schizophrenia, Molecular Psychiatry, 2013, pp. 1185-1192, vol. 18.

Won, et al., Autistic-like social behaviour in Shank2-mutant mice improved by restoringNMDA receptor function, Nature, Jun. 14, 2012, pp. 261-265, vol. 486.

Yang, et al., Reduced brain infarct volume and improved neurological outcome by inhibition of the NR2B subunit of NMDA receptors by using CP101,606-27 alone and in combination with rt-PA in a thromboembolic stroke model in rats, J. Neurosurg, Feb. 2003, pp. 397-403, vol. 98 Issue 2.

Youssif, S. "Recent trends in the chemistry of pyridine N-oxides" ARKIVOC, 2001, pp. 242-268.

Yuan, et al., Context-Dependent GluN2B-Selective Inhibitors of NMDA Receptor Function Are Neuroprotective with Minimal Side Effects, Neuron, Mar. 18, 2015, pp. 1305-1318, vol. 85 Issue 6.

Zarate, et al., A Randomized Trail of an N-methyl_D-aspartate Antagonist in Treatment-Resistant Major Depression, Arch Gen Psychiatry, 2006, pp. 856-864, vol. 63.

PYRIDINE CARBAMATES AND THEIR USE AS GLUN2B RECEPTOR MODULATORS

1. CROSS-REFERENCE TO RELATED APPLICATIONS

This application claims the priority benefit of U.S. provisional application No. 62/861,634, filed Jun. 14, 2019, the contents of which are incorporated herein in their entireties by reference thereto.

2. BACKGROUND

Glutamate is one of the major excitatory neurotransmitters that is widely spread in the brain. First indication of its role as an excitatory messenger was in the 1950's when it was observed that intravenous administration of glutamate induces convulsions. However, the detection of the whole glutamatergic neurotransmitter system with its various receptors did not take place before the 1970's and 1980's when numerous antagonists were developed or, as in the case of PCP and ketamine, were identified as antagonists. Finally, in the 1990's molecular biology provided the tools for the classification of the glutamatergic receptors.

N-methyl-D-aspartate (NMDA) receptors are a subtype of ionotropic glutamate receptors that mediate excitatory synaptic transmission in the brain. NMDA receptors are ubiquitously distributed throughout the brain and play a key role in synaptic plasticity, synaptogenesis, excitotoxicity, memory acquisition and learning. NMDA receptors are distinct from other major subtypes of ionotropic glutamate receptors (AMPA and kainate receptors) in that they are blocked by $Mg^{2+}$ at resting membrane potentials, are highly $Ca^{2+}$ permeable, and require co-activation by two distinct neurotransmitters: glutamate and glycine (or D-serine) (Traynelis S F et al., *Pharmacol Rev.* 2010; 62(3):405-96). The influx of $Ca^{2+}$ through NMDA receptors triggers signaling cascades and regulates gene expression that is critical for different forms of synaptic plasticity including both long-term potentiation of synapse efficacy (LTP) (Berberich S et al., *Neuropharmacology* 2007; 52(1):77-86) and long-term depression (LTD) (Massey, P V et al., *J Neurosci.* 2004 Sep. 8; 24(36):7821-8).

The vast majority of the mammalian NMDA receptors form a heterotetramer made of two obligatory GluN1 units and two variable GluN2 receptor subunits encoded by the GRIN1 gene and one of four GRIN2 genes, respectively. One or both GluN2 subunits can be potentially replaced by a GluN3A or a GluN3B subunit. The GRIN1 gene product has 8 splice variants while there are 4 different GRIN2 genes (GRIN2A-D) encoding four distinct GluN2 subunits. The glycine binding site is present on the GluN1 subunit and the glutamate binding site is present on the GluN2 subunit.

The GluN2B subunits (also known as NR2B; see, Collingridge, et al, *Neuropharmacology*, 2009, 56:2-5) play a dominant role in determining the functional and pharmacological properties of the NMDA receptor assembly and exhibit distinct distribution in different areas of the brain. For instance, GluN2B subunits are expressed primarily in the forebrain in the adult mammalian brain (Paoletti P et al., *Nat Rev Neurosci.* 2013; 14(6):383-400; Watanabe M et al., *J Comp Neurol.* 1993; 338(3):377-90) and are implicated in learning, memory processing, mood, attention, emotion and pain perception (Cull-Candy S et al., *Curr Opin Neurobiol.* 2001; 11(3):327-35).

Compounds that modulate GluN2B-containing NMDA receptor function can be useful in treatment of many neurological and psychiatric disorders including but not limited to bipolar disorder (Martucci L et al., *Schizophrenia Res*, 2006; 84(2-3):214-21), major depressive disorder (Miller O H et al., *eLife.* 2014; 3:e03581; Li N et al., *Biol Psychiatry.* 2011; 69(8):754-61), treatment-resistant depression (Preskorn S H et al. *J Clin Psychopharmacol.* 2008; 28(6): 631-7) and other mood disorders (including schizophrenia (Grimwood S et al., *Neuroreport.* 1999; 10(3):461-5; Weickert C S et al. *Molecular Psychiatry* (2013) 18, 1185-1192), ante- and postpartum depression, seasonal affective disorder and the like), Alzheimer's disease (Hanson J E et al., *Neurobiol Dis.* 2015; 74:254-62; Li S et al., *J Neurosci.* 2011; 31(18):6627-38) and other dementias (Orgogozo J M et al. *Stroke* 2002, 33: 1834-1839), Parkinson's disease (Duty S, CNS Drugs. 2012; 26(12):1017-32; Steece-Collier K et al., *Exp Neurol.* 2000; 163(1):239-43; Leaver K R et al. *Clin Exp Pharmaco Physiol.* 2008; 35(11):1388-94), Huntington's chorea (Tang T S et al., *Proc Nat Acad Sci USA.* 2005; 102(7):2602-7; Li L et al., *J Neurophysiol.* 2004; 92(5):2738-46), multiple sclerosis (Grasselli G et al., *Br J Pharmacol.* 2013; 168(2):502-17; Farjam M et al., *Iran J Pharm Res.* 2014; 13(2):695-705), cognitive impairment (Wang D et al. 2014, *Expert Opin Ther Targets Expert Opin Ther Targets.* 2014; 18(10):1121-30), head injury (Bullock M R et al., *Ann N Y Acad Sci.* 1999; 890:51-8), spinal cord injury, stroke (Yang Y et al., *J Neurosurg.* 2003; 98(2):397-403), epilepsy (Naspolini A P et al., *Epilepsy Res.* 2012 June; 100(1-2):12-9), movement disorders (e.g. dyskinesias) (Morissette M et al., *Mov Disord.* 2006; 21(1):9-17), various neurodegenerative diseases (e.g. amyotrophic lateral sclerosis (Fuller P I et al., *Neurosci Lett.* 2006; 399(1-2):157-61) or neurodegeneration associated with bacterial or chronic infections), glaucoma (Naskar R et al. *Semin Ophthalmol.* 1999 September; 14(3):152-8), pain (e.g. chronic, cancer, post-operative and neuropathic pain (Wu L J and Zhuo M, Neurotherapeutics. 2009; 6(4):693-702), diabetic neuropathy, migraine (Peeters M et al., *J Pharmacol Exp Ther.* 2007; 321(2):564-72), cerebral ischemia (Yuan H et al., *Neuron.* 2015; 85(6):1305-18), encephalitis (Dalmau J. et al., *Lancet Neurol.* 2008; 7(12):1091-8.), autism and autism spectrum disorders (Won H. et al., *Nature.* 2012; 486(7402):261-5), memory and learning disorders (Tang, Y. P. et al., *Nature.* 1999; 401(6748):63-9), obsessive compulsive disorder (Arnold P D et al., *Psychiatry Res.* 2009; 172(2):136-9.), attention deficit hyperactivity disorder (ADHD) (Dorval K M et al., *Genes Brain Behav.* 2007; 6(5):444-52), PTSD (Haller J et al. *Behav Pharmacol.* 2011; 22(2):113-21; Leaderbrand K et al. *Neurobiol Learn Mem.* 2014; 113:35-40), tinnitus (Guitton M J, and Dudai Y, *Neural Plast.* 2007; 80904; Hu S S et al. 2016; 273(2): 325-332), sleep disorders (like narcolepsy or excessive daytime sleepiness, patent WO 2009058261 A1), vertigo and nystagmus (Straube A. et al., *Curr Opin Neurol.* 2005; 18(1):11-4; Starck M et al. *J Neurol.* 1997 January; 244(1):9-16), anxiety autoimmunological disorders like neuropsychiatric systemic lupus erythematosus (Kowal C et al. *Proc. Natl. Acad. Sci. U.S.A.* 2006; 103, 19854-19859) and addictive illnesses (e.g. alcohol addiction, drug addiction) (Nagy J, 2004, *Curr Drug Targets CNS Neurol Disord.* 2004; 3(3):169-79.; Shen H et al., *Proc Nat Acad Sci USA.* 2011; 108(48):19407-12).

In view of the clinical importance of GluN2B, the identification of compounds that modulate GluN2B receptor function represents an attractive avenue into the development of new therapeutic agents. Such compounds are provided herein.

3. SUMMARY

In one aspect, this disclosure provides compounds of Formula (I):

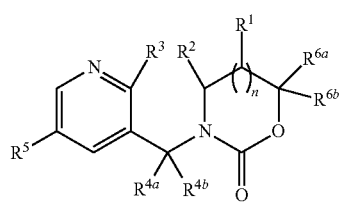

and pharmaceutically acceptable salts, solvates, isotopic variants, and N-oxides thereof, wherein:

n is 0 or 1;

$R^1$, when present, is H; or $R^1$, together with $R^2$ and the carbon atoms to which they are attached, forms a phenyl ring;

$R^2$, when not forming a phenyl ring with $R^1$ and the carbon atoms to which they are attached, is H or alkyl;

$R^3$ is H, halogen, alkyl, haloalkyl, O-alkyl, or O-haloalkyl;

$R^{4a}$ and $R^{4b}$ are, each independent from the other, H or alkyl;

$R^5$ is aryl which is optionally substituted with one, two, or three substituents each of which is independently halogen, alkyl, haloalkyl, or O-haloalkyl; pyridinyl which is optionally substituted with one substituent which is haloalkyl; or thienyl which is optionally substituted with one substituent which is halogen or haloalkyl; and $R^{6a}$ and $R^{6b}$ are, each independent from the other, H or alkyl which is optionally substituted with one substituent which is heterocycloalkyl; or $R^{6a}$ and $R^{6b}$ together with the carbon atom to which they are attached form a cycloalkyl ring or a heterocycloalkyl ring.

In certain embodiments, the compounds of Formula (I) are compounds selected from those species described or exemplified in the detailed description below.

In another aspect, the disclosure provides pharmaceutically acceptable prodrugs of compounds of Formula (I) and pharmaceutically active metabolites of compounds of Formula (I).

In a further aspect, the disclosure provides enantiomers and diastereomers of the compounds of Formula (I), as well as the pharmaceutically acceptable salts, solvates, isotopic variants, N-oxides, pharmaceutically acceptable prodrugs and pharmaceutically active metabolites of compounds of such enantiomers and diastereomers.

Exemplary features of the compounds of the disclosure (which include, for example, compounds of Formula (I), salts of compounds of Formula (I), solvates of compounds of Formula (I), isotopic variants of compounds of Formula (I), N-oxides of compounds of Formula (I), prodrugs of compounds of Formula (I), metabolites of compounds of Formula (I), enantiomers and diastereomers of compounds of Formula (I) etc.), are described in Section 4.3 and numbered embodiments, 1 to 226, infra.

In another aspect, the disclosure provides pharmaceutical compositions comprising a compound of the disclosure. Such pharmaceutical compositions can be used, for example, for treating a disease, disorder, or medical condition mediated by GluN2B receptor activity. In some embodiments, a pharmaceutical composition of the disclosure comprises at least one compound selected from compounds of Formula (I), pharmaceutically acceptable salts of compounds of Formula (I), solvates of compounds of Formula (I), isotopic variants of compounds of Formula (I), and N-oxides of compounds of Formula (I). Pharmaceutical compositions of the disclosure typically comprise one or more pharmaceutically acceptable excipients. Exemplary features of pharmaceutical compositions of the disclosure are described in Section 4.4 and numbered embodiments 227 to 233, infra.

In another aspect, the disclosure is directed to a method for modulating GluN2B receptor activity, including when such receptor is in a subject, comprising exposing GluN2B receptors to an effective amount of at least one compound of the disclosure (e.g., at least one compound selected from compounds of Formula (I), pharmaceutically acceptable salts of compounds of Formula (I), solvates of compounds of Formula (I), isotopic variants of compounds of Formula (I), and N-oxides of compounds of Formula (I)). In some aspects, the disclosure is directed to a method of treating a subject suffering from, or diagnosed with a disease, disorder, or medical condition mediated by GluN2B receptor activity, comprising administering to the subject an effective amount of at least one compound of the disclosure (e.g., at least one compound selected from compounds of Formula (I), pharmaceutically acceptable salts of compounds of Formula (I), solvates of compounds of Formula (I), isotopic variants of compounds of Formula (I), and N-oxides of compounds of Formula (I)). Exemplary features of methods for using compounds of the disclosure to treat diseases, disorders, and medical conditions mediated by GluN2B receptor activity are described in Section 4.5 and numbered embodiments 234 to 245, infra.

Additional aspects of this disclosure include methods of making compounds of the disclosure. Exemplary methods for making compounds of the disclosure are described in Sections 4.3 and 4.6.

4. DETAILED DESCRIPTION

In various aspects, this disclosure provides compounds, for example compounds of Formula (I) as described in the Summary and Section 4.3, pharmaceutical compositions comprising at least one compound of the disclosure, for example, as described in Section 4.4, methods of using the compounds of the disclosure, for example, as described in Section 4.5, and methods of making compounds of the disclosure, for example as described in Section 4.6.

4.1. Definitions

Abbreviations, acronyms, and trademarks used in this disclosure include the following:

TABLE 1

| Term | Acronym/Abbreviation/Trademark |
|---|---|
| [1,1'-bis(diphenylphosphino)ferrocene]dichloropalladium(II) | Pd(dppf)Cl$_2$ |
| [1,1'-bis(diphenylphosphino)ferrocene]dichloropalladium(II), complex with dichloromethane | Pd(dppf)Cl$_2$·CH$_2$Cl$_2$ |
| [1,1'-Bis(di-tert-butylphosphino)ferrocene]dichloropalladium(II) | PdCCl$_2$(dtbpf) |

TABLE 1-continued

| Term | Acronym/Abbreviation/Trademark |
|---|---|
| (2-Dicyclohexylphospino-2',6'-diisopropoxy-1,1'-biphenyl)[3-(3]-amino-1,1'biphenyl)] palladium(II) methanesulfonate, RuPhos-G3-Palladacycle | RuPhos Pd G3 |
| Acetonitrile | ACN |
| Azobisisobutyronitirile | AIBN |
| Broad | br |
| Di-tert-butyl decarbonate | $Boc_2O$ |
| Carbon tetrachloride | $CCl_4$ |
| Cesium carbonate | $Cs_2CO_3$ |
| Diatomaceous Earth | Celite ® 545, Celite ® |
| 1,1'-Carbonyl-diimidazole | CDI |
| (Diethylamino)sulfur trifluoride | DAST |
| Dichlorethane | DCE |
| Methylene chloride, dichloromethane | DCM |
| Bis(2-methoxyethyl)aminosulfur trifluoride | Deoxo-Fluor ® |
| N,N-Dimethylformamide | DMF |
| Deutero-dimethyl sulfoxide | $DMSO-d_6$ |
| Electrospray Ionization | ESI |
| Diethyl ether | $Et_2O$ |
| Ethyl Acetate | EtOAc, or EA, or AcOEt |
| Ethanol | EtOH |
| Flash Column Chromatography | FCC |
| Grams | g |
| Hours | h |
| High-pressure liquid chromatography | HPLC |
| Hertz | Hz |
| Isopropyl Alcohol | iPrOH |
| Potassium fluoride | KF |
| Potassium acetate | KOAc |
| Potassium carbonate | $K_2CO_3$ |
| Lithium aluminum hydride | LAH |
| Liquid chromatography and mass spectrometry | LCMS |
| Lithium aluminum deuteride | $LiAlD_4$ |
| Lithium borohydride | $LiBH_4$ |
| Molar | M |
| Mass to charge ratio | m/z |
| Milligrams | mg |
| Minute | min |
| Milliliter | mL |
| Microliter | μL |
| Mass spectrometry | MS |
| Deteromethanol | $MeOD-d_4$ |
| Methanol | MeOH |
| Sodium borohydride | $NaBH_4$ |
| Sodium borodeuteride | $NaBD_4$ |
| Sodium carbonate | $Na_2CO_3$ |
| Sodium hydride | NaH |
| N-Bromosuccinimide | NBS |
| Nuclear magnetic resonance | NMR |
| Precipitate | ppt |
| Tetrakis(triphenylphosphine)palladium(0) | $Pd(PPh_3)_4$ |
| Room temperature | rt |
| Saturated | sat |
| Supercritical Fluid Chromatography | SFC |
| Thionyl chloride | $SOCl_2$ |
| Triethyl amine | TEA |
| Trifluoroacetic acid | TFA |
| Tetrahydrofuran | THF |

"Alkyl" refers to a straight- or branched-chain alkyl group having from 1 to 12 carbon atoms in the chain. Examples of alkyl groups include methyl (Me, which also can be structurally depicted by the symbol, "P"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_{1-6}$alkyl as used here refers to a straight- or branched-chain alkyl group having from 1 to 6 carbon atoms in the chain. The term $C_{1-4}$alkyl as used here refers to a straight- or branched-chain alkyl group having from 1 to 4 carbon atoms in the chain. The term $C_{1-3}$alkyl as used here refers to a straight- or branched-chain alkyl group having from 1 to 3 carbon atoms in the chain. The term $C_{1-2}$alkyl as used here refers to an alkyl group having from 1 to 2 carbon atoms in the chain.

"Aryl" refers to a monocyclic, aromatic carbocycle (ring structure having ring atoms that are all carbon) having 6 atoms per ring. Carbon atoms in the aryl groups are $sp^2$ hybridized.

"Compounds of Formula (I)" refers to compounds encompassed by Formula (I) as described in the Summary. Unless required otherwise by context, the term "compounds of Formula (I)" encompasses compounds of Formula (Ia), Formula (Ib), Formula (Ic), Formula (Id), Formula (Ie), and Formula (If) as described in this disclosure. Thus, unless required otherwise by context, disclosure of an embodiment relating to a "compound of Formula (I)" is also a disclosure of an embodiment relating a compound of Formula (Ia), a disclosure of an embodiment relating to a compound of Formula (Ib), a disclosure of an embodiment relating to a compound of Formula (Ic), a disclosure of an embodiment relating to a compound of Formula (Id), a disclosure of an embodiment relating to a compound of Formula (Ie), and a disclosure of an embodiment relating to a compound of Formula (If).

"Cycloalkyl" refers to a saturated or partially saturated carbocycle having from 3 to 12 ring atoms per carbocycle. Illustrative examples of cycloalkyl groups include the following entities, in the form of properly bonded moieties:

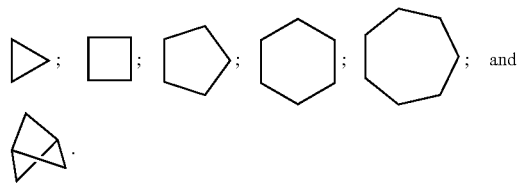

"Effective amount" means an amount or dose of an agent (e.g., a compound of the disclosure or a pharmaceutical composition of the disclosure) sufficient to generally bring about the desired therapeutic or prophylactic benefit in a subject in need of treatment for a designated disease, disorder, or condition. Effective amounts or doses of the compounds or pharmaceutical compositions of the disclosure can be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician.

"Halo" or "halogen" represents chloro, fluoro, bromo or iodo.

"Haloalkyl" refers to a straight- or branched-chain alkyl group having from 1 to 12 carbon atoms in the chain optionally substituting hydrogens with halogens. The term "$C_{1-6}$haloalkyl" as used here refers to a straight- or branched-chain alkyl group having from 1 to 6 carbon atoms in the chain, substituting one or more hydrogens with halogens. The term "$C_{1-3}$haloalkyl" as used here refers to a straight- or branched-chain alkyl group having from 1 to 3 carbon atoms in the chain, substituting one or more hydrogens with halogens. Examples of haloalkyl groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl (—$CF(CF_3)_2$), and groups that in light of the ordinary skill in the art and the teachings provided herein would be considered equivalent to any one of the foregoing examples.

"Heteroaryl" refers to a monocyclic or fused bicyclic heterocycle (ring structure having ring atoms selected from carbon atoms and up to four heteroatoms selected from nitrogen, oxygen, and sulfur) having from 3 to 9 ring atoms per heterocycle. Illustrative examples of heteroaryl groups include the following entities, in the form of properly bonded moieties:

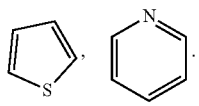

"Heterocycloalkyl" or "heterocycloalkyl ring" refers to a monocyclic ring structure that is saturated or partially saturated and has from 4 to 7 ring atoms per ring structure selected from carbon atoms and up to two heteroatoms selected from nitrogen, oxygen, and sulfur. Illustrative entities, in the form of properly bonded moieties, include:

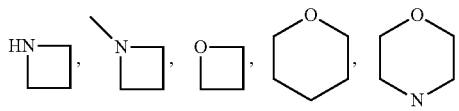

"Isotopic variant" refers to a compound of the disclosure (e.g., a compound of Formula (I)) that is isotopically labeled. Isotopic variants have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorus, sulfur, fluorine, chlorine, and iodine such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively.

"Para," "meta," and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on a phenyl ring, the 2 different ortho positions can be designated as ortho and ortho' and the 2 different meta positions as meta and meta' as illustrated below.

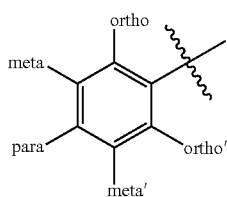

When referring to substituents on a pyridyl group, the terms "para", "meta", and "ortho" refer to the placement of a substituent relative to the point of attachment of the pyridyl ring. For example the structure below is described as 3-pyridyl with the $X^1$ substituent in the ortho position, the $X^2$ substituent in the meta position, and $X^3$ substituent in the para position:

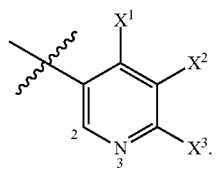

"Pharmaceutically acceptable" means approved or approvable by a regulatory agency of Federal or a state government or the corresponding agency in countries other than the United States, or that is listed in the U. S. Pharmacopoeia or other generally recognized pharmacopoeia for use in animals, and more particularly, in humans.

"Pharmaceutically active metabolite" means a pharmacologically active product of metabolism in the body of a compound.

"Phenyl" refers to the following moiety:

"Prodrug" means a precursor of a compound that, following administration to a subject, yields the compound in vivo via a chemical or physiological process such as solvolysis or enzymatic cleavage, or under physiological conditions (e.g., a prodrug on being brought to physiological pH is converted to a compound of Formula (I). A "pharmaceutically acceptable prodrug" is a prodrug that is biologically tolerable and otherwise biologically suitable for administration to a subject.

"Substituted" means that the specified group or moiety bears one or more substituents. "Unsubstituted" means that the specified group bears no substituents. "Optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

"Subject" refers to a mammalian subject, preferably a human.

"Treat," "treatment" or "treating" refers to administration of a compound or pharmaceutical composition of the disclosure to a subject for the purpose of affecting a therapeutic or prophylactic benefit. Unless required otherwise by context, treating includes reversing, ameliorating, alleviating, inhibiting the progress of, lessening the severity of, or preventing a disease, disorder, or condition, or one or more symptoms of such disease, disorder or condition.

Those skilled in the art will recognize that the species of groups listed or illustrated in this Section are not exhaustive, and that additional species within the scope of these defined terms can also be selected.

4.2. Additional Terminology

To provide a more concise description, some of the quantitative expressions given in this disclosure are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Chemical structural formulae are provided throughout the disclosure. For a given formula, this disclosure encompasses the compound(s) depicted by the formula as well as certain variations and forms thereof. For example, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (e.g., cis and trans isomers), as tautomers, or as atropisomers.

The compounds of this disclosure may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enantiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

The symbols  and  are used as meaning the same spatial arrangement in chemical structures shown herein. Analogously, the symbols  and  are used as meaning the same spatial arrangement in chemical structures shown herein.

When referring to any formula given herein, the selection of a particular moiety from a list of possible species for a specified variable is not intended to define the same choice of the species for the variable appearing elsewhere. In other words, where a variable appears more than once, the choice of a species from a specified list is independent of the choice of another species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this disclosure given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. Shorter terminology, such as, "$S^1_{example}$ is one of $S_1$ and $S_2$, and $S^2_{example}$ is one of $S_3$ and $S_4$," is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^3$, $R^{4a}$, $R^{4b}$, $R^5$, $R^{6a}$, $R^{6b}$, $R^7$, $R^8$, $R^9$, $R^{10}$, $R^{11}$, $R^{12}$, and any other generic substituent symbol used herein.

Furthermore, when more than one assignment is given for any member or substituent, embodiments of this disclosure comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this disclosure for which $S_{example}$ is $S$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. Shorter terminology, such as "$S_{example}$ is one of $S_1$, $S_2$, and $S_3$," is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^3$, $R^4$, $R^{4b}$, $R^5$, $R^{6a}$, $R^{6b}$, $R^7$, $R^8$, $R^9$, $R^{10}$, $R^{11}$, $R^{12}$, and any other generic substituent symbol used herein.

The nomenclature "$C_{i-j}$" with $j>i$, when applied herein to a class of substituents, is meant to refer to embodiments of this disclosure for which each and every one of the number of carbon members, from i to j including i and j, is independently realized. By way of example, the term $C_{1-4}$ refers independently to embodiments that have one carbon member ($C_1$), embodiments that have two carbon members ($C_2$), embodiments that have three carbon members ($C_3$), and embodiments that have four carbon members ($C_4$).

4.3. Compounds of the Disclosure

In one aspect, this disclosure provides compounds of Formula (I):

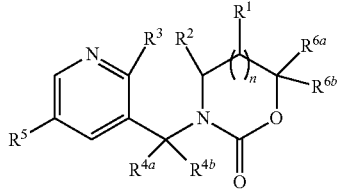

(I)

and pharmaceutically acceptable salts, solvates, isotopic variants, and N-oxides of compounds of Formula (I), wherein:

n is 0 or 1;

$R^1$, when present, is H; or $R^1$, together with $R^2$ and the carbon atoms to which they are attached, forms a phenyl ring;

$R^2$, when not forming a phenyl ring with $R^1$ and the carbon atoms to which they are attached, is H or alkyl;

$R^3$ is H, halogen, alkyl, haloalkyl, O-alkyl, or O-haloalkyl;

$R^{4a}$ and $R^{4b}$ are, each independent from the other, H or alkyl;

$R^5$ is aryl which is optionally substituted with one, two, or three substituents each of which is independently halogen, alkyl, haloalkyl, or O-haloalkyl; pyridinyl which is optionally substituted with one substituent which is haloalkyl; or thienyl which is optionally substituted with one substituent which is halogen or haloalkyl; and $R^{6a}$ and $R^{6b}$ are, each independent from the other, H or alkyl which is optionally substituted with one substituent which is heterocycloalkyl; or $R^{6a}$ and $R^{6b}$ together with the carbon atom to which they are attached form a cycloalkyl ring or a heterocycloalkyl ring.

In some embodiments, the compound of Formula (I) is a compound of Formula (Ia):

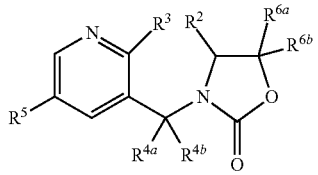

(Ia)

In other embodiments, the compound of Formula (I) is a compound of Formula (Ib):

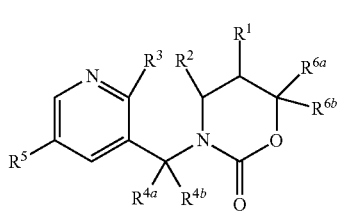

(Ib)

In other embodiments, the compound of Formula (I) is a compound of Formula (Ic):

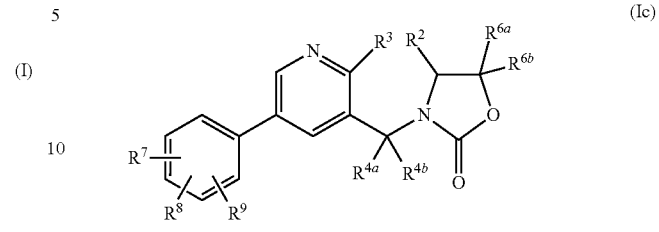

(Ic)

wherein each of $R^7$, $R^8$, and $R^9$ is, independent from the others, H, halogen, alkyl, haloalkyl, or O-haloalkyl.

In other embodiments, the compound of Formula (I) is a compound of Formula (Id):

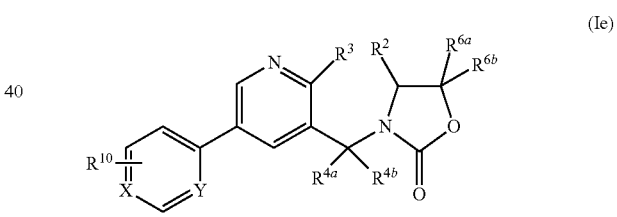

(Id)

wherein each of $R^1$, $R^8$, and $R^9$ is, independent from the others, H, halogen, alkyl, haloalkyl, or O-haloalkyl.

In other embodiments, the compound of Formula (I) is a compound of Formula (Ie):

(Ie)

wherein one of X and Y is N and the other is H, and wherein $R^1$ is $C_1$-$C_6$haloalkyl.

In other embodiments, the compound of Formula (I) is a compound of Formula (If):

(If)

wherein $R^{11}$ is halo or $C_1$-$C_6$haloalkyl.

In another aspect, the disclosure provides enantiomers of compounds of Formula (I).

In another aspect, the disclosure provides diastereomers of compounds of Formula (I).

In another aspect, the disclosure provides pharmaceutically acceptable prodrugs of compounds of Formula (I).

In another aspect, the disclosure provides pharmaceutically active metabolites of compounds of Formula (I).

Further embodiments relating to variables $R^1$, $R^2$, $R^3$, $R^{4a}$, $R^{4b}$, $R^5$, $R^{6a}$, and $R^{6b}$ are described in Sections 4.3.1 to 4.3.6. It should be understood that an embodiment relating to a given variable described in one of Sections 4.3.1 to 4.3.6 can be combined with one or more embodiments in one or more of the other of Sections 4.3.1 to 4.3.6 (e.g., an embodiment relating to $R^1$ described in Section 4.3.1 can be combined with an embodiment relating to $R^2$ described in Section 4.3.2, an embodiment relating to $R^3$ described in Section 4.3.3, an embodiment relating to $R^{4a}$ and $R^{4b}$ described in Section 4.3.4, an embodiment relating to $R^5$ described in Section 4.3.5, and an embodiment relating to $R^{6a}$ and $R^{6b}$ described in Section 4.3.6), and that such combinations are within the scope of the disclosure.

4.3.1. $R^1$

In some embodiments of the compounds of the disclosure, $R^1$, when present, is H.

In other embodiments of the compounds of the disclosure, $R^1$, when present, forms a phenyl ring with $R^2$ and the atoms to which $R^1$ and $R^2$ are attached.

4.3.2. $R^2$

In some embodiments of the compounds of the disclosure, $R^2$, when not forming a phenyl ring with $R^1$ and the carbon atoms to which they are attached, is H or alkyl, for example, $C_1$-$C_6$alkyl or $C_1$-$C_3$alkyl. In some embodiments, $R^2$ is H. In other embodiments, $R^2$ is —$CH_3$. In other embodiments, $R^2$ is —$CH(CH_3)_2$.

In some embodiments of compounds of the disclosure, the stereochemistry at the carbon to which $R^2$ is attached is (R). In other embodiments of compounds of the disclosure, the stereochemistry at the carbon to which $R^2$ is attached is (S).

4.3.3. $R^3$

In some embodiments of the compounds of the disclosure, $R^3$ is H, halogen (e.g., F, C, or Br), alkyl (e.g., $C_1$-$C_6$alkyl or $C_1$-$C_3$alkyl), haloalkyl (e.g., $C_1$-$C_6$haloalkyl or $C_1$-$C_3$haloalkyl), O-alkyl (e.g., O—$C_1$-$C_6$alkyl or O—$C_1$-$C_3$alkyl), or O-haloalkyl (e.g., O—$C_1$-$C_6$haloalkyl or O—$C_1$-$C_3$haloalkyl).

In some embodiments of the compounds of the disclosure, $R^3$ is H.

In some embodiments of the compounds of the disclosure, $R^3$ is halogen (e.g., F, Cl, or Br). In some embodiments of the compounds of the disclosure, $R^3$ is F.

In other embodiments of the compounds of the disclosure, $R^3$ is alkyl (e.g., $C_1$-$C_6$alkyl, $C_1$-$C_3$alkyl, or $C_1$-$C_2$alkyl). In some embodiments of the compounds of the disclosure, $R^3$ is —$CH_3$.

In other embodiments of the compounds of the disclosure, $R^3$ is haloalkyl (e.g., $C_1$-$C_6$haloalkyl, $C_1$-$C_3$haloalkyl, or $C_1$-$C_2$haloalkyl). In some embodiments of the compounds of the disclosure, the haloalkyl comprises one or more (e.g., one or two) F atoms. In some embodiments of the compounds of the disclosure, $R^3$ is —$CHF_2$. In other embodiments of the compounds of the disclosure, $R^3$ is —$CF_2CH_3$.

In other embodiments of the compounds of the disclosure, $R^3$ is O-alkyl (e.g., —$OC_1$-$C_6$alkyl, —$OC_1$-$C_3$alkyl, or —$OC_1$-$C_2$alkyl). In some embodiments of the compounds of the disclosure, $R^3$ is —$OCH_3$.

In other embodiments of the compounds of the disclosure, $R^3$ is O-haloalkyl (e.g., O—$C_1$-$C_6$haloalkyl, O—$C_1$-$C_3$haloalkyl, or O—$C_1$-$C_2$haloalkyl). In some embodiments of the compounds of the disclosure, the O-haloalkyl comprises one or more (e.g., one or two) F atoms. In some embodiments of the compounds of the disclosure, $R^3$ is —$OCHF_2$.

In some embodiments, $R^3$ is H, F, —$CH_3$, —$CHF_2$, —$CF_2CH_3$, —$OCH_3$, or —$OCHF_2$.

In some embodiments, $R^3$ is H, —$CH_3$, —$CHF_2$, —$CF_2CH_3$, —$OCH_3$, or —$OCHF_2$.

4.3.4. $R^{4a}$ and $R^{4b}$

In some embodiments of the compounds of the disclosure, $R^{4a}$ and $R^{4b}$ are both H (e.g., $^1H$ or $^2H$). In some embodiments of the compounds of the disclosure, $R^{4a}$ and $R^{4b}$ are both $^1H$. In other embodiments of the compounds of the disclosure, one of $R^{4a}$ and $R^{4b}$ is $^1H$ and the other is $^2H$. In other embodiments of the compounds of the disclosure, $R^{4a}$ and $R^{4b}$ are both $^2H$.

In other embodiments of the compounds of the disclosure, $R^{4a}$ is H (e.g., $^1H$ or $^2H$) and $R^{4b}$ is alkyl (e.g., $C_1$-$C_6$alkyl, $C_1$-$C_3$alkyl or $C_1$-$C_2$alkyl). In other embodiments of the compounds of the disclosure, $R^{4b}$ is —$CH_3$.

In some embodiments of the compounds of the disclosure, when $R^{4a}$ and $R^{4b}$ are different, the stereochemistry at the carbon to which $R^{4a}$ and $R^{4b}$ are attached is (R). In other embodiments of the compounds of the disclosure, when $R^{4a}$ and $R^{4b}$ are different, the stereochemistry at the carbon to which $R^{4a}$ and $R^{4b}$ are attached is (S).

4.3.5. $R^5$

4.3.5.1. Aryl $R^5$ Groups

In some embodiments of the compounds of the disclosure, $R^5$ is aryl which is optionally substituted with one, two, or three substituents each of which is independently halogen (e.g., F or Cl), alkyl (e.g., $C_1$-$C_6$alkyl, $C_1$-$C_3$alkyl, or $C_1$-$C_2$alkyl), haloalkyl (e.g., $C_1$-$C_6$haloalkyl, $C_1$-$C_3$haloalkyl, or $C_1$-$C_2$haloalkyl), or O-haloalkyl (e.g., O—$C_1$-$C_6$haloalkyl, O—$C_1$-$C_3$haloalkyl, or O—$C_1$-$C_2$haloalkyl). In some embodiments of the compounds of the disclosure, $R^5$ is aryl substituted with one substituent. In other embodiments of the compounds of the disclosure, $R^5$ is aryl substituted with two substituents. In yet other embodiments of the compounds of the disclosure, $R^5$ is aryl substituted with three substituents.

In some embodiments of the compounds of the disclosure, $R^5$ is

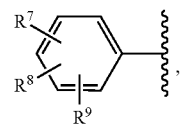

wherein each of $R^7$, $R^8$, and $R^9$ is, independent from the others, H, halogen (e.g., F or Cl), alkyl (e.g., $C_1$-$C_6$alkyl, $C_1$-$C_3$alkyl, or $C_1$-$C_2$alkyl), haloalkyl (e.g., $C_1$-$C_6$haloalkyl, $C_1$-$C_6$haloalkyl, or $C_1$-$C_2$haloalkyl), or O-haloalkyl (e.g., O—$C_1$-$C_6$haloalkyl, O—$C_1$-$C_3$haloalkyl, or O—$C_1$-$C_2$haloalkyl).

In some embodiments of the compounds of the disclosure, each of $R^7$, $R^8$, and $R^9$ is, independent from the others, H, F, C, $CH_3$, —$CHF_2$, —$CF_2CH_3$, —$CF_3$, —$OCHF_2$, or —$OCF_3$.

In some embodiments of the compounds of the disclosure, $R^7$ is in the ortho position, $R^8$ is in the ortho position, and $R^9$ in the meta position. In other embodiments of the compounds of the disclosure, $R^7$ is in the ortho position, $R^8$ is in the ortho position, and $R^9$ in the para position. In other embodiments of the compounds of the disclosure, $R^7$ is in the ortho position, $R^8$ is in the meta position, and $R^9$ in the para position. In other embodiments of the compounds of the disclosure, $R^7$ is in the ortho position, $R^8$ is in the meta position, and $R^9$ in the meta position. In other embodiments of the compounds of the disclosure, $R^7$ is in the meta position, $R^8$ is in the meta position, and $R^9$ in the para position.

In some embodiments of the compounds of the disclosure, $R^5$ is:

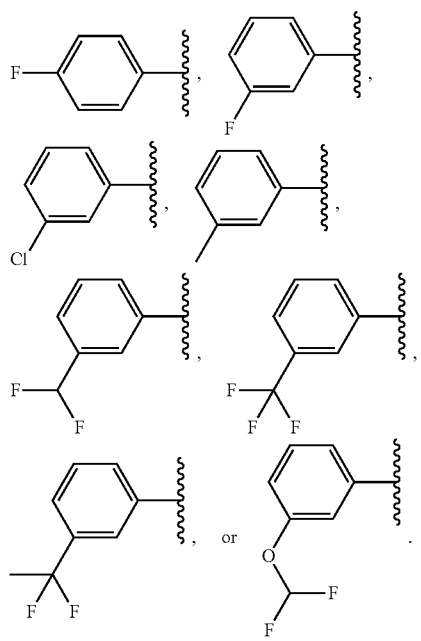

In other embodiments of the compounds of the disclosure, $R^5$ is

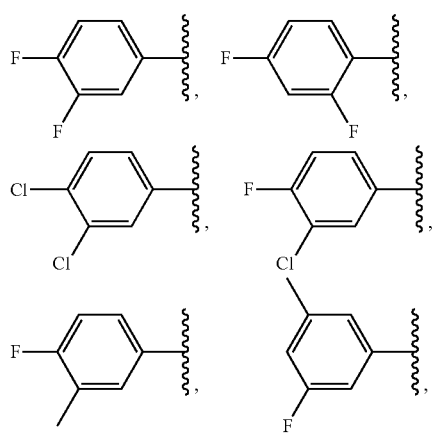

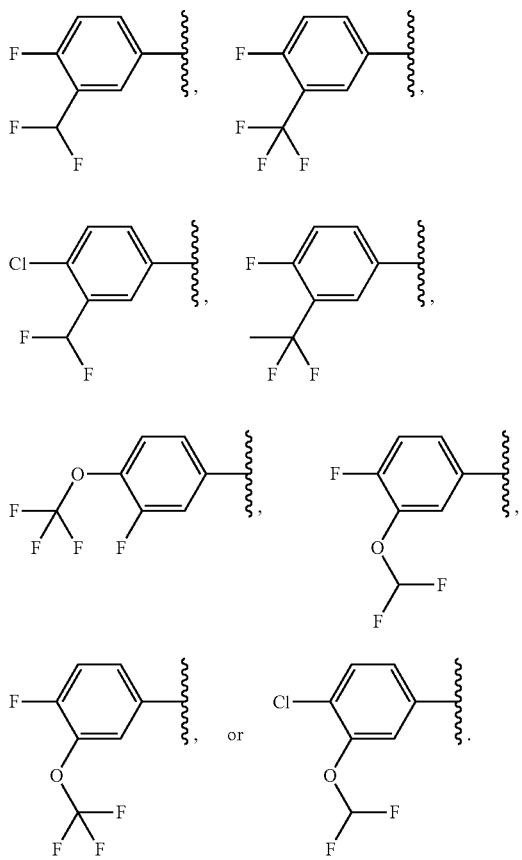

In other embodiments of the compounds of the disclosure, $R^5$ is

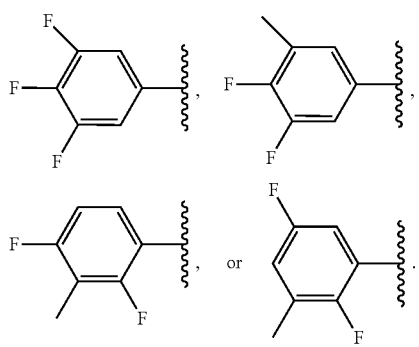

4.3.5.2. Pyridinyl $R^5$ Groups

In some embodiments of the compounds of the disclosure, $R^5$ is pyridinyl which is optionally substituted with one substituent which is haloalkyl (e.g., $C_1$-$C_6$haloalkyl or $C_1$-$C_6$haloalkyl). In some embodiments of the compounds of the disclosure, $R^5$ is pyridinyl substituted with one substituent which is haloalkyl (e.g., $C_1$-$C_6$haloalkyl or $C_1$-$C_6$haloalkyl). In some embodiments of the compounds of the disclosure, $R^5$ is pyridinyl substituted with one substituent which is-$CF_3$.

In some embodiments of the compounds of the disclosure, $R^5$ is

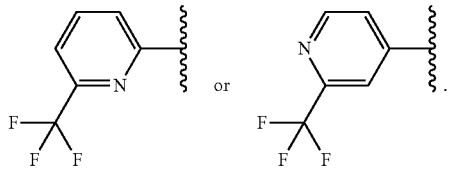 [SMILES: *c1cccc(C(F)(F)F)n1 ; *c1ccnc(C(F)(F)F)c1]

4.3.5.3. Thineyl $R^5$ Groups

In some embodiments of the compounds of the disclosure, $R^5$ is thienyl which is optionally substituted with one substituent which is halogen (e.g., Cl) or haloalkyl (e.g., $C_1$-$C_6$haloalkyl).

In some embodiments of the compounds of the disclosure, $R^5$ is thienyl which is substituted with one substituent which is halogen (e.g., Cl). In some embodiments of the compounds of the disclosure, $R^5$ is

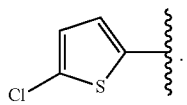

In other embodiments of the compounds of the disclosure, $R^5$ is thienyl which is substituted with one substituent which is haloalkyl (e.g., $C_1$-$C_6$haloalkyl). In other embodiments of the compounds of the disclosure, $R^5$ is thienyl which is substituted with one substituent which is —$CHF_2$ or —$CF_3$. In some embodiments of the compounds of the disclosure, $R^5$ is

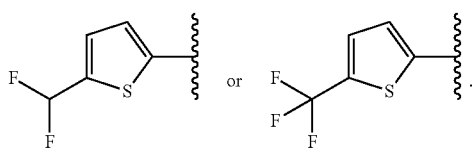 [SMILES: *c1ccc(C(F)F)s1 ; *c1ccc(C(F)(F)F)s1]

4.3.6. $R^{6a}$ and $R^{6b}$

In some embodiments of the compounds of the disclosure, $R^{6a}$ and $R^{6b}$ are, each independent from the other, H or alkyl which is optionally substituted with one substituent which is heterocycloalkyl; or $R^{6a}$ and $R^{6b}$ together with the carbon atom to which they are attached form a cycloalkyl ring or a heterocycloalkyl ring.

In some embodiments of the compounds of the disclosure, $R^{6a}$ and $R^{6b}$ are, each independent from the other, H or $C_1$-$C_6$alkyl which is optionally substituted with one substituent which is 4 to 6 membered heterocycloalkyl; or $R^{6a}$ and $R^{6b}$ together with the carbon atom to which they are attached form a $C_3$-$C_6$cycloalkyl ring or a 4 to 6 membered heterocycloalkyl ring.

In some embodiments of the compounds of the disclosure, $R^{6a}$ and $R^{6b}$ are both H.

In some embodiments of the compounds of the disclosure, one of $R^{6a}$ and $R^{6b}$ is H and the other is alkyl (e.g., $C_1$-$C_6$alkyl or $C_1$-$C_6$alkyl) which is optionally substituted with one substituent which is heterocycloalkyl (e.g., 4 to 6 membered heterocycloalkyl).

In some embodiments of the compounds of the disclosure, one of $R^{6a}$ and $R^{6b}$ is H and the other is —$CH_3$.

In other embodiments of the compounds of the disclosure, one of $R^{6a}$ and $R^{6b}$ is H and the other is —$CH(CH_3)_2$.

In other embodiments of the compounds of the disclosure, one of $R^{6a}$ and $R^{6b}$ is H and the other is —$CH_2R^{12}$, where $R^{12}$ is 4 to 6 membered heterocycloalkyl. In some embodiments of the compounds of the disclosure, $R^{12}$ is

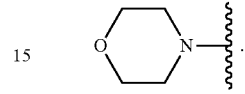

In other embodiments of the compounds of the disclosure, $R^{6a}$ and $R^{6b}$ are both alkyl (e.g., $C_1$-$C_6$alkyl, $C_1$-$C_3$alkyl, or $C_1$-$C_2$alkyl). In some embodiments of the compounds of the disclosure, $R^{6a}$ and $R^{6b}$ are both -$CH_3$.

In other embodiments of the compounds of the disclosure, $R^{6a}$ and $R^{6b}$ together with the carbon atom to which they are attached form a cycloalkyl ring (e.g., a $C_3$-$C_6$cycloalkyl ring) or a heterocycloalkyl ring (e.g., a 4 to 6 membered heterocycloalkyl ring). In some embodiments of the compounds of the disclosure, $R^{6a}$ and $R^{6b}$ together with the carbon atom to which they are attached form a cyclopropyl or cyclobutyl ring. In other embodiments of the compounds of the disclosure, $R^{6a}$ and $R^{6b}$ together with the carbon atom to which they are attached form

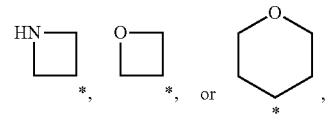

wherein * denotes the point of attachment of the ring to the remainder of the molecule.

In some embodiments of the compounds of the disclosure, the stereochemistry at the carbon to which $R^{6a}$ and $R^{6b}$ are attached is (R). In other embodiments of the compounds of the disclosure the stereochemistry at the carbon to which $R^{6a}$ and $R^{6b}$ are attached is (S).

4.3.7. Compound Forms

A compounds of the disclosure can be, for example, a compound of Formula (I) in the form of a free acid or a free base. A compound of the disclosure can also be a compound of Formula (I) in the form of a pharmaceutically acceptable salt. A compound of the disclosure can also be a compound of Formula (I) in the form of a solvate. A compound of the disclosure can also be an isotopic variant of a compound of Formula (I). A compound of the disclosure can also be in the form of an N-oxide of a compound of Formula (I). A compound of the disclosure can also be in the form of a prodrug of a compound of Formula (I). A compound of the disclosure can also be in the form of a metabolite of a compound of Formula (I).

4.3.7.1. Pharmaceutically Acceptable Salts

In some embodiments, a compound of Formula (I) is the form of a pharmaceutically acceptable salt. Pharmaceutically acceptable salts are preferably salts that are non-toxic, biologically tolerable, or otherwise biologically suitable for administration to a subject. Preferably, a pharmaceutically acceptable salt of a compound of Formula (I) possesses the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., *"Pharmaceutical Salts", J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compound of Formula (I) is a base, a desired pharmaceutically acceptable salt can be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as aurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, a desired pharmaceutically acceptable salt can be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

4.3.7.2. Solvates

In some embodiments, a compound of Formula (I) is in the form of a solvate. Many organic compounds can form solvates with solvents in which they are reacted or from which they are precipitated or crystallized. Solvates include those formed from the interaction or complexation of compounds of the disclosure with one or more solvents, either in solution or as a solid or crystalline form. In some embodiments, the solvent is water and the solvates are hydrates.

4.3.7.3. Isotopic Variants

In some embodiments, a compound of Formula (I) is the form of an isotopic variant, e.g., a deuterated compound of Formula (I). Such isotopic variants are useful in metabolic studies (preferably with $^{14}C$), reaction kinetic studies (with, for example deuterium (abbreviated "D" or "$^{2}H$"); or tritium (abbreviated "T" or "$^{3}H$")), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound can be particularly preferred for PET or SPECT studies. Further, substitution with heavier isotopes such as deuterium can afford certain therapeutic advantages resulting from greater metabolic stability, for example increased in vivo half-life or reduced dosage requirements. Isotopically labeled compounds of this disclosure can generally be prepared by carrying out the procedures disclosed in the schemes or in the examples described herein by substituting a readily available isotopically labeled reagent for a non-isotopically labeled reagent.

4.3.7.4. N-Oxides

In some embodiments, a compound of Formula (I) is the form of an N-oxide. N-oxides can be prepared according to techniques known in the art. See, e.g., Yousif, S., Arkivoc, 2001, 2001(1):242-268.

4.3.7.5. Prodrugs and Pharmaceutically Active Metabolites

The disclosure also provides pharmaceutically acceptable prodrugs of the compounds of Formula (I) and treatment methods employing such pharmaceutically acceptable prodrugs. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

The present disclosure also relates to pharmaceutically active metabolites of the compounds of Formula (I). Prodrugs and active metabolites of a compound can be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, Drug Dev Res. 1995, 34, 220-230; Bodor, *Adv Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

4.3.8. Exemplary Compounds of Formula (I)

Exemplary compounds of the disclosure are listed in Table 2, below. In various aspects, the disclosure provides, for example, pharmaceutically acceptable salts, solvates, isotopic variants, and N-oxides of the compounds listed in Table 2.

TABLE 2

| Example # | Compound Name |
|---|---|
| 1 | 3-[[5[3-(Difluoromethoxy)-4-fluoro-phenyl]-3-pyridyl]methyl]-1,3-oxazinan-2-one; |
| 2 | 3-[[5-[3-(Difluoromethoxy)-4-fluoro-phenyl]-3-pyridyl]methyl]oxazolidin-2-one; |
| 3 | (4S)-3-[[5-[3-(Difluoromethoxy)-4-fluoro-phenyl]-3-pyridyl]methyl]-4-isopropyl-oxazolidin-2-one; |
| 4 | 1-[[5-[3-(Difluoromethoxy)-4-fluoro-phenyl]-3-pyridyl]methyl]-4H-3,1-benzoxazin-2-one; |
| 5 | (R/S)-3-[[5-[3-(Difluoromethoxy)-4-fluoro-phenyl]-3-pyridyl]methyl]-4-methyl-oxazolidin-2-one; |
| 6 | (R/S)-3-[[5-[3-(Difluoromethoxy)-4-fluoro-phenyl]-3-pyridyl]methyl]-5-methyl-oxazolidin-2-one; |
| 7 | (S*)-3-[[5-[3-(Difluoromethoxy)-4-fluoro-phenyl]-3-pyridyl]methyl]-5-methyl-oxazolidin-2-one; |
| 8 | (R*)-3-[[5-[3-(Difluoromethoxy)-4-fluoro-phenyl]-3-pyridyl]methyl]-5-methyl-oxazolidin-2-one; |
| 9 | 5-[[5-[3-(Difluoromethoxy)-4-fluoro-phenyl]-3-pyridyl]methyl]-7-oxa-5-azaspiro[2.4]heptan-6-one; |
| 10 | 3-[[5-[3-(Difluoromethoxy)-4-fluoro-phenyl]-3-pyridyl]methyl]-6,6-dimethyl-1,3-oxazinan-2-one; |
| 11 | (4R)-3-[[5-[3-(Difluoromethoxy)-4-fluoro-phenyl]-3-pyridyl]methyl]-4-isopropyl-oxazolidin-2-one; |
| 12 | 6-[[5-[3-(Difluoromethoxy)-4-fluoro-phenyl]-3-pyridyl]methyl]-8-oxa-6-azaspiro[3.4]octan-7-one; |
| 13 | 6-[[5-[3-(Difluoromethoxy)-4-fluoro-phenyl]-3-pyridyl]methyl]-2,8-dioxa-6-azaspiro[3.4]octan-7-one; |
| 14 | (R/S)-3-[[5-[3-(Difluoromethoxy)-4-fluoro-phenyl]-3-pyridyl]methyl]-5-isopropyl-oxazolidin-2-one; |
| 15 | (R*)-3-[[5-[3-(Difluoromethoxy)-4-fluoro-phenyl]-3-pyridyl]methyl]-5-isopropyl-oxazolidin-2-one; |
| 16 | (S*)-3-[[5-[3-(Difluoromethoxy)-4-fluoro-phenyl]-3-pyridyl]methyl]-5-isopropyl-oxazolidin-2-one; |
| 17 | (R/S)-3-[[5-[3-(Difluoromethoxy)-4-fluoro-phenyl]-3-pyridyl]methyl]-5-(morpholinomethyl)oxazolidin-2-one; |
| 18 | (R*)-3-[[5-[3-(Difluoromethoxy)-4-fluoro-phenyl]-3-pyridyl]methyl]-5-(morpholinomethyl)oxazolidin-2-one; |
| 19 | (S*)-3-[[5-[3-(Difluoromethoxy)-4-fluoro-phenyl]-3-pyridyl]methyl]-5-(morpholinomethyl)oxazolidin-2-one; |
| 20 | 2-[[5-[3-(Difluoromethoxy)-4-fluoro-phenyl]-3-pyridyl]methyl]-4,8-dioxa-2-azaspiro[4.5]decan-3-one; |
| 21 | 6-[[5-[3-(Difluoromethyl)-4-fluoro-phenyl]-3-pyridyl]methyl]-8-oxa-2,6-diazaspiro[3.4]octan-7-one; |
| 22 | 3-[[5-[3-(Difluoromethyl)-4-fluoro-phenyl]-3-pyridyl]methyl]oxazolidin-2-one; |
| 23 | (4S)-3-[[5-[3-(Difluoromethyl)-4-fluoro-phenyl]-3-pyridyl]methyl]-4-isopropyl-oxazolidin-2-one; |
| 24 | 1-[[5-[3-(Difluoromethyl)-4-fluoro-phenyl]-3-pyridyl]methyl]-4H-3,1-benzoxazin-2-one; |
| 25 | (R/S)-3-[[5-[3-(Difluoromethyl)-4-fluoro-phenyl]-3-pyridyl]methyl]-4-methyl-oxazolidin-2-one; |
| 26 | (R/S)-3-[[5-[3-(Difluoromethyl)-4-fluoro-phenyl]-3-pyridyl]methyl]-5-methyl-oxazolidin-2-one; |
| 27 | (S*)-3-[[5-[3-(Difluoromethyl)-4-fluoro-phenyl]-3-pyridyl]methyl]-5-methyl-oxazolidin-2-one; |
| 28 | (R*)-3-[[5-[3-(Difluoromethyl)-4-fluoro-phenyl]-3-pyridyl]methyl]-5-methyl-oxazolidin-2-one; |
| 29 | 5-[[5-[3-(Difluoromethyl)-4-fluoro-phenyl]-3-pyridyl]methyl]-7-oxa-5-azaspiro[2.4]heptan-6-one; |
| 30 | 3-[[5-[3-(Difluoromethyl)-4-fluoro-phenyl]-3-pyridyl]methyl]-6,6-dimethyl-1,3-oxazinan-2-one; |
| 31 | (4R)-3-[[5-[3-(Difluoromethyl)-4-fluoro-phenyl]-3-pyridyl]methyl]-4-isopropyl-oxazolidin-2-one; |
| 32 | 6-[[5-[3-(Difluoromethyl)-4-fluoro-phenyl]-3-pyridyl]methyl]-8-oxa-6-azaspiro[3.4]octan-7-one; |
| 33 | (5R)-3-[[5-[3-(Difluoromethyl)-4-fluoro-phenyl]-3-pyridyl]methyl]-5-methyl-oxazolidin-2-one; |
| 34 | 6-[[5-[3-(Difluoromethyl)-4-fluoro-phenyl]-3-pyridyl]methyl]-2,8-dioxa-6-azaspiro[3.4]octan-7-one; |
| 35 | (R/S)-3-[[5-[3-(Difluoromethyl)-4-fluoro-phenyl]-3-pyridyl]methyl]-5-isopropyl-oxazolidin-2-one; |
| 36 | (R*)-3-[[5-[3-(Difluoromethyl)-4-fluoro-phenyl]-3-pyridyl]methyl]-5-isopropyl-oxazolidin-2-one; |
| 37 | (S*)-3-[[5-[3-(Difluoromethyl)-4-fluoro-phenyl]-3-pyridyl]methyl]-5-isopropyl-oxazolidin-2-one; |
| 38 | 3-[[5-[3-(Difluoromethyl)-4-fluoro-phenyl]-3-pyridyl]methyl]-1,3-oxazinan-2-one; |
| 39 | (R/S)-3-[[5-[3-(Difluoromethyl)-4-fluoro-phenyl]-3-pyridyl]methyl]-5-(morpholinomethyl)oxazolidin-2-one; |
| 40 | (R*)-3-[[5-[3-(Difluoromethyl)-4-fluoro-phenyl]-3-pyridyl]methyl]-5-(morpholinomethyl)oxazolidin-2-one; |
| 41 | (S*)-3-[[5-[3-(Difluoromethyl)-4-fluoro-phenyl]-3-pyridyl]methyl]-5-(morpholinomethyl)oxazolidin-2-one; |
| 42 | 2-[[5-[3-(Difluoromethyl)-4-fluoro-phenyl]-3-pyridyl]methyl]-4,8-dioxa-2-azaspiro[4.5]decan-3-one; |
| 43 | 6-[[5-[3-(Difluoromethoxy)-4-fluoro-phenyl]-3-pyridyl]methyl]-8-oxa-2,6-diazaspiro[3.4]octan-7-one; |
| 44 | 3-[[5-(4-Fluoro-3-methyl-phenyl)-3-pyridyl]methyl]oxazolidin-2-one; |
| 45 | 3-[[5-(2,4-Difluoro-3-methyl-phenyl)-3-pyridyl]methyl]oxazolidin-2-one; |
| 46 | 3-[[5-[3-(Trifluoromethyl)phenyl]-3-pyridyl]methyl]oxazolidin-2-one; |
| 47 | 3-[[5-[4-Chloro-3-(difluoromethoxy)phenyl]-3-pyridyl]methyl]oxazolidin-2-one; |
| 48 | 3-[[5-[3-Fluoro-4-(trifluoromethoxy)phenyl]-3-pyridyl]methyl]oxazolidin-2-one; |
| 49 | 3-[[5-[3-(1,1-Difluoroethyl)-4-fluoro-phenyl]-3-pyridyl]methyl]oxazolidin-2-one; |
| 50 | 3-[[5-[6-(Trifluoromethyl)-2-pyridyl]-3-pyridyl]methyl]oxazolidin-2-one; |
| 51 | 3-[[5-[2-(Trifluoromethyl)-4-pyridyl]-3-pyridyl]methyl]oxazolidin-2-one; |
| 52 | 3-[[5-[4-Fluoro-3-(trifluoromethyl)phenyl]-3-pyridyl]methyl]-1,3-oxazinan-2-one; |
| 53 | 3-[[5-[4-chloro-3-(difluoromethoxy)phenyl]-3-pyridyl]methyl]-1,3-oxazinan-2-one; |
| 54 | 3-[Dideuterio-[5-[3-(difluoromethyl)-4-fluoro-phenyl]-3-pyridyl]methyl]oxazolidin-2-one; |
| 55 | 3-[Dideuterio-[5-[3-(difluoromethoxy)-4-fluoro-phenyl]-3-pyridyl]methyl]-1,3-oxazinan-2-one; |
| 56 | 3-[Dideuterio-[5-[3-(difluoromethoxy)-4-fluoro-phenyl]-2-methyl-3-pyridyl]methyl]-1,3-oxazinan-2-one; |
| 57 | 3-[Dideuterio-[5-(4-fluoro-3-methyl-phenyl)-2-methyl-3-pyridyl]methyl]-1,3-oxazinan-2-one; |
| 58 | 3-[Dideuterio-[5-[3-(difluoromethyl)-4-fluoro-phenyl]-2-methyl-3-pyridyl]methyl]-1,3-oxazinan-2-one; |
| 59 | 3-[Dideuterio-[5-[3-(difluoromethyl)-4-fluoro-phenyl]-2-methyl-3-pyridyl]methyl]oxazolidin-2-one; |

TABLE 2-continued

| Example # | Compound Name |
|---|---|
| 60 | (R/S)-3-[1-[5-[3-(difluoromethyl)-4-fluoro-phenyl]-3-pyridyl]ethyl]oxazolidin-2-one trifluoroacetate salt; |
| 61 | (R/S)-3-[1-[5-[3-(difluoromethyl)-4-fluoro-phenyl]-3-pyridyl]ethyl]-1,3-oxazinan-2-one; |
| 62 | 3-[[5-[3-(Difluoromethyl)phenyl]-2-methyl-3-pyridyl]methyl]-1,3-oxazinan-2-one; |
| 63 | 3-[[5-[3-(Difluoromethoxy)phenyl]-2-methyl-3-pyridyl]methyl]-1,3-oxazinan-2-one; |
| 64 | 3-[[5-(3-Chlorophenyl)-2-methyl-3-pyridyl]methyl]-1,3-oxazinan-2-one; |
| 65 | 3-[[5-(3-Chloro-4-fluoro-phenyl)-2-methyl-3-pyridyl]methyl]-1,3-oxazinan-2-one; |
| 66 | 3-[[5-(4-Fluoro-3-methyl-phenyl)-2-methyl-3-pyridyl]methyl]-1,3-oxazinan-2-one; |
| 67 | 3-[[5-(3,4-Difluorophenyl)-2-methyl-3-pyridyl]methyl]-1,3-oxazinan-2-one; |
| 68 | 3-[[5-(4-Fluorophenyl)-2-methyl-3-pyridyl]methyl]-1,3-oxazinan-2-one; |
| 69 | 3-[[5-(3-Fluorophenyl)-2-methyl-3-pyridyl]methyl]-1,3-oxazinan-2-one; |
| 70 | 3-[[5-(3,4-Difluoro-5-methyl-phenyl)-2-methyl-3-pyridyl]methyl]-1,3-oxazinan-2-one; |
| 71 | 3-[[5-(2,4-Difluoro-3-methyl-phenyl)-2-methyl-3-pyridyl]methyl]-1,3-oxazinan-2-one; |
| 72 | 3-[[5-(2,4-Difluorophenyl)-2-methyl-3-pyridyl]methyl]-1,3-oxazinan-2-one; |
| 73 | 3-[[5-(3,4-Dichlorophenyl)-2-methyl-3-pyridyl]methyl]-1,3-oxazinan-2-one; |
| 74 | 3-[[2-Methyl-5-[3-(Trifluoromethyl)phenyl]-3-pyridyl]methyl]-1,3-oxazinan-2-one; |
| 75 | 3-[[5-4-Fluoro-3-(trifluoromethyl)phenyl]-2-methyl-3-pyridyl]methyl]-1,3-oxazinan-2-one; |
| 76 | 3-[[5-(4-Fluoro-3-methyl-phenyl)-2-methyl-3-pyridyl]methyl]oxazolidin-2-one; |
| 77 | 3-[[5-(2,4-Difluoro-3-methyl-phenyl)-2-methyl-3-pyridyl]methyl]oxazolidin-2-one; |
| 78 | 3-[[5-[3-(1,1-Difluoroethyl)-4-fluoro-phenyl]-2-methyl-3-pyridyl]methyl]oxazolidin-2-one; |
| 79 | 3-[[5-[3-(Difluoromethoxy)-4-fluoro-phenyl]-2-methyl-3-pyridyl]methyl]oxazolidin-2-one; |
| 80 | (R/S)-3-[[5-[3-(Difluoromethoxy)-4-fluoro-phenyl]-2-methyl-3-pyridyl]methyl]-5-methyl-oxazolidin-2-one; |
| 81 | (R/S)-3-[[5-[3-(Difluoromethoxy)-4-fluoro-phenyl]-2-methyl-3-pyridyl]methyl]-4-methyl-oxazolidin-2-one; |
| 82 | (R*)-3-[[5-[3-(Difluoromethoxy)-4-fluoro-phenyl]-2-methyl-3-pyridyl]methyl]-4-methyl-oxazolidin-2-one; |
| 83 | (S*)-3-[[5-[3-(Difluoromethoxy)-4-fluoro-phenyl]-2-methyl-3-pyridyl]methyl]-4-methyl-oxazolidin-2-one; |
| 84 | 5-[[5-[3-(Difluoromethoxy)-4-fluoro-phenyl]-2-methyl-3-pyridyl]methyl]-7-oxa-5-azaspiro[2.4]heptan-6-one; |
| 85 | 6-[[5-[3-(Difluoromethoxy)-4-fluoro-phenyl]-2-methyl-3-pyridyl]methyl]-8-oxa-6-azaspiro[3.4]octan-7-one; |
| 86 | (5R)-3-[[5-[3-(Difluoromethoxy)-4-fluoro-phenyl]-2-methyl-3-pyridyl]methyl]-5-methyl-oxazolidin-2-one; |
| 87 | 3-[[5-[3-(Difluoromethoxy)-4-fluoro-phenyl]-2-methyl-3-pyridyl]methyl]-5,5-dimethyl-oxazolidin-2-one; |
| 88 | 3-[[5-[3-(Difluoromethoxy)-4-fluoro-phenyl]-2-methyl-3-pyridyl]methyl]-1,3-oxazinan-2-one; |
| 89 | 3-[[5-[4-Chloro-3-(difluoromethoxy)phenyl]-2-methyl-3-pyridyl]methyl]oxazolidin-2-one; |
| 90 | 3-[[5-[3-(Difluoromethyl)-4-fluoro-phenyl]-2-methyl-3-pyridyl]methyl]oxazolidin-2-one; |
| 91 | 6-[[5-[3-(Difluoromethyl)-4-fluoro-phenyl]-2-methyl-3-pyridyl]methyl]-8-oxa-6-azaspiro[3.4]octan-7-one; |
| 92 | (5R)-3-[[5-[3-(Difluoromethyl)-4-fluoro-phenyl]-2-methyl-3-pyridyl]methyl]-5-methyl-oxazolidin-2-one; |
| 93 | 3-[[5-[3-(Difluoromethyl)-4-fluoro-phenyl]-2-methyl-3-pyridyl]methyl]-5,5-dimethyl-oxazolidin-2-one; |
| 94 | (R/S)-3-[[5-[3-(Difluoromethyl)-4-fluoro-phenyl]-2-methyl-3-pyridyl]methyl]-5-methyl-oxazolidin-2-one; |
| 95 | (R/S)-3-[[5-[3-(difluoromethyl)-4-fluoro-phenyl]-2-methyl-3-pyridyl]methyl]-4-methyl-oxazolidin-2-one; |
| 96 | 5-[[5-[3-(Difluoromethyl)-4-fluoro-phenyl]-2-methyl-3-pyridyl]methyl]-7-oxa-5-azaspiro[2.4]heptan-6-one; |
| 97 | 3-[[5-[3-(Difluoromethyl)-4-fluoro-phenyl]-2-methyl-3-pyridyl]methyl]-1,3-oxazinan-2-one; |
| 98 | 3-[[5-(5-Chloro-2-thienyl)-2-methyl-3-pyridyl]methyl]oxazolidin-2-one; |
| 99 | 3-[[2-Methyl-5-[5-(trifluoromethyl)-2-thienyl]-3-pyridyl]methyl]oxazolidin-2-one; |
| 100 | 3-[[5-[5-(Difluoromethyl)-2-thienyl]-2-methyl-3-pyridyl]methyl]oxazolidin-2-one; |
| 101 | 3-[[2-Methoxy-5-[3-(trifluoromethyl)phenyl]-3-pyridyl]methyl]oxazolidin-2-one; |
| 102 | 3-[[2-Methoxy-5-(3,4,5-trifluorophenyl)-3-pyridyl]methyl]oxazolidin-2-one; |
| 103 | 3-[[5-(2,4-Difluoro-3-methyl-phenyl)-2-methoxy-3-pyridyl]methyl]oxazolidin-2-one; |
| 104 | 3-[[5-(3-Fluoro-5-methyl-phenyl)-2-methoxy-3-pyridyl]methyl]oxazolidin-2-one; |
| 105 | 3-[[2-Methoxy-5-(m-tolyl)-3-pyridyl]methyl]oxazolidin-2-one; |
| 106 | 3-[[5-(3,4-Dichlorophenyl)-2-methoxy-3-pyridyl]methyl]oxazolidin-2-one; |
| 107 | 3-[[5-[4-Chloro-3-(difluoromethoxy)phenyl]-2-methoxy-3-pyridyl]methyl]oxazolidin-2-one; |
| 108 | 3-[[5-(3-Chloro-4-fluoro-phenyl)-2-methoxy-3-pyridyl]methyl]oxazolidin-2-one; |
| 109 | 3-[[5-(3-Chlorophenyl)-2-methoxy-3-pyridyl]methyl]oxazolidin-2-one; |
| 110 | 3-[[5-[3-(1,1-Difluoroethyl)-4-fluoro-phenyl]-2-methoxy-3-pyridyl]methyl]oxazolidin-2-one; |
| 111 | 3-[[5-[3-(1,1-Difluoroethyl)phenyl]-2-methoxy-3-pyridyl]methyl]oxazolidin-2-one; |
| 112 | 3-[[5-(3,4-Difluoro-5-methyl-phenyl)-2-methoxy-3-pyridyl]methyl]oxazolidin-2-one; |
| 113 | 3-[[5-[4-Fluoro-3-(trifluoromethoxy)phenyl]-2-methoxy-3-pyridyl]methyl]oxazolidin-2-one; |
| 114 | 3-[[5-(2,5-Difluoro-3-methyl-phenyl)-2-methoxy-3-pyridyl]methyl]oxazolidin-2-one; |
| 115 | 3-[[5-[4-Chloro-3-(difluoromethyl)phenyl]-2-methoxy-3-pyridyl]methyl]oxazolidin-2-one; |
| 116 | 3-[[5-(4-Fluoro-3-methyl-phenyl)-2-methoxy-3-pyridyl]methyl]oxazolidin-2-one; |
| 117 | (4S)-3-[[5-[3-(Difluoromethoxy)-4-fluoro-phenyl]-2-methoxy-3-pyridyl]methyl]-4-methyl-oxazolidin-2-one; |
| 118 | (4R)-3-[[5-[3-(Difluoromethoxy)-4-fluoro-phenyl]-2-methoxy-3-pyridyl]methyl]-4-methyl-oxazolidin-2-one; |
| 119 | 3-[[5-[3-(Difluoromethoxy)-4-fluoro-phenyl]-2-methoxy-3-pyridyl]methyl]oxazolidin-2-one; |
| 120 | (4S)-3-[[5-[3-(Difluoromethyl)-4-fluoro-phenyl]-2-methoxy-3-pyridyl]methyl]-4-methyl-oxazolidin-2-one; |
| 121 | (4R)-3-[[5-[3-(Difluoromethyl)-4-fluoro-phenyl]-2-methoxy-3-pyridyl]methyl]-4-methyl-oxazolidin-2-one; |
| 122 | 3-[[5-[3-(Difluoromethyl)-4-fluoro-phenyl]-2-methoxy-3-pyridyl]methyl]oxazolidin-2-one; |
| 123 | 3-[[2-(Difluoromethyl)-5-[3-(difluoromethyl)-4-fluoro-phenyl]-3-pyridyl]methyl]-1,3-oxazinan-2-one; |
| 124 | 3-[[2-(Difluoromethyl)-5-[3-(difluoromethyl)-4-fluoro-phenyl]-3-pyridyl]methyl]oxazolidin-2-one; |
| 125 | 3-[[5-[3-(Difluoromethoxy)-4-fluoro-phenyl]-2-(difluoromethyl)-3-pyridyl]methyl]oxazolidin-2-one; |
| 126 | 3-[[5-[3-(Difluoromethoxy)-4-fluoro-phenyl]-2-(difluoromethyl)-3-pyridyl]methyl]-1,3-oxazinan-2-one; |
| 127 | 3-[[2-(Difluoromethyl)-5-(4-fluoro-3-methyl-phenyl)-3-pyridyl]methyl]-1,3-oxazinan-2-one; |
| 128 | 3-[[2-(Difluoromethyl)-5-(4-fluoro-3-methyl-phenyl)-3-pyridyl]methyl]oxazolidin-2-one; |
| 129 | 3-[[5-[4-Chloro-3-(difluoromethoxy)phenyl]-2-(difluoromethyl)-3-pyridyl]methyl]-1,3-oxazinan-2-one; |
| 130 | 3-[[5-[4-Chloro-3-(difluoromethoxy)phenyl]-2-(difluoromethyl)-3-pyridyl]methyl]oxazolidin-2-one; |
| 131 | 3-[[2-(Difluoromethoxy)-5-[3-(difluoromethyl)-4-fluoro-phenyl]-3-pyridyl]methyl]oxazolidin-2-one; |
| 132 | (4R)-3-[[2-(Difluoromethoxy)-5-[3-(difluoromethyl)-4-fluoro-phenyl]-3-pyridyl]methyl]-4-methyl-oxazolidin-2-one; |
| 133 | 3-[[2-(Difluoromethoxy)-5-[3-(difluoromethoxy)-4-fluoro-phenyl]-3-pyridyl]methyl]oxazolidin-2-one; |
| 134 | (4R)-3-[[-(Difluoromethoxy)-5-[3-(difluoromethoxy)-4-fluoro-phenyl]-3-pyridyl]methyl]-4-methyl-oxazolidin-2-one; |
| 135 | 3-[[2-(1,1-Difluoroethyl)-5-[3-(difluoromethyl)-4-fluoro-phenyl]-3-pyridyl]methyl]oxazolidin-2-one; |

TABLE 2-continued

| Example # | Compound Name |
|---|---|
| 136 | 3-[[2-(1,1-Difluoroethyl)-5-[3-(difluoromethyl)-4-fluoro-phenyl]-3-pyridyl]methyl]-1,3-oxazinan-2-one; |
| 137 | 3-[[2-(1,1-Difluoroethyl)-5-[3-(difluoromethoxy)-4-fluoro-phenyl]-3-pyridyl]methyl]-1,3-oxazinan-2-one; |
| 138 | 6-[[2-(1,1-Difluoroethyl)-5-[3-(difluoromethyl)-4-fluoro-phenyl]-3-pyridyl]methyl]-8-oxa-6-azaspiro[3.4]octan-7-one; |
| 139 | (5R)-3-[[2-(1,1-Difluoroethyl)-5-[3-(difluoromethyl)-4-fluoro-phenyl]-3-pyridyl]methyl]-5-methyl-oxazolidin-2-one; |
| 140 | (5S)-3-[[2-(1,1-Difluoroethyl)-5-[3-(difluoromethyl)-4-fluoro-phenyl]-3-pyridyl]methyl]-5-methyl-oxazolidin-2-one; |
| 141 | 5-[[2-(1,1-Difluoroethyl)-5-[3-(difluoromethyl)-4-fluoro-phenyl]-3-pyridyl]methyl]-7-oxa-5-azaspiro[2.4]heptan-6-one; |
| 142 | (4S)-3-[[2-(1,1-Difluoroethyl)-5-[3-(difluoromethyl)-4-fluoro-phenyl]-3-pyridyl]methyl]-4-methyl-oxazolidin-2-one; |
| 143 | (4R)-3-[[2-(1,1-Difluoroethyl)-5-[3-(difluoromethyl)-4-fluoro-phenyl]-3-pyridyl]methyl]-4-methyl-oxazolidin-2-one; |
| 144 | (4R)-3-[[2-(1,1-Difluoroethyl)-5-[3-(difluoromethoxy)-4-fluoro-phenyl]-3-pyridyl]methyl]-4-methyl-oxazolidin-2-one; |
| 145 | (4S)-3-[[2-(1,1-Difluoroethyl)-5-[3-(difluoromethoxy)-4-fluoro-phenyl]-3-pyridyl]methyl]-4-methyl-oxazolidin-2-one; |
| 146 | 5-[[2-(1,1-Difluoroethyl)-5-[3-(difluoromethoxy)-4-fluoro-phenyl]-3-pyridyl]methyl]-7-oxa-5-azaspiro[2.4]heptan-6-one; |
| 147 | 6-[[2-(1,1-Difluoroethyl)-5-[3-(difluoromethoxy)-4-fluoro-phenyl]-3-pyridyl]methyl]-8-oxa-6-azaspiro[3.4]octan-7-one; |
| 148 | (5S)-3-[[2-(1,1-Difluoroethyl)-5-[3-(difluoromethoxy)-4-fluoro-phenyl]-3-pyridyl]methyl]-5-methyl-oxazolidin-2-one; |
| 149 | (5R)-3-[[2-(1,1-Difluoroethyl)-5-[3-(difluoromethoxy)-4-fluoro-phenyl]-3-pyridyl]methyl]-5-methyl-oxazolidin-2-one; |
| 150 | 3-((5-(3-(Difluoromethoxy)-4-fluorophenyl)-2-fluoropyridin-3-yl)methyl)oxazolidin-2-one; and |
| 151 | 3-((5-(3-(Difluoromethoxy)-4-fluorophenyl)-2-fluoropyridin-3-yl)methyl)-1,3-oxazinan-2-one. |

In the event of an inconsistency between a compound name shown in Table 2 and a structure provided herein for the compound, the structure shall control unless it is clear from context that the structure is incorrect.

Exemplary compounds of the disclosure are listed in Table 3, below. In various aspects, the disclosure provides, for example, pharmaceutically acceptable salts, solvates, isotopic variants, and N-oxides of the compounds listed in Table 3.

TABLE 3

| Example # | Compound Name |
|---|---|
| 1 | 3-[[5-[3-(Difluoromethoxy)-4-fluoro-phenyl]-3-pyridyl]methyl]-1,3-oxazinan-2-one; |
| 22 | 3-[[5-[3-(Difluoromethyl)-4-fluoro-phenyl]-3-pyridyl]methyl]oxazolidin-2-one; |
| 27 | (S*)-3-[[5-[3-(Difluoromethyl)-4-fluoro-phenyl]-3-pyridyl]methyl]-5-methyl-oxazolidin-2-one; |
| 38 | 3-[[5-[3-(Difluoromethyl)-4-fluoro-phenyl]-3-pyridyl]methyl]-1,3-oxazinan-2-one; |
| 53 | 3-[[5-[4-chloro-3-(difluoromethoxy)phenyl]-3-pyridyl]methyl]-1,3-oxazinan-2-one; |
| 54 | 3-[Dideuterio-5-[3-difluomethyl)-4-fluoro-phenyl]-3-pyridyl]methyl]oxazolidin-2-one; |
| 60 | (R/S)-3-[1-[5-[3-(difluoromethyl)-4-fluoro-phenyl]-3-pyridyl]ethyl]oxazolidin-2-one trifluoroacetate salt; |
| 90 | 3-[[5-[3-(Difluoromethyl)-4-fluoro-phenyl]-2-methyl-3-pyridyl]methyl]oxazolidin-2-one; and |
| 97 | 3-[[5-[3-(Difluoromethyl)-4-fluoro-phenyl]-2-methyl-3-pyridyl]methyl]-1,3-oxazinan-2-one. |

In the event of an inconsistency between a compound name shown in Table 2 and a structure provided herein for the compound, the structure shall control unless it is clear from context that the structure is incorrect.

4.4. Pharmaceutical Compositions

The disclosure further provides pharmaceutical compositions comprising a compound of the disclosure (e.g., a compound of Formula (I) or a pharmaceutically acceptable salt, solvate, isotopic variant, or N-oxide thereof). Pharmaceutical compositions of the disclosure can comprise a single compound of the disclosure or more than one compound of the disclosure. Pharmaceutical compositions of the disclosure typically comprise at least one pharmaceutically acceptable excipient (e.g., one or more than one pharmaceutically acceptable excipient).

In some embodiments, a pharmaceutical composition of the disclosure comprises at least one compound selected from compounds of Formula (I), pharmaceutically acceptable salts of compounds of Formula (I), solvates of compounds of Formula (I), isotopic variants of compounds of Formula (I), N-oxides of compounds of Formula (I) and solvates of compounds of Formula (I), pharmaceutically acceptable prodrugs of compounds of Formula (I), and pharmaceutically active metabolites of compounds of Formula (I); and at least one pharmaceutically acceptable excipient.

In some further embodiments, a pharmaceutical composition of the disclosure comprises at least one compound selected from compounds of Formula (Ia), pharmaceutically acceptable salts of compounds of Formula (Ia), solvates of compounds of Formula (Ia), isotopic variants of compounds of Formula (Ia), N-oxides of compounds of Formula (Ia) and solvates of compounds of Formula (Ia), pharmaceutically acceptable prodrugs of compounds of Formula (a), and pharmaceutically active metabolites of compounds of Formula (Ia); and at least one pharmaceutically acceptable excipient.

In some further embodiments, a pharmaceutical composition of the disclosure comprises at least one compound selected from compounds of Formula (Ib), pharmaceutically acceptable salts of compounds of Formula (Ib), solvates of compounds of Formula (Ib), isotopic variants of compounds of Formula (Ib), N-oxides of compounds of Formula (Ib) and solvates of compounds of Formula (Ib), pharmaceutically acceptable prodrugs of compounds of Formula (Ib), and pharmaceutically active metabolites of compounds of Formula (Ib); and at least one pharmaceutically acceptable excipient.

In some further embodiments, a pharmaceutical composition of the disclosure comprises at least one compound selected from compounds of Formula (Ic), pharmaceutically acceptable salts of compounds of Formula (Ic), solvates of compounds of Formula (Ic), isotopic variants of compounds of Formula (Ic), N-oxides of compounds of Formula (Ic) and solvates of compounds of Formula (Ic), pharmaceutically acceptable prodrugs of compounds of Formula (Ic), and pharmaceutically active metabolites of compounds of Formula (Ic); and at least one pharmaceutically acceptable excipient.

In some further embodiments, a pharmaceutical composition of the disclosure comprises at least one compound selected from compounds of Formula (Id), pharmaceutically acceptable salts of compounds of Formula (Id), solvates of compounds of Formula (Id), isotopic variants of compounds of Formula (Id), N-oxides of compounds of Formula (Id) and solvates of compounds of Formula (Id), pharmaceutically acceptable prodrugs of compounds of Formula (Id), and pharmaceutically active metabolites of compounds of Formula (Id); and at least one pharmaceutically acceptable excipient.

In some further embodiments, a pharmaceutical composition of the disclosure comprises at least one compound selected from compounds of Formula (Ie), pharmaceutically acceptable salts of compounds of Formula (Ie), solvates of compounds of Formula (Ie), isotopic variants of compounds of Formula (Ie), N-oxides of compounds of Formula (Ie) and solvates of compounds of Formula (Ie), pharmaceutically acceptable prodrugs of compounds of Formula (Ie), and pharmaceutically active metabolites of compounds of Formula (Ie); and at least one pharmaceutically acceptable excipient.

In some further embodiments, a pharmaceutical composition of the disclosure comprises at least one compound selected from compounds of Formula (If), pharmaceutically acceptable salts of compounds of Formula (If), solvates of compounds of Formula (If), isotopic variants of compounds of Formula (If), N-oxides of compounds of Formula (If) and solvates of compounds of Formula (If), pharmaceutically acceptable prodrugs of compounds of Formula (If), and pharmaceutically active metabolites of compounds of Formula (If); and at least one pharmaceutically acceptable excipient.

In some embodiments, a pharmaceutical composition of the disclosure comprises at least compound selected from compounds in Table 2, pharmaceutically acceptable salts, solvates, isotopic variants, and N-oxides of compounds in Table 2, pharmaceutically acceptable prodrugs of compounds in Table 2, and pharmaceutically active metabolites of compounds in Table 2; and at least one pharmaceutically acceptable excipient.

The pharmaceutically acceptable excipient(s) included in the pharmaceutical compositions of the disclosure are preferably non-toxic, biologically tolerable, and otherwise biologically suitable for administration to a subject. Pharmaceutically acceptable excipients include inert substances, which can be added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Pharmaceutical compositions of the disclosure can be formulated for various routes of delivery, e.g., oral, parenteral, rectal, topical, or ocular routes, or by inhalation.

Pharmaceutical compositions can be in the form of tablets, capsules, sachets, dragees, powders, granules, lozenges, powders for reconstitution, liquid preparations, or suppositories. Pharmaceutical compositions can be formulated, for example, for intravenous infusion, topical administration, or oral administration.

For oral administration, the compounds of the disclosure can be provided in the form of tablets or capsules, or as a solution, emulsion, or suspension. Oral tablets can include a compound according to the disclosure mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents can include starch and gelatin. The lubricating agent, if present, can be magnesium stearate, stearic acid or talc. If desired, the tablets can be coated with a material, such as glyceryl monostearate or glyceryl distearate, to delay absorption in the gastrointestinal tract, or can be coated with an enteric coating.

Capsules for oral administration include hard and soft gelatin capsules. To prepare hard gelatin capsules, compounds of the disclosure can be mixed with a solid, semi-solid, or liquid diluent. Soft gelatin capsules can be prepared by mixing the compound of the disclosure with water, an oil such as peanut oil or olive oil, liquid paraffin, a mixture of mono and di-glycerides of short chain fatty acids, polyethylene glycol 400, propylene glycol, or am mixture of any of the foregoing.

Liquids for oral administration can be in the form of suspensions, solutions, emulsions or syrups or can be lyophilized or presented as a dry product for reconstitution with water or other suitable vehicle before use. Such liquid compositions can optionally contain, for example: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compounds of the disclosure can also be administered by non-oral routes. For example, the compositions can be formulated for rectal administration as a suppository. For parenteral use, including intravenous, intramuscular, intraperitoneal, or subcutaneous routes, the compounds of the disclosure can be provided in sterile aqueous solutions or suspensions, buffered to an appropriate pH and isotonicity or in parenterally acceptable oil. Suitable aqueous vehicles include Ringer's solution and isotonic sodium chloride. Such forms can be presented in unit-dose form such as ampules or disposable injection devices, in multi-dose forms such as vials from which the appropriate dose can be withdrawn, or in a solid form or pre-concentrate that can be used to prepare an injectable formulation.

For topical pharmaceutical compositions, compounds of the disclosure can be mixed with a pharmaceutical carrier. Another mode of administering the compounds of the disclosure can utilize a patch formulation to affect transdermal delivery.

Compounds of the disclosure can alternatively be administered in methods of this disclosure by inhalation, via the nasal or oral routes, e.g., in a spray formulation also containing a suitable carrier.

4.5. Uses of Compounds of the Disclosure

Compounds of the disclosure are useful as modulators of the GluN2B receptor. As such modulators, the compounds can act, for example, as antagonists, agonists, or inverse agonists. The term "modulators" include both inhibitors and activators, where "inhibitors" refer to compounds that decrease, prevent, inactivate, desensitize, or down-regulate the GluN2B receptor expression or activity, and "activators" are compounds that increase, activate, facilitate, sensitize, or up-regulate GluN2B receptor expression or activity.

In one aspect, the disclosure provides methods of treating a subject suffering from or diagnosed with a disease, disorder, or medical condition mediated by GluN2B receptor activity, comprising administering to the subject a therapeutically effective amount of a compound of the disclosure, for example a compound of Formula (I) or a pharmaceutically acceptable salt, solvate, isotopic variant, or N-oxide thereof, or a therapeutically effective amount of a pharmaceutical composition of the disclosure, for example a unit dosage form as described in Section 4.4. The treatment methods described herein can comprise, for example, administering at least one (e.g., one) compound of the disclosure or at least one (e.g., one) pharmaceutical composition of the disclosure) to the subject.

In some embodiments, the disease, disorder, or medical condition comprises bipolar disorder, major depressive disorder, treatment-resistant depression, a mood disorder, postpartum depression, seasonal affective disorder, Alzheimer's disease, Parkinson's disease, Huntington's chorea, multiple sclerosis, cognitive impairment, head injury, spinal cord injury, stroke, epilepsy, dyskinesias, amyotrophic lateral sclerosis, neurodegeneration associated with a bacterial or chronic infection, pain, diabetic neuropathy, migraine, cerebral ischemia, schizophrenia, encephalitis, autism or an autism spectrum disorder, a memory disorder, a learning disorder, obsessive compulsive disorder, attention deficit hyperactivity disorder (ADHD) or an addictive illness.

In some embodiments, the disease, disorder, or medical condition is selected from: neurologic and psychiatric disorders including, but not limited to: (1) mood disorders and mood affective disorders; (2) neurotic, stress-related and somatoform disorders including anxiety disorders; (3) disorders of psychological development; (4) behavioral syndromes associated with physiological disturbances and physical factors; (5) extrapyramidal and movement disorders; (6) episodic and paroxysmal disorders, epilepsy; (7) pain; (8) forms of neurodegeneration; (9) cerebrovascular diseases, acute and chronic; and any sequelae of cerebrovascular diseases.

Examples of mood disorders and mood affective disorders that can be treated according to the present disclosure include, but are not limited to, bipolar disorder I depressed, hypomanic, manic and mixed form; bipolar disorder II; depressive disorders, such as single depressive episode or recurrent major depressive disorder, minor depressive disorder, treatment-resistant depression, depressive disorder with postpartum onset, depressive disorders with psychotic symptoms; persistent mood disorders, such as cyclothymia, dysthymia, euthymia; and premenstrual dysphoric disorder. In specific embodiments, the mood disorders and mood affective disorders that can be treated according to the present disclosure are major depressive disorder, treatment-resistant depression and bipolar disorder.

Examples of disorders belonging to the neurotic, stress-related and somatoform disorders that can be treated according to the present disclosure include, but are not limited to, anxiety disorders, general anxiety disorder, panic disorder with or without agoraphobia, specific phobia, social anxiety disorder, chronic anxiety disorders; obsessive compulsive disorder; reaction to sever stress and adjustment disorders, such as post-traumatic stress disorder (PTSD); other neurotic disorders such as depersonalisation-derealisation syndrome.

Examples of disorders of psychological development that can be treated according to the present disclosure include, but are not limited to pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills.

Examples of behavioral syndromes associated with physiological disturbances and physical factors according to the present disclosure include, but are not limited to mental and behavioral disorders associated with childbirth, including but not limited to postnatal (postpartum) and prenatal depression; eating disorders, including but not limited to anorexia nervosa, bulimia nervosa, pica and binge eating disorder.

Examples of extrapyramidal and movement disorders that can be treated according to the present disclosure include, but are not limited to Parkinson's disease; second Parkinsonism, such as postencephalitic Parkinsonism; Parkinsonism comprised in other disorders; Lewis body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor; restless leg syndrome, Stiff-man syndrome.

Further examples of movement disorders with malfunction and/or degeneration of basal ganglia that can be treated according to the present disclosure include, but are not limited to dystonia including but not limited to focal dystonia, multiple-focal or segmental dystonia, torsion dystonia, hemispheric, generalised and tardive dystonia (induced by psychopharmacological drugs). Focal dystonia includes cervical dystonia (torticolli), blepharospasm (cramp of the eyelid), appendicular dystonia (cramp in the extremities, like the writer's cramp), oromandibular dystonia and spasmodic dysphonia (cramp of the vocal cord).

Examples for episodic and paroxysmal disorders that can be treated according to the present disclosure include, but are not limited to epilepsy, including localization-related (focal)(partial) idiopathic epilepsy and epileptic syndromes with seizures of localized onset, localization-related (focal) (partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes including but not limited to myoclonic epilepsy in infancy, neonatal convulsions (familial), childhood absence epilepsy (pyknolepsy), epilepsy with grand mal seizures on awakening, absence epilepsy, myoclonic epilepsy (impulsive petit mal) and nonspecific atonic, clonic, myoclonic, tonic, tonic-clonic epileptic seizures.

Further examples of epilepsy that can be treated according to the present disclosure include, but are not limited to epilepsy with myoclonic absences, myoclonic-astatic seizures, infantile spasms, Lennox-Gastaut syndrome, Salaam attacks, symptomatic early myoclonic encephalopathy, West's syndrome, petit and grand mal seizures; status epilepticus.

Examples of pain include, but are not limited to pain disorders related to psychological factors, such as persistent somatoform disorders; acute, chronic and chronic intractable pain, headache; acute and chronic pain related to physiological processes and physical disorders including but not limited to back pain, tooth pain, abdominal pain, low back pain, pain in joints; acute and chronic pain that is related to diseases of the musculoskeletal system and connective tissue including, but not limited to rheumatism, myalgia, neuralgia and fibromyalgia; acute and chronic pain that is related to nerve, nerve root and plexus disorders, such as trigeminal pain, postzoster neuralgia, phantom limb syndrome with pain, carpal tunnel syndrome, lesion of sciatic nerve, diabetic mononeuropathy; acute and chronic pain that is related to polyneuropathies and other disorders of the peripheral nervous system, such as hereditary and idiopathic neuropathy, inflammatory polyneuropathy, polyneuropathy induced by drugs, alcohol or toxic agents, polyneuropathy in neoplastic disease, diabetic polyneuropathy.

Examples of diseases that include forms of neurodegeneration include, but are not limited to, acute neurodegeneration, such as intracranial brain injuries, such as stroke, diffuse and local brain injuries, epidural, subdural and subarachnoid haemorrhage, and chronic neurodegeneration, such as Alzheimer's disease, Huntington's disease, multiple sclerosis and ALS.

Examples of cerebrovascular diseases include, but are not limited to, subarachnoid haemorrhage, intracerebral haemorrhage and other nontraumatic intracranial haemorrhage, cerebral infarction, stroke, occlusion and stenosis or precerebral and cerebral arteries, not resulting in cerebral infarction, dissection of cerebral arteries, cerebral aneurysm, cerebral atherosclerosis, progressive vascular leukoencephalopathy, hypertensive encephalopathy, non-pyogenic thrombosis of intracranial venous system, cerebral arteritis, cerebral amyloid angiopathy and sequelae of cerebrovascular diseases.

Once improvement of a subject's disease, disorder, or condition has occurred, the dose can be adjusted for preventative or maintenance treatment. For example, the dosage or the frequency of administration, or both, can be reduced as a function of the symptoms, to a level at which the desired therapeutic or prophylactic effect is maintained. Of course, if symptoms have been alleviated to an appropriate level, treatment may cease. Subjects may, however, require intermittent treatment on a long-term basis upon any recurrence of symptoms.

In some embodiments, administration of a compound of the disclosure (e.g., a compound of Formula (I) or a pharmaceutically acceptable salt thereof), is effective in preventing the disease or delaying onset of symptoms of the disease; for example, preventing a disease, condition or disorder or a symptom thereof in an individual who may be predisposed to the disease, condition or disorder but does not yet experience or display the pathology or symptomatology of the disease.

Compounds and pharmaceutical compositions of the disclosure can be administered as monotherapy, or they can be administered in combination with one or more additional active agents. For example, the additional active agent can be an agent known or discovered to be effective in the treatment of conditions, disorders, or diseases mediated by GluN2B activity, such as another GluN2B modulator or a compound active against another target associated with a subject's particular condition, disorder, or disease. The combination may serve to increase efficacy (e.g., by including in the combination a compound potentiating the potency or effectiveness of a compound of the disclosure), decrease one or more side effects, or decrease the required dose of a compound of the disclosure.

4.6. Exemplary Methods of Making Compounds of the Disclosure

Illustrative synthetic schemes for the general preparation of compounds of Formula (I) are described below. Artisans will recognize that, to obtain the various compounds described herein, starting materials can be suitably selected so that the ultimately desired substituents will be carried through the reaction scheme with or without protection as appropriate to yield the desired product. Alternatively, it can be desirable to employ, in the place of the ultimately desired substituent, a suitable group that can be carried through the reaction scheme and replaced as appropriate with the desired substituent. Unless otherwise specified, the variables are as defined above in reference to Formula (I). Reactions can be performed between the melting point and the reflux temperature of the solvent, and preferably between 0° C. and the reflux temperature of the solvent. Reactions can be heated employing conventional heating or microwave heating. Reactions can also be conducted in sealed pressure vessels above the normal reflux temperature of the solvent.

Compounds of Formula (I) can be converted to their corresponding salts using methods known to one of ordinary skill in the art. For example, an amine of Formula (I) can be treated with trifluoroacetic acid, HCl, or citric acid in a solvent such as $Et_2O$, $CH_2Cl_2$, THF, MeOH, chloroform, or isopropanol to provide the corresponding salt form. Alternately, trifluoroacetic acid or formic acid salts can be obtained as a result of reverse phase HPLC purification conditions. Crystalline forms of pharmaceutically acceptable salts of compounds of Formula (I) can be obtained in crystalline form by recrystallization from polar solvents (including mixtures of polar solvents and aqueous mixtures of polar solvents) or from non-polar solvents (including mixtures of non-polar solvents).

Where the compounds according to this disclosure have at least one chiral center, they can accordingly exist as enantiomers. Where the compounds possess two or more chiral centers, they can additionally exist as diastereomers. It is to be understood that all such isomers and mixtures thereof are encompassed within the scope of the present disclosure.

Compounds prepared according to the schemes described below can be obtained as single forms, such as single enantiomers, by form-specific synthesis, or by resolution.

Compounds prepared according to the schemes below can alternately be obtained as mixtures of various forms, such as racemic (1:1) or non-racemic (not 1:1) mixtures. Where racemic and non-racemic mixtures of enantiomers are obtained, single enantiomers can be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers can be separated using conventional methods such as chromatography or crystallization.

SCHEME 1

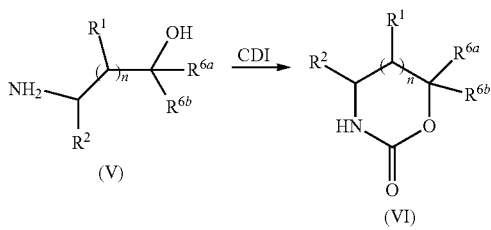

(V) → (VI)

According to SCHEME 1, a compound of formula (VI), where $R^1$, $R^2$, n, $R^{6a}$, and $R^{6b}$ are as defined in the Summary, is commercially available or synthetically accessible from a compound of formula (V). A compound of formula (V), where n is 0 or 1; $R^1$ is H when present; $R^2$ is H or alkyl; $R^{6a}$ and $R^{6b}$ are independently H or alkyl, can be cyclized with a reagent such as CDI, triphosgene, diethyl carbonate, and the like; in a suitable solvent such as THF, DCM, DMF, and the like; at temperatures ranging from room temperature to 100° C.; for a period of 1 h to 2 days; to provide a compound of formula (VI). In a preferred embodiment, the reagent employed for cyclization is CDI, the solvent is THF and the reaction is stirred at room temperature for 2 days.

SCHEME 2

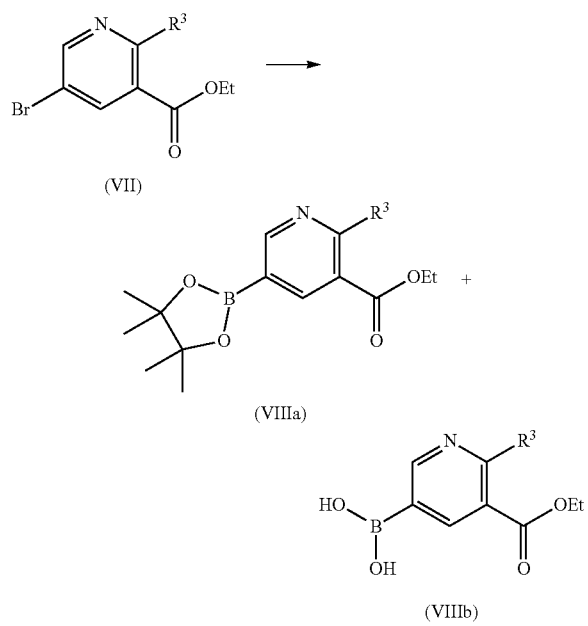

According to SCHEME 2, a compound of formula (VII), where $R^3$ is $CH_3$ or $OCH_3$, can be borylated employing palladium catalyzed borylation conditions as described in U.S. Pat. No. 10,150,747 (Yeung et al; Dec. 11, 2018). For example, a compound of formula (VII), where $R^3$ is $OCH_3$ or $CH_3$, can be reacted with a borylation reagent such as 4,4,4',4',5,5,5',5'-octamethyl-2,2'-bi-1,3,2-(bis(pinacolato)diboron), and the like; potassium acetate; a palladium catalyst such as $PdCl_2(dppf)\text{-}CH_2Cl_2$, and the like; in a suitable solvent such as THF, DMF, 1,4-dioxane, or a mixture thereof; at a temperature ranging from 23 to 90° C.; for a period of about 1-4 h, to provide compounds of formula (VIIIa) and formula (VIIIb).

SCHEME 3

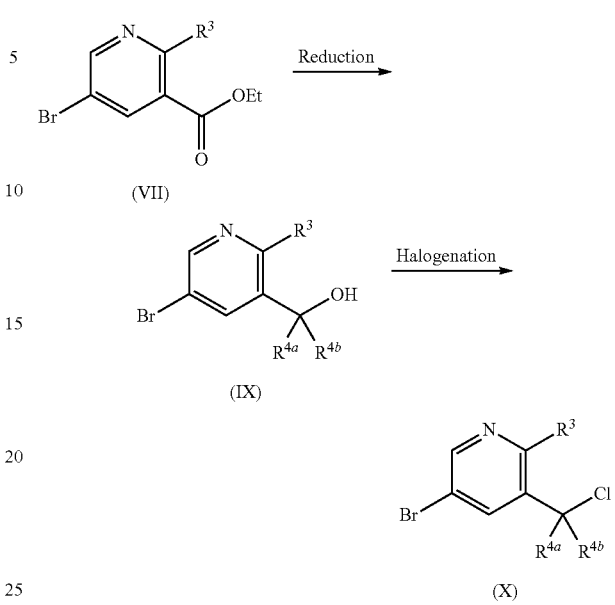

According to SCHEME 3, a compound of formula (IX), where $R^{4b}$ and $R^{4b}$ are $^1H$, deuterium, or alkyl, is commercially available or synthetically accessible from a compound of formula (VII), where $R^3$ is H, alkyl, O-alkyl, O-haloalkyl, haloalkyl. Under conditions known to one skilled in the art, a compound of formula (VII), where $R^3$ is H, alkyl, O-alkyl, O-haloalkyl, or haloalkyl, can be reduced with a reducing agent such as $NaBH_4$, $NaBD_4$, $LiAlH_4$, $LiBH_4$, $LiAlD_4$, diisobutylaluminum hydride (DIBAL or DIBAL-H), and the like; in a suitable solvent such as tetrahydrofuran (THF), THF-$d_8$, methanol (MeOH), ethanol (EtOH), and the like; at temperatures ranging from −78 to −40° C.; for a period of 30 min to 16 h; to provide a compound of formula (IX). A compound of formula (IX), where $R^{4a}$ and $R^{4b}$ are $^1H$, deuterium, or alkyl; can be chlorinated with thionyl chloride; in a suitable solvent such as dichloromethane (DCM), and the like; at temperatures ranging from 0 to 30° C.; for a period of 30 min to 18 h; to provide a compound of formula (X).

SCHEME 4

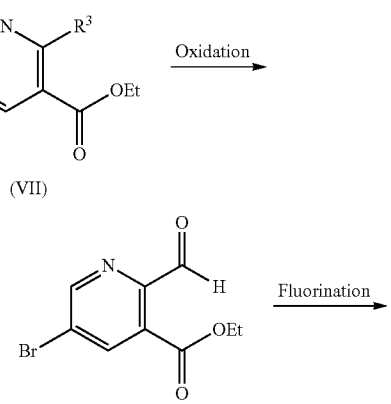

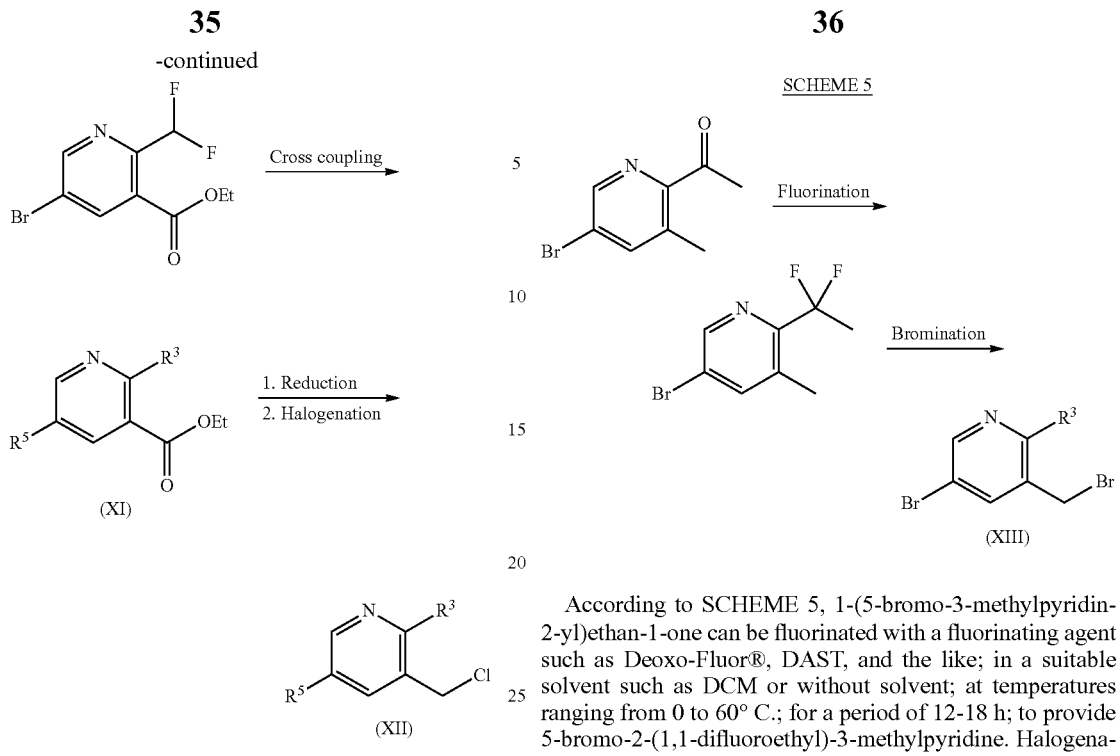

According to SCHEME 4, a commercially available or synthetically accessible compound of formula (VII), where $R^3$ is $CH_3$, can be oxidized employing conditions known to one skilled in the art. For example, ethyl 5-bromo-2-methylnicotinate, can be oxidized with an oxidizing agent such as $SeO_2$, and the like; in a suitable solvent such as 1,4-dioxane, and the like; employing microwave heating at 120° C.; for a period of 20 minutes to provide ethyl 5-bromo-2-formylnicotinate. Fluorination of ethyl 5-bromo-2-formylnicotinate, is described in U.S. Pat. No. 8,648,200 (Hughes et al; Feb. 11, 2014). For example ethyl 5-bromo-2-formylnicotinate can be fluorinated with a fluorinating agent such as DAST, and the like; in a suitable solvent such as DCM, and the like; at temperatures ranging from 0° C. to room temperature; for a period of 16 h to 24 h; to provide ethyl 5-bromo-2-(difluoromethyl)nicotinate. Ethyl 5-bromo-2-(difluoromethyl)nicotinate can then be reacted under metal-mediated cross coupling conditions such as Suzuki reaction conditions known to one skilled in the art. For example, ethyl 5-bromo-2-(difluoromethyl)nicotinate, can be reacted with a commercially available or synthetically accessible suitably substituted aryl or heteroaryl boronic acid or boronic ester; in the presence of a palladium catalyst such as RuPhos Pd G3, $Pd(PPh_3)_4$, $Pd(dppf)Cl_2$, $PdCl_2(dppf)$-$CH_2Cl_2$, $PdCl_2(dtbpf)$, and the like; a suitable base such a KF, $Na_2CO_3$, potassium phosphate, $Cs_2CO_3$, $K_2CO_3$, and the like; in a solvent such as 1,4-dioxane, water, or a mixture thereof; employing conventional or microwave heating; at temperatures ranging from room temperature to 100° C.; for a period of 1 h to 18 h, to give a compound of formula (XI), where $R^3$ is $CHF_2$ and $R^5$ is as defined in the Summary. A compound of formula (XI), where $R^3CHF_2$ or $OCHF_2$, and $R^5$ is as defined in the Summary can be reduced employing conditions previously described to provide the alcohol intermediate, which is subsequently chlorinated employing conditions previously described to provide a compound of formula (XII).

According to SCHEME 5, 1-(5-bromo-3-methylpyridin-2-yl)ethan-1-one can be fluorinated with a fluorinating agent such as Deoxo-Fluor®, DAST, and the like; in a suitable solvent such as DCM or without solvent; at temperatures ranging from 0 to 60° C.; for a period of 12-18 h; to provide 5-bromo-2-(1,1-difluoroethyl)-3-methylpyridine. Halogenation of 5-bromo-2-(1,1-difluoroethyl)-3-methylpyridine is achieved under conditions known to one skilled in the art to provide a compound of formula (XIII). For example, reaction of 5-bromo-2-(1,1-difluoroethyl)-3-methylpyridine with a brominating agent such as NBS, in the presence of 2,2'-azobisisobutyronitrile (AIBN), in a solvent such as $CCl_4$, under refluxing conditions, provides a compound of formula (XIII), where $R^3$ is $CHF_2(CH_3)$.

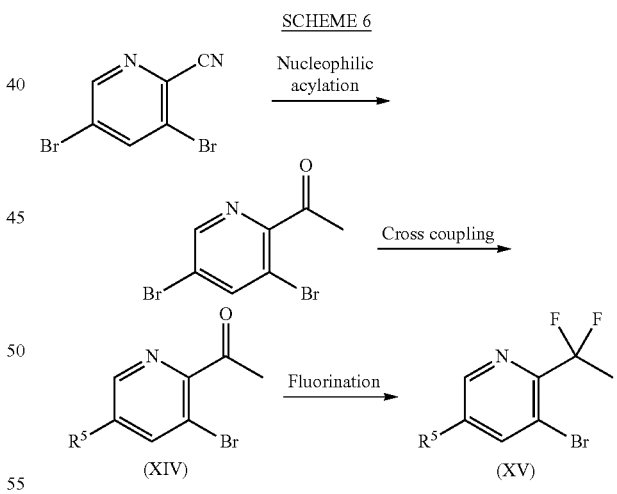

According to SCHEME 6, 3,5-dibromopicolinonitrile is commercially available and is reacted through a nucleophilic acylation reaction with an alkylmagnesium or alkyllithium reagent, such as MeMgBr, MeLi, and the like; in a suitable solvent such as toluene, THF, $Et_2O$, and the like; at −78° C. to room temperature; for a period of 30 minutes to 6 h; to afford the imine intermediate which is readily hydrolyzed under acidic conditions to provide 1-(3,5-dibromopyridin-2-yl)ethan-1-one. In a preferred embodiment, the alkylmagnesium reagent is MeMgBr, the solvent is toluene, and the reaction is conducted at a temperature of −10° C. for 1 h.

1-(3,5-Dibromopyridin-2-yl)ethan-1-one can then be reacted under metal mediated cross coupling conditions as previously described, with an aryl or heteroaryl boronic ester or boronic acid to afford a compound of formula (XIV), where $R^5$ is as defined in the Summary. Fluorination of a compound of formula (XIV) under conditions previously described affords compound of formula (XV).

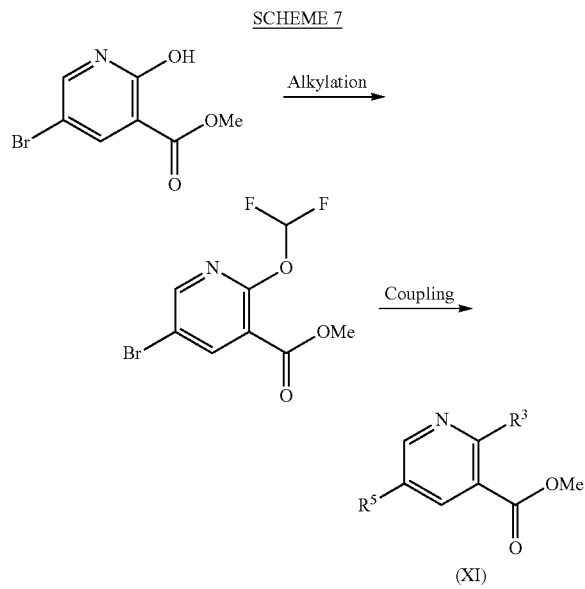

According to SCHEME 7, a compound of formula (XI), where $R^3$ is $OCF_2H$, is accessible in two steps through alkylation of methyl 5-bromo-2-hydroxynicotinate with a reagent such as fluorosulfonyldifluoroacetic acid, sodium chlorodifluoroacetate, and the like; in the presence of a base such as $NaHCO_3$, and the like; in a solvent such as acetonitrile (ACN), and the like; at room temperature; for a period of 76 h; to provide methyl 5-bromo-2-(difluoromethoxy)nicotinate. In a second step, methyl 5-bromo-2-(difluoromethoxy)nicotinate can be reacted with a commercially available or synthetically accessible suitably substituted aryl or heteroaryl boronic acid or boronic ester, under metal-mediated cross coupling conditions, such as Suzuki reaction conditions known to one skilled in the art, as previously described to provide a compound of formula (XI), where $R^3$ is $OCF_2H$.

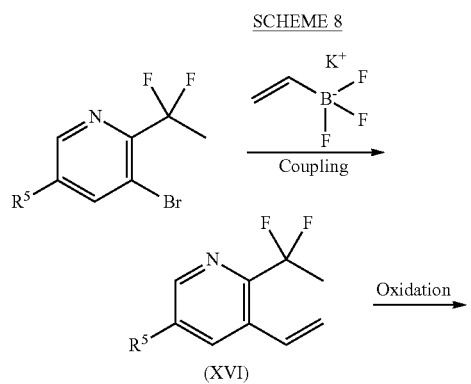

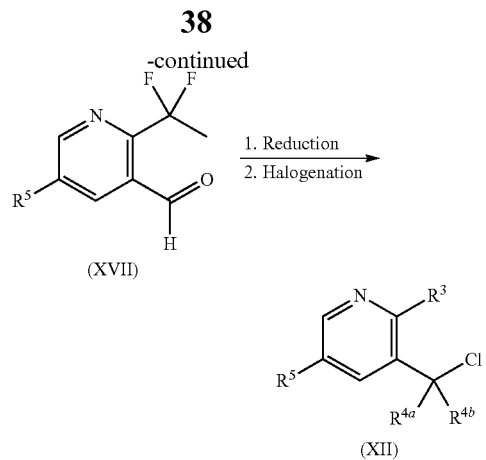

According to SCHEME 8, a compound of formula (XV) is reacted in a metal-mediated cross coupling reaction such as a Suzuki reaction, to provide a compound of formula (XVI). For example, a compound of formula (XV), where $R^5$ is as defined in the Summary, can be reacted with potassium vinyltrifluoroborate; a palladium catalyst such as $Pd(dppf)Cl_2$; a base such as sodium carbonate, and the like; in a suitable solvent such as 1,4-dioxane, ACN, water, or a mixture thereof; at a temperature of about 80 to 100° C.; for a period of 2 to 18 h; to provide a vinyl compound of formula (XVI). A vinyl compound of formula (XVI) can be treated with osmium tetroxide and sodium periodate; in a suitable solvent such as 1,4-dioxane, THF, water, or a mixture thereof; to provide an aldehyde compound of formula (XVII). A compound of formula (XII) can be prepared in two steps from a compound of formula (XVII), employing reduction and halogenation conditions previously described.

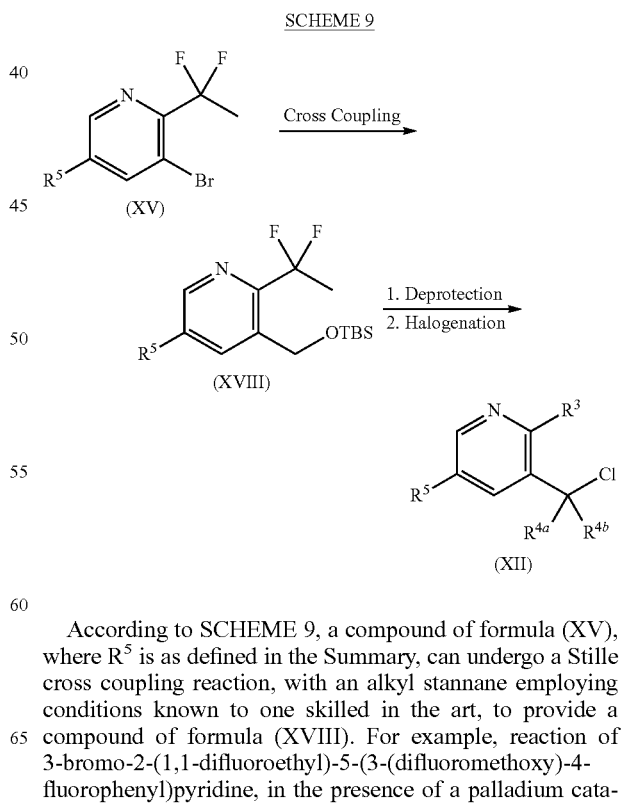

According to SCHEME 9, a compound of formula (XV), where $R^5$ is as defined in the Summary, can undergo a Stille cross coupling reaction, with an alkyl stannane employing conditions known to one skilled in the art, to provide a compound of formula (XVIII). For example, reaction of 3-bromo-2-(1,1-difluoroethyl)-5-(3-(difluoromethoxy)-4-fluorophenyl)pyridine, in the presence of a palladium catalyst such as Pd(Ph₃)₄, and the like; KF; and an alkyl stananne, such as tert-butyl-dimethyl-(tributylstannyl-methoxy)silane; in a suitable solvent such as 1,4-dioxane, toluene, DMF, and the like; at temperatures ranging from 50 to 120° C.; for a period of 22 hours; provides 3-(((tert-butyldimethylsilyl)oxy)methyl)-2-(1,1-difluoroethyl)-5-(3-(difluoromethoxy)-4-fluorophenyl)pyridine. Deprotection of the trialkyl silyl protecting group on compound of formula (XVIII) is achieved employing established methodologies, such as those described in T. W. Greene and P. G. M. Wuts, "Protective Groups in Organic Synthesis," 3 ed., John Wiley & Sons, 1999, for example, with an acid such as TFA, HCl, and the like; in a suitable solvent such as DCM, and the like. Subsequent chlorination, employing conditions known to one skilled in the art, or as previously described, provides a compound of formula (XII), where $R^3$ is $CF_2H(CF_3)$.

palladium catalyst such as RuPhos Pd G3, Pd(PPh₃)₄, Pd(dppf)Cl₂, PdCl₂(dppf)-CH₂Cl₂, PdCl₂(dtbpf), and the like; a suitable base such a Na₂CO₃, potassium phosphate, Cs₂CO₃, K₂CO₃, and the like; in a solvent such as 1,4-dioxane, water, or a mixture thereof; employing conventional or microwave heating; at temperatures ranging from room temperature to 100° C.; for a period of 1 h to 18 h, to give a compound of Formula (I).

Alternatively, under conditions known to one skilled in the art, a compound of formula (XIX), where $R^{4a}$ and $R^{4b}$ are H, and $R^3$ is O-alkyl; can be borylated, employing conditions previously described, to provide the corresponding boronic ester and boronic acid as a mixture. For example, reaction of 3-[(5-bromo-2-methoxy-3-pyridyl)methyl]oxazolidin-2-one under a metal mediated cross coupling reaction with bis(pinacolato)diboron, in the presence of a palladium catalyst such as Pd(dppf)Cl₂, and the like; a base such as KOAc, and the like; in a suitable solvent such as 1,4-dioxane, and the like; at a temperature of 80° C.; for a period of 4 h; provides [6-methoxy-5-[(2-oxooxazolidin-3-yl)methyl]-3-pyridyl]boronic acid and 3-[[2-methoxy-5-(4,4,5,5-tetramethyl-1,3,2-dioxaborolan-2-yl)-3-pyridyl]methyl]oxazolidin-2-one. Subsequent metal mediated cross coupling reaction with a commercially available or synthetically accessible differentially substituted aryl or heteroaryl halide; in the presence of a palladium catalyst such as Pd(PPh₃)₄, and the like; a base such as K₂CO₃, and the like; in a suitable solvent such as 1,4-dioxane, water, or a mixture thereof; at a temperature of 90° C.; for a period of 6 h; provides a compound of Formula (I).

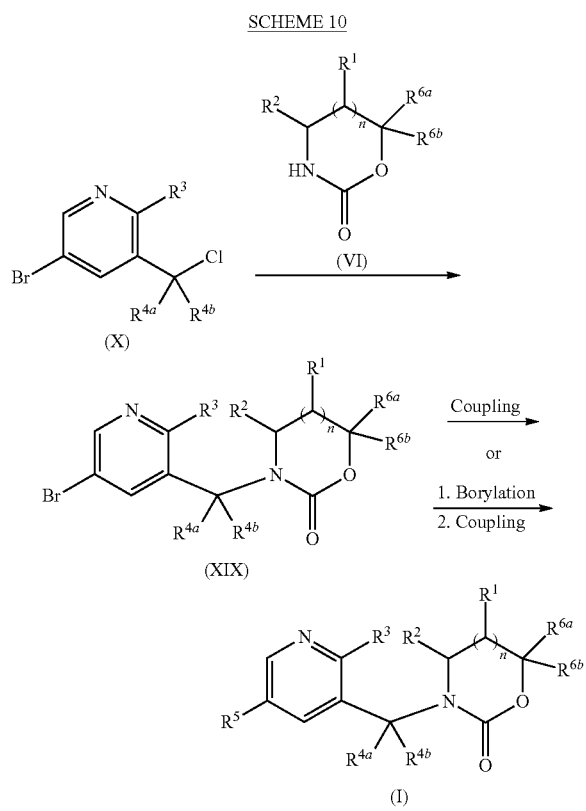

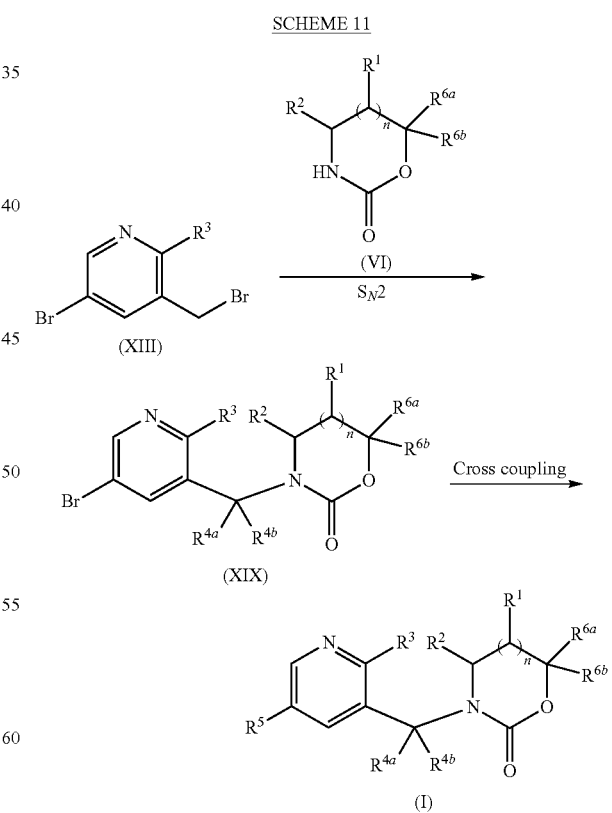

According to SCHEME 10, a commercially available or synthetically accessible 2-substituted pyridine of formula (X), where $R^3$ is H, alkyl, Oalkyl, Ohaloalkyl, or haloalkyl, $R^{4a}$ and $R^{4b}$ are ¹H, deuterium, or alkyl, is reacted with a commercially available or synthetically accessible carbamate of formula (VI), where $R^1$, $R^2$, n, $R^{6a}$ an $R^{6b}$ are as defined in the Summary, in the presence of a base such as NaH, K₂CO₃, Cs₂CO₃, and the like; in a solvent such as dimethylformamide (DMF), acetonitrile (ACN), DCM, and the like; for a period of 30 min to 18 h; at room temperature; to provide a compound of formula (XIX). A compound of formula (XIX) can then be reacted under metal-mediated cross coupling conditions such as Suzuki reaction conditions known to one skilled in the art. For example, a compound of formula (XIX), can be reacted with a commercially available or synthetically accessible suitably substituted aryl or heteroaryl boronic acid or boronic ester; in the presence of a According to SCHEME 11, an $S_N2$ reaction of a compound of formula (XIII), with a commercially available or synthetically accessible carbamate of formula (VI); in the presence of a base such as Na$_2$CO$_3$, NaH, K$_2$CO$_3$, Cs$_2$CO$_3$, and the like; in a solvent such as DMF, ACN, DCM, and the like; for a period of 30 min to 18 hours; at room temperature; provides the bromopyridine intermediate compound of formula (XIX). A compound of formula (XIX) can be reacted in a metal mediated cross coupling reaction as previously described, with a commercially available or synthetically accessible differentially substituted aryl or heteroaryl halide to provide a compound of Formula (I).

SCHEME 12

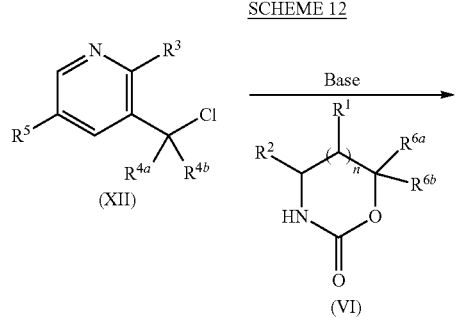

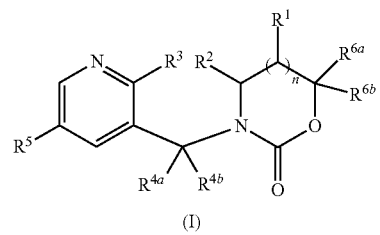

An S$_N$2 reaction of a compound of formula (XII), with a commercially available or synthetically accessible carbamate of formula (VI), where R$^1$, R$^2$, n, R$^{6a}$, and R$^{6b}$ are as defined in the Summary, can be performed in the presence of a base such as Na$_2$CO$_3$, NaH, K$_2$CO$_3$, Cs$_2$CO$_3$, and the like; in a suitable solvent such as DMF, ACN, DCM, and the like; for a period of 30 min to 18 hours; at room temperature; to provide a compound of Formula (I).

SCHEME 13

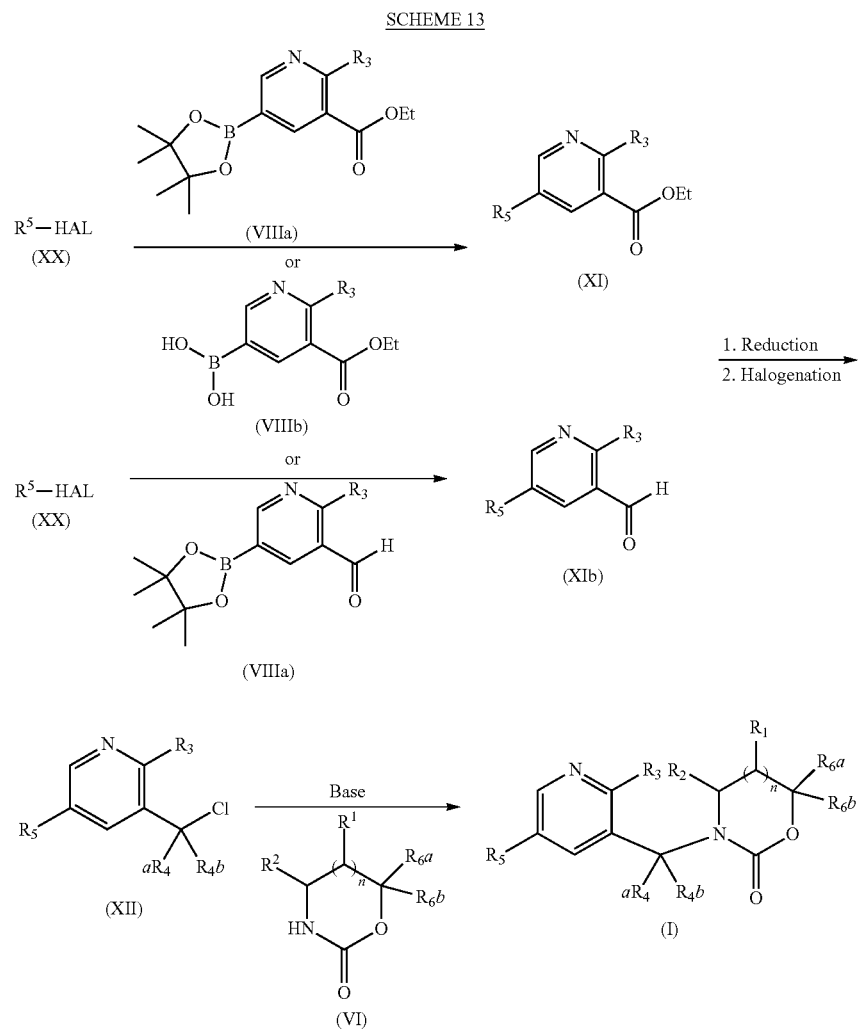

According to SCHEME 13, a commercially available or synthetically accessible aryl or heteroaryl halide compound of formula (XX), where R is as defined in the Summary and HAL is Br or Cl; is reacted in a metal mediated cross coupling reaction with commercially available or synthetically accessible boronic acid (VIIIb) or boronic ester (VIIIa), where $R^3$ is H, alkyl, Oalkyl, Ohaloalkyl, or haloalkyl; in the presence of a palladium catalyst such as $Pd(PPh_3)_4$, $Pd(dppf)C_2$, and the like; and abase such as $Na_2CO_3$, $Cs_2CO_3$, $K_2O_3$, KF, and the like; in a suitable solvent such as 1,4-dioxane, ACN, with or without water; at temperatures ranging from 80-90° C.; for a period of 1 h to 18 hours, to give a compound of formula (XI). A compound of formula (XII) can be prepared in two steps from a compound of formula (XI), employing reduction and halogenation conditions previously described.

For example, a compound of formula (XI), can be reduced with a reducing agent such as $NaBH_4$, $NaBD_4$, $LiAlH_4$, $LiAlD_4$, $LiBH_4$, DIBAL, and the like; in a suitable solvent such as THF, THF-$d_8$, MeOH, EtOH, and the like; at temperatures ranging from −78-45° C.; for a period of 30 min to 40 h; to provide the alcohol intermediate, which is chlorinated with thionyl chloride, as previously described. An $S_N2$ reaction of a compound of formula (XII), with a commercially available or synthetically accessible carbamate of formula (VI), employing conditions previously described provides a compound of Formula (I).

According to SCHEME 13, a commercially available or synthetically accessible aryl or heteroaryl halide compound of formula (XX), where R is as defined in the Summary and HAL is Br or Cl; is reacted in a metal mediated cross coupling reaction with commercially available or synthetically accessible boronic ester (VIIIc), where $R^3$ is F; in the presence of a palladium catalyst such as $Pd(PPh_3)_4$, $Pd(dpp)Cl_2$, and the like; and abase such as $Na_2CO_3$, $Cs_2CO_3$, $K_2CO_3$, KF, and the like; in a suitable solvent such as 1,4-dioxane, ACN; at a temperature of 90° C.; for a period of 18 hours, to give a compound of formula (XIb). A compound of formula (XII) can be prepared in two steps from a compound of formula (XIb), employing reduction and halogenation conditions.

For example, a compound of formula (XIb), can be reduced with a reducing agent such as $NaBH_4$, $LiAlH_4$, $LiBH_4$, DIBAL, and the like; in a suitable solvent such as THF, MeOH, EtOH, and the like; at temperatures ranging from 0-25° C.; for a period of 60 min; to provide the alcohol intermediate, which is reacted with a chlorination reagent such as oxalyl chloride, thionyl chloride, and the like; in a solvent such as dichloromethane (DCM), dichloroethane (DCE) and the like; at a temperature of 25-60° C. An $S_N2$ reaction of a compound of formula (XII), with a commercially available or synthetically accessible carbamate of formula (VI), employing conditions previously described provides a compound of Formula (I).

The following specific examples are provided to further illustrate the invention and various preferred embodiments.

5. EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$.

Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

Normal-phase silica gel chromatography (FCC) was performed on silica gel ($SiO_2$) using prepacked cartridges.

Preparative reverse-phase high performance liquid chromatography (RP HPLC) was performed with:

METHOD A. A Gilson HPLC with an XBridge C18 column (5 µm, 50×100 mm or 50×250 mm), mobile phase of 5-99% ACN in 20 mM $NH_4OH$ over 10 min and then hold at 99% ACN for 2 min, at a flow rate of 80 mL/min.

or

METHOD B. A Teledyne ACCQPrep HP125 with an XBridge C18 column (5 µm, 50×100 mm or 50×250 mm), mobile phase of 0-100% ACN in 20 mM $NH_4OH$ over 16 min or 42 min and then hold at 100% ACN for 2 min, at a flow rate of 80 mL/min.

or

METHOD C. A Teledyne ACCQPrep HP125 with a Sunfire Prep C18 column (5 µm, 30×250 mm), mobile phase of 5-100% ACN with 0.05% TFA in water with 0.05% TFA over 22 min and then hold at 100% ACN for 2 min, at a flow rate of 42.5 mL/min.

or

METHOD D. A Wufeng LC100 equipped with a manual Rheodyne 3725i sampler with a Gemini-NX C18 column (5 µM, 30×100 mm), and a mobile phase of 0-90% ACN: 8 mM $(NH_4)HCO_3$ (9:1) in 10 mM aqueous $(NH_4)HCO_3$ over 8 min or 21 min, with a flow rate of 30 mL/min.

or

METHOD E. A Wufeng LC100 equipped with a manual Rheodyne 3725i sampler with a Gemini-NX C18 column (5 µM, 30×100 mm), and a mobile phase of 0-90% ACN: 10 mM $(NH_4)HCO_3$ (9:1) in 10 mM aqueous $(NH_4)HCO_3$ with 0.1% $NH_4OH$ over 16 min or 18 min, with a flow rate of 30 mL/min.

or

METHOD F. A Wufeng LC100 equipped with a manual Rheodyne 3725i sampler with a Gemini-NX C18 column (5 µM, 30×100 mm), and a mobile phase of 0-90% MeOH: 50 mM $NH_4HCO_2$ (9:1) in 50 mM aqueous $NH_4HCO_2$ with 0.1% $HCO_2H$ over 10 min, with a flow rate of 30 mL/min.

or

METHOD G. An Agilent HPLC with an Xterra Prep RP18 column (5 µM, 30×100 or 50×150 mm) or an XBridge C18 OBD column (5 µM, 30×100, 50×100, or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

Preparative supercritical fluid high performance liquid chromatography (SFC) was performed on a Jasco preparative SFC system, an APS 1010 system from Berger instruments, or a SFC-PICLAB-PREP 200 (PIC SOLUTION, Avignon, France). The separations were conducted at 100-150 bar with a flow rate ranging from 40-60 mL/min. The column was heated to 35-40° C.

Mass spectra (MS) were obtained on an Agilent series 1100 MSD using electrospray ionization (ESI) in positive mode unless otherwise indicated. Calculated (calcd.) mass corresponds to the exact mass.

Analytical LC/MS method was performed on:

An Agilent 1200 system with a variable wavelength detector and Agilent 6140 single quadrupole mass spectrometer, alternating positive and negative ion scans. Retention times were determined from the extracted 220 nm UV chromatogram. HPLC column: Kinetex, 2.6 μm, C18, 50×2.1 mm, maintained at 40° C. HPLC Gradient: 1.0 mL/min, 95:5:0.1 water:acetonitrile:formic acid to 5:95:0.1 water:acetonitrile:formic acid in 2.0 min, maintaining for 0.5 min.
or
A Shimadzu system with a variable wavelength detector and Shimadzu LCMS-2020 single quadrupole mass spectrometer, alternating positive and negative ion scans. Retention times were determined from the extracted 220 nm UV chromatogram. HPLC column: Kinetex, 2.6 μm, C18, 50×2.1 mm, maintained at 40° C. HPLC Gradient: 1.0 mL/min, 95:5 water:acetonitrile (with 10 mmol ammonium bicarbonate) to 20:80 water:acetonitrile (with 10 mmol ammonium bicarbonate) in 2.0 min, maintaining for 0.5 min.
or
A Shimadzu system with a variable wavelength detector and Shimadzu LCMS-2020 single quadrupole mass spectrometer, alternating positive and negative ion scans. Retention times were determined from the extracted 205 nm UV chromatogram. HPLC column: Kinetex, 2.6 μm, C18, 50×2.1 mm, maintained at 40° C. HPLC Gradient: 1.0 mL/min, 95:5 water:acetonitrile (with 10 mmol ammonium bicarbonate) to 20:80 water:acetonitrile (with 10 mmol ammonium bicarbonate) in 2.0 min, maintaining for 0.5 min.
or
A Shimadzu system with a variable wavelength detector and Shimadzu LCMS-2020 single quadrupole mass spectrometer, alternating positive and negative ion scans. Retention times were determined from the extracted 220 nm UV chromatogram. HPLC column: Kinetex, 2.6 μm, C18, 50×2.1 mm, maintained at 40° C. HPLC Gradient: 1.0 mL/min, 95:5 water:acetonitrile (with 5 mmol ammonium carbonate) to 20:80 water:acetonitrile (with 5 mmol ammonium carbonate) in 2.0 min, maintaining for 0.5 min.
or
A Shimadzu system with a variable wavelength detector and Shimadzu LCMS-2020 single quadrupole mass spectrometer, alternating positive and negative ion scans. Retention times were determined from the extracted 220 nm UV chromatogram. HPLC column: Kinetex, 2.6 μm, C18, 50×2.1 mm, maintained at 40° C. HPLC Gradient: 1.0 mL/min, 95:5:0.1 water:acetonitrile:formic acid to 5:95:0.1 water:acetonitrile:formic acid in 2.0 min, maintaining for 0.5 min.

Analytical HPLC was performed on the systems mentioned in the Examples or either: A Waters 1525 Binary HPLC Pump with Waters 2487 Dual A absorbance detector. Retention times were determined from the extracted 220 nm UV chromatogram. HPLC column: Gemini NX, 5 μm, C$_{18}$, 10×4.6 mm, maintained at ambient temperature. HPLC Gradient: 1.0 mL/min, 82:18 water:acetonitrile containing 10 mM ammonium bicarbonate to 10:90 water:acetonitrile containing 10 mM ammonium bicarbonate in 10 min, maintaining for 2.0 min.
or
A Waters 1525 Binary HPLC Pump with Waters 2487 Dual A absorbance detector. Retention times were determined from the extracted 220 nm UV chromatogram. HPLC column: Kinetex EVO, 5 μm, C$_{18}$, 150×4.6 mm, maintained at ambient temperature. HPLC Gradient: 1.0 mL/min, 95:5 water:acetonitrile to 0:100 water:acetonitrile in 15 min, maintaining for 2.0 min.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 17.1 (CambridgeSoft Corp., Cambridge, Mass.) or OEMetaChem V1.4.0.4 (Open Eye).

Compounds designated as R* or S* are enantiopure compounds where the absolute configuration was not determined.

5.1. Intermediates: Intermediates 1-44

Intermediate 1: 6,6-Dimethyl-1,3-oxazinan-2-one

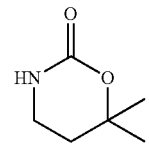

A solution of 4-amino-2-methylbutan-2-ol (245 mg, 2.38 mmol) and CDI (385 mg, 2.38 mmol) in THF (7.9 mL) at room temperature was stirred for 2 days. The crude reaction was concentrated to a clear residue and subjected directly to purification. Purification via silica gel chromatography (0-10% methanol in DCM) gave the title compound (270 mg, 2.09 mmol, 88%) as a white solid. $^1$H NMR (400 MHz, Methanol-d$_4$) δ 3.34 (t, J=6.4 Hz, 2H), 1.85 (t, J=6.4 Hz, 2H), 1.39 (s, 6H).

Intermediate 2: 4-Oxa-6-azaspiro[2.4]heptan-5-one

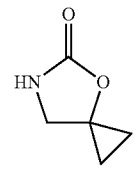

Prepared analogous to 6,6-Dimethyl-1,3-oxazinan-2-one (Intermediate 1), using 1-(aminomethyl)cyclopropan-1-ol. $^1$H NMR (400 MHz, Methanol-d$_4$) δ 3.66 (s, 2H), 1.18-1.08 (m, 2H), 0.81-0.74 (m, 2H).

Intermediate 3:2,5-Dioxa-7-azaspiro[3.4]octan-6-one

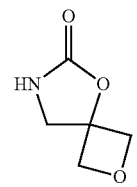

Prepared analogous to 6,6-Dimethyl-1,3-oxazinan-2-one (Intermediate 1), using 3-(aminomethyl)oxetan-3-ol. $^1$H NMR (400 MHz, Methanol-d₄) δ 4.87 (dd, J=7.7, 1.2 Hz, 2H), 4.74 (dd, J=7.7, 1.2 Hz, 2H), 3.86 (s, 2H).

Intermediate 4: Racemic 5-Isopropyloxazolidin-2-one

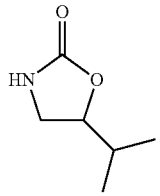

Prepared analogous to 6,6-Dimethyl-1,3-oxazinan-2-one (Intermediate 1), using 1-amino-3-methylbutan-2-ol. ¹H NMR (400 MHz, Methanol-d₄) δ 4.53-4.10 (m, 1H), 3.61 (t, J=8.8 Hz, 1H), 3.37-3.27 (m, 1H), 2.01-1.77 (m, J=6.8 Hz, 1H), 1.01 (d, J=6.7 Hz, 3H), 0.94 (d, J=6.8 Hz, 3H).

Intermediate 5: Racemic 5-(Morpholinomethyl)oxazolidin-2-one

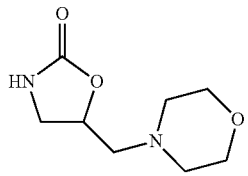

Prepared analogous to 6,6-Dimethyl-1,3-oxazinan-2-one (Intermediate 1), using racemic 1-amino-3-morpholinopropan-2-ol. ¹H NMR (400 MHz, Chloroform-d) δ 5.81 (s, 1H), 4.95-4.66 (m, 1H), 3.72-3.60 (m, 5H), 3.45-3.33 (m, 1H), 2.76-2.64 (m, 1H), 2.64-2.47 (m, 5H).

Intermediate 6: 1,8-Dioxa-3-azaspiro[4.5]decan-2-one

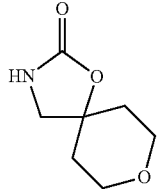 [SMILES: O=C1NCC2(CCOCC2)O1]

Prepared analogous to 6,6-Dimethyl-1,3-oxazinan-2-one (Intermediate 1), using 4-(aminomethyl)tetrahydro-2H-pyran-4-ol. ¹H NMR (400 MHz, Methanol-d₄) δ 3.90-3.70 (m, 4H), 3.39 (s, 2H), 1.95-1.78 (m, 4H).

Intermediate 7: tert-Butyl 6-oxo-5-oxa-2,7-diazaspiro[3.4]octane-2-carboxylate

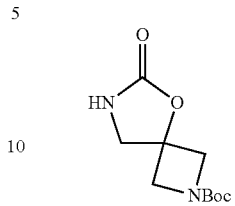

Prepared analogous to 6,6-Dimethyl-1,3-oxazinan-2-one (Intermediate 1), using tert-butyl 3-(aminomethyl)-3-hydroxyazetidine-1-carboxylate. ¹H NMR (400 MHz, Methanol-d₄) δ 4.24-4.07 (m, 4H), 3.78 (s, 2H), 1.45 (s, 9H).

Intermediate 8: 2-(3,4-Difluoro-5-methylphenyl)-4,4,5,5-tetramethyl-1,3,2-dioxaborolane

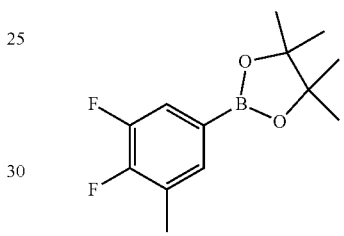

A mixture of 5-bromo-1,2-difluoro-3-methylbenzene (1 g, 4.83 mmol), bis(pinacolato)diboron (1.35 g, 5.32 mmol), [1,1'-bis(diphenylphosphino)ferrocene]dichloropalladium (II) (353 mg, 0.48 mmol), and KOAc (1.42 g, 14.5 mmol) in degassed 1,4-dioxane (9 mL) was stirred at 90° C. for 2 h under argon. The reaction mixture was filtered through Celite® and washed with 1,4-dioxane (5×5 mL). The filtrate was concentrated and subjected directly to purification. Purification via silica gel chromatography (0-10% EtOAc in hexanes) gave the title compound (1.08 g, 4.25 mmol, 88%) as a yellow liquid.

Intermediate 9: 2-Bromo-5-(difluoromethyl)thiophene

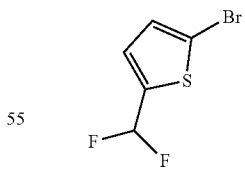

To neat DAST (13.8 mL, 105 mmol) was added 5-bromothiophene-2-carbaldehyde (5.0 g, 26.2 mmol) dropwise at 0° C. under argon. The reaction mixture was allowed to warm to room temperature and stirred for 22 h. The reaction was quenched carefully by the dropwise addition of 2 M NaOH (25 mL) at 0° C. The aqueous layer was extracted with EtOAc (2×50 mL). The combined organic layers were dried over Na₂SO₄, filtered and evaporated. The residue was purified by silica gel column chromatography, eluting with petroleum ether to give a first crop of the title compound (2.58 g, 12.1 mmol, 46%) as a pale yellow liquid. Fractions from the same column were collected to give a second crop of the title compound (69 mg, 0.324 mmol, 1%) as a colorless liquid.

Intermediate 10: Ethyl 2-methyl-5-(4,4,5,5-tetramethyl-1,3,2-dioxaborolan-2-yl)pyridine-3-carboxylate and (5-(ethoxycarbonyl)-6-methylpyridin-3-yl) boronic Acid

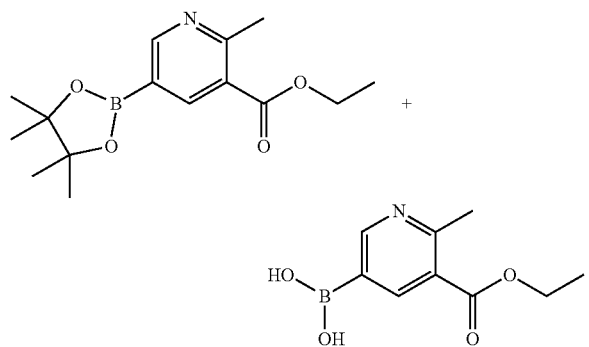

A mixture of ethyl 5-bromo-2-methyl-pyridine-3-carboxylate (5.5 g, 22.5 mmol), bis(pinacolato)diboron (6.29 g, 24.8 mmol), [1,1'-bis(diphenylphosphino)ferrocene]dichloropalladium(II) (825 mg, 1.13 mmol) and KOAc (6.63 g, 67.6 mmol) in degassed 1,4-dioxane (55 mL) was stirred at 90° C. for 2 h under argon. The reaction mixture was poured onto crushed ice (80 mL), concentrated to remove the 1,4-dioxane, and extracted with ethyl acetate (3×200 mL). The combined organic layers were dried over MgSO$_4$, filtered and evaporated to give a mixture of ethyl 2-methyl-5-(4,4,5,5-tetramethyl-1,3,2-dioxaborolan-2-yl)pyridine-3-carboxylate and (5-ethoxycarbonyl-6-methyl-3-pyridyl)boronic acid (9.13 g, 43.7 mmol, crude) as a brown oil, which was used without further purification. (5-Ethoxycarbonyl-6-methyl-3-pyridyl)boronic acid: MS (ESI): mass calcd. for $C_9H_{12}BNO_4$, 209.1; m/z found, 210.1 [M+H]$^+$.

Intermediate 11: 3-Bromo-5-(chloromethyl-d$_2$)pyridine

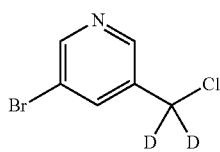 [SMILES: [2H]C([2H])(Cl)c1cncc(Br)c1]

Step A: 5-Bromonicotinic (ethyl carbonic) anhydride

To a suspension of 5-bromonicotinic acid (385 mg, 1.91 mmol) in toluene (8 mL) was added Et$_3$N (0.3 mL, 2.02 mmol), and the reaction mixture was stirred at room temperature for 5 minutes. Then, ethyl chloroformate (0.19 mL, 2.02 mmol) was added dropwise and the reaction mixture was further stirred at room temperature for 80 minutes to form the mixed anhydride, at which time the triethylamine hydrochloride salt precipitated and was filtered off. The filtrate was collected and concentrated to give the mixed anhydride, which was used without further purification.

Step B: (5-Bromopyridin-3-yl)methan-d$_2$-ol

The crude 5-bromonicotinic (ethyl carbonic) anhydride from step A was re-dissolved in THF (8 mL) and cooled to 0° C., and NaBD$_4$ (266 mg, 5.72 mmol) was added portionwise followed by the dropwise addition of methanol-d$_4$ (12 mL). Upon complete addition, the reaction was stirred at 0° C. for 20 minutes. Then, the reaction was quenched with water and concentrated to remove the organics. The crude material was re-dissolved in EtOAc and brine, and the organic layer was separated. The aqueous layer was further extracted with EtOAc (3×). The organics were combined and concentrated to give a yellow residue that solidified upon standing. Purification via silica gel chromatography (0-50% EtOAc (with 10% methanol) in hexanes) gave the title compound (153 mg, 0.81 mmol, 42%). MS (ESI): mass calcd. for $C_6H_4D_2BrNO$, 189.0; m/z found, 189.9 [M+H]$^+$.

Step C: 3-Bromo-5-(chloromethyl-d$_2$)pyridine

To a solution of (5-bromopyridin-3-yl)methan-d$_2$-ol (152 mg, 0.8 mmol) in DCM (3.2 mL) at 0° C. was added thionyl chloride (0.06 mL, 0.88 mmol), and the reaction mixture was slowly warmed to room temperature and stirred overnight. Then, the crude reaction mixture was slowly poured into a cold solution of saturated aqueous NaHCO$_3$ until bubbling ceased. The organics were removed, and the aqueous layer was further extracted with DCM (3×). The combined organics were dried (MgSO$_4$), filtered and concentrated to yield the title compound as a yellow solid (124 mg), which was used without further purification. MS (ESI): mass calcd. for $C_6H_3D_2BrClN$, 207.0; m/z found, 207.9 [M+H]$^+$.

Intermediate 12: 5-Bromo-3-(chloromethyl-d2)-2-methylpyridine

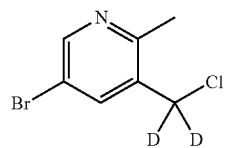

Prepared analogous to 3-Bromo-5-(chloromethyl-d$_2$)pyridine (Intermediate 11), using ethyl 5-bromo-2-methylnicotinate in Step A. $^1$H NMR (400 MHz, Chloroform-d) δ 8.52 (d, J=2.3 Hz, 1H), 7.77 (d, J=2.3 Hz, 1H), 2.59 (s, 3H).

Intermediate 13: 5-Bromo-3-(chloromethyl)-2-methoxy-pyridine

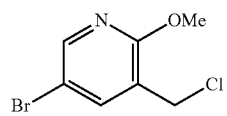 [SMILES: COc1ncc(Br)cc1CCl]

Step A: (5-Bromo-2-methoxy-3-pyridyl)methanol

To a solution of methyl 5-bromo-2-methoxy-pyridine-3-carboxylate (10 g, 40.6 mmol) in tetrahydrofuran (100 mL)

and methanol (5 mL, 124 mmol) was added sodium borohydride (3.08 g, 81.4 mmol) portion-wise, and upon complete addition the reaction mixture was stirred at 40° C. for 2 h. The reaction mixture was cooled to 5° C. and diluted carefully with water (60 mL) and stirred at room temperature for 15 min. The organics were evaporated, and the aqueous layer was extracted with chloroform (3×35 mL). The combined organic layers were dried over MgSO$_4$, filtered and evaporated, and the residue was triturated with a hot mixture of n-heptane:ethyl acetate (10:1, 40 mL) to give the title compound (6.89 g, 31.6 mmol, 78%) as a white powder. MS (ESI): mass calcd. for C$_7$H$_8$BrNO$_2$, 217.0; m/z found, 218.0 [M+H]$^+$.

Step B:
5-Bromo-3-(chloromethyl)-2-methoxy-pyridine

To a solution of (5-bromo-2-methoxy-3-pyridyl)methanol (6.89 g, 31.6 mmol) in dichloromethane (70 mL) was added thionyl chloride (6.88 mL, 94.8 mmol) dropwise at 0° C. The mixture was stirred at room temperature for 1.5 h and then concentrated. To the residue was added water (30 mL) and the mixture was basified to pH 8 with saturated sodium bicarbonate. The aqueous layer was extracted with chloroform (4×20 mL) and the combined organic layers were dried over MgSO$_4$, filtered and evaporated to give the title compound (6.84 g, 28.9 mmol, 92%) as a pale yellow oil.

Intermediate 14: 3-Bromo-5-(1-chloroethyl)pyridine

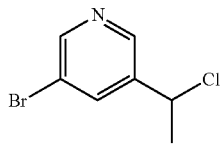

To a solution of 3-bromo-5-(1-hydroxyethyl)pyridine (300 mg, 1.49 mmol) in DCM (2.5 mL) at 0° C. was added thionyl chloride (0.32 mL, 4.45 mmol), and the reaction mixture was slowly warmed to room temperature and stirred for 5 h. Then, the crude reaction mixture was slowly poured into a cold solution of saturated aqueous NaHCO$_3$ until bubbling ceased. The organics were removed, and the aqueous layer was further extracted with DCM (3×). The combined organics were dried (Na$_2$SO$_4$), filtered and concentrated to yield the title compound as a red-brown liquid (315 mg), which was used without further purification. MS (ESI): mass calcd. for C$_7$H$_7$BrClN, 219.0; m/z found, 219.9 [M+H]$^+$.

Intermediate 15: 5-Bromo-3-(chloromethyl)-2-methylpyridine

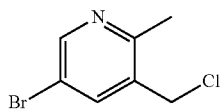

To a solution of (5-bromo-2-methyl-3-pyridyl)methanol (2.71 g, 13.4 mmol, prepared according to U.S. Pat. No. 9,695,168 (Konkol et al., Jul. 4, 2017)), in dichloromethane (50 mL) was added thionyl chloride (2.92 mL, 40.3 mmol) dropwise at 0° C. The reaction mixture was stirred at room temperature for 1 h and concentrated. Then, diethyl ether (3×10 mL) was added until a precipitate formed. The precipitate was collected to give the title compound (2.97 g, 13.5 mmol, 50%) as a brown powder. MS (ESI): mass calcd. for C$_7$H$_7$BrClN, 219.0; m/z found, 220.0 [M+H]$^+$.

Intermediate 16: 5-Bromo-3-(bromomethyl)-2-(1,1-difluoroethyl)pyridine

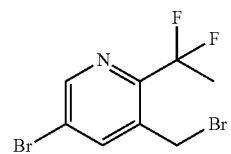

Step A:
5-Bromo-2-(1,1-difluoroethyl)-3-methylpyridine

Deoxo-Fluor® (7.5 mL, 40.7 mmol) was added dropwise to neat 1-(5-bromo-3-methylpyridin-2-yl)ethan-1-one (1.09 g, 5.08 mmol) at 0° C. Upon complete addition, the reaction mixture was heated to 60° C. overnight. Then, the reaction was cooled to 0° C. and slowly quenched with an aqueous solution of 3 N NaOH (3 mL), followed by extraction with Et$_2$O (3×). The combined organic layers were dried (Na$_2$SO$_4$), filtered and concentrated. Purification via silica gel chromatography (100% hexanes) gave the title compound as a clear liquid (777 mg, 3.29 mmol, 65%). $^1$H NMR (400 MHz, Chloroform-d) δ 8.44 (d, J=1.3 Hz, 1H), 7.72 (d, J=2.1 Hz, 1H), 2.75-2.38 (m, 3H), 2.05 (t, J=19.3 Hz, 3H).

Step B: 5-Bromo-3-(bromomethyl)-2-(1,1-difluoroethyl)pyridine

To a solution of 5-bromo-2-(1,1-difluoroethyl)-3-methylpyridine (256 mg, 1.08 mmol) and NBS (289 mg, 1.63 mmol) in CCl$_4$ (4.3 mL) was added AIBN (177.9 mg, 1.08 mmol), and the reaction mixture was heated to reflux for 2 h. The reaction mixture was cooled to room temperature, filtered through Celite® and washed with DCM. The filtrate was further washed with a saturated aqueous solution of NaHCO$_3$ (2×). The organics were combined, dried (Na$_2$SO$_4$), filtered, and concentrated. Purification via silica gel chromatography (100% hexanes) gave a mixture of the title compound and unreacted 5-bromo-2-(1,1-difluoroethyl)-3-methylpyridine (ca. 40% by $^1$HNMR analysis). The material was used in the next step without further purification. $^1$H NMR (500 MHz, Chloroform-d) δ 8.54 (d, J=2.2 Hz, 1H), 8.06 (d, J=2.1 Hz, 1H), 4.71 (s, 2H), 2.09 (t, J=19.4 Hz, 3H).

Intermediate 17:3-(Chloromethyl)-5-(3-(difluoromethoxy)-4-fluorophenyl)-2-methylpyridine hydrochloride.

53

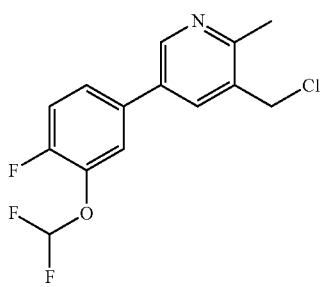 [SMILES: Cc1ncc(-c2ccc(F)c(OC(F)F)c2)cc1CCl]

Step A: Ethyl 5-[3-(difluoromethoxy)-4-fluoro-phenyl]-2-methyl-pyridine-3-carboxylate To a solution of ethyl 5-bromo-2-methyl-pyridine-3-carboxylate (2.0 g, 8.19 mmol) in ACN (57 mL) and water (9 mL) was added 2-[3-(difluoromethoxy)-4-fluoro-phenyl]-4,4,5,5-tetramethyl-1,3,2-dioxaborolane (2.48 g, 8.60 mmol), $Na_2CO_3$ (2.61 g, 24.6 mmol) and [1,1'-bis(diphenylphosphino)ferrocene]dichloropalladium(II) (780 mg, 1.07 mmol). The reaction mixture was split evenly into 5 portions and all portions were stirred at 80° C. for 1 h under argon. Upon completion, the reaction mixtures were combined and concentrated. The residue was taken up in EtOAc (80 mL) and the organic layer was washed with water (1×70 mL). The aqueous layer was extracted with EtOAc (2×70 mL) and the combined organic layers were dried over $Na_2SO_4$, filtered and concentrated. Purification via silica gel chromatography (0-5% MeOH in DCM) gave the title compound, which contained trace impurities. The material was further purified via silica gel chromatography (0-40% EtOAc in n-heptane) to yield the title compound (1.83 g, 5.63 mmol, 69%) as a light brown powder. MS (ESI): mass calcd. for $C_{16}H_{14}F_3NO_3$, 325.1; m/z found, 326.1 $[M+H]^+$.

Step B: [5-[3-(Difluoromethoxy)-4-fluoro-phenyl]-2-methyl-3-pyridyl]methanol To a solution of ethyl 5-[3-(difluoromethoxy)-4-fluorophenyl]-2-methyl-pyridine-3-carboxylate (2.02 g, 6.21 mmol) in THF (40.5 mL) was added $LiAlH_4$ (6.52 mL, 6.52 mmol, 1 M in THF) dropwise at −78° C. under argon. The reaction mixture was stirred at −78° C. for 1 h under argon and quenched carefully with EtOAc (200 mL) at −70° C. The organic layer was washed with saturated $NaHCO_3$ (1×50 mL), water (1×50 mL), dried over $MgSO_4$, filtered and concentrated. The residue was triturated with $Et_2O$ (15 mL) to afford the title compound (1.50 g, 5.30 mmol, 85%) as a white powder. MS (ESI): mass calcd. for $C_{14}H_{12}F_3NO_2$, 283.1; m/z found, 284.1 $[M+H]^+$.

Step C: 3-(Chloromethyl)-5-(3-(difluoromethoxy)-4-fluorophenyl)-2-methylpyridine hydrochloride To a solution of [5-[3-(difluoromethoxy)-4-fluoro-phenyl]-2-methyl-3-pyridyl]methanol (1.5 g, 5.296 mmol) in DCM (20 mL) was added thionyl chloride (1.2 mL, 15.8 mmol) at 0° C. The reaction mixture was stirred at room temperature for 2 h and then concentrated. The residue was triturated with $Et_2O$ (10 mL) to afford the title compound (1.72 g, 5.09 mmol, 96%), as the hydrochloride salt, as a white powder. MS (ESI): mass calcd. for $C_{14}H_{11}ClF_3NO_2$, 301.1; m/z found, 302.1 $[M+H]^+$.

54

Intermediate 18: 3-(Chloromethyl)-5-(4-fluoro-3-methylphenyl)-2-methoxypyridine hydrochloride

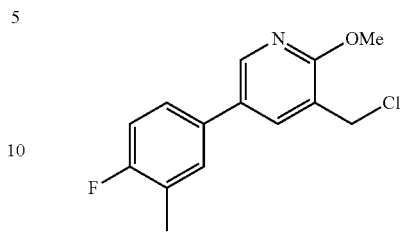

Step A: Methyl 5-(4-fluoro-3-methyl-phenyl)-2-methoxy-pyridine-3-carboxylate A mixture of methyl 5-bromo-2-methoxy-pyridine-3-carboxylate (2.00 g, 8.13 mmol, synthesized by the method described in US Application 4,980,357 (Goldstein et al, Dec. 25, 1990)), 4-fluoro-3-methylphenylboronic acid (1.4 g, 9.09 mmol), [1,1'-bis(diphenylphosphino)ferrocene]dichloropalladium (658 mg, 0.899 mmol) and potassium carbonate (2.2 g, 15.9 mmol) in 1,4-dioxane (26 mL) and water (2.6 mL) was stirred at 80° C. for 4 h under argon. The reaction mixture was evaporated and the residue was purified by silica gel column chromatography, eluting with n-hexane:ethyl acetate (4:1), to afford the title compound (1.55 g, 5.63 mmol, 69%) as a white powder. MS (ESI): mass calcd. for $C_{15}H_{14}FNO_3$, 275.1; m/z found, 276.2 $[M+H]^+$.

Step B: [5-(4-Fluoro-3-methyl-phenyl)-2-methoxy-3-pyridyl]methanol

To a solution of methyl 5-(4-fluoro-3-methyl-phenyl)-2-methoxy-pyridine-3-carboxylate (1.50 g, 5.45 mmol) in tetrahydrofuran (15 mL) and methanol (647 μL, 16 mmol) was added sodium borohydride (420 mg, 11.1 mmol) in small portions and the reaction mixture was stirred at 45° C. for 40 h. The mixture was cooled to 5° C. and carefully diluted with water (10 mL). The mixture was stirred at room temperature for 30 min and then tetrahydrofuran (15 mL) was evaporated from the mixture. The aqueous layer was extracted with ethyl acetate (4×15 mL) and the combined organic layers were washed with water (1×8 mL). The organic layer was dried over $MgSO_4$, filtered and evaporated to give the title compound (1.05 g, 4.25 mmol, 77%) as a white powder. MS (ESI): mass calcd. for $C_{14}H_{14}FNO_2$, 247.1; m/z found, 248.2 $[M+H]^+$.

Step C: 3-(Chloromethyl)-5-(4-fluoro-3-methylphenyl)-2-methoxypyridine hydrochloride To a solution of [5-(4-fluoro-3-methyl-phenyl)-2-methoxy-3-pyridyl]methanol (170 mg, 0.688 mmol) in dichloromethane (2 mL) was added thionyl chloride (150 μL, 2.07 mmol) dropwise at 0° C. and the reaction mixture was stirred at room temperature for 2 h. The reaction mixture was evaporated and the residue was triturated with diethyl ether (1 mL) to afford the title compound (160 mg, 0.529 mmol, 76%) as a white powder. MS (ESI): mass calcd. for $C_{14}H_{13}ClFNO$, 265.1; m/z found, 266.1 $[M+H]^+$. $^1H$ NMR (300 MHz, DMSO-$d_6$) δ 8.50-8.43 (m, 1H), 8.17-8.10 (m, 1H), 7.67-7.57 (m, 1H), 7.56-7.46 (m, 1H), 7.23 (t, J=9.1 Hz, 1H), 4.82-4.70 (m, 2H), 3.97 (s, 3H), 2.34-2.27 (m, 3H).

Intermediate 19: 3-(Chloromethyl-d$_2$)-5-(3-(difluoromethyl)-4-fluorophenyl)-2-methylpyridine DCl Salt

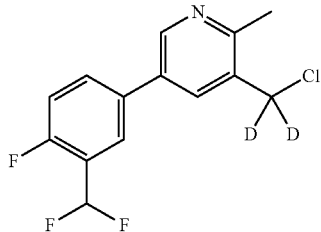 [SMILES: [2H]C([2H])(Cl)c1cc(-c2ccc(F)c(C(F)F)c2)cnc1C]

Step A: Ethyl 5-[3-(difluoromethyl)-4-fluoro-phenyl]-2-methyl-pyridine-3-carboxylate To a solution of ethyl 5-bromo-2-methyl-pyridine-3-carboxylate (3.00 g, 12.3 mmol) in degassed acetonitrile (87 mL) and water (13.5 mL) was added 2-[3-(difluoromethyl)-4-fluoro-phenyl]-4,4,5,5-tetramethyl-1,3,2-dioxaborolane (3.51 g, 12.9 mmol), [1,1'-bis(diphenylphosphino)ferrocene]dichloropalladium(II) (1.17 g, 1.60 mmol) and sodium carbonate (3.91 g, 36.9 mmol). The reaction mixture was stirred at 80° C. for 1 h under argon and evaporated. The residue was taken up in water (100 mL) and extracted with ethyl acetate (3×100 mL). The combined organic layers were dried over sodium sulfate, filtered and evaporated. The residue was purified by gradient silica gel column chromatography, eluting with n-heptane:ethyl acetate (1:0→0:1), to give the title compound (3.29 g, 10.6 mmol, 87%) as an off-white powder. MS (ESI): mass calcd. for $C_{16}H_{14}F_3NO_2$, 309.1; m/z found, 310.1 [M+H]$^+$.

Step B: Dideuterio-[5-[3-(difluoromethyl)-4-fluorophenyl]-2-methyl-3-pyridyl]methanol To a solution of ethyl 5-[3-(difluoromethyl)-4-fluorophenyl]-2-methyl-pyridine-3-carboxylate (1 g, 3.23 mmol) in tetrahydrofuran-d$_8$ (18 mL) was added lithium aluminum deuteride (143 mg, 3.41 mmol) in portions at −30° C. under argon. The reaction mixture was stirred at −30° C. for 30 min under argon. The reaction mixture was quenched with deuterium oxide (1 mL) at −70° C., allowed to warm to room temperature and stirred for 21 h. The mixture was diluted with freshly distilled dichloromethane (20 mL) and filtered through a pad of Celite®. The Celite® pad was washed with freshly distilled dichloromethane (4×10 mL). The combined filtrates were evaporated and the residue was triturated with diethyl ether (15 mL) to afford the title compound (793 mg, 2.93 mmol, 91%) as a pale yellow powder. MS (ESI): mass calcd. for $C_{14}H_{10}D_2F_3NO$, 269.1; m/z found, 270.3 [M+H]$^+$.

Step C: 3-(Chloromethyl-d$_2$)-5-(3-(difluoromethyl)-4-fluorophenyl)-2-methylpyridine To a suspension dideuterio-[5-[3-(difluoromethyl)-4-fluoro-phenyl]-2-methyl-3-pyridyl]methanol (27 mg, 0.099 mmol) in DCM (0.7 mL) was added thionyl chloride (2 μL, 0.3 mmol) at 0° C. The reaction mixture was stirred at room temperature for 2 h and then concentrated. The residue was triturated with Et$_2$O (1 mL) to afford the title compound (27 mg, 0.094 mmol, 83%). MS (ESI): mass calcd. for $C_{14}H_9D_2ClF_3N$, 287.1; m/z found, 288.2 [M+H]$^+$.

Intermediate 20: 3-(Chloromethyl)-5-(5-(difluoromethyl)thiophen-2-yl)-2-methylpyridine hydrochloride

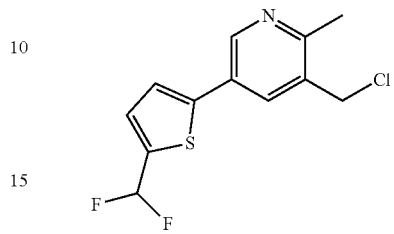

Step A: Ethyl 5-[5-(difluoromethyl)-2-thienyl]-2-methyl-pyridine-3-carboxylate To a solution of 2-bromo-5-(difluoromethyl)thiophene (Intermediate 9, 2.48 g, 11.6 mmol) in degassed 1,4-dioxane (181 mL) and water (54.6 mL) was added (5-ethoxycarbonyl-6-methyl-3-pyridyl)boronic acid (Intermediate 10, 3.41 g, 16.3 mmol), potassium fluoride (2.03 g, 34.9 mmol) and tetrakis(triphenylphosphine)palladium(0) (942 mg, 0.815 mmol). The reaction mixture was stirred at 80° C. for 21 h under argon. The reaction was concentrated to remove 1,4-dioxane, diluted with water (30 mL) and extracted with dichloromethane (3×100 mL). The combined organic layers were dried over sodium sulfate, filtered and evaporated. Purification via silica gel column chromatography (10-20% EtOAc in n-heptane) gave the title compound (1.80 g, 6.05 mmol, 52%) as a pale yellow powder. MS (ESI): mass calcd. for $C_{14}H_{13}F_2NO_2S$, 297.1; m/z found, 298.1 [M+H]$^+$.

Step B: [5-[5-(Difluoromethyl)-2-thienyl]-2-methyl-3-pyridyl]methanol

To a solution of ethyl 5-[5-(difluoromethyl)-2-thienyl]-2-methyl-pyridine-3-carboxylate (1.80 g, 6.05 mmol) in THF (38 mL) was added lithium aluminum hydride (6.35 mL, 6.35 mmol, 1 M in THF) dropwise at −78° C. under argon. The reaction mixture was allowed to warm to −40° C. and stirred for 2 h under argon. The reaction mixture was quenched carefully with ethyl acetate (200 mL) at −78° C. The organic layer was washed with saturated sodium bicarbonate (1×50 mL), water (1×50 mL), dried over MgSO$_4$, filtered, and evaporated. The residue was triturated with diethyl ether (8 mL) to afford a first crop of the title compound (1.04 g, 4.07 mmol, 67%) as an orange powder. The diethyl ether was evaporated to afford a second crop of the title compound (508 mg, 1.99 mmol, 33%) as an orange powder. MS (ESI): mass calcd. for $C_{12}H_{11}F_2NOS$, 255.1; m/z found, 256.1 [M+H]$^+$. $^1$H NMR (300 MHz, DMSO-d$_6$) δ 8.69 (d, J=2.4 Hz, 1H), 7.97 (d, J=2.3 Hz, 1H), 7.65-7.56 (m, 1H), 7.56-7.48 (m, 1H), 7.34 (t, J=55.2 Hz, 1H), 5.39 (t, J=5.4 Hz, 1H), 4.57 (d, J=5.4 Hz, 2H), 2.44 (s, 3H).

Step C: 3-(Chloromethyl)-5-(5-(difluoromethyl)thiophen-2-yl)-2-methylpyridine hydrochloride Prepared analogous to 3-(Chloromethyl)-5-(3-(difluoromethoxy)-4-fluorophenyl)-2-methylpyridine hydrochloride (Intermediate 17, Step C), using [5-[5-(difluoromethyl)-

2-thienyl]-2-methyl-3-pyridyl]methanol. ¹H NMR (300 MHz, DMSO-d₆) δ 10.08-9.09 (m, 1H), 8.97 (d, J=2.3 Hz, 1H), 8.50 (d, J=2.3 Hz, 1H), 7.80-7.74 (m, 1H), 7.63-7.54 (m, 1H), 7.38 (t, J=55.0 Hz, 1H), 4.96 (s, 2H), 2.71 (s, 3H).

Intermediate 21: 3-(Chloromethyl)-5-(3-(difluoromethoxy)-4-fluorophenyl)-2-methoxypyridine hydrochloride

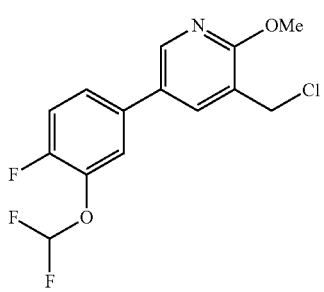 [SMILES: COc1ncc(-c2ccc(F)c(OC(F)F)c2)cc1CCl]

Step A: Methyl 5-[3-(difluoromethoxy)-4-fluoro-phenyl]-2-methoxy-pyridine-3-carboxylate A mixture of methyl 2-methoxy-5-(4,4,5,5-tetramethyl-1,3,2-dioxaborolan-2-yl)pyridine-3-carboxylate (2.5 g, 8.53 mmol) (synthesized by the method described in U.S. Pat. No. 10,150,747 (Yeung et al; Dec. 11, 2018)), 4-bromo-2-(difluoromethoxy)-1-fluorobenzene (2.47 g, 10.2 mmol), [1,1'-bis(diphenylphosphino)ferrocene]dichloropalladium (624 mg, 0.853 mmol) and potassium carbonate (2.36 g, 17.1 mmol) in 1,4-dioxane (33 mL) and water (3.3 mL) was stirred at 80° C. for 4 h under argon. The reaction mixture was evaporated and the residue was purified by silica gel column chromatography, eluting with n-heptane:ethyl acetate (4:1). The residue was triturated with diisopropyl ether (10 mL) to give the title compound (1.77 g, 5.41 mmol, 63%) as an off-white powder. MS (ESI): mass calcd. for C₁₅H₁₂F₃NO₄, 327.1; m/z found, 328.2 [M+H]⁺.

Step B: [5-[3-(Difluoromethoxy)-4-fluoro-phenyl]-2-methoxy-3-pyridyl]methanol

To a solution of methyl 5-[3-(difluoromethoxy)-4-fluoro-phenyl]-2-methoxy-pyridine-3-carboxylate (1.77 g, 5.41 mmol) in tetrahydrofuran (17.7 mL) and methanol (656 μL, 16.2 mmol) was added sodium borohydride (614 mg, 16.2 mmol) in small portions and the reaction mixture was stirred at 40° C. for 13 h, then at room temperature for 36 h. The mixture was cooled to 5° C. and carefully diluted with water (20 mL), then stirred at room temperature for 30 min. The tetrahydrofuran was evaporated from the mixture and the aqueous layer was extracted with ethyl acetate (3×20 mL). The combined organic layers were washed with water (1×15 mL), dried over MgSO₄, filtered and evaporated. The residue was triturated with diisopropyl ether (6 mL) to give a first crop of the title compound (1.04 g, 3.47 mmol, 64%) as a white powder. The trituration solvent was evaporated to give a second crop of the title compound (430 mg, 1.437 mmol, 27%) as a white powder. MS (ESI): mass calcd. for C₁₄H₁₂F₃NO₃, 299.1; m/z found, 300.2 [M+H]⁺.

Step C: 3-(Chloromethyl)-5-[3-(difluoromethoxy)-4-fluoro-phenyl]-2-methoxy-pyridine hydrochloride To a solution of [5-[3-(difluoromethoxy)-4-fluoro-phenyl]-2-methoxy-3-pyridyl]methanol (250 mg, 0.835 mmol) in dichloromethane (3 mL) was added thionyl chloride (175 μL, 2.41 mmol) dropwise at 0° C. and the reaction mixture was stirred at room temperature for 2 h. The reaction mixture was evaporated and the residue was triturated with diethyl ether (1 mL) to afford the title compound (227 mg, 0.641 mmol, 76%) as a white powder. ¹H NMR (300 MHz, DMSO-d₆) δ 8.52 (d, J=2.5 Hz, 1H), 8.20 (d, J=2.5 Hz, 1H), 7.73-7.66 (m, 1H), 7.65-7.57 (m, 1H), 7.56-7.47 (m, 1H), 7.35 (t, J=73.3 Hz, 1H), 4.76 (s, 2H), 3.98 (s, 3H).

Intermediate 22: 3-(Chloromethyl)-2-(difluoromethoxy)-5-[3-(difluoromethyl)-4-fluoro-phenyl]pyridine hydrochloride Salt

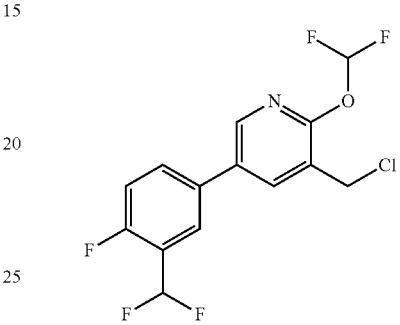

Step A: Methyl 5-bromo-2-(difluoromethoxy)pyridine-3-carboxylate

A mixture of methyl-5-bromo-2-hydroxynicotinate (50 mg, 0.215 mmol), 2-fluorosulfonyldifluoroacetic acid (46 mg, 0.258 mmol) and sodium bicarbonate (36 mg, 0.429 mmol) in acetonitrile (1 mL) was stirred at room temperature for 76 h. To the reaction mixture was added water (1 mL) and the mixture was evaporated. The residue was purified by gradient silica gel column chromatography, eluting with (14-25% EtOAc in n-heptane), to afford the title compound (16 mg, 0.057 mmol, 27%) as an off-white crystalline solid. MS (ESI): mass calcd. for C₈H₆BrF₂NO₃, 281.0; m/z found, 282.0 [M+H]⁺. ¹H NMR (300 MHz, DMSO-d₆) δ 8.64 (d, J=2.5 Hz, 1H), 8.48 (d, J=2.6 Hz, 1H), 7.73 (t, J=71.8 Hz, 1H), 3.87 (s, 3H).

Step B: Methyl 2-(difluoromethoxy)-5-[3-(difluoromethyl)-4-fluoro-phenyl]pyridine-3-carboxylate A mixture of methyl 5-bromo-2-(difluoromethoxy)pyridine-3-carboxylate (1.4 g, 4.96 mmol), 2-[3-(difluoromethyl)-4-fluoro-phenyl]-4,4,5,5-tetramethyl-1,3,2-dioxaborolane (1.4 g, 5.15 mmol), [1,1'-bis(diphenylphosphino)ferrocene] dichloropalladium(II) (365 mg, 0.499 mmol) and potassium carbonate (1.38 g, 9.99 mmol) in 1,4-dioxane (20 mL) and water (2 mL) was stirred at 80° C. for 4 h under argon. The reaction mixture was evaporated and the residue was purified by gradient silica gel column chromatography, eluting with (0-20% EtOAc in n-heptane), to give the title compound (1.20 g, 3.46 mmol, 69%) as a white solid. MS (ESI): mass calcd. for C₁₅H₁₀F₅NO₃, 347.1; m/z found, 348.1 [M+H]⁺.

Step C: [2-(Difluoromethoxy)-5-[3-(difluoromethyl)-4-fluoro-phenyl]-3-pyridyl]methanol To a solution of methyl 2-(difluoromethoxy)-5-[3-(difluoromethyl)-4-fluoro-phenyl]pyridine-3-carboxylate (1.20 g, 3.46 mmol) in tetrahydrofuran (20 mL) was added lithium borohydride (152 mg, 6.98 mmol) in small portions and the reaction mixture was stirred at room temperature for 3 h. The mixture was cooled to 5° C. and diluted carefully with water (0.5 mL) and stirred at room temperature for 30 min. The tetrahydrofuran was evaporated from the mixture and the aqueous layer was extracted with chloroform (3×4 mL). The combined organic layers were dried over MgSO$_4$, filtered and evaporated. The residue was purified by column chromatography, eluting with (0-20% EtOAc in n-heptane), to give the title compound (770 mg, 2.41 mmol, 69%) as a white powder. MS (ESI): mass calcd. for $C_{14}H_{10}F_5NO_2$, 319.1; m/z found, 320.1 [M+H]$^+$.

Step D: 3-(Chloromethyl)-2-(difluoromethoxy)-5-[3-(difluoromethyl)-4-fluoro-phenyl]pyridine hydrochloride Salt To a solution of [2-(difluoromethoxy)-5-[3-(difluoromethyl)-4-fluoro-phenyl]-3-pyridyl]methanol (770 mg, 2.41 mmol) in dichloromethane (10 mL) was added thionyl chloride (2.6 mL, 35.8 mmol) dropwise at 0° C. The reaction mixture was stirred at room temperature for 20 h and evaporated to afford the title compound (800 mg, 2.37 mmol, 98%) as a yellow oil. MS (ESI): mass calcd. for $C_{14}H_9ClF_5NO$, 337.0 m/z found, 338.0 [M+H]$^+$. $^1$H NMR (300 MHz, DMSO-d$_6$) δ 8.61 (d, J=2.5 Hz, 1H), 8.44 (d, J=2.5 Hz, 1H), 8.03-7.92 (m, 2H), 7.83 (t, J=71.9 Hz, 1H), 7.60-7.48 (m, 1H), 7.27 (t, J=54.1 Hz, 1H), 4.81 (s, 2H).

Intermediate 23:3-[[2-Methoxy-5-(4,4,5,5-tetramethyl-1,3,2-dioxaborolan-2-yl)-3-pyridyl]methyl]oxazolidin-2-one and [6-methoxy-5-[(2-oxooxazolidin-3-yl)methyl]-3-pyridyl]boronic Acid

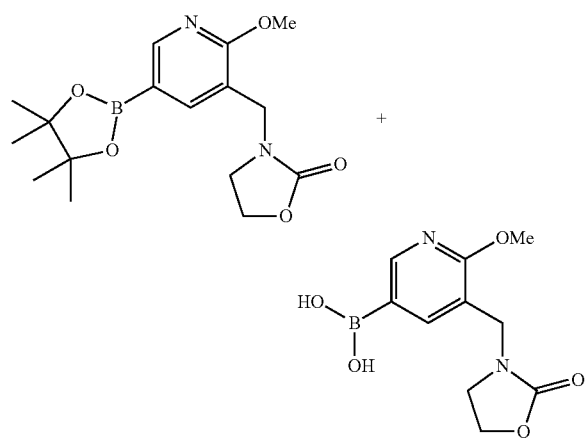

Step A: 3-[(5-Bromo-2-methoxy-3-pyridyl)methyl]oxazolidin-2-one

To a solution of 2-oxazolidinone (2.21 g, 25.4 mmol) in dry N,N-dimethylformamide (700 μL) was added cesium carbonate (13.8 g, 42.3 mmol) under argon and the mixture was stirred at room temperature for 10 min. To the mixture was added 5-bromo-3-(chloromethyl)-2-methoxy-pyridine (Intermediate 13, 5.00 g, 21.1 mmol) and the reaction mixture was stirred at room temperature for 18 h. Then, water (250 mL) was added and the mixture was extracted with ethyl acetate (3×100 mL). The combined organic layers were dried over MgSO$_4$, filtered and evaporated. The residue was triturated with diisopropyl ether (4 mL) to afford the title compound (5.09 g, 17.7 mmol, 84%) as a pale yellow powder. MS (ESI): mass calcd. for $C_{10}H_{11}BrN_2O_3$, 286.0; m/z found, 287.0 [M+H]$^+$. $^1$H NMR (300 MHz, DMSO-d$_6$) δ 8.24 (d, J=2.5 Hz, 1H), 7.79 (d, J=2.5 Hz, 1H), 4.37-4.25 (m, 2H), 4.28 (s, 2H), 3.89 (s, 3H), 3.56-3.45 (m, 2H).

Step B: 3-[[2-Methoxy-5-(4,4,5,5-tetramethyl-1,3,2-dioxaborolan-2-yl)-3-pyridyl]methyl]oxazolidin-2-one and [6-methoxy-5-[(2-oxooxazolidin-3-yl)methyl]-3-pyridyl]boronic Acid A mixture of 3-[(5-bromo-2-methoxy-3-pyridyl)methyl]oxazolidin-2-one (2.00 g, 6.97 mmol), bis(pinacolato)diboron (3.54 g, 13.9 mmol), [1,1'-bis(diphenylphosphino)ferrocene]dichloropalladium (255 mg, 0.348 mmol), and potassium acetate (1.71 g, 17.4 mmol) in 1,4-dioxane (20 mL) was stirred at 80° C. for 4 h under argon. The reaction mixture was evaporated and the residue was purified by gradient silica gel column chromatography, eluting with (0-67% EtOAc in n-heptane). The residue was triturated with n-hexane (5 mL) to give a first crop of the title compounds (544 mg, 1.63 mmol, 23%) as a pale orange crystalline solid. The collected fractions were evaporated and the residue was triturated with n-hexane (8 mL) to give a second crop of the title compounds (713 mg, 2.13 mmol, 31%) as a pale orange crystalline solid. 3-[[2-Methoxy-5-(4,4,5,5-tetramethyl-1,3,2-dioxaborolan-2-yl)-3-pyridyl]methyl]oxazolidin-2-one: MS (ESI): mass calcd. for $C_{17}H_{23}BN_2O_5$, 334.2; m/z found, 335.2 [M+H]$^+$, and [6-methoxy-5-[(2-oxooxazolidin-3-yl)methyl]-3-pyridyl]boronic acid: MS (ESI): mass calcd. for $C_{10}H_{13}BN_2O_5$, 252.1; m/z found, 253.1 [M+H]$^+$ Intermediate 24: 3-(Chloromethyl)-2-(difluoromethyl)-5-(3-(difluoromethyl)-4-fluorophenyl)pyridine hydrochloride

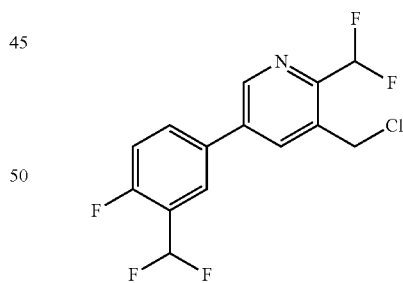

Step A: Ethyl 5-bromo-2-formylnicotinate

A mixture of ethyl 5-bromo-2-methylnicotinate (25 g, 102 mmol) and SeO$_2$ (14.8 g, 133 mmol) in 1,4-dioxane (64 mL) was heated to 180° C. for 20 min in a microwave reactor. The completed reaction was concentrated under reduced pressure and subjected directly to purification. Purification via silica gel chromatography (0-1% MeOH in DCM) yielded the title compound (20.75 g, 80.4 mmol, 79%). MS (ESI): mass calcd. for $C_9H_3BrNO_3$, 257.0; m/z found, 258.0 [M+H].

Step B: Ethyl 5-bromo-2-(difluoromethyl)nicotinate

To a solution of ethyl 5-bromo-2-formylnicotinate (3.99 g, 15.46 mmol) in DCM (38 mL) was added DAST (3.06 mL, 23.16 mmol) dropwise at 0° C. under argon. The reaction mixture was allowed to warm to room temperature and stirred overnight. The completed reaction was cooled to 0° C. and carefully quenched with 2 M NaOH (10 mL), and then diluted with DCM (200 mL). The reaction was washed with water (3×60 mL). The organic layers were combined, dried over MgSO$_4$, filtered, and concentrated under reduced pressure. Purification via silica gel chromatography (100% DCM) afforded the title compound (3.48 g, 13.6 mmol, 80%). MS (ESI): mass calcd. for C$_9$H$_3$BrF$_2$NO$_2$, 279.0; m/z found, 280.0 [M+H].

Step C: Ethyl 2-(difluoromethyl)-5-(3-(difluoromethyl)-4-fluorophenyl)nicotinate A solution of ethyl 5-bromo-2-(difluoromethyl)nicotinate (1.96 g, 6.998 mmol) in degassed 1,4-dioxane (35 mL) and water (12 mL) was charged with 2-(3-(difluoromethyl)-4-fluorophenyl)-4,4,5,5-tetramethyl-1,3,2-dioxaborolane (Intermediate 39) (2.09 g, 7.682 mmol), KF (1.22 g, 20.999 mmol) and Pd(PPh$_3$)$_4$ (404 mg, 0.35 mmol). The resulting mixture was stirred at 80° C. for 17 h under argon. The completed reaction was concentrated under reduced pressure to remove 1,4-dioxanes. The resulting concentrate was diluted with water (20 mL) and extracted into EtOAc (3×50 mL). The combined organics were dried over Na$_2$SO$_4$, filtered and concentrated under reduced pressure. Purification via silica gel chromatography (10-80% EtOAc in n-heptanes) afforded the title compound (1.38 g, 3.996 mmol, 76%). MS (ESI): mass calcd. for C$_{16}$H$_{12}$F$_5$NO$_2$, 345.1; m/z found, 346.1 [M+H].

Step D: (2-(Difluoromethyl)-5-(3-(difluoromethyl)-4-fluorophenyl)pyridin-3-yl)methanol A solution of ethyl 2-(difluoromethyl)-5-(3-(difluoromethyl)-4-fluorophenyl)nicotinate (1.83 g, 5.3 mmol) in freshly distilled THF (32 mL) was charged with LAH (5.57 mL, 5.57 mmol, 1 M in THF) dropwise at −78° C. under argon. The reaction mixture stirred for 2 hours under argon warming to −40° C. The reaction mixture was quenched carefully with ethyl acetate (200 mL) at −78° C. The organic layer was washed with a saturated aqueous solution of NaHCO$_3$ (1×50 mL), water (1×50 mL), dried over MgSO$_4$, filtered, and concentrated under reduced pressure. Purification via silica gel chromatography (10-80% EtOAc in n-heptanes) afforded the title compound (0.90 g, 2.97 mmol, 55%). MS (ESI): mass calcd. for C$_{14}$H$_{10}$F$_5$NO, 303.1; m/z found, 304.1 [M+H].

Step E: 3-(Chloromethyl)-2-(difluoromethyl)-5-(3-(difluoromethyl)-4-fluorophenyl)pyridine hydrochloride Salt A solution of (2-(difluoromethyl)-5-(3-(difluoromethyl)-4-fluorophenyl)pyridin-3-yl)methanol (450 mg, 1.48 mmol) in DCM (5 mL) was cooled to 0° C. and thionyl chloride (323 μL, 4.45 mmol) was added dropwise. The reaction mixture was stirred for 2 h at room temperature. The completed reaction mixture was concentrated under reduced pressure to yield the title compound, which was carried forward without further purification (0.411 g, 1.28 mmol, 90%). MS (ESI): mass calcd. for C$_{14}$H$_9$ClF$_5$N, 321.0; m/z found, 322.0 [M+H].

Intermediate 25: 3-(Chloromethyl)-2-(1,1-difluoroethyl)-5-(3-(difluoromethyl)-4-fluorophenyl)pyridine hydrochloride

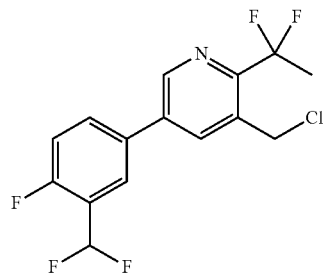 [SMILES: CC(F)(F)c1ncc(-c2ccc(F)c(C(F)F)c2)cc1CCl]

Step A: 1-(3,5-Dibromopyridin-2-yl)ethan-1-one

To a solution of 3,5-dibromopicolinonitrile (5.2 g, 19.9 mmol) in toluene (60 mL) was added methylmagnesium bromide (12 mL, 36 mmol, 3.0 M in diethyl ether) at −10° C. under argon. The reaction mixture was stirred at −10° C. for 1 h. HCl (12.7 mL, 147 mmol, 11.6 M) in water (34 mL) was added and the mixture was stirred at room temperature for 1 h. To the mixture was added 10% sodium bicarbonate (25 mL) and the mixture was stirred for 30 minutes. The organic layer was washed with 10% sodium sulfate (1×25 mL), water (1×25 mL) and evaporated. The residue was taken up in toluene (2×20 mL), evaporated, taken up in methanol (2×20 mL) and evaporated to give the title compound (5.49 g, 20.0 mmol, 99%) as a yellow crystalline solid. MS (ESI): mass calcd. for C$_7$H$_5$Br$_2$NO, 276.9; m/z found, 279.9 [M+H]$^+$.

Step B: 1-(3-Bromo-5-(3-(difluoromethyl)-4-fluorophenyl)pyridin-2-yl)ethan-1-one To a solution of 1-(3,5-dibromopyridin-2-yl)ethan-1-one (6.09 g, 21.8 mmol) in degassed acetonitrile (158 mL) and water (24.9 mL) was added 2-[3-(difluoromethyl)-4-fluorophenyl]-4,4,5,5-tetramethyl-1,3,2-dioxaborolane (6.24 g, 22.9 mmol), [1,1'-bis(diphenylphosphino)ferrocene]dichloropalladium(II) (2.08 g, 2.84 mmol) and sodium carbonate (6.94 g, 65.5 mmol). The reaction mixture was stirred at 80° C. for 2 h under argon. The reaction mixture was evaporated and the residue was taken up in ethyl acetate (60 mL). The organic layer was washed with water (1×40 mL) and the aqueous layer was extracted with ethyl acetate (2×60 mL). The combined organic layers were dried over sodium sulfate, filtered and evaporated. Purification via silica gel chromatography (0-10% EtOAc in n-heptanes) afforded the isomer, 1-[5-bromo-3-[3-(difluoromethyl)-4-fluoro-phenyl]-2-pyridyl]ethanone (1.57 g, 4.56 mmol, 21%) as a white powder, and the desired title compound (1.92 g, 5.58 mmol, 26%) as a white powder. MS (ESI): mass calcd. for C$_{14}$H$_9$BrF$_3$NO, 343.0; m/z found, 344.0 [M+H]$^+$. $^1$H NMR (500 MHz, DMSO-d$_6$) δ 9.03 (d, J=2.0 Hz, 1H), 8.59 (d, J=2.0 Hz, 1H), 8.16-8.09 (m, 2H), 7.61-7.55 (m, 1H), 7.25 (t, J=54.0 Hz, 1H), 2.66 (s, 3H).

Step C: 3-Bromo-2-(1,1-difluoroethyl)-5-(3-(difluoromethyl)-4-fluorophenyl)pyridine To 1-(3-bromo-5-(3-(difluoromethyl)-4-fluorophenyl)pyridin-2-yl)ethan-1-one (1.11 g, 3.23 mmol) was added DAST (6.8 mL, 51.5 mmol) at 0° C. under argon. The reaction mixture was allowed to warm to room temperature and stirred for 17 h. Complete conversion was not observed and additional DAST (6.8 mL, 51.5 mmol) was added and the reaction was stirred at room temperature for 24 h. Additional DAST (6.8 mL, 51.5 mmol) was added and the reaction was stirred at room temperature for 72 h. The reaction mixture was quenched carefully with the dropwise addition of 2 M NaOH (50 mL) at 0° C. The crude reaction mixture was extracted with dichloromethane (1×50 mL). The organic layer was washed with water (3×70 mL), dried over sodium sulfate, filtered, and evaporated. Purification via silica gel chromatography (0-10% EtOAc in n-heptanes) gave the title compound (978 mg, 2.67 mmol, 83%) as a light brown powder. MS (ESI): mass calcd. for $CH_9BrF_5N$, 365.0; m/z found, 366.0 [M+H]+.

Step D: 2-(1,1-Difluoroethyl)-5-(3-(difluoromethyl)-4-fluorophenyl)-3-vinylpyridine To a mixture of 3-bromo-2-(1,1-difluoroethyl)-5-(3-(difluoromethyl)-4-fluorophenyl)pyridine (978 mg, 2.67 mmol), potassium vinyltrifluoroborate (537 mg, 4.01 mmol) and [1,1'-bis(diphenylphosphino)ferrocene]dichloropalladium(II) (195 mg, 0.266 mmol) in degassed 1,4-dioxane (9.8 mL) was added triethylamine (1.86 mL, 13.3 mmol) at room temperature. The reaction mixture was stirred at 100° C. for 18 h under argon. The reaction mixture was evaporated and the residue was taken up in ethyl acetate (30 mL). The organic layer was washed with half saturated brine (1×30 mL). The aqueous layer was extracted with ethyl acetate (3×30 mL) and the combined organic layers were dried over sodium sulfate, filtered and evaporated. Purification via silica gel chromatography (0-10% EtOAc in n-heptanes) gave the title compound (606 mg, 1.93 mmol, 72%) as a pale yellow powder. MS (ESI): mass calcd. for $C_{16}H_{12}F_5N$, 313.1; m/z found, 314.1 [M+H]+.

Step E: 2-(1,1-Difluoroethyl)-5-(3-(difluoromethyl)-4-fluorophenyl)nicotinaldehyde To a suspension of 2-(1,1-difluoroethyl)-5-(3-(difluoromethyl)-4-fluorophenyl)-3-vinylpyridine (606 mg, 1.93 mmol) and sodium periodate (2.48 g, 11.6 mmol) in 1,4-dioxane (97.2 mL) and water (48.1 mL) was added osmium tetroxide (25 mg, 0.0983 mmol). The reaction mixture was stirred at room temperature for 22 h and concentrated to 48 mL. The aqueous layer was extracted with ethyl acetate (3×80 mL). The combined organic layers were dried over sodium sulfate, filtered and evaporated. Purification via silica gel chromatography (0-10% EtOAc in n-heptanes) gave the title compound (557 mg, 1.77 mmol, 92%) as a white powder. MS (ESI): mass calcd. for $C_{15}H_{10}F_5NO$, 315.1; m/z found, 316.1 [M+H]+.

Step F: (2-(1,1-Difluoroethyl)-5-(3-(difluoromethyl)-4-fluorophenyl)pyridin-3-yl)methanol To a solution of 2-(1,1-difluoroethyl)-5-(3-(difluoromethyl)-4-fluorophenyl) nicotinaldehyde (327 mg, 1.04 mmol) in methanol (3.5 mL) was added lithium borohydride (19 mg, 0.872 mmol) at 0° C. and the reaction mixture was stirred at 0° C. for 30 min. The reaction was quenched with water (407 µL) and evaporated. The residue was taken up in water (1 mL) and extracted with ethyl acetate (3×2 mL). The combined organic layers were dried over sodium sulfate, filtered and evaporated. Purification via silica gel chromatography (0-10% EtOAc in n-heptanes) gave the title compound (275 mg, 0.867 mmol, 99%) as a pale yellow powder. MS (ESI): mass calcd. for $C_{15}H_{12}F_5NO$, 317.1; m/z found, 318.1 [M+H]+.

Step G: 3-(Chloromethyl)-2-(1,1-difluoroethyl)-5-(3-(difluoromethyl)-4-fluorophenyl)pyridine hydrochloride To a solution of (2-(1,1-difluoroethyl)-5-(3-(difluoromethyl)-4-fluorophenyl)pyridin-3-yl)methanol (275 mg, 0.867 mmol) in dichloromethane (2.75 mL) was added thionyl chloride (377 µL, 5.2 mmol) dropwise at 0° C. The reaction mixture was stirred at room temperature for 2 h and evaporated to afford the title compound (289 mg, 0.777 mmol, 90%) as a yellow oil. MS (ESI): mass calcd. for $C_{15}H_{11}ClF_5N$, 335.1 m/z found, 336.1 [M+H]+. 1H NMR (300 MHz, DMSO-$d_6$) δ 9.02-8.92 (m, 1H), 8.51-8.43 (m, 1H), 8.14-7.99 (m, 2H), 7.65-7.51 (m, 1H), 7.29 (t, J=54.1 Hz, 1H), 5.01 (s, 2H), 2.12 (t, J=19.6 Hz, 3H).

Intermediate 26: 3-(Chloromethyl)-2-(1,1-difluoroethyl)-5-[3-(difluoromethoxy)-4-fluoro-phenyl]pyridine hydrochloride

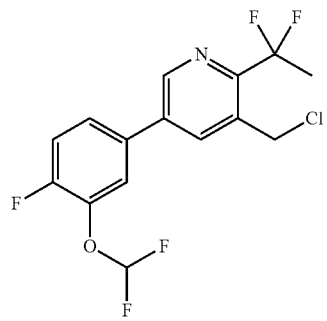 [SMILES: CC(F)(F)c1ncc(-c2ccc(F)c(OC(F)F)c2)cc1CCl]

Step A: 1-(3-Bromo-5-(3-(difluoromethoxy)-4-fluorophenyl)pyridin-2-yl)ethan-1-one To a solution of 1-(3,5-dibromo-2-pyridyl)ethanone (5.57 g, 20.0 mmol) in degassed acetonitrile (145 mL) and water (23 mL) was added 2-[3-(difluoromethoxy)-4-fluoro-phenyl]-4,4,5,5-tetramethyl-1,3,2-dioxaborolane (6.04 g, 21.0 mmol), [1,1'-bis(diphenylphosphino)ferrocene]dichloropalladium(II) (Pd(dppf)Cl$_2$) (1.90 g, 2.60 mmol) and sodium carbonate (6.35 g, 59.9 mmol). The reaction mixture was stirred at 80° C. for 2 h under argon. The reaction mixture was evaporated, taken up in water (65 mL) and extracted with ethyl acetate (3×80 mL). The combined organic layers were dried over sodium sulfate, filtered and evaporated. Purification via silica gel chromatography (0-10% EtOAc in n-heptanes) gave the title compound (2.62 g, 7.27 mmol, 36%) as a white powder. MS (ESI): mass calcd. for $C_{14}H_9BrF_3NO_2$, 359.0; m/z found, 360.0 [M+H]+.

Step B: 3-Bromo-2-(1,1-difluoroethyl)-5-(3-(difluoromethoxy)-4-fluorophenyl)pyridine To 1-(3-bromo-5-(3-(difluoromethoxy)-4-fluorophenyl)pyridin-2-yl)ethan-1-one (2.62 g, 7.27 mmol) was added DAST® (15.4 mL, 117 mmol) at 0° C. under argon. The reaction mixture was allowed to warm to room temperature and stirred for 46 h. The reaction mixture was quenched carefully by the dropwise addition of 2 M NaOH (70 mL) at 0° C. and diluted with dichloromethane (70 mL). The organic layer was washed with water (3×50 mL), dried over MgSO$_4$, filtered, and evaporated. Purification via silica gel chromatography (0-10% EtOAc in n-heptanes) gave the title compound (2.03 g, 5.31 mmol, 73%) as a yellow powder. MS (ESI): mass calcd. for $C_{14}H_9BrF_5NO$, 381.0; m/z found, 382.0 [M+H]$^+$.

Step C: 3-(((tert-Butyldimethylsilyl)oxy)methyl)-2-(1,1-difluoroethyl)-5-(3-(difluoromethoxy)-4-fluorophenyl)pyridine To a solution of 3-bromo-2-(1,1-difluoroethyl)-5-(3-(difluoromethoxy)-4-fluorophenyl)pyridine (1.78 g, 4.66 mmol) in degassed 1,4-dioxane (22 mL) was added tert-butyl-dimethyl-(tributylstannylmethoxy)silane (2.44 g, 5.605 mmol), Pd(Ph$_3$)$_4$ (324 mg, 0.280 mmol) and KF (812 mg, 14 mmol). The reaction mixture was split evenly into two portions and both portions were stirred at 120° C. for 22 h under argon. Complete conversion was not observed and additional tert-butyl-dimethyl-(tributylstannyl-methoxy)silane (400 mg, 0.919 mmol) and Pd(Ph$_3$)$_4$ (324 mg, 0.280 mmol) were added. The reaction mixtures were stirred at 120° C. for 22 h under argon. A third equivalent of tert-butyl-dimethyl-(tributylstannylmethoxy)silane (400 mg, 0.919 mmol) and Pd(Ph$_3$)$_4$ (324 mg, 0.280 mmol) were added, and the reaction mixtures were stirred at 120° C. for 44 h under argon. The combined reaction mixtures were evaporated and the crude residue was subjected to purification. Purification via silica gel chromatography (0-8% EtOAc in n-heptanes) gave the title compound (480 mg) as a colorless oil, which was contaminated with impurities. Fractions from the same column were collected to give a second crop of the title compound (495 mg) as a pale yellow powder, which was contaminated with impurities. The batches of material were used as is in the next step without further purification. MS (ESI): mass calcd. for $C_{21}H_{26}F_5NO_2Si$, 447.2; m/z found, 448.2 [M+H]$^+$.

Step D: (2-(1,1-Difluoroethyl)-5-(3-(difluoromethoxy)-4-fluorophenyl)pyridin-3-yl)methanol To a solution of 3-(((tert-butyldimethylsilyl)oxy)methyl)-2-(1,1-difluoroethyl)-5-(3-(difluoromethoxy)-4-fluorophenyl)pyridine (900 mg, 2.01 mmol) in dichloromethane (40 mL) was added HCl (5 mL, 23.5 mmol, 4.7 M in 1,4-dioxane). The reaction mixture was stirred at room temperature for 18 h. The reaction mixture was evaporated and the residue was taken up in saturated sodium bicarbonate (50 mL). The aqueous layer was extracted with ethyl acetate (2×50 mL). The combined organic layers were dried over sodium sulfate, filtered and evaporated. Purification via silica gel chromatography (0-4% EtOAc in n-heptanes) gave the title compound (489 mg, 1.47 mmol, 73%) as a yellow oil. MS (ESI): mass calcd. for $C_{15}H_{12}F_5NO_2$, 333.1; m/z found, 334.1 [M+H]$^+$.

Step E: 3-(Chloromethyl)-2-(1,1-difluoroethyl)-5-[3-(difluoromethoxy)-4-fluoro-phenyl]pyridine hydrochloride To a solution of [2-(1,1-difluoroethyl)-5-[3-(difluoromethoxy)-4-fluoro-phenyl]-3-pyridyl]methanol (489 mg, 1.47 mmol) in dichloromethane (7 mL) was added thionyl chloride (2 mL, 27.6 mmol) dropwise at 0° C. The reaction mixture was allowed to warm to room temperature and stirred for 2 h. The reaction mixture was evaporated to afford the title compound (511 mg, 1.32 mmol, 90%) as an off-white powder. MS (ESI): mass calcd. for $C_{15}H_{11}ClF_5NO$, 351.0; m/z found, 352.2 [M+H]*. $^1$H NMR (500 MHz, DMSO-d$_6$) δ 8.96 (d, J=2.1 Hz, 1H), 8.44 (d, J=2.2 Hz, 1H), 7.85 (dd, J=7.6, 2.2 Hz, 1H), 7.80-7.73 (m, 1H), 7.60 (dd, J=10.5, 8.7 Hz, 1H), 7.37 (t, J=73.1 Hz, 1H), 5.00 (s, 2H), 2.11 (t, J=19.6 Hz, 3H).

Intermediate 27: 3-(Chloromethyl)-5-(5-chlorothiophen-2-yl)-2-methylpyridine hydrochloride

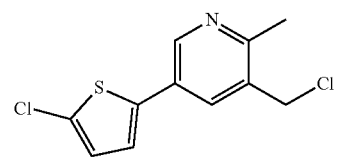

Prepared analogous to 3-(chloromethyl)-5-(3-(difluoromethoxy)-4-fluorophenyl)-2-methylpyridine hydrochloride (Intermediate 17), using (5-chlorothiophen-2-yl)boronic acid. MS (ESI): mass calcd. for $C_{11}H_9Cl_2NS$, 257.0; m/z found, 258.0 [M+H]$^+$.

Intermediate 28: 3-(Chloromethyl)-2-methyl-5-(5-(trifluoromethyl)thiophen-2-yl)pyridine hydrochloride

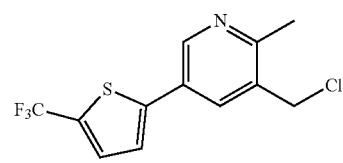

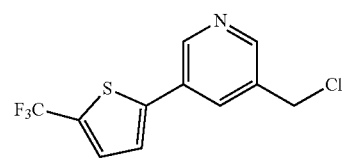

Prepared analogous to 3-(chloromethyl)-5-(3-(difluoromethoxy)-4-fluorophenyl)-2-methylpyridine hydrochloride (Intermediate 17), using 2-bromo-5-trifluoromethylthiophene. MS (ESI): mass calcd. for $C_{12}H_9ClF_3NS$, 291.0; m/z found, 292.0 [M+H]$^+$.

Intermediate 29:3-(Chloromethyl)-5-(3-(difluoromethoxy)-4-fluorophenyl)-2-(difluoromethyl)pyridine hydrochloride

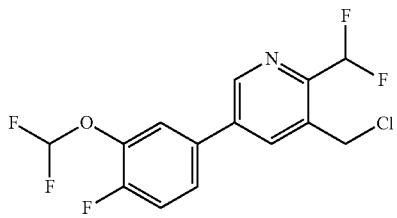 [SMILES: Fc1ccc(-c2cnc(C(F)F)c(CCl)c2)cc1OC(F)F]

Prepared analogous to 3-(chloromethyl)-2-(difluoromethyl)-5-(3-(difluoromethyl)-4-fluorophenyl)pyridine hydrochloride salt (Intermediate 24), using 2-(3-(difluoromethoxy)-4-fluorophenyl)-4,4,5,5-tetramethyl-1,3,2-dioxaborolane (Intermediate 42) in Step C. MS (ESI): mass calcd. for $C_{14}H_9ClF_5NO$, 337.0; m/z found, 338.0 [M+H].

Intermediate 30: 3-(Chloromethyl)-2-(difluoromethyl)-5-(4-fluoro-3-methylphenyl)pyridine hydrochloride

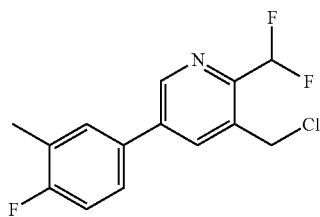 [SMILES: Cc1cc(-c2cnc(C(F)F)c(CCl)c2)ccc1F]

Prepared analogous to 3-(chloromethyl)-2-(difluoromethyl)-5-(3-(difluoromethyl)-4-fluorophenyl)pyridine hydrochloride salt (Intermediate 24), using (4-fluoro-3-methylphenyl)boronic acid in step C. MS (ESI): mass calcd. for $C_{14}H_{11}ClF_3N$, 285.1; m/z found, 286.1 [M+H]. $^1H$ NMR (500 MHz, DMSO-$d_6$) δ 8.96 (d, J=2.1 Hz, 1H), 8.38-8.33 (m, 1H), 7.79-7.73 (m, 1H), 7.69-7.64 (m, 1H), 7.34-7.27 (m, 1H), 7.20 (t, J=53.4 Hz, 1H), 5.00 (s, 2H), 2.35-2.29 (m, 3H).

Intermediate 31: 5-(4-Chloro-3-(difluoromethoxy)phenyl)-3-(chloromethyl)-2-(difluoromethyl)pyridine hydrochloride

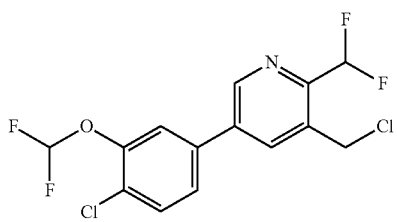 [SMILES: FC(F)Oc1cc(-c2cnc(C(F)F)c(CCl)c2)ccc1Cl]

Prepared analogous to 3-(chloromethyl)-2-(difluoromethyl)-5-(3-(difluoromethyl)-4-fluorophenyl)pyridine hydrochloride salt (Intermediate 24), using 2-(3-(difluoromethoxy)-4-chlorophenyl)-4,4,5,5-tetramethyl-1,3,2-dioxaborolane in step C. MS (ESI): mass calcd. for $C_{14}H_9Cl_2F_4NO$, 353.0; m/z found, 354.0 [M+H]. $^1H$ NMR (500 MHz, DMSO-$d_6$) δ 9.03 (d, J=2.1 Hz, 1H), 8.44 (d, J=2.2 Hz, 1H), 7.85-7.79 (m, 1H), 7.79-7.69 (m, 2H), 7.41 (t, J=73.0 Hz, 1H), 7.19 (t, J=53.4 Hz, 1H), 5.01 (s, 2H).

Intermediate 32: 3-(Chloromethyl)-2-(difluoromethoxy)-5-(3-(difluoromethoxy)-4-fluorophenyl)pyridine hydrochloride

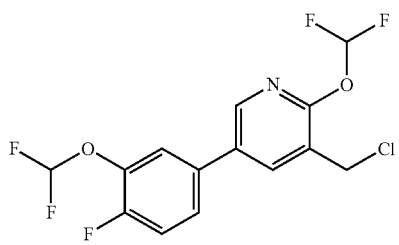 [SMILES: Fc1ccc(-c2cnc(OC(F)F)c(CCl)c2)cc1OC(F)F]

Prepared analogous to 3-(chloromethyl)-2-(difluoromethoxy)-5-[3-(difluoromethyl)-4-fluoro-phenyl]pyridine hydrochloride salt (Intermediate 22), using 2-[3-(difluoromethoxy)-4-fluoro-phenyl]-4,4,5,5-tetramethyl-1,3,2-dioxaborolane in Step B. MS (ESI): mass calcd. for $C_{14}H_9ClF_5NO_2$, 353.0; m/z found, 354.0 [M+H]$^+$.

Intermediate 33: 5-(4-Chloro-3-(difluoromethoxy)phenyl)-3-(chloromethyl)-2-methylpyridine hydrochloride

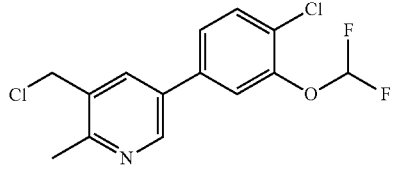 [SMILES: Cc1ncc(-c2ccc(Cl)c(OC(F)F)c2)cc1CCl]

Prepared analogous to 3-(chloromethyl)-5-(3-(difluoromethoxy)-4-fluorophenyl)-2-methylpyridine hydrochloride (Intermediate 17), using 2-(4-chloro-3-(difluoromethoxy)phenyl)-4,4,5,5-tetramethyl-1,3,2-dioxaborolane (Intermediate 43). MS (ESI): mass calcd. for $C_{14}H_{11}Cl_2F_2NO$, 317.0; m/z found, 318.0 [M+H]$^+$.

Intermediate 34:3-(Chloromethyl)-5-(3-(difluoromethyl)-4-fluorophenyl)-2-methylpyridine

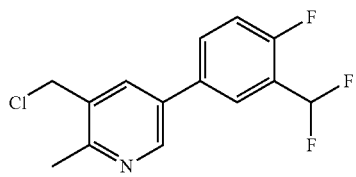 [SMILES: Cc1ncc(-c2ccc(F)c(C(F)F)c2)cc1CCl]

Prepared analogous to 3-(chloromethyl)-5-(3-(difluoromethoxy)-4-fluorophenyl)-2-methylpyridine hydrochloride (Intermediate 17), using 2-(3-(difluoromethyl)-4-fluorophenyl)-4,4,5,5-tetramethyl-1,3,2-dioxaborolane Intermediate 35: 3-(Chloromethyl)-5-(3-(difluoromethyl)-4-fluorophenyl)-2-methoxypyridine hydrochloride

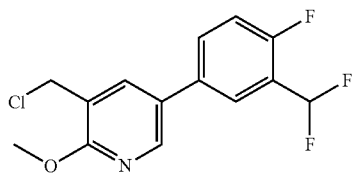 [SMILES: COc1ncc(-c2ccc(F)c(C(F)F)c2)cc1CCl]

Prepared analogous to 3-(chloromethyl)-5-(3-(difluoromethoxy)-4-fluorophenyl)-2-methoxypyridine hydrochloride (Intermediate 21), using 2-(3-(difluoromethyl)-4-fluorophenyl)-4,4,5,5-tetramethyl-1,3,2-dioxaborolane (Intermediate 39) in Step A. MS (ESI): mass calcd. for $C_{14}H_{11}ClF_3NO$, 301.1; m/z found, 302.1 [M+H]$^+$.

Intermediate 36: 3-((5-Bromo-2-methylpyridin-3-yl)methyl-d$_2$)-1,3-oxazinan-2-one

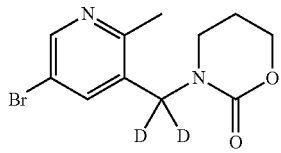

Prepared analogous to Example 1, Step A, using 5-bromo-3-(chloromethyl-d$_2$)-2-methylpyridine (Intermediate 12). $^1$H NMR (500 MHz, Chloroform-d) δ 8.49 (d, J=2.3 Hz, 1H), 7.61 (d, J=2.3 Hz, 1H), 4.43-4.27 (m, 2H), 3.37-3.12 (m, 2H), 2.50 (s, 3H), 2.19-2.01 (m, 2H).

Intermediate 37: 3-[(5-Bromo-2-methyl-3-pyridyl)methyl]-1,3-oxazinan-2-one

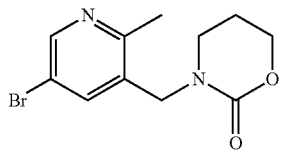 [SMILES: Cc1ncc(Br)cc1CN1CCCOC1=O]

Prepared analogous to Example 1, using 5-bromo-3-(chloromethyl)-2-methylpyridine (Intermediate 15) in Step A. MS (ESI): mass calcd. for $C_{11}H_{111}BrN_2O_2$, 284.0; m/z found, 285.0 [M+H]$^+$.

Intermediate 38: 3-((5-Bromo-2-methylpyridin-3-yl)methyl)oxazolidin-2-one

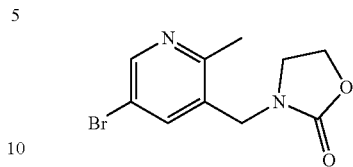

Prepared analogous to Example 22, using 5-bromo-3-(chloromethyl)-2-methylpyridine (Intermediate 15) in Step A. MS (ESI): mass calcd. for $C_{10}H_{11}BrN_2O_2$, 270.0; m/z found, 271.0 [M+H].

Intermediate 39: 2-(3-(Difluoromethyl)-4-fluorophenyl)-4,4,5,5-tetramethyl-1,3,2-dioxaborolane

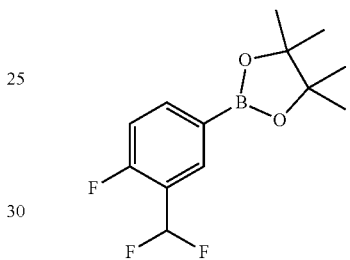

A solution of 4-bromo-2-(difluoromethyl)-1-fluorobenzene (20 g, 88.9 mmol), bis(pinacolato)diboron (24.8 g, 97.8 mmol), potassium acetate (26.2 g, 267 mmol), and [1,1'-bis(diphenylphosphino)ferrocene]-dichloropalladium(II) (3.12 g, 4.44 mmol) in 1,4-dioxane (400 mL) was purged with N$_2$, and the reaction mixture was stirred at 90° C. overnight. Upon completion, the reaction mixture was cooled to room temperature, filtered through Celite®, and rinsed with EtOAc. The filtrate was washed with water and brine. The combined organics were dried with Na$_2$SO$_4$, filtered and concentrated to yield a clear oil (22.1 g, 81.0 mmol, 91%), which solidified upon standing. $^1$H NMR (400 MHz, Chloroform-d) δ 8.12-8.00 (m, 1H), 7.96-7.85 (m, 1H), 7.17-7.06 (m, 1H), 6.88 (t, J=54.9 Hz, 1H), 1.35 (s, 12H). MS (ESI): mass calcd. for $C_{13}H_{16}BF_3O_2$, 272.1; m/z found, 273.0 [M+H]$^+$.

Intermediate 40: 2-(3-(1,1-Difluoroethyl)-4-fluorophenyl)-4,4,5,5-tetramethyl-1,3,2-dioxaborolane

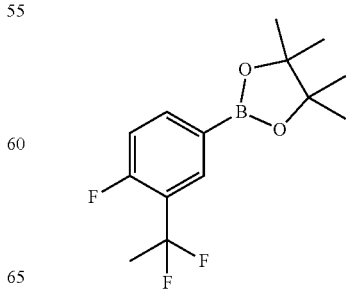

Step A: 4-Bromo-2-(1,1-difluoroethyl)-1-fluorobenzene

In a round bottom flask, a mixture of 1-(5-bromo-2-fluorophenyl)-1-ethanone (2.5 g, 11.5 mmol, 1 equiv) and DAST (1.9 mL, 14.4 mmol, 1.25 equiv) was heated at 60° C. for 16 h. Then a sat. aq. solution of NaHCO$_3$ was slowly added at 0° C. and the mixture was extracted with DCM. The organic layers were combined, dried over MgSO$_4$, filtered, and partially concentrated (product is volatile). The crude product was purified by flash column chromatography (silica; 100% DCM) to give the title compound (3 g, 7.5 mmol, purity 60%, 65%) as a brown oil. $^1$H NMR (300 MHz, CDCl$_3$) δ 7.73-7.61 (m, 1H), 7.60-7.48 (m, 1H), 7.02 (t, J=9.4 Hz, 1H), 1.98 (t, J=18.6 Hz, 3H).

Step B: 2-(3-(1,1-Difluoroethyl)-4-fluorophenyl)-4,4,5,5-tetramethyl-1,3,2-dioxaborolane In a round bottom flask, bis(pinacolato)diboron (2.87 g, 11.3 mmol, 1.5 equiv), potassium acetate (2.22 g, 22.6 mmol, 3 equiv), and [1,1'-bis(diphenylphosphino)ferrocene]-dichloropalladium(II) (615 mg, 0.75 mmol, 0.1 equiv) were added to a solution of 4-bromo-2-(1,1-difluoroethyl)-1-fluorobenzene (3 g, 7.5 mmol, 1 equiv) in dry 1,4-dioxane (40 mL). The mixture was purged with nitrogen and stirred at 90° C. for 16 h. Then, a sat. aq. solution of NaHCO$_3$ was added and the mixture was extracted with EtOAc. The combined organics were dried with MgSO$_4$, filtered and concentrated to yield a brown oil (2.15 g, 7.53 mmol), which was used in the next step without further purification. MS (ESI): mass calcd. for C$_{14}$H$_{18}$BF$_3$O$_2$, 286.1; m/z found, 287.1 [M+H]$^+$.

Intermediate 41: 2-(3-(1,1-Difluoroethyl)phenyl)-4,4,5,5-tetramethyl-1,3,2-dioxaborolane

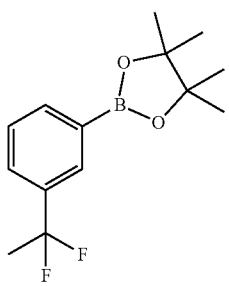 [SMILES: CC(F)(F)c1cccc(B2OC(C)(C)C(C)(C)O2)c1]

The title compound was prepared in a manner analogous to 2-(3-(Difluoromethyl)-4-fluorophenyl)-4,4,5,5-tetramethyl-1,3,2-dioxaborolane (Intermediate 39) using 1-bromo-3-(1,1-difluoroethyl)benzene instead of 4-bromo-2-(difluoromethyl)-1-fluorobenzene.

Intermediate 42: 2-(3-(Difluoromethoxy)-4-fluorophenyl)-4,4,5,5-tetramethyl-1,3,2-dioxaborolane

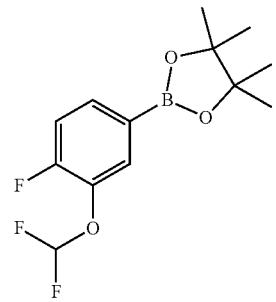 [SMILES: CC1(C)OB(c2ccc(F)c(OC(F)F)c2)OC1(C)C]

The title compound was prepared in a manner analogous to 2-(3-(difluoromethyl)-4-fluorophenyl)-4,4,5,5-tetramethyl-1,3,2-dioxaborolane (Intermediate 39) using 4-bromo-2-(difluoromethoxy)-1-fluorobenzene instead of 4-bromo-2-(difluoromethyl)-1-fluorobenzene. MS (ESI): mass calcd. for C$_{13}$H$_{16}$BF$_3$O$_3$, 288.1; m/z found, 289.0 [M+H]$^+$.

Intermediate 43: 2-(4-Chloro-3-(difluoromethoxy)phenyl)-4,4,5,5-tetramethyl-1,3,2-dioxaborolane

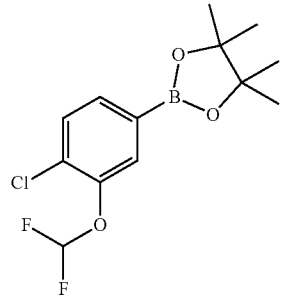 [SMILES: CC1(C)OB(c2ccc(Cl)c(OC(F)F)c2)OC1(C)C]

The title compound was prepared in a manner analogous to 2-(3-(difluoromethyl)-4-fluorophenyl)-4,4,5,5-tetramethyl-1,3,2-dioxaborolane (Intermediate 39) using 4-bromo-1-chloro-2-(difluoromethoxy)benzene instead of 4-bromo-2-(difluoromethyl)-1-fluorobenzene. $^1$H NMR (500 MHz, CDCl$_3$) δ 7.62-7.56 (m, 2H), 7.44 (d, J=7.9 Hz, 1H), 6.56 (t, J=73.6 Hz, 1H), 1.34 (s, 12H).

Intermediate 44: 3-(Chloromethyl)-5-(3-(difluoromethoxy)-4-fluorophenyl)-2-fluoropyridine

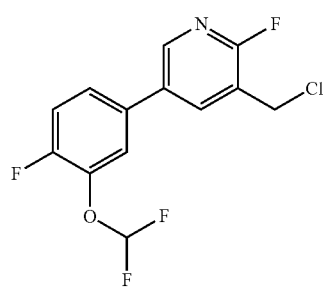 [SMILES: Fc1ccc(-c2cnc(F)c(CCl)c2)cc1OC(F)F]

Step A: 5-(3-(Difluoromethoxy)-4-fluorophenyl)-2-fluoronicotinaldehyde

A mixture of 5-bromo-2-fluoronicotinaldehyde (750 mg, 3.68 mmol), 2-(3-(difluoromethoxy)-4-fluorophenyl)-4,4,5,5-tetramethyl-1,3,2-dioxaborolane (1.59 g, 5.52 mmol), [1,1'-bis(diphenylphosphino)ferrocene]dichloropalladium (II), complex with dichloromethane (211 mg, 0.26 mmol) and cesium carbonate (2.40 g, 7.35 mmol) in 1,4-dioxane (11 mL) was stirred at 90° C. under nitrogen. After 16 hours, the reaction mixture was evaporated and purification (FCC, SiO$_2$, 0-90% EtOAc in hexanes) afforded the title compound (367 mg, 35%). MS (ESI): mass calcd. for $C_{13}H_7F_4NO_2$, 285.0; m/z found, 286.0 [M+H]$^+$. $^1$H NMR (500 MHz, DMSO-d$_6$) δ 10.21 (s, 1H), 8.87 (dd, J=2.7, 1.1 Hz, 1H), 8.67 (dd, J=8.9, 2.7 Hz, 1H), 7.86 (dd, J=7.5, 2.3 Hz, 1H), 7.78-7.73 (m, 1H), 7.58 (dd, J=10.5, 8.6 Hz, 1H), 7.38 (t, J=73.2 Hz, 1H).

Step B: (5-(3-(Difluoromethoxy)-4-fluorophenyl)-2-fluoropyridin-3-yl)methanol Sodium borohydride (45 mg, 1.2 mmol) was added to a mixture of 5-(3-(difluoromethoxy)-4-fluorophenyl)-2-fluoronicotinaldehyde (337 mg, 1.2 mmol) in THF (34 mL) at 0° C. under nitrogen. After 1 h, a saturated aqueous solution of ammonium chloride (20 mL) followed by water (40 mL) were added to the reaction mixture. The resulting mixture was extracted using EtOAc (3×80 mL). The combined organics were dried over MgSO$_4$, filtered and evaporated. Purification (FCC, SiO$_2$, 0-99% EtOAc in hexanes) afforded the title compound (282 mg, 83%). MS (ESI): mass calcd. for $C_{13}H_9F_4NO_2$, 287.1; m/z found, 288.0 [M+H]$^+$. $^1$H NMR (400 MHz, DMSO-d$_6$) δ 8.46-8.42 (m, 1H), 8.27-8.22 (m, 1H), 7.75-7.70 (m, 1H), 7.68-7.62 (m, 1H), 7.55 (dd, J=10.5, 8.6 Hz, 1H), 7.37 (t, J=73.2 Hz, 1H), 5.50 (t, J=5.6 Hz, 1H), 4.60 (d, J=5.2 Hz, 2H).

Step C: 3-(Chloromethyl)-5-(3-(difluoromethoxy)-4-fluorophenyl)-2-fluoropyridine Thionyl chloride (0.08 mL, 1.1 mmol) was added to a mixture of (5-(3-(difluoromethoxy)-4-fluorophenyl)-2-fluoropyridin-3-yl)methanol (232 mg, 0.8 mmol) in DCE (2.5 mL) under nitrogen. Upon addition, the reaction mixture was heated to 60° C. After 2 h, the reaction mixture was cooled to room temperature and a saturated aqueous solution of sodium bicarbonate (20 mL) was added. The resulting mixture was extracted using EtOAc (3×30 mL). The combined organics were dried over MgSO$_4$, filtered and evaporated. Purification (FCC, SiO$_2$, 0-99% EtOAc in hexanes) afforded the title compound (167 mg, 68%). MS (ESI): mass calcd. for $C_{13}H_3ClF_4NO$, 305.0; m/z found, 306.0 [M+H]$^+$. $^1$H NMR (500 MHz, DMSO-d$_6$) δ 8.59-8.57 (m, 1H), 8.47 (dd, J=9.2, 2.6 Hz, 1H), 7.77 (dd, J=7.6, 2.3 Hz, 1H), 7.70-7.66 (m, 1H), 7.56 (dd, J=10.5, 8.6 Hz, 1H), 7.36 (t, J=73.2 Hz, 1H), 4.85 (s, 2H).

5.2. Compounds of Formula (I): Examples 1-151

Example 1: 3-[[5-[3-(Difluoromethoxy)-4-fluorophenyl]-3-pyridyl]methyl]-1,3-oxazinan-2-one

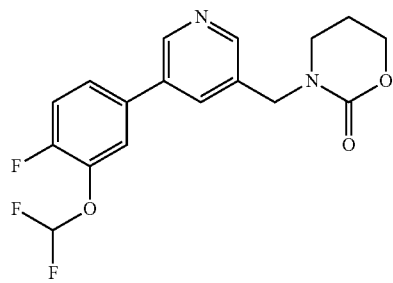 [SMILES: O=C1OCCCN1Cc1cncc(-c2ccc(F)c(OC(F)F)c2)c1]

Step A: 3-((5-Bromopyridin-3-yl)methyl)-1,3-oxazinan-2-one

To a solution of 1,3-oxazinan-2-one (137.1 mg, 1.36 mmol) in DMF (3.4 mL) was added NaH (60% dispersion in mineral oil, 81.4 mg, 2.03 mmol), and the reaction mixture was stirred at room temperature for 15 minutes. Then, 3-bromo-5-(chloromethyl)pyridine (70 mg, 0.34 mmol) was added and the reaction was stirred at room temperature overnight. The reaction mixture was diluted with H$_2$O and extracted with EtOAc (3×). The organic layers were combined, dried (Na$_2$SO$_4$), concentrated, and subjected directly to purification. Purification via silica gel chromatography (0-5% methanol in DCM) gave the title compound (59 mg, 0.22 mmol, 64%). MS (ESI) mass calcd. for $C_{10}H_{11}BrN_2O_2$, 270.0; m/z found 271.0 [M+H]$^+$.

Step B: 3-[[5-[3-(Difluoromethoxy)-4-fluoro-phenyl]-3-pyridyl]methyl]-1,3-oxazinan-2-one To a solution of 3-((5-bromopyridin-3-yl)methyl)-1,3-oxazinan-2-one (30 mg, 0.11 mmol), 2-(3-(difluoromethoxy)-4-fluorophenyl)-4,4,5,5-tetramethyl-1,3,2-dioxaborolane (Intermediate 42) (38.3 mg, 0.13 mmol) and Cs$_2$CO$_3$ (108.4 mg, 0.33 mmol) in 1,4-dioxane (1.3 mL) was added RuPhos Pd G3 (5.2 mg, 6.2 μmol), and the reaction mixture was heated to 95° C. overnight. The crude reaction mixture was cooled, filtered through a pad of Celite®, and the filtrate was concentrated. The crude material was re-dissolved in water and EtOAc, and the organic layer was separated. The aqueous layer was further extracted with EtOAc (2×). The organics were combined, dried (Na$_2$SO$_4$), filtered, and concentrated. The crude product was purified by preparative HPLC (Method A) to yield the title compound (25 mg, 0.071 mmol, 64%). MS (ESI): mass calcd. for $C_{17}H_{15}F_3N_2O_3$, 352.1; m/z found, 353.1 [M+H]$^+$. $^1$H NMR (500 MHz, Methanol-d$_4$) δ 8.74 (d, J=2.2 Hz, 1H), 8.54 (d, J=2.0 Hz, 1H), 8.17-7.96 (m, 1H), 7.63-7.60 (m, 1H), 7.60-7.57 (m, 1H), 7.40 (dd, J=10.3, 8.6 Hz, 1H), 6.96 (t, J=73.4 Hz, 1H), 4.65 (s, 2H), 4.42-4.18 (m, 2H), 3.42 (t, J=6.2 Hz, 2H), 2.19-1.95 (m, 2H).

Example 2: 3-[[5-[3-(Difluoromethoxy)-4-fluoro-phenyl]-3-pyridyl]methyl]oxazolidin-2-one

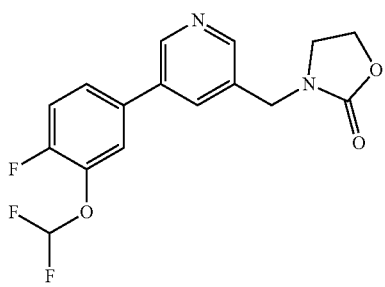 [SMILES: O=C1OCCN1Cc1cncc(-c2ccc(F)c(OC(F)F)c2)c1]

Prepared analogous to Example 1, using 2-oxazolidone in Step A. MS (ESI): mass calcd. for $C_{16}H_{13}F_3N_2O_3$, 338.1; m/z found, 339.0 [M+H]$^+$. $^1$H NMR (500 MHz, Methanol-$d_4$) δ 8.78 (d, J=2.2 Hz, 1H), 8.55 (d, J=2.1 Hz, 1H), 8.11-8.04 (m, 1H), 7.96-7.85 (m, 2H), 7.43-7.36 (m, 1H), 7.06 (t, J=54.6 Hz, 1H), 4.57 (s, 2H), 4.45-4.34 (m, 2H), 3.72-3.54 (m, 2H).

Example 3: (4S)-3-[[5-[3-(Difluoromethoxy)-4-fluoro-phenyl]-3-pyridyl]methyl]-4-isopropyl-oxazo-lidin-2-one

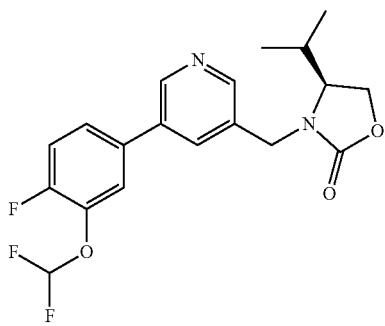 [SMILES: CC(C)[C@H]1COC(=O)N1Cc1cncc(-c2ccc(F)c(OC(F)F)c2)c1]

Prepared analogous to Example 1, using (S)-4-isopropyl-2-oxazolidinone (3 equiv) and NaH (5 equiv) in Step A. MS (ESI): mass calcd. for $C_{19}H_{19}F_3N_2O_3$, 380.1; m/z found, 381.1 [M+H]$^+$. $^1$H NMR (400 MHz, Methanol-$d_4$) δ 8.75 (d, J=2.2 Hz, 1H), 8.56 (d, J=2.0 Hz, 1H), 8.17-8.00 (m, 1H), 7.69-7.54 (m, 2H), 7.40 (dd, J=10.3, 8.5 Hz, 1H), 6.95 (t, J=73.3 Hz, 1H), 4.75 (d, J=15.6 Hz, 1H), 4.39 (d, J=15.7 Hz, 1H), 4.36-4.28 (m, 1H), 4.29-4.15 (m, 1H), 3.91-3.73 (m, 1H), 2.26-2.10 (m, 1H), 0.89 (d, J=7.0 Hz, 3H), 0.85 (d, J=6.8 Hz, 3H).

Example 4: 1-[[5-[3-(Difluoromethoxy)-4-fluoro-phenyl]-3-pyridyl]methyl]-4H-3,1-benzoxazin-2-one

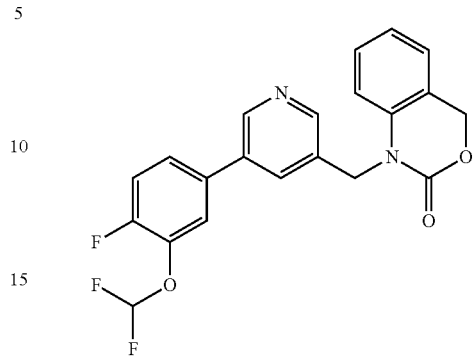

Prepared analogous to Example 1, using 1,4-dihydro-2H-benzo[d][1,3]oxazin-2-one (1 equiv) and NaH (1.2 equiv) in Step A. MS (ESI): mass calcd. for $C_{21}H_{15}F_3N_2O_3$, 400.1; m/z found, 401.1 [M+H]$^+$. $^1$H NMR (400 MHz, Methanol-$d_4$) δ 8.70 (d, J=2.2 Hz, 1H), 8.51 (d, J=2.0 Hz, 1H), 8.06-7.93 (m, 1H), 7.63-7.45 (m, 2H), 7.37 (dd, J=10.3, 8.5 Hz, 1H), 7.32-7.23 (m, 2H), 7.15-6.73 (m, 3H), 5.37 (s, 2H), 5.30 (s, 2H).

Example 5: (R/S)-3-[[5-[3-(Difluoromethoxy)-4-fluoro-phenyl]-3-pyridyl]methyl]-4-methyl-oxazoli-din-2-one

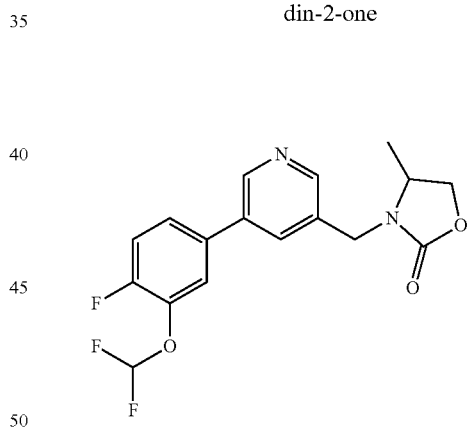

Prepared analogous to Example 1, using racemic 4-methyloxazolidin-2-one (2 equiv) and NaH (4 equiv) in Step A. In Step B, complete conversion was not observed and additional 2-(3-(difluoromethoxy)-4-fluorophenyl)-4,4,5,5-tetramethyl-1,3,2-dioxaborolane (Intermediate 42) (1.2 equiv) and RuPhos Pd G3 (0.05 equiv) were added, and the reaction mixture was stirred at 95° C. for an additional 3 h. MS (ESI): mass calcd. for $C_{17}H_{15}F_3N_2O_3$, 352.1; m/z found, 353.1 [M+H]$^+$. $^1$H NMR (400 MHz, Methanol-$d_4$) δ 8.74 (d, J=2.2 Hz, 1H), 8.55 (d, J=2.0 Hz, 1H), 8.13-7.95 (m, 1H), 7.68-7.54 (m, 2H), 7.40 (dd, J=10.3, 8.5 Hz, 1H), 6.95 (t, J=73.4 Hz, 1H), 4.81-4.38 (m, 3H), 4.07-3.83 (m, 2H), 1.28 (d, J=5.9 Hz, 3H).

Example 6: (R/S)-3-[[5-[3-(Difluoromethoxy)-4-fluoro-phenyl]-3-pyridyl]methyl]-5-methyl-oxazolidin-2-one

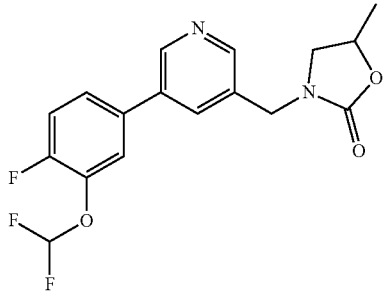 [SMILES: CC1CN(Cc2cncc(-c3ccc(F)c(OC(F)F)c3)c2)C(=O)O1]

Prepared analogous to Example 1, using racemic 5-methyloxazolidin-2-one (1.5 equiv) and NaH (1.5 equiv) in Step A. MS (ESI): mass calcd. for $C_{17}H_{15}F_3N_2O_3$, 352.1; m/z found, 353.1 [M+H]$^+$. $^1$H NMR (400 MHz, Methanol-$d_4$) δ 8.76 (d, J=2.2 Hz, 1H), 8.53 (d, J=2.0 Hz, 1H), 8.12-7.96 (m, 1H), 7.65-7.60 (m, 1H), 7.60-7.56 (m, 1H), 7.40 (dd, J=10.3, 8.5 Hz, 1H), 6.96 (t, J=73.4 Hz, 1H), 4.78-4.64 (m, 1H), 4.64-4.47 (m, 2H), 3.70 (t, J=8.5 Hz, 1H), 3.24-3.10 (m, 1H), 1.39 (d, J=6.2 Hz, 3H).

Example 7: (S*)-3-[[5-[3-(Difluoromethoxy)-4-fluoro-phenyl]-3-pyridyl]methyl]-5-methyl-oxazolidin-2-one

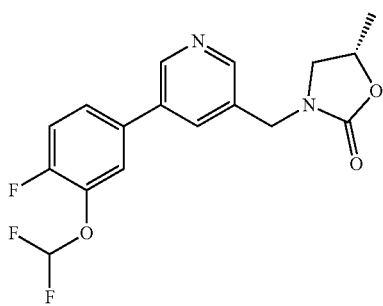 [SMILES: C[C@H]1CN(Cc2cncc(-c3ccc(F)c(OC(F)F)c3)c2)C(=O)O1]

The title compound was obtained as a single enantiomer by Chiral SFC purification of Example 6 performed using a Whelk O1 SS column (5 um 250×21 mm), mobile phase of 20% MeOH:iPrOH (1:1) with 0.2% iPrNH$_2$, 80% CO$_2$, and a flow rate of 42 mL/min (Temperature=40° C.). Elution was monitored following absorbance at 254 nm. The enantiomeric purity was confirmed by analytical SFC using a Whelk O1 SS column (5 um 250×4.6 mm), mobile phase of 20% MeOH:iPrOH (1:1) with 0.2% iPrNH$_2$, 80% CO$_2$, and a flow rate of 2 mL/min over 20 minutes. Elution was monitored following absorbance at 254 nm, enantiopurity 100%, retention time of 15.59 min. MS (ESI): mass calcd. for $C_{17}H_{15}F_3N_2O_3$, 352.1; m/z found, 353.1 [M+H]$^+$. $^1$HNMR is in agreement with Example 6.

Example 8: (R*)-3-[[5-[3-(Difluoromethoxy)-4-fluoro-phenyl]-3-pyridyl]methyl]-5-methyl-oxazolidin-2-one

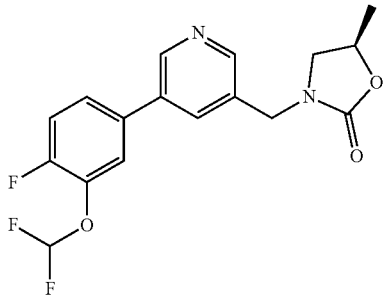 [SMILES: C[C@@H]1CN(Cc2cncc(-c3ccc(F)c(OC(F)F)c3)c2)C(=O)O1]

The title compound was obtained as a single enantiomer by Chiral SFC purification of Example 6 performed using a Whelk O1 SS column (5 um 250×21 mm), mobile phase of 20% MeOH:iPrOH (1:1) with 0.2% iPrNH$_2$, 80% CO$_2$, and a flow rate of 42 mL/min (Temperature=40° C.). Elution was monitored following absorbance at 254 nm. The enantiomeric purity was confirmed by analytical SFC using a Whelk O1 SS column (5 um 250×4.6 mm), mobile phase of 20% MeOH:iPrOH (1:1) with 0.2% iPrNH$_2$, 80% CO$_2$, and a flow rate of 2 mL/min over 20 minutes. Elution was monitored following absorbance at 254 nm, enantiopurity 100%, retention time of 15.67 min. MS (ESI): mass calcd. for $C_{17}H_{15}F_3N_2O_3$, 352.1; m/z found, 353.1 [M+H]$^+$. $^1$HNMR is in agreement with Example 6.

Example 9: 5-[[5-[3-(Difluoromethoxy)-4-fluoro-phenyl]-3-pyridyl]methyl]-7-oxa-5-azaspiro[2.4]heptan-6-one

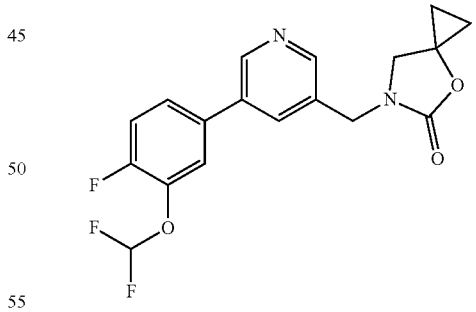

Prepared analogous to Example 1, using 4-oxa-6-azaspiro[2.4]heptan-5-one (Intermediate 2) (1.5 equiv) and NaH (2 equiv) in Step A. MS (ESI): mass calcd. for $C_{18}H_{15}F_3N_2O_3$, 364.1; m/z found, 365.1 [M+H]$^+$. $^1$H NMR (500 MHz, Methanol-$d_4$) δ 8.77 (d, J=2.2 Hz, 1H), 8.55 (d, J=2.0 Hz, 1H), 8.07-7.96 (m, 1H), 7.63 (dd, J=7.3, 2.3 Hz, 1H), 7.61-7.55 (m, 1H), 7.41 (dd, J=10.3, 8.5 Hz, 1H), 6.96 (t, J=73.3 Hz, 1H), 4.61 (s, 2H), 3.67 (s, 2H), 1.28-1.02 (m, 2H), 0.86-0.70 (m, 2H).

Example 10: 3-[[5-[3-(Difluoromethoxy)-4-fluoro-phenyl]-3-pyridyl]methyl]-6,6-dimethyl-1,3-oxazinan-2-one

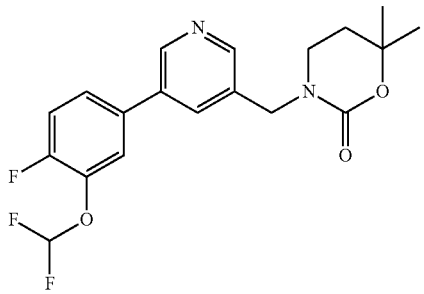 [SMILES: CC1(C)CCN(Cc2cncc(-c3ccc(F)c(OC(F)F)c3)c2)C(=O)O1]

Prepared analogous to Example 1, using 6,6-dimethyl-1,3-oxazinan-2-one (Intermediate 1) (1.5 equiv) and NaH (2 equiv) in Step A. MS (ESI): mass calcd. for $C_{19}H_{19}F_3N_2O_3$, 380.1; m/z found, 381.1 [M+H]$^+$. $^1$H NMR (500 MHz, Methanol-d$_4$) δ 8.75 (d, J=2.2 Hz, 1H), 8.54 (d, J=2.0 Hz, 1H), 8.06-7.96 (m, 1H), 7.63-7.59 (m, 1H), 7.59-7.55 (m, 1H), 7.41 (dd, J=10.3, 8.5 Hz, 1H), 6.96 (t, J=73.3 Hz, 1H), 4.67 (s, 2H), 3.43 (t, J=6.4 Hz, 2H), 1.96 (t, J=6.4 Hz, 2H), 1.38 (s, 6H).

Example 11: (4R)-3-[[5-[3-(Difluoromethoxy)-4-fluoro-phenyl]-3-pyridyl]methyl]-4-isopropyl-oxazolidin-2-one

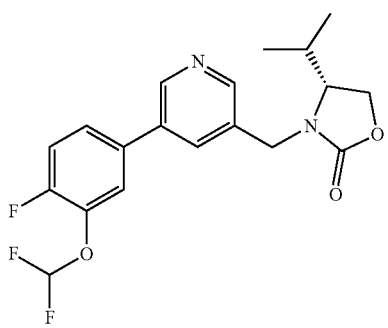 [SMILES: CC(C)[C@@H]1COC(=O)N1Cc1cncc(-c2ccc(F)c(OC(F)F)c2)c1]

Prepared analogous to Example 1, using (R)-4-isopropyl-2-oxazolidinone (1.5 equiv) and NaH (2 equiv) in Step A. MS (ESI): mass calcd. for $C_{19}H_{19}F_3N_2O_3$, 380.1; m/z found, 381.1 [M+H]$^+$. $^1$H NMR (400 MHz, Methanol-d$_4$) δ 8.75 (d, J=2.2 Hz, 1H), 8.56 (d, J=2.1 Hz, 1H), 8.16-7.95 (m, 1H), 7.70-7.53 (m, 2H), 7.40 (dd, J=10.3, 8.5 Hz, 1H), 6.96 (t, J=73.4 Hz, 1H), 4.75 (d, J=15.6 Hz, 1H), 4.39 (d, J=15.7 Hz, 1H), 4.35-4.28 (m, 1H), 4.27-4.14 (m, 1H), 3.89-3.72 (m, 1H), 2.31-2.05 (m, 1H), 0.89 (d, J=7.0 Hz, 3H), 0.85 (d, J=6.8 Hz, 3H).

Example 12: 6-[[5-[3-(Difluoromethoxy)-4-fluoro-phenyl]-3-pyridyl]methyl]-8-oxa-6-azaspiro[3.4]octan-7-one

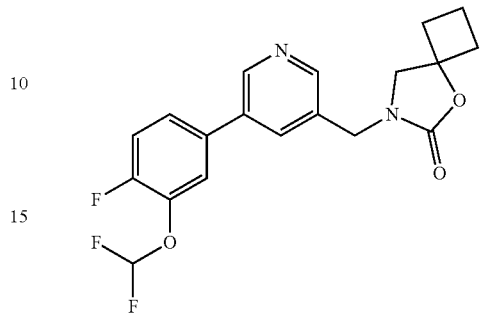

Prepared analogous to Example 1, using 5-oxa-7-azaspiro[3.4]octan-6-one (1.5 equiv) and NaH (2 equiv) in Step A. MS (ESI): mass calcd. for $C_{19}H_{17}F_3N_2O_3$, 378.1; m/z found, 379.2 [M+H]$^+$. $^1$H NMR (400 MHz, Methanol-d$_4$) δ 8.76 (d, J=2.3 Hz, 1H), 8.51 (d, J=2.0 Hz, 1H), 8.12-7.94 (m, 1H), 7.66-7.60 (m, 1H), 7.60-7.55 (m, 1H), 7.41 (dd, J=10.3, 8.5 Hz, 1H), 6.95 (t, J=73.3 Hz, 1H), 4.54 (s, 2H), 3.64 (s, 2H), 2.59-2.40 (m, 2H), 2.30-2.14 (m, 2H), 1.96-1.78 (m, 1H), 1.76-1.55 (m, 1H).

Example 13: 6-[[5-[3-(Difluoromethoxy)-4-fluoro-phenyl]-3-pyridyl]methyl]-2,8-dioxa-6-azaspiro[3.4]octan-7-one

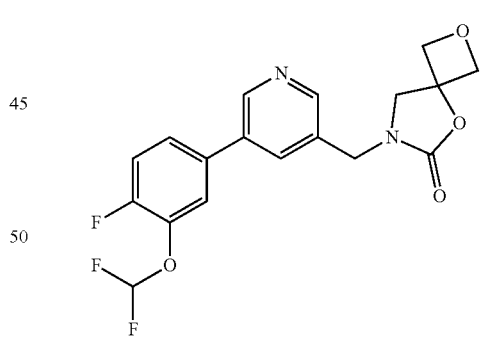

Prepared analogous to Example 1, using 2,5-dioxa-7-azaspiro[3.4]octan-6-one (Intermediate 3) (1.5 equiv) and NaH (2 equiv) in Step A. MS (ESI): mass calcd. for $C_{18}H_{15}F_3N_2O_4$, 380.1; m/z found, 381.1 [M+H]$^+$. $^1$H NMR (400 MHz, Methanol-d$_4$) δ 8.76 (d, J=2.2 Hz, 1H), 8.53 (d, J=2.0 Hz, 1H), 8.10-7.98 (m, 1H), 7.66-7.56 (m, 2H), 7.41 (dd, J=10.3, 8.5 Hz, 1H), 6.95 (t, J=73.4 Hz, 1H), 4.90-4.82 (m, 2H), 4.71 (dd, J=7.9, 1.2 Hz, 2H), 4.54 (s, 2H), 3.86 (s, 2H).

Example 14: (R/S)-3-[[5-[3-(Difluoromethoxy)-4-fluoro-phenyl]-3-pyridyl]methyl]-5-isopropyl-oxazolidin-2-one

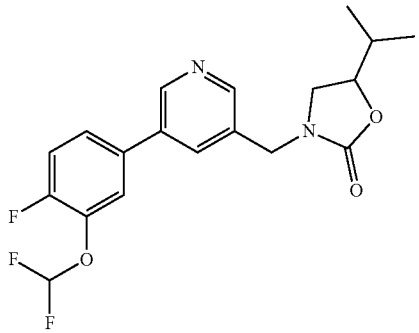 [SMILES: CC(C)C1CN(Cc2cncc(-c3ccc(F)c(OC(F)F)c3)c2)C(=O)O1]

Prepared analogous to Example 1, using racemic 5-isopropyloxazolidin-2-one (Intermediate 4) in Step A. In Step B, complete conversion was not observed and additional 2-(3-(difluoromethoxy)-4-fluorophenyl)-4,4,5,5-tetramethyl-1,3,2-dioxaborolane (Intermediate 42) (1.2 equiv) and RuPhos Pd G3 (0.05 equiv) were added, and the reaction mixture was stirred at 95° C. overnight. MS (ESI): mass calcd. for $C_{19}H_{19}F_3N_2O_3$, 380.1; m/z found, 381.1 [M+H]$^+$. Analytical HPLC was obtained on an Agilent 1100 Series using a XBridge C18 column (5 um, 100×4.6 mm), mobile phase of 10-100% ACN in 20 mM NH$_4$OH over 2 min and then hold at 100% ACN for 2 min, at a flow rate of 2.5 mL/min (Temperature=45° C.). R$_t$=2.03 min at 254 nm.

Example 15: (R*)-3-[[5-[3-(Difluoromethoxy)-4-fluoro-phenyl]-3-pyridyl]methyl]-5-isopropyl-oxazolidin-2-one

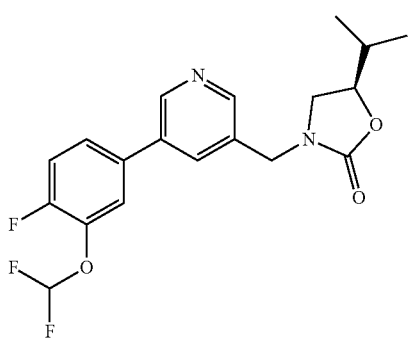 [SMILES: CC(C)[C@@H]1CN(Cc2cncc(-c3ccc(F)c(OC(F)F)c3)c2)C(=O)O1]

The title compound was obtained as a single enantiomer by Chiral SFC purification of Example 14 performed using a Whelk O1 SS column (5 um, 250×21 mm), mobile phase of 28% MeOH, 72% CO$_2$, and a flow rate of 42 mL/min (Temperature=40° C.). Elution was monitored following absorbance at 254 nm. The enantiomeric purity was confirmed by analytical SFC using a Whelk O1 SS column (5 um, 250×4.6 mm), mobile phase of 30% MeOH, 70% CO$_2$, and a flow rate of 2 mL/min over 20 minutes. Elution was monitored following absorbance at 254 nm, enantiopurity 100%, retention time of 6.03 min. MS (ESI): mass calcd. for $C_{19}H_{19}F_3N_2O_3$, 380.1; m/z found, 381.1 [M+H]$^+$. Analytical HPLC was obtained on an Agilent 1100 Series using a XBridge C18 column (5 um, 100×4.6 mm), mobile phase of 10-100% ACN in 20 mM NH$_4$OH over 2 min and then hold at 100% ACN for 2 min, at a flow rate of 2.5 mL/min (Temperature=45° C.). R$_t$=2.03 min at 254 nm.

Example 16: (S*)-3-[[5-[3-(Difluoromethoxy)-4-fluoro-phenyl]-3-pyridyl]methyl]-5-isopropyl-oxazolidin-2-one

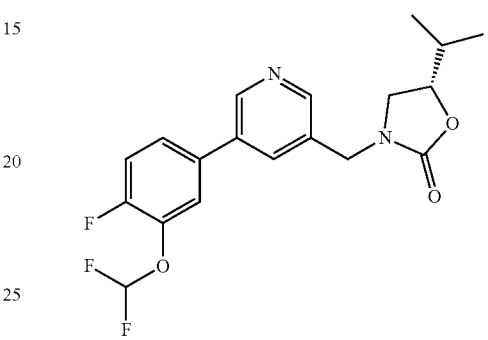

The title compound was obtained as a single enantiomer by Chiral SFC purification of Example 14 performed using a Whelk O1 SS column (5 um, 250×21 mm), mobile phase of 28% MeOH, 72% CO$_2$, and a flow rate of 42 mL/min (Temperature=40° C.). Elution was monitored following absorbance at 254 nm. The enantiomeric purity was confirmed by analytical SFC using a Whelk O1 SS column (5 um, 250×4.6 mm), mobile phase of 30% MeOH, 70% CO$_2$, and a flow rate of 2 mL/min over 20 minutes. Elution was monitored following absorbance at 254 nm, enantiopurity 100%, retention time of 7.16 min. MS (ESI): mass calcd. for $C_{19}H_{19}F_3N_2O_3$, 380.1; m/z found, 381.1 [M+H]$^+$. Analytical HPLC was obtained on an Agilent 1100 Series using a XBridge C18 column (5 um, 100×4.6 mm), mobile phase of 10-100% ACN in 20 mM NH$_4$OH over 2 min and then hold at 100% ACN for 2 min, at a flow rate of 2.5 mL/min (Temperature=45° C.). R$_t$=2.05 min at 254 nm.

Example 17: (R/S)-3-[[5-[3-(Difluoromethoxy)-4-fluoro-phenyl]-3-pyridyl]methyl]-5-(morpholinomethyl)oxazolidin-2-one

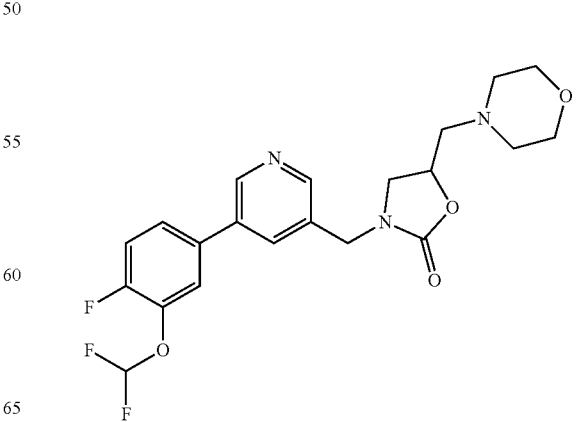

Prepared analogous to Example 1, using racemic 5-(morpholinomethyl)oxazolidin-2-one (Intermediate 5) (1.5 equiv) and NaH (2 equiv) in Step A. In Step B, complete conversion was not observed and additional 2-(3-(difluoromethoxy)-4-fluorophenyl)-4,4,5,5-tetramethyl-1,3,2-dioxaborolane (Intermediate 42) (1.2 equiv) and RuPhos Pd G3 (0.05 equiv) were added, and the reaction mixture was stirred at 95° C. for 4 h. Analytical HPLC was obtained on an Agilent 1100 Series using a XBridge C18 column (5 um, 100×4.6 mm), mobile phase of 10-100% ACN in 20 mM NH$_4$OH over 2 min and then hold at 100% ACN for 2 min, at a flow rate of 2.5 mL/min (Temperature=45° C.). R$_t$=1.819 min at 254 nm.

Example 18: (R*)-3-[[5-[3-(Difluoromethoxy)-4-fluoro-phenyl]-3-pyridyl]methyl]-5-(morpholinomethyl)oxazolidin-2-one

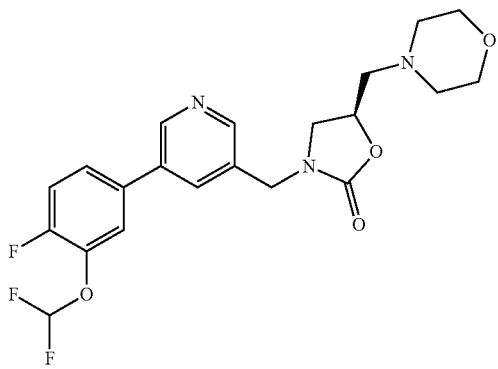 [SMILES: O=C1O[C@H](CN2CCOCC2)CN1Cc1cncc(-c2ccc(F)c(OC(F)F)c2)c1]

The title compound was obtained as a single enantiomer by Chiral SFC purification of Example 17 performed using a Whelk O1 SS column (5 um, 250×21 mm), mobile phase of 30% MeOH with 0.3% iPrNH$_2$, 70% CO$_2$, and a flow rate of 42 mL/min (Temperature=40° C.). Elution was monitored following absorbance at 254 nm. The enantiomeric purity was confirmed by analytical SFC using a Whelk O1 SS column (3 um, 100×4.6 mm), mobile phase of 40% MeOH with 0.3% iPrNH$_2$, 60% CO$_2$, and a flow rate of 3.5 mL/min over 3 minutes. Elution was monitored following absorbance at 243 nm, enantiopurity 100%, retention time of 1.43 min. MS (ESI): mass calcd. for C$_{21}$H$_{22}$F$_3$N$_3$O$_4$, 437.2; m/z found, 438.1 [M+H]$^+$. $^1$H NMR (400 MHz, Methanol-d$_4$) 8.77 (d, J=2.2 Hz, 1H), 8.56 (d, J=2.0 Hz, 1H), 8.13-7.97 (m, 1H), 7.67-7.56 (m, 2H), 7.41 (dd, J=10.3, 8.5 Hz, 1H), 6.96 (t, J=73.4 Hz, 1H), 4.81-4.70 (m, 1H), 4.65-4.48 (m, 2H), 3.67 (t, J=8.7 Hz, 1H), 3.63-3.53 (m, 4H), 3.41-3.33 (m, 1H), 2.66-2.59 (m, 2H), 2.57-2.45 (m, 4H).

Example 19: (S*)-3-[[5-[3-(Difluoromethoxy)-4-fluoro-phenyl]-3-pyridyl]methyl]-5-(morpholinomethyl)oxazolidin-2-one

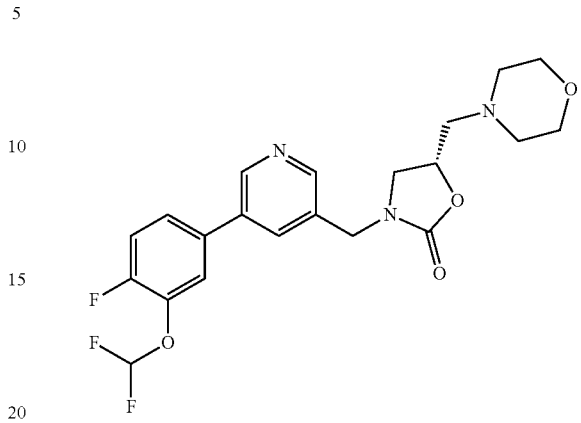

The title compound was obtained as a single enantiomer by Chiral SFC purification of Example 17 performed using a Whelk O1 SS column (5 um, 250×21 mm), mobile phase of 30% MeOH with 0.3% iPrNH$_2$, 70% CO$_2$, and a flow rate of 42 mL/min (Temperature=40° C.). Elution was monitored following absorbance at 254 nm. The enantiomeric purity was confirmed by analytical SFC using a Whelk O1 SS column (3 um, 100×4.6 mm), mobile phase of 40% MeOH with 0.3% iPrNH$_2$, 60% CO$_2$, and a flow rate of 3.5 mL/min over 3 minutes. Elution was monitored following absorbance at 243 nm, enantiopurity 100%, retention time of 1.61 min. MS (ESI): mass calcd. for C$_{21}$H$_{22}$F$_3$N$_3$O$_4$, 437.2; m/z found, 438.1 [M+H]$^+$. $^1$H NMR (400 MHz, Methanol-d$_4$) 8.77 (d, J=2.2 Hz, 1H), 8.56 (d, J=2.0 Hz, 1H), 8.09-7.99 (m, 1H), 7.69-7.53 (m, 2H), 7.41 (dd, J=10.3, 8.5 Hz, 1H), 6.96 (t, J=73.4 Hz, 1H), 4.82-4.71 (m, 1H), 4.65-4.49 (m, 2H), 3.67 (t, J=8.8 Hz, 1H), 3.62-3.54 (m, 4H), 3.41-3.32 (m, 1H), 2.68-2.59 (m, 2H), 2.56-2.43 (m, 4H).

Example 20: 2-[[5-[3-(Difluoromethoxy)-4-fluoro-phenyl]-3-pyridyl]methyl]-4,8-dioxa-2-azaspiro[4.5]decan-3-one

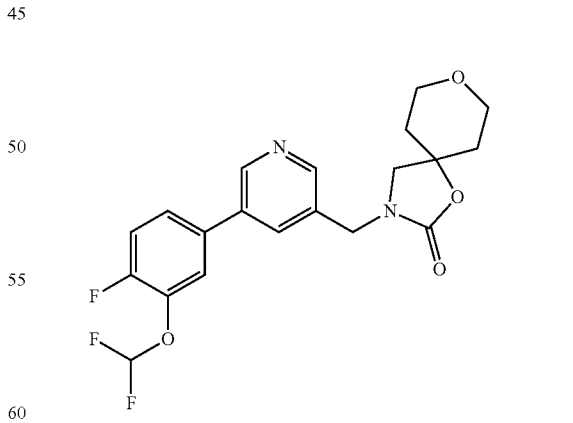

Prepared analogous to Example 1, using 1,8-dioxa-3-azaspiro[4.5]decan-2-one (Intermediate 6) (1.5 equiv) and NaH (2 equiv) in Step A. MS (ESI): mass calcd. for C$_{20}$H$_{19}$F$_3$N$_2$O$_4$, 408.1; m/z found, 409.1 [M+H]$^+$. $^1$H NMR (400 MHz, Methanol-d$_4$) δ 8.77 (d, J=2.2 Hz, 1H), 8.53 (d, J=2.0 Hz, 1H), 8.11-7.92 (m, 1H), 7.70-7.52 (m, 2H), 7.41

(dd, J=10.3, 8.5 Hz, 1H), 6.96 (t, J=73.3 Hz, 1H), 4.57 (s, 2H), 3.93-3.62 (m, 4H), 3.40 (s, 2H), 1.97-1.73 (m, 4H).

Example 21: 6-[[5-[3-(Difluoromethyl)-4-fluoro-phenyl]-3-pyridyl]methyl]-8-oxa-2,6-diazaspiro[3.4]octan-7-one Trifluoroacetate Salt

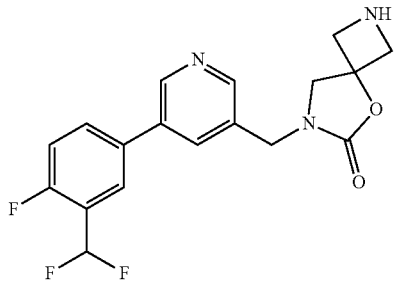 [SMILES: O=C1OC2(CNC2)CN1Cc1cncc(-c2ccc(F)c(C(F)F)c2)c1]

Step A: tert-Butyl 7-((5-bromopyridin-3-yl)methyl)-6-oxo-5-oxa-2,7-diazaspiro[3.4]octane-2-carboxylate Prepared analogous to Example 22, using tert-butyl 6-oxo-5-oxa-2,7-diazaspiro[3.4]octane-2-carboxylate (Intermediate 7). MS (ESI): mass calcd. for $C_{17}H_{20}BrN_3O_4$, 397.1; m/z found, 342.0 [M+H-tBu]$^+$.

Step B: tert-Butyl 7-((5-(3-(difluoromethyl)-4-fluorophenyl)pyridin-3-yl)methyl)-6-oxo-5-oxa-2,7-diazaspiro[3.4]octane-2-carboxylate To a solution of tert-butyl 7-((5-bromopyridin-3-yl)methyl)-6-oxo-5-oxa-2,7-diazaspiro[3.4]octane-2-carboxylate (50 mg, 0.13 mmol), 2-(3-(difluoromethyl)-4-fluorophenyl)-4,4,5,5-tetramethyl-1,3,2-dioxaborolane (Intermediate 39) (44 mg, 0.16 mmol) and $Cs_2CO_3$ (123 mg, 0.38 mmol) in DCE (1.3 mL) was added RuPhos Pd G3 (6 mg, 7 µmol). The vial was purged with $N_2$, sealed, and the reaction mixture was heated to 80° C. overnight. Complete conversion was not observed and additional 2-(3-(difluoromethyl)-4-fluorophenyl)-4,4,5,5-tetramethyl-1,3,2-dioxaborolane (Intermediate 39) (44 mg, 0.16 mmol) and RuPhos Pd G3 (6 mg, 7 µmol) were added, and the reaction mixture was further stirred at 80° C. overnight. Then, the crude reaction mixture was cooled, filtered through a pad of Celite®, and the filtrate was concentrated. The crude material was re-dissolved in water and EtOAc, and the organic layer was separated. The aqueous layer was further extracted with EtOAc (2×). The organics were combined, dried ($Na_2SO_4$), filtered, and concentrated. The crude product was purified by preparative HPLC (Method C) to yield the title compound (6 mg, 0.013 mmol, 10%) as a white solid. MS (ESI): mass calcd. for $C_{23}H_{24}F_3N_3O_4$, 463.2; m/z found, 464.3 [M+H]$^+$.

Step C: 6-[[5-[3-(Difluoromethyl)-4-fluoro-phenyl]-3-pyridyl]methyl]-8-oxa-2,6-diazaspiro[3.4]octan-7-one To a solution of tert-butyl 7-((5-(3-(difluoromethyl)-4-fluorophenyl)pyridin-3-yl)methyl)-6-oxo-5-oxa-2,7-diazaspiro[3.4]octane-2-carboxylate (6 mg, 0.013 mmol) in DCM (0.13 mL) was added 1 drop of TFA, and the reaction mixture was stirred at room temperature overnight. The volatiles were removed to yield the title compound as the TFA salt. MS (ESI): mass calcd. for $C_{18}H_{16}F_3N_3O_2$, 363.1; m/z found, 364.2 [M+H]$^+$. $^1$H NMR (400 MHz, Methanol-$d_4$) δ 9.05 (s, 1H), 8.77 (s, 1H), 8.63-8.50 (m, 1H), 8.10-8.01 (m, 1H), 8.00-7.94 (m, 1H), 7.53-7.40 (m, 1H), 7.09 (t, J=54.5 Hz, 1H), 4.67 (s, 2H), 4.40 (s, 4H), 3.92 (s, 2H).

Example 22: 3-[[5-[3-(Difluoromethyl)-4-fluoro-phenyl]-3-pyridyl]methyl]oxazolidin-2-one

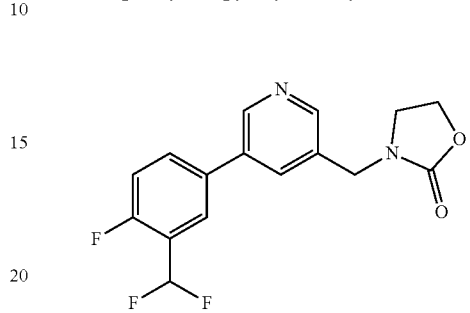

Step A: 3-((5-Bromopyridin-3-yl)methyl)oxazolidin-2-one

To a solution of 2-oxazolidone (189.8 mg, 2.18 mmol) and 3-bromo-5-(chloromethyl)pyridine (300 mg, 1.45 mmol) in DMF (7.3 mL) was added NaH (60% dispersion in mineral oil, 116 mg, 2.91 mmol), and the reaction mixture was stirred at room temperature for 1 h. The reaction mixture was diluted with $H_2O$ and EtOAc. The organic layer was separated, and the aqueous layer further extracted with EtOAc (3×). The organic layers were combined, dried ($Na_2SO_4$), concentrated, and subjected directly to purification. Purification via silica gel chromatography (0-10% methanol in DCM) gave the title compound, which was contaminated with a small amount of unreacted 2-oxazolidone. Further purification via silica gel chromatography (0-70% EtOAc (with 10% MeOH) in hexanes) gave the title compound (283 mg, 1.1 mmol, 76%). MS (ESI) mass calcd. for $C_9H_9BrN_2O2$, 255.98; m/z found 257.0 [M+H]$^+$.

Step B: 3-[[5-[3-(Difluoromethyl)-4-fluoro-phenyl]-3-pyridyl]methyl]oxazolidin-2-one To a solution of 3-((5-bromopyridin-3-yl)methyl)oxazolidin-2-one (283 mg, 1.1 mmol), 2-(3-(difluoromethyl)-4-fluorophenyl)-4,4,5,5-tetramethyl-1,3,2-dioxaborolane (Intermediate 39) (359.3 mg, 1.32 mmol) and $Cs_2CO_3$ (1.08 g, 3.31 mmol) in 1,4-dioxane (12 mL) was added RuPhos Pd G3 (52.2 mg, 0.062 mmol). The vial was purged with $N_2$, sealed, and the reaction mixture was heated to 95° C. overnight. The crude reaction mixture was cooled, filtered through a pad of Celite®, and the filtrate was concentrated. The crude material was re-dissolved in water and EtOAc, and the organic layer was separated. The aqueous layer was further extracted with EtOAc (2×). The organics were combined, dried ($Na_2SO_4$), filtered, and concentrated. The crude product was purified by preparative HPLC (Method B) to yield the title compound (271 mg, 0.84 mmol, 76%). MS (ESI): mass calcd. for $C_{16}H_{13}F_3N_2O_2$, 322.1; m/z found, 323.1 [M+H]$^+$. $^1$H NMR (400 MHz, Methanol-$d_4$) δ 8.78 (d, J=2.2 Hz, 1H), 8.55 (d, J=2.1 Hz, 1H), 8.10-8.00 (m, 1H), 7.99-7.80 (m, 2H), 7.47-7.30 (m, 1H), 7.06 (t, J=54.6 Hz, 1H), 4.57 (s, 2H), 4.44-4.29 (m, 2H), 3.67-3.52 (m, 2H).

Example 23: (4S)-3-[[5-[3-(Difluoromethyl)-4-fluoro-phenyl]-3-pyridyl]methyl]-4-isopropyl-oxazolidin-2-one

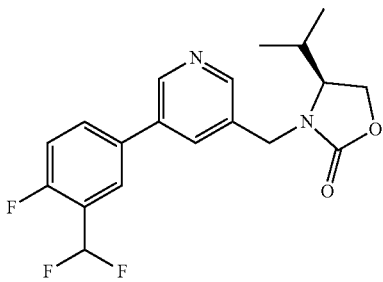 [SMILES: CC(C)[C@H]1COC(=O)N1Cc1cncc(-c2ccc(F)c(C(F)F)c2)c1]

Prepared analogous to Example 22, using (S)-4-isopropyl-2-oxazolidinone (3 equiv) and NaH (5 equiv) in Step A. MS (ESI): mass calcd. for $C_{19}H_{19}F_3N_2O_2$, 364.1; m/z found, 365.1 [M+H]$^+$. $^1$H NMR (400 MHz, Methanol-d$_4$) δ 8.78 (d, J=2.2 Hz, 1H), 8.57 (d, J=2.1 Hz, 1H), 8.16-8.04 (m, 1H), 7.97-7.82 (m, 2H), 7.47-7.34 (m, 1H), 7.06 (t, J=54.6 Hz, 1H), 4.76 (d, J=15.7 Hz, 1H), 4.47-4.28 (m, 2H), 4.27-4.17 (m, 1H), 3.87-3.76 (m, 1H), 2.25-2.12 (m, 1H), 0.89 (d, J=7.0 Hz, 3H), 0.86 (d, J=6.8 Hz, 3H).

Example 24: 1-[[5-[3-(Difluoromethyl)-4-fluoro-phenyl]-3-pyridyl]methyl]-4H-3,1-benzoxazin-2-one

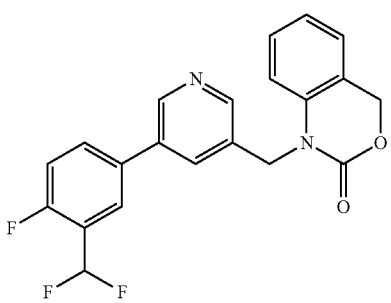 [SMILES: O=C1OCc2ccccc2N1Cc1cncc(-c2ccc(F)c(C(F)F)c2)c1]

Prepared analogous to Example 22, using 1,4-dihydro-2H-benzo[d][1,3]oxazin-2-one (1 equiv) and NaH (1.2 equiv) in Step A. MS (ESI): mass calcd. for $C_{21}H_{15}F_3N_2O_2$, 384.1; m/z found, 385.0 [M+H]$^+$. $^1$H NMR (400 MHz, Methanol-d$_4$) δ 8.72 (d, J=2.2 Hz, 1H), 8.56-8.45 (m, 1H), 8.13-7.99 (m, 1H), 7.92-7.78 (m, 2H), 7.42-7.33 (m, 1H), 7.32-7.24 (m, 2H), 7.23-6.88 (m, 3H), 5.37 (s, 2H), 5.31 (s, 2H).

Example 25: (R/S)-3-[[5-[3-(Difluoromethyl)-4-fluoro-phenyl]-3-pyridyl]methyl]-4-methyl-oxazolidin-2-one

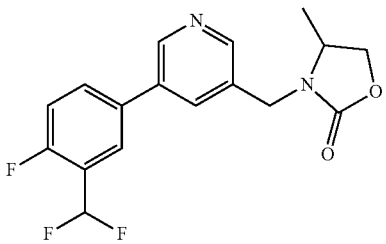 [SMILES: CC1COC(=O)N1Cc1cncc(-c2ccc(F)c(C(F)F)c2)c1]

Prepared analogous to Example 22, using racemic 4-methyloxazolidin-2-one (2 equiv) and NaH (4 equiv) in Step A. In Step B, complete conversion was not observed and additional 2-(3-(difluoromethyl)-4-fluorophenyl)-4,4,5,5-tetramethyl-1,3,2-dioxaborolane (Intermediate 39) (1.2 equiv) and RuPhos Pd G3 (0.05 equiv) were added, and the reaction mixture was stirred at 95° C. for an additional 3 h. MS (ESI): mass calcd. for $C_{17}H_{15}F_3N_2O_2$, 336.1; m/z found, 337.1 [M+H]$^+$. $^1$H NMR (400 MHz, Methanol-d$_4$) δ 8.77 (d, J=2.2 Hz, 1H), 8.56 (d, J=2.1 Hz, 1H), 8.14-7.96 (m, 1H), 7.92-7.79 (m, 2H), 7.44-7.33 (m, 1H), 7.05 (t, J=54.6 Hz, 1H), 4.73-4.41 (m, 3H), 4.04-3.82 (m, 2H), 1.28 (d, J=6.0 Hz, 3H).

Example 26: (R/S)-3-[[5-[3-(Difluoromethyl)-4-fluoro-phenyl]-3-pyridyl]methyl]-5-methyl-oxazolidin-2-one

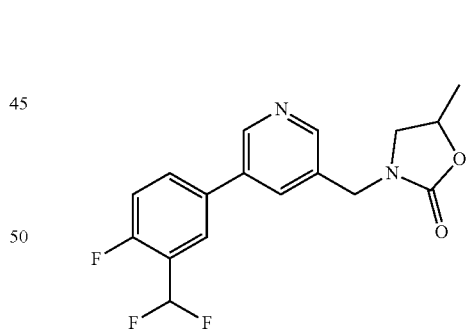

Prepared analogous to Example 22, using racemic 5-methyloxazolidin-2-one in Step A. MS (ESI): mass calcd. for $C_{17}H_{15}F_3N_2O_2$, 336.1; m/z found, 337.1 [M+H]$^+$. $^1$H NMR (400 MHz, Methanol-d$_4$) δ 8.78 (d, J=2.3 Hz, 1H), 8.54 (d, J=2.0 Hz, 1H), 8.13-7.98 (m, 1H), 7.96-7.80 (m, 2H), 7.47-7.33 (m, 1H), 7.06 (t, J=54.6 Hz, 1H), 4.77-4.65 (m, 1H), 4.66-4.42 (m, 2H), 3.74-3.67 (m, 1H), 3.22-3.13 (m, 1H), 1.39 (d, J=6.2 Hz, 3H).

Example 27: (S*)-3-[[5-[3-(Difluoromethyl)-4-fluoro-phenyl]-3-pyridyl]methyl]-5-methyl-oxazolidin-2-one

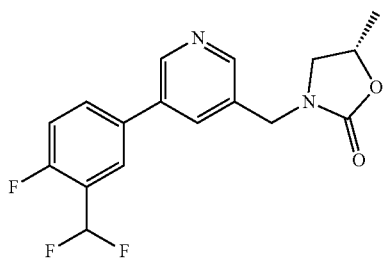 [SMILES: C[C@H]1CN(Cc2cncc(-c3ccc(F)c(C(F)F)c3)c2)C(=O)O1]

The title compound was obtained as a single enantiomer by Chiral SFC purification of Example 26 performed using a Whelk O1 SS column (5 um 250×21 mm), mobile phase of 20% MeOH:iPrOH (1:1) with 0.2% iPrNH$_2$, 80% CO$_2$, and a flow rate of 42 mL/min (Temperature=40° C.). Elution was monitored following absorbance at 254 nm. The enantiomeric purity was confirmed by analytical SFC using a Whelk O1 SS column (5 um 250×4.6 mm), mobile phase of 20% MeOH:iPrOH (1:1) with 0.2% iPrNH$_2$, 80% CO$_2$, and a flow rate of 2 mL/min over 20 minutes. Elution was monitored following absorbance at 254 nm, enantiopurity 100%, retention time of 13.75 min. MS (ESI): mass calcd. for C$_{17}$H$_{15}$F$_3$N$_2$O$_2$, 336.1; m/z found, 337.0 [M+H]$^+$. $^1$HNMR is in agreement with Example 26.

Example 28: (R*)-3-[[5-[3-(Difluoromethyl)-4-fluoro-phenyl]-3-pyridyl]methyl]-5-methyl-oxazolidin-2-one

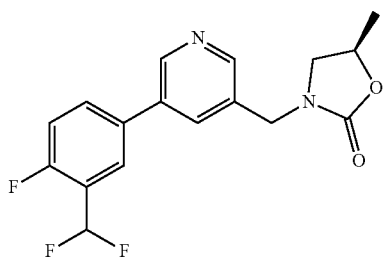 [SMILES: C[C@@H]1CN(Cc2cncc(-c3ccc(F)c(C(F)F)c3)c2)C(=O)O1]

The title compound, whose stereochemistry was confirmed by Example 33, was obtained as a single enantiomer by Chiral SFC purification of Example 26 performed using a Whelk O1 SS column (5 um 250×21 mm), mobile phase of 20% MeOH:iPrOH (1:1) with 0.2% iPrNH$_2$, 80% CO$_2$, and a flow rate of 42 mL/min (Temperature=40° C.). Elution was monitored following absorbance at 254 nm. The enantiomeric purity was confirmed by analytical SFC using a Whelk O1 SS column (5 um 250×4.6 mm), mobile phase of 20% MeOH:iPrOH (1:1) with 0.2% iPrNH$_2$, 80% CO$_2$, and a flow rate of 2 mL/min over 20 minutes. Elution was monitored following absorbance at 254 nm, enantiopurity 100%, retention time of 15.9 min. MS (ESI): mass calcd. for C$_{17}$H$_{15}$F$_3$N$_2$O$_2$, 336.1; m/z found, 337.1 [M+H]$^+$. $^1$HNMR is in agreement with Example 26.

Example 29: 5-[[5-[3-(Difluoromethyl)-4-fluoro-phenyl]-3-pyridyl]methyl]-7-oxa-5-azaspiro[2.4]heptan-6-one

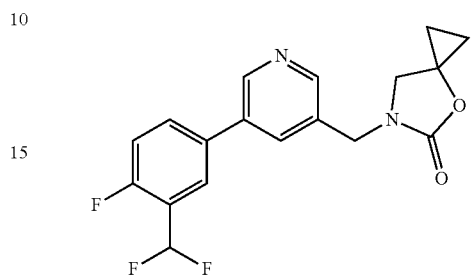

Prepared analogous to Example 22, using 4-oxa-6-azaspiro[2.4]heptan-5-one (Intermediate 2) in Step A. MS (ESI): mass calcd. for C$_{18}$H$_{15}$F$_3$N$_2$O$_2$, 348.1; m/z found, 349.1 [M+H]$^+$. $^1$H NMR (500 MHz, Methanol-d$_4$) δ 8.79 (d, J=2.2 Hz, 1H), 8.56 (d, J=2.0 Hz, 1H), 8.13-8.01 (m, 1H), 7.95-7.90 (m, 1H), 7.90-7.84 (m, 1H), 7.46-7.33 (m, 1H), 7.06 (t, J=54.6 Hz, 1H), 4.62 (s, 2H), 3.67 (s, 2H), 1.32-0.93 (m, 2H), 0.89-0.60 (m, 2H).

Example 30: 3-[[5-[3-(Difluoromethyl)-4-fluoro-phenyl]-3-pyridyl]methyl]-6,6-dimethyl-1,3-oxazinan-2-one

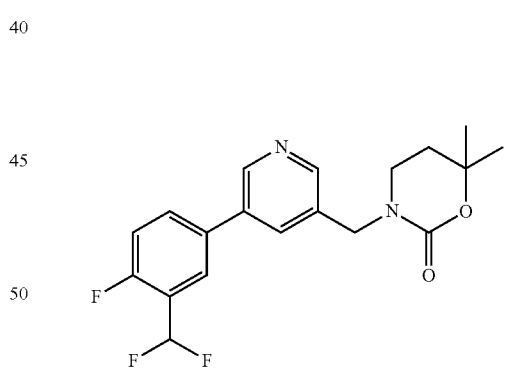

Prepared analogous to Example 22, using 6,6-dimethyl-1,3-oxazinan-2-one (Intermediate 1) in Step A. MS (ESI): mass calcd. for C$_{19}$H$_{19}$F$_3$N$_2$O$_2$, 364.1; m/z found, 365.1 [M+H]$^+$. $^1$H NMR (500 MHz, Methanol-d$_4$) δ 8.77 (d, J=2.2 Hz, 1H), 8.55 (d, J=2.1 Hz, 1H), 8.07-8.04 (m, 1H), 7.92-7.88 (m, 1H), 7.88-7.85 (m, 1H), 7.43-7.35 (m, 1H), 7.06 (t, J=54.6 Hz, 1H), 4.67 (s, 2H), 3.43 (t, J=6.4 Hz, 2H), 1.96 (t, J=6.4 Hz, 2H), 1.38 (s, 6H).

Example 31: (4R)-3-[[5-[3-(Difluoromethyl)-4-fluoro-phenyl]-3-pyridyl]methyl]-4-isopropyl-oxazolidin-2-one

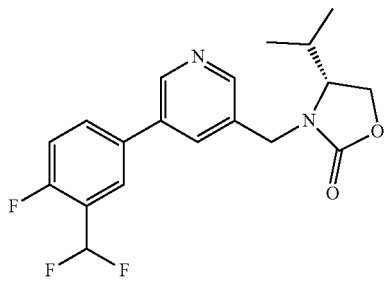 [SMILES: CC(C)[C@@H]1COC(=O)N1Cc1cncc(-c2ccc(F)c(C(F)F)c2)c1]

Prepared analogous to Example 22, using (R)-4-isopropyl-2-oxazolidinone in Step A. MS (ESI): mass calcd. for $C_{19}H_{19}F_3N_2O_2$, 364.1; m/z found, 365.1 [M+H]$^+$. $^1$H NMR (400 MHz, Methanol-d$_4$) δ 8.77 (d, J=2.2 Hz, 1H), 8.57 (d, J=2.0 Hz, 1H), 8.20-8.01 (m, 1H), 7.96-7.80 (m, 2H), 7.47-7.31 (m, 1H), 7.05 (t, J=54.6 Hz, 1H), 4.76 (d, J=15.7 Hz, 1H), 4.44-4.27 (m, 2H), 4.25-4.15 (m, 1H), 3.84-3.77 (m, 1H), 2.24-2.12 (m, 1H), 0.89 (d, J=7.0 Hz, 3H), 0.85 (d, J=6.8 Hz, 3H).

Example 32: 6-[[5-[3-(Difluoromethyl)-4-fluoro-phenyl]-3-pyridyl]methyl]-8-oxa-6-azaspiro[3.4]octan-7-one

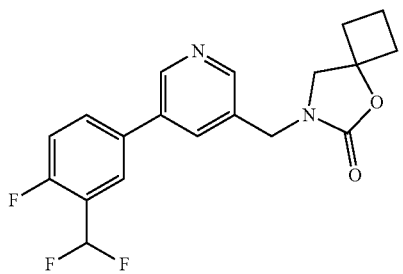 [SMILES: O=C1OC2(CCC2)CN1Cc1cncc(-c2ccc(F)c(C(F)F)c2)c1]

Prepared analogous to Example 22, using 5-oxa-7-azaspiro[3.4]octan-6-one in Step A. MS (ESI): mass calcd. for $C_{19}H_{17}F_3N_2O_2$, 362.1; m/z found, 363.1 [M+H]$^+$. $^1$H NMR (400 MHz, Methanol-d$_4$) δ 8.78 (d, J=2.3 Hz, 1H), 8.53 (d, J=2.0 Hz, 1H), 8.11-8.01 (m, 1H), 7.96-7.83 (m, 2H), 7.47-7.32 (m, 1H), 7.06 (t, J=54.6 Hz, 1H), 4.55 (s, 2H), 3.65 (s, 2H), 2.59-2.40 (m, 2H), 2.28-2.13 (m, 2H), 1.96-1.77 (m, 1H), 1.73-1.55 (m, 1H).

Example 33: (5R)-3-[[5-[3-(Difluoromethyl)-4-fluoro-phenyl]-3-pyridyl]methyl]-5-methyl-oxazolidin-2-one

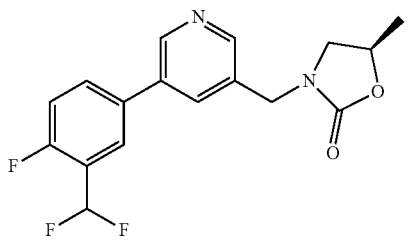 [SMILES: C[C@@H]1CN(Cc2cncc(-c3ccc(F)c(C(F)F)c3)c2)C(=O)O1]

Prepared analogous to Example 22, using (R)-5-methyl-oxazolidin-2-one in Step A. MS (ESI): mass calcd. for $C_{17}H_{15}F_3N_2O_2$, 336.1; m/z found, 337.0 [M+H]$^+$. $^1$H NMR (400 MHz, Methanol-d$_4$) δ 8.78 (d, J=2.2 Hz, 1H), 8.54 (d, J=2.1 Hz, 1H), 8.08-8.01 (m, 1H), 7.95-7.85 (m, 2H), 7.45-7.36 (m, 1H), 7.06 (t, J=54.6 Hz, 1H), 4.78-4.65 (m, 1H), 4.64-4.44 (m, 2H), 3.74-3.59 (m, 1H), 3.21-3.12 (m, 1H), 1.39 (d, J=6.3 Hz, 3H).

Example 34: 6-[[5-[3-(Difluoromethyl)-4-fluoro-phenyl]-3-pyridyl]methyl]-2,8-dioxa-6-azaspiro[3.4]octan-7-one

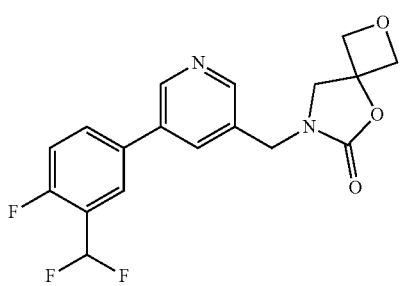 [SMILES: O=C1OC2(COC2)CN1Cc1cncc(-c2ccc(F)c(C(F)F)c2)c1]

Prepared analogous to Example 22, using 2,5-dioxa-7-azaspiro[3.4]octan-6-one (Intermediate 3) in Step A. MS (ESI): mass calcd. for $C_{18}H_{15}F_3N_2O_3$, 364.1; m/z found, 365.1 [M+H]$^+$. $^1$H NMR (400 MHz, Methanol-d$_4$) δ 8.78 (d, J=2.2 Hz, 1H), 8.54 (d, J=2.1 Hz, 1H), 8.07-8.03 (m, 1H), 7.97-7.83 (m, 2H), 7.50-7.32 (m, 1H), 7.06 (t, J=54.6 Hz, 1H), 4.88-4.85 (m, 2H), 4.71 (dd, J=7.9, 1.2 Hz, 2H), 4.55 (s, 2H), 3.86 (s, 2H).

Example 35: (R/S)-3-[[5-[3-(Difluoromethyl)-4-fluoro-phenyl]-3-pyridyl]methyl]-5-isopropyl-oxazolidin-2-one

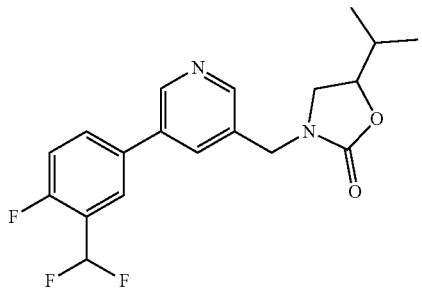 [SMILES: CC(C)C1CN(Cc2cncc(-c3ccc(F)c(C(F)F)c3)c2)C(=O)O1]

Prepared analogous to Example 22, using racemic 5-isopropyloxazolidin-2-one (Intermediate 4) in Step A. In Step B, complete conversion was not observed and additional 2-(3-(difluoromethyl)-4-fluorophenyl)-4,4,5,5-tetramethyl-1,3,2-dioxaborolane (Intermediate 39) (1.2 equiv) and RuPhos Pd G3 (0.05 equiv) were added, and the reaction mixture was stirred at 95° C. overnight. MS (ESI): mass calcd. for $C_{19}H_{19}F_3N_2O_2$, 364.1; m/z found, 365.2 [M+H]+. Analytical HPLC was obtained on an Agilent 1100 Series using a XBridge C18 column (5 um, 100×4.6 mm), mobile phase of 10-100% ACN in 20 mM NH4OH over 2 min and then hold at 100% ACN for 2 min, at a flow rate of 2.5 mL/min (Temperature=45° C.). $R_t$=1.99 min at 254 nm.

Example 36: (R*)-3-[[5-[3-(Difluoromethyl)-4-fluoro-phenyl]-3-pyridyl]methyl]-5-isopropyl-oxazolidin-2-one

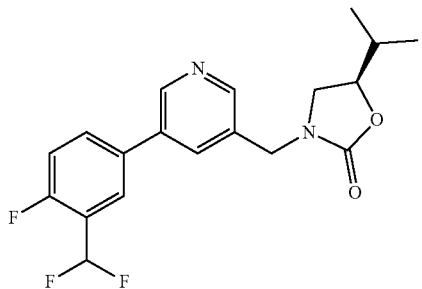 [SMILES: CC(C)[C@@H]1CN(Cc2cncc(-c3ccc(F)c(C(F)F)c3)c2)C(=O)O1]

The title compound was obtained as a single enantiomer by Chiral SFC purification of Example 35 performed using a Whelk O1 SS column (5 um, 250×21 mm), mobile phase of 28% MeOH, 72% CO2, and a flow rate of 42 mL/min (Temperature=40° C.). Elution was monitored following absorbance at 254 nm. The enantiomeric purity was confirmed by analytical SFC using a Whelk O1 SS column (5 um, 250×4.6 mm), mobile phase of 30% MeOH, 70% CO2, and a flow rate of 2 mL/min over 20 minutes. Elution was monitored following absorbance at 254 nm, enantiopurity 100%, retention time of 6.14 min. MS (ESI): mass calcd. for $C_{19}H_{19}F_3N_2O_2$, 364.1; m/z found, 365.1 [M+H]+. Analytical HPLC was obtained on an Agilent 1100 Series using a XBridge C18 column (5 um, 100×4.6 mm), mobile phase of 10-100% ACN in 20 mM NH4OH over 2 min and then hold at 100% ACN for 2 min, at a flow rate of 2.5 mL/min (Temperature=45° C.). $R_t$=2.04 min at 254 nm.

Example 37: (S*)-3-[[5-[3-(Difluoromethyl)-4-fluoro-phenyl]-3-pyridyl]methyl]-5-isopropyl-oxazolidin-2-one

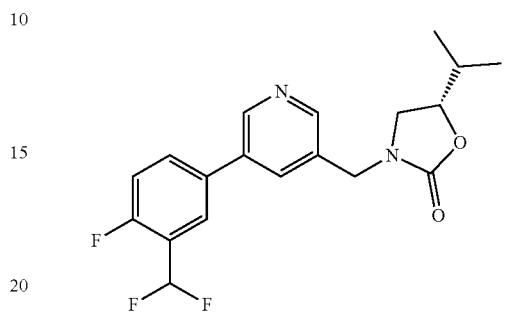

The title compound was obtained as a single enantiomer by Chiral SFC purification of Example 35 performed using a Whelk O1 SS column (5 um, 250×21 mm), mobile phase of 28% MeOH, 72% CO2, and a flow rate of 42 mL/min (Temperature=40° C.). Elution was monitored following absorbance at 254 nm. The enantiomeric purity was confirmed by analytical SFC using a Whelk O1 SS column (5 um, 250×4.6 mm), mobile phase of 30% MeOH, 70% CO2, and a flow rate of 2 mL/min over 20 minutes. Elution was monitored following absorbance at 254 nm, enantiopurity 100%, retention time of 7.33 min. MS (ESI): mass calcd. for $C_{19}H_{19}F_3N_2O_2$, 364.1; m/z found, 365.1 [M+H]+. Analytical HPLC was obtained on an Agilent 1100 Series using a XBridge C18 column (5 um, 100×4.6 mm), mobile phase of 10-100% ACN in 20 mM NH4OH over 2 min and then hold at 100% ACN for 2 min, at a flow rate of 2.5 mL/min (Temperature=45° C.). $R_t$=2.04 min at 254 nm.

Example 38: 3-[[5-[3-(Difluoromethyl)-4-fluoro-phenyl]-3-pyridyl]methyl]-1,3-oxazinan-2-one

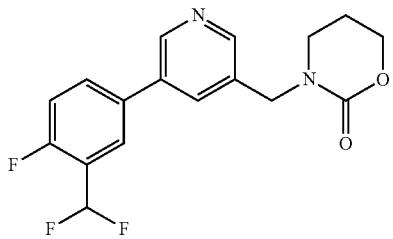 [SMILES: O=C1OCCCN1Cc1cncc(-c2ccc(F)c(C(F)F)c2)c1]

Prepared analogous to Example 22, using 1,3-oxazinan-2-one in Step A. MS (ESI): mass calcd. for $C_{17}H_{15}F_3N_2O_2$, 336.1; m/z found, 337.0 [M+H]+. 1H NMR (500 MHz, Methanol-$d_4$) δ 8.76 (d, J=2.2 Hz, 1H), 8.55 (d, J=2.0 Hz, 1H), 8.20-8.00 (m, 1H), 7.93-7.89 (m, 1H), 7.89-7.85 (m, 1H), 7.59-7.25 (m, 1H), 7.06 (t, J=54.6 Hz, 1H), 4.66 (s, 2H), 4.49-4.25 (m, 2H), 3.42 (t, J=6.2 Hz, 2H), 2.20-1.94 (m, 2H).

Example 39: (R/S)-3-[[5-[3-(Difluoromethyl)-4-fluoro-phenyl]-3-pyridyl]methyl]-5-(morpholinomethyl)oxazolidin-2-one

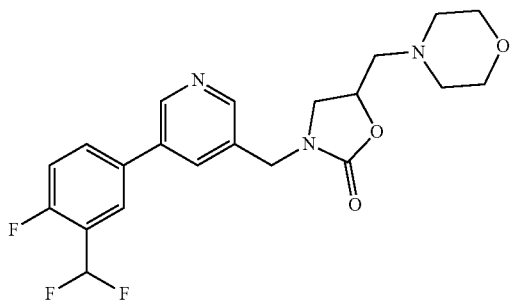 [SMILES: O=C1OC(CN2CCOCC2)CN1Cc1cncc(-c2ccc(F)c(C(F)F)c2)c1]

Prepared analogous to Example 22, using racemic 5-(morpholinomethyl)oxazolidin-2-one (Intermediate 5) in Step A. In Step B, complete conversion was not observed and additional 2-(3-(difluoromethyl)-4-fluorophenyl)-4,4,5,5-tetramethyl-1,3,2-dioxaborolane (Intermediate 39) (1.2 equiv) and RuPhos Pd G3 (0.05 equiv) were added, and the reaction mixture was stirred at 95° C. for 4 h. MS (ESI): mass calcd. for $C_{21}H_{22}F_3N_3O_3$, 421.2; m/z found, 422.1 [M+H]$^+$. Analytical HPLC was obtained on an Agilent 1100 Series using a XBridge C18 column (5 um, 100×4.6 mm), mobile phase of 10-100% ACN in 20 mM NH$_4$OH over 2 min and then hold at 100% ACN for 2 min, at a flow rate of 2.5 mL/min (Temperature=45° C.). $R_t$=1.797 min at 254 nm.

Example 40: (R*)-3-[[5-[3-(Difluoromethyl)-4-fluoro-phenyl]-3-pyridyl]methyl]-5-(morpholinomethyl)oxazolidin-2-one

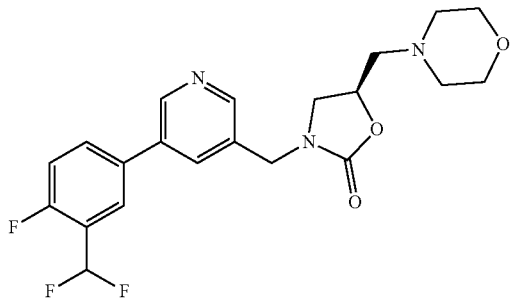 [SMILES: O=C1O[C@H](CN2CCOCC2)CN1Cc1cncc(-c2ccc(F)c(C(F)F)c2)c1]

The title compound was obtained as a single enantiomer by Chiral SFC purification of Example 39 performed using a Whelk O1 SS column (5 um, 250×21 mm), mobile phase of 30% MeOH with 0.3% iPrNH$_2$, 70% CO$_2$, and a flow rate of 42 mL/min (Temperature=40° C.). Elution was monitored following absorbance at 254 nm. The enantiomeric purity was confirmed by analytical SFC using a Whelk O1 SS column (3 um, 100×4.6 mm), mobile phase of 40% MeOH with 0.3% iPrNH$_2$, 60% CO$_2$, and a flow rate of 3.5 mL/min over 3 minutes. Elution was monitored following absorbance at 243 nm, enantiopurity 100%, retention time of 1.49 min. MS (ESI): mass calcd. for $C_{21}H_{22}F_3N_3O_3$, 421.2; m/z found, 422.1 [M+H]$^+$. $^1$H NMR (400 MHz, Methanol-d$_4$) δ 8.79 (d, J=2.2 Hz, 1H), 8.57 (d, J=2.0 Hz, 1H), 8.09-8.03 (m, 1H), 7.95-7.84 (m, 2H), 7.47-7.33 (m, 1H), 7.06 (t, J=54.6 Hz, 1H), 4.82-4.72 (m, 1H), 4.68-4.48 (m, 2H), 3.67 (t, J=8.7 Hz, 1H), 3.63-3.54 (m, 4H), 3.41-3.33 (m, 1H), 2.70-2.60 (m, 2H), 2.58-2.49 (m, 4H).

Example 41: (S*)-3-[[5-[3-(Difluoromethyl)-4-fluoro-phenyl]-3-pyridyl]methyl]-5-(morpholinomethyl)oxazolidin-2-one

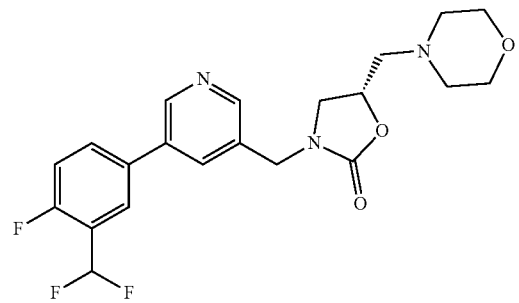 [SMILES: O=C1O[C@@H](CN2CCOCC2)CN1Cc1cncc(-c2ccc(F)c(C(F)F)c2)c1]

The title compound was obtained as a single enantiomer by Chiral SFC purification of Example 39 performed using a Whelk O1 SS column (5 um, 250×21 mm), mobile phase of 30% MeOH with 0.3% iPrNH$_2$, 70% CO$_2$, and a flow rate of 42 mL/min (Temperature=40° C.). Elution was monitored following absorbance at 254 nm. The enantiomeric purity was confirmed by analytical SFC using a Whelk O1 SS column (3 um, 100×4.6 mm), mobile phase of 40% MeOH with 0.3% iPrNH$_2$, 60% CO$_2$, and a flow rate of 3.5 mL/min over 3 minutes. Elution was monitored following absorbance at 243 nm, enantiopurity 100%, retention time of 1.68 min. MS (ESI): mass calcd. for $C_{21}H_{22}F_3N_3O_3$, 421.2; m/z found, 422.2 [M+H]$^+$. $^1$H NMR (400 MHz, Methanol-d$_4$) δ 8.79 (d, J=2.2 Hz, 1H), 8.57 (d, J=2.0 Hz, 1H), 8.16-8.00 (m, 1H), 7.96-7.73 (m, 2H), 7.48-7.33 (m, 1H), 7.06 (t, J=54.6 Hz, 1H), 4.83-4.72 (m, 1H), 4.67-4.51 (m, 2H), 3.67 (t, J=8.8 Hz, 1H), 3.63-3.54 (m, 4H), 3.42-3.32 (m, 1H), 2.64-2.59 (m, 2H), 2.55-2.48 (m, 4H).

Example 42: 2-[[5-[3-(Difluoromethyl)-4-fluoro-phenyl]-3-pyridyl]methyl]-4,8-dioxa-2-azaspiro[4.5]decan-3-one

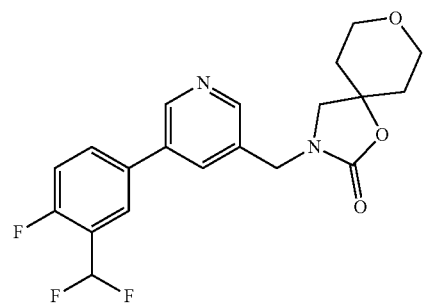 [SMILES: O=C1OC2(CCOCC2)CN1Cc1cncc(-c2ccc(F)c(C(F)F)c2)c1]

Prepared analogous to Example 22, using 1,8-dioxa-3-azaspiro[4.5]decan-2-one (Intermediate 6) in Step A. MS (ESI): mass calcd. for $C_{20}H_{19}F_3N_2O_3$, 392.1; m/z found, 393.1 [M+H]$^+$. $^1$H NMR (400 MHz, Methanol-d$_4$) δ 8.79 (d, J=2.2 Hz, 1H), 8.54 (d, J=2.0 Hz, 1H), 8.11-7.98 (m, 1H), 7.96-7.80 (m, 2H), 7.56-7.26 (m, 1H), 7.06 (t, J=54.6 Hz, 1H), 4.58 (s, 2H), 3.86-3.67 (m, 4H), 3.40 (s, 2H), 1.96-1.76 (m, 4H).

Example 43: 6-[[5-[3-(Difluoromethoxy)-4-fluorophenyl]-3-pyridyl]methyl]-8-oxa-2,6-diazaspiro[3.4]octan-7-one Trifluoroacetate Salt

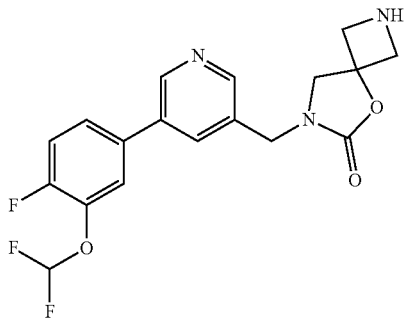 [SMILES: O=C1OC2(CNC2)CN1Cc1cncc(-c2ccc(F)c(OC(F)F)c2)c1]

Prepared analogous to Example 21, using 2-(3-(difluoromethoxy)-4-fluorophenyl)-4,4,5,5-tetramethyl-1,3,2-dioxaborolane (Intermediate 42) in Step B. MS (ESI): mass calcd. for $C_{18}H_{16}F_3N_3O_3$, 379.1; m/z found, 380.1 [M+H]$^+$. $^1$H NMR (400 MHz, Methanol-d$_4$) δ 9.02 (s, 1H), 8.76 (s, 1H), 8.61-8.48 (m, 1H), 7.74 (dd, J=7.3, 2.3 Hz, 1H), 7.72-7.67 (m, 1H), 7.47 (dd, J=10.2, 8.6 Hz, 1H), 6.97 (t, J=73.2 Hz, 1H), 4.67 (s, 2H), 4.40 (s, 4H), 3.92 (s, 2H).

Example 44: 3-[[5-(4-Fluoro-3-methyl-phenyl)-3-pyridyl]methyl]oxazolidin-2-one

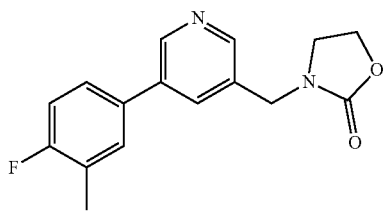 [SMILES: Cc1cc(-c2cncc(CN3CCOC3=O)c2)ccc1F]

Prepared analogous to Example 22, using (4-fluoro-3-methylphenyl)boronic acid in Step B. MS (ESI): mass calcd. for $C_{16}H_{15}FN_2O_2$, 286.1; m/z found, 287.1 [M+H]$^+$. $^1$H NMR (400 MHz, Methanol-d$_4$) δ 8.73 (d, J=2.2 Hz, 1H), 8.49 (d, J=2.0 Hz, 1H), 8.06-7.89 (m, 1H), 7.60-7.53 (m, 1H), 7.54-7.45 (m, 1H), 7.23-7.07 (m, 1H), 4.55 (s, 2H), 4.43-4.30 (m, 2H), 3.69-3.52 (m, 2H), 2.35 (d, J=2.0 Hz, 3H).

Example 45: 3-[[5-(2,4-Difluoro-3-methyl-phenyl)-3-pyridyl]methyl]oxazolidin-2-one

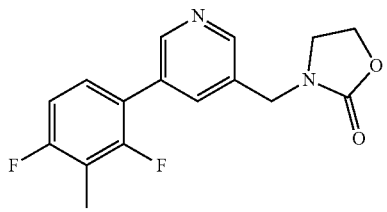 [SMILES: Cc1c(F)ccc(-c2cncc(CN3CCOC3=O)c2)c1F]

Prepared analogous to Example 22, using (2,4-difluoro-3-methylphenyl)boronic acid in Step B. MS (ESI): mass calcd. for $C_{16}H_{14}F_2N_2O_2$, 304.1; m/z found, 305.1 [M+H]$^+$*. $^1$H NMR (400 MHz, Methanol-d$_4$) δ 8.71-8.63 (m, 1H), 8.53 (d, J=2.1 Hz, 1H), 8.07-7.78 (m, 1H), 7.47-7.31 (m, 1H), 7.07 (td, J=8.7, 1.5 Hz, 1H), 4.55 (s, 2H), 4.46-4.19 (m, 2H), 3.69-3.44 (m, 2H), 2.42-2.05 (m, 3H).

Example 46: 3-[[5-[3-(Trifluoromethyl)phenyl]-3-pyridyl]methyl]oxazolidin-2-one

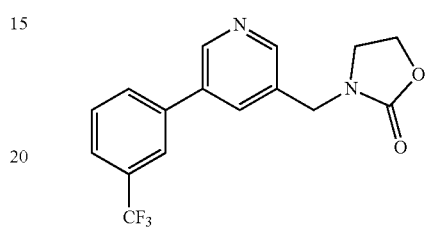

Prepared analogous to Example 22, using 3-(trifluoromethyl)phenylboronic acid in Step B. MS (ESI): mass calcd. for $C_{16}H_{13}F_3N_2O_2$, 322.1; m/z found, 323.1 [M+H]$^+$. $^1$H NMR (400 MHz, Methanol-d$_4$) δ 8.94-8.76 (m, 1H), 8.68-8.53 (m, 1H), 8.21-8.11 (m, 1H), 8.08-7.93 (m, 2H), 7.85-7.72 (m, 2H), 4.62 (s, 2H), 4.51-4.34 (m, 2H), 3.77-3.53 (m, 2H).

Example 47: 3-[[5-[4-Chloro-3-(difluoromethoxy)phenyl]-3-pyridyl]methyl]oxazolidin-2-one

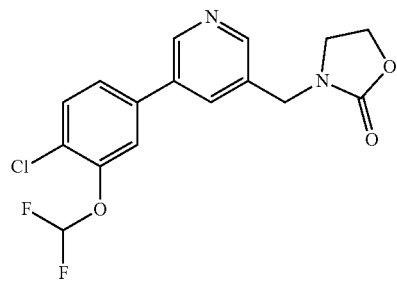 [SMILES: O=C1OCCN1Cc1cncc(-c2ccc(Cl)c(OC(F)F)c2)c1]

Prepared analogous to Example 22, using 2-(4-chloro-3-(difluoromethoxy)phenyl)-4,4,5,5-tetramethyl-1,3,2-dioxaborolane (Intermediate 43) in Step B. MS (ESI): mass calcd. for $C_{16}H_{13}ClF_2N_2O_3$, 354.1; m/z found, 355.0 [M+H]$^+$. $^1$H NMR (400 MHz, Methanol-d$_4$) δ 8.82 (d, J=1.9 Hz, 1H), 8.60 (d, J=1.7 Hz, 1H), 8.16-7.96 (m, 1H), 7.74-7.54 (m, 3H), 7.24-6.74 (m, 1H), 4.60 (s, 2H), 4.46-4.29 (m, 2H), 3.76-3.55 (m, 2H).

Example 48: 3-[[5-[3-Fluoro-4-(trifluoromethoxy)phenyl]-3-pyridyl]methyl]oxazolidin-2-one

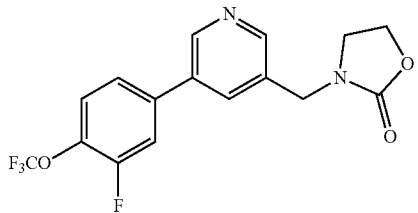 [SMILES: O=C1OCCN1Cc1cncc(-c2ccc(OC(F)(F)F)c(F)c2)c1]

Prepared analogous to Example 22, using (3-fluoro-4-(trifluoromethoxy)phenyl)boronic acid in Step B. MS (ESI): mass calcd. for $C_{16}H_{12}F_4N_2O_3$, 356.1; m/z found, 357.1 [M+H]$^+$. $^1$H NMR (400 MHz, Methanol-d$_4$) δ 8.81 (d, J=2.2 Hz, 1H), 8.57 (d, J=2.0 Hz, 1H), 8.12-8.04 (m, 1H), 7.74 (dd, J=11.3, 2.1 Hz, 1H), 7.68-7.45 (m, 2H), 4.57 (s, 2H), 4.43-4.30 (m, 2H), 3.72-3.50 (m, 2H).

Example 49: 3-[[5-[3-(1,1-Difluoroethyl)-4-fluorophenyl]-3-pyridyl]methyl]oxazolidin-2-one

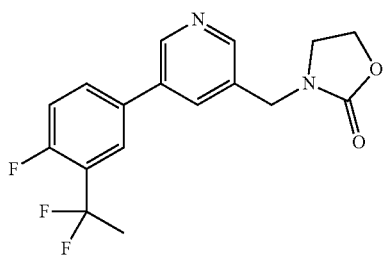 [SMILES: CC(F)(F)c1cc(-c2cncc(CN3CCOC3=O)c2)ccc1F]

Prepared analogous to Example 22, using 2-(3-(1,1-difluoroethyl)-4-fluorophenyl)-4,4,5,5-tetramethyl-1,3,2-dioxaborolane (Intermediate 40) in Step B. MS (ESI): mass calcd. for $C_{17}H_{15}F_3N_2O_2$, 336.1; m/z found, 337.1 [M+H]$^+$. $^1$H NMR (400 MHz, Methanol-d$_4$) δ 8.77 (d, J=2.2 Hz, 1H), 8.55 (d, J=2.0 Hz, 1H), 8.10-7.97 (m, 1H), 7.88-7.77 (m, 2H), 7.42-7.29 (m, 1H), 4.57 (s, 2H), 4.43-4.32 (m, 2H), 3.67-3.55 (m, 2H), 2.04 (td, J=18.7, 1.0 Hz, 3H).

Example 50: 3-[[5-[6-(Trifluoromethyl)-2-pyridyl]-3-pyridyl]methyl]oxazolidin-2-one

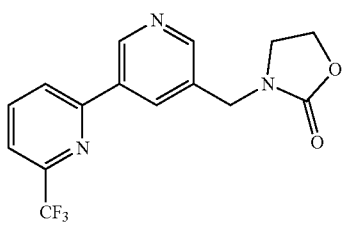 [SMILES: O=C1OCCN1Cc1cncc(-c2cccc(C(F)(F)F)n2)c1]

Prepared analogous to Example 22, using (6-(trifluoromethyl)pyridin-2-yl)boronic acid in Step B. In Step B, complete conversion was not observed and additional (6-(trifluoromethyl)pyridin-2-yl)boronic acid (1.2 equiv) and RuPhos Pd G3 (0.05 equiv) were added, and the reaction mixture was stirred at 95° C. for an additional 4 h. MS (ESI): mass calcd. for $C_{15}H_{12}F_3N_3O_2$, 323.1; m/z found, 324.1 [M+H]$^+$. $^1$H NMR (400 MHz, Methanol-d$_4$) δ 9.23 (d, J=2.2 Hz, 1H), 8.64 (d, J=2.1 Hz, 1H), 8.53-8.48 (m, 1H), 8.29-8.12 (m, 2H), 7.83 (dd, J=7.7, 0.9 Hz, 1H), 4.61 (s, 2H), 4.47-4.25 (m, 2H), 3.73-3.55 (m, 2H).

Example 51: 3-[[5-[2-(Trifluoromethyl)-4-pyridyl]-3-pyridyl]methyl]oxazoidin-2-one

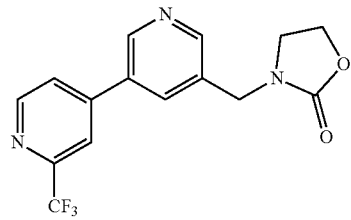 [SMILES: O=C1OCCN1Cc1cncc(-c2ccnc(C(F)(F)F)c2)c1]

Prepared analogous to Example 22, using (2-(trifluoromethyl)pyridin-4-yl)boronic acid in Step B. In Step B, complete conversion was not observed and additional (2-(trifluoromethyl)pyridin-4-yl)boronic acid (1.2 equiv) and RuPhos Pd G3 (0.05 equiv) were added, and the reaction mixture was stirred at 95° C. for an additional 4 h. MS (ESI): mass calcd. for $C_{15}H_{12}F_3N_3O_2$, 323.1; m/z found, 324.1 [M+H]$^+$. $^1$H NMR (400 MHz, Methanol-d$_4$) δ 8.96 (d, J=2.2 Hz, 1H), 8.83 (d, J=5.1 Hz, 1H), 8.67 (d, J=2.0 Hz, 1H), 8.27-8.22 (m, 1H), 8.21-8.15 (m, 1H), 8.02 (dd, J=5.1, 1.7 Hz, 1H), 4.60 (s, 2H), 4.47-4.25 (m, 2H), 3.75-3.52 (m, 2H).

Example 52: 3-[[5-[4-Fluoro-3-(trifluoromethyl)phenyl]-3-pyridyl]methyl]-1,3-oxazinan-2-one

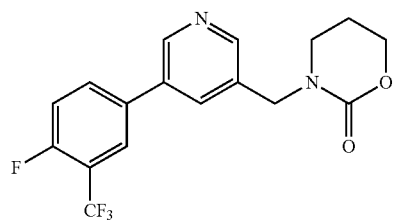 [SMILES: O=C1OCCCN1Cc1cncc(-c2ccc(F)c(C(F)(F)F)c2)c1]

Prepared analogous to Example 22, using 1,3-oxazinan-2-one (1.5 equiv) and NaH (2 equiv) in Step A, and (4-fluoro-3-(trifluoromethyl)phenyl)boronic acid in Step B. MS (ESI): mass calcd. for $C_{17}H_{14}F_4N_2O_2$, 354.1; m/z found, 355.0 [M+H]$^+$. $^1$H NMR (400 MHz, Methanol-d$_4$) δ 8.78 (d, J=2.2 Hz, 1H), 8.57 (d, J=2.0 Hz, 1H), 8.12-8.03 (m, 1H), 8.03-7.93 (m, 2H), 7.57-7.41 (m, 1H), 4.66 (s, 2H), 4.42-4.21 (m, 2H), 3.43 (t, J=6.2 Hz, 2H), 2.13-1.99 (m, 2H).

Example 53: 3-[[5-[4-chloro-3-(difluoromethoxy)phenyl]-3-pyridyl]methyl]-1,3-oxazinan-2-one

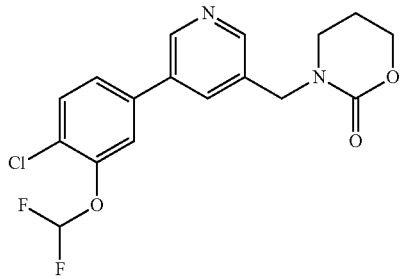 [SMILES: O=C1OCCCN1Cc1cncc(-c2ccc(Cl)c(OC(F)F)c2)c1]

Prepared analogous to Example 22, using 1,3-oxazinan-2-one (1.5 equiv) and NaH (2 equiv) in Step A, and 2-(4-chloro-3-(difluoromethoxy)phenyl)-4,4,5,5-tetramethyl-1,3,2-dioxaborolane (Intermediate 43) in Step B. MS (ESI): mass calcd. for $C_{17}H_{15}ClF_2N_2O_3$, 368.1; m/z found, 369.1 [M+H]$^+$. Analytical HPLC was obtained on an Agilent 1100 Series using a XBridge C18 column (5 um, 100×4.6 mm), mobile phase of 10-100% ACN in 20 mM NH$_4$OH over 2 min and then hold at 100% ACN for 2 min, at a flow rate of 2.5 mL/min (Temperature=45° C.). R$_t$=1.88 min at 254 nm.

Example 54: 3-[Dideuterio-[5-[3-(difluoromethyl)-4-fluoro-phenyl]-3-pyridyl]methyl]oxazolidin-2-one

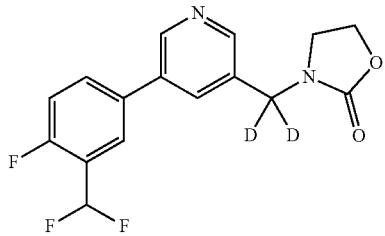 [SMILES: [2H]C([2H])(c1cncc(-c2ccc(F)c(C(F)F)c2)c1)N1CCOC1=O]

Prepared analogous to Example 22, using 3-bromo-5-(chloromethyl-d$_2$)pyridine (Intermediate 11) in Step A. MS (ESI): mass calcd. for $C_{16}H_{11}D_2F_3N_2O_2$, 324.1; m/z found, 325.1 [M+H]$^+$. $^1$H NMR (400 MHz, Methanol-d$_4$) δ 8.78 (d, J=2.2 Hz, 1H), 8.55 (d, J=2.0 Hz, 1H), 8.12-8.01 (m, 1H), 7.94-7.83 (m, 2H), 7.44-7.33 (m, 1H), 7.05 (t, J=54.6 Hz, 1H), 4.47-4.27 (m, 2H), 3.66-3.54 (m, 2H).

Example 55: 3-[Dideuterio-[5-[3-(difluoromethoxy)-4-fluoro-phenyl]-3-pyridyl]methyl]-1,3-oxazinan-2-one

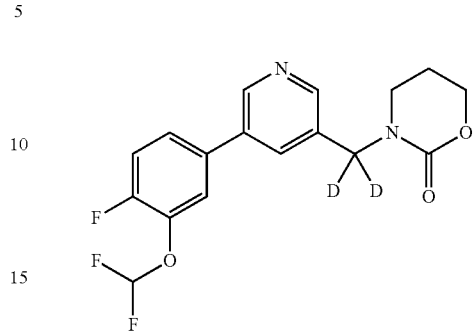

Prepared analogous to Example 1, using 3-bromo-5-(chloromethyl-d$_2$)pyridine (Intermediate 11), 1,3-oxazinan-2-one (1.5 equiv), and NaH (2 equiv) in Step A. MS (ESI): mass calcd. for $C_{17}H_{13}D_2F_3N_2O_3$, 354.1; m/z found, 355.1 [M+H]$^+$. $^1$H NMR (400 MHz, Methanol-d$_4$) δ 8.74 (d, J=2.3 Hz, 1H), 8.54 (d, J=2.0 Hz, 1H), 8.13-7.93 (m, 1H), 7.66-7.60 (m, 1H), 7.62-7.54 (m, 1H), 7.40 (dd, J=10.3, 8.5 Hz, 1H), 6.96 (t, J=73.4 Hz, 1H), 4.42-4.28 (m, 2H), 3.50-3.36 (m, 2H), 2.14-1.93 (m, 2H).

Example 56: 3-[Dideuterio-[5-[3-(difluoromethoxy)-4-fluoro-phenyl]-2-methyl-3-pyridyl]methyl]-1,3-oxazinan-2-one

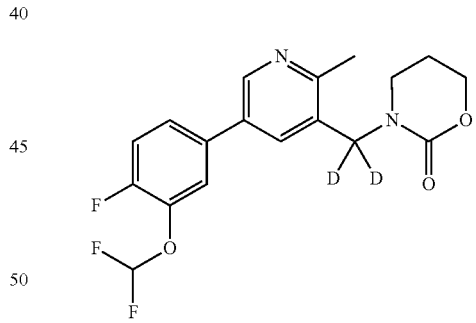

Prepared analogous to Example 62, using 3-((5-bromo-2-methylpyridin-3-yl)methyl-d$_2$)-1,3-oxazinan-2-one (Intermediate 36) and 2-(3-(difluoromethoxy)-4-fluorophenyl)-4,4,5,5-tetramethyl-1,3,2-dioxaborolane (Intermediate 42) in Step B. MS (ESI): mass calcd. for $C_{18}H_{15}D_2F_3N_2O_3$, 368.1; m/z found, 369.1 [M+H]$^+$. $^1$H NMR (500 MHz, Chloroform-d) δ 8.60 (d, J=2.3 Hz, 1H), 7.61 (d, J=2.3 Hz, 1H), 7.43-7.35 (m, 2H), 7.31-7.23 (m, 1H), 6.62 (t, J=73.3 Hz, 1H), 4.47-4.19 (m, 2H), 3.39-3.11 (m, 2H), 2.60 (s, 3H), 2.19-1.99 (m, 2H).

Example 57: 3-[Dideuterio-[5-(4-fluoro-3-methylphenyl)-2-methyl-3-pyridyl]methyl]-1,3-oxazinan-2-one

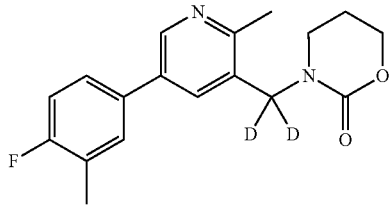 [SMILES: [2H]C([2H])(c1cc(-c2ccc(F)c(C)c2)cnc1C)N1CCCOC1=O]

Prepared analogous to Example 56, using (4-fluoro-3-methylphenyl)boronic acid in Step B. MS (ESI): mass calcd. for $C_{18}H_{17}D_2FN_2O_2$, 316.2; m/z found, 317.2 [M+H]$^+$. $^1$H NMR (500 MHz, CDCl$_3$) δ 8.60 (d, J=2.3 Hz, 1H), 7.63 (d, J=2.3 Hz, 1H), 7.36-7.30 (m, 2H), 7.16-7.04 (m, 1H), 4.45-4.18 (m, 2H), 3.33-3.17 (m, 2H), 2.59 (s, 3H), 2.35 (d, J=2.0 Hz, 3H), 2.16-1.99 (m, 2H).

Example 58: 3-[Dideuterio-[5-[3-(difluoromethyl)-4-fluoro-phenyl]-2-methyl-3-pyridyl]methyl]-1,3-oxazinan-2-one

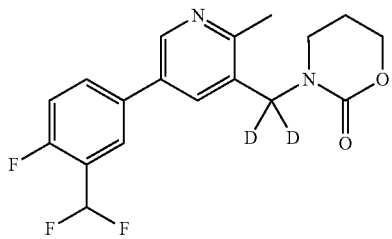 [SMILES: [2H]C([2H])(c1cc(-c2ccc(F)c(C(F)F)c2)cnc1C)N1CCCOC1=O]

Prepared analogous to Example 56, using 2-(3-(difluoromethyl)-4-fluorophenyl)-4,4,5,5-tetramethyl-1,3,2-dioxaborolane (Intermediate 39) in Step B. MS (ESI): mass calcd. for $C_{18}H_{15}D_2F_3N_2O_2$, 352.1; m/z found, 353.3 [M+H]$^+$. $^1$H NMR (500 MHz, CDCl$_3$) δ 8.62 (d, J=2.3 Hz, 1H), 7.77-7.71 (m, 1H), 7.67-7.61 (m, 2H), 7.25-7.19 (m, 1H), 6.95 (t, J=54.9 Hz, 1H), 4.43-4.18 (m, 2H), 3.53-3.10 (m, 2H), 2.61 (s, 3H), 2.19-1.99 (m, 2H).

Example 59: 3-[Dideuterio-[5-[3-(difluoromethyl)-4-fluoro-phenyl]-2-methyl-3-pyridyl]methyl]oxazolidin-2-one

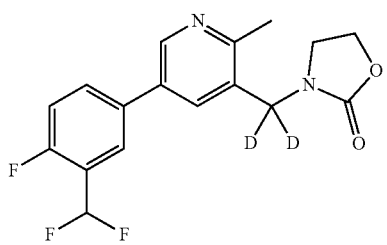 [SMILES: [2H]C([2H])(c1cc(-c2ccc(F)c(C(F)F)c2)cnc1C)N1CCOC1=O]

Prepared analogous to Example 79, using 3-(chloromethyl-d$_2$)-5-(3-(difluoromethyl)-4-fluorophenyl)-2-methylpyridine DCl salt (Intermediate 19). MS (ESI): mass calcd. for $C_{17}H_{13}D_2F_3N_2O_2$, 338.1; m/z found, 339.3 [M+H]$^+$. $^1$H NMR (500 MHz, DMSO-d$_6$) δ 8.73 (d, J=2.4 Hz, 1H), 8.00-7.94 (m, 2H), 7.92 (d, J=2.3 Hz, 1H), 7.56-7.48 (m, 1H), 7.26 (t, J=54.1 Hz, 1H), 4.32-4.25 (m, 2H), 3.47-3.41 (m, 2H), 2.52 (s, 3H).

Example 60: (R/S)-3-[1-[5-[3-(difluoromethyl)-4-fluoro-phenyl]-3-pyridyl]ethyl]oxazolidin-2-one

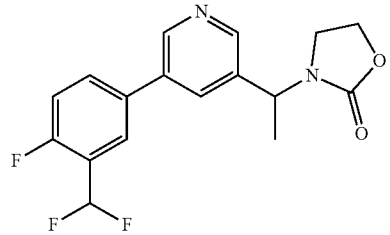 [SMILES: CC(c1cncc(-c2ccc(F)c(C(F)F)c2)c1)N1CCOC1=O]

Prepared analogous to Example 22, using 3-bromo-5-(1-chloroethyl)pyridine (Intermediate 14) in Step A. MS (ESI): mass calcd. for $C_{17}H_{15}F_3N_2O_2$, 336.1; m/z found, 337.0 [M+H]$^+$. $^1$H NMR (400 MHz, Chloroform-d) δ 8.77 (d, J=2.2 Hz, 1H), 8.64 (d, J=2.1 Hz, 1H), 7.84-7.80 (m, 1H), 7.80-7.75 (m, 1H), 7.71-7.59 (m, 1H), 7.32-7.22 (m, 1H), 6.96 (t, J=54.8 Hz, 1H), 5.35-5.22 (m, 1H), 4.55-4.16 (m, 2H), 3.71-3.48 (m, 1H), 3.36-3.07 (m, 1H), 1.69 (d, J=7.2 Hz, 3H).

Example 61: (R/S)-3-[1-[5-[3-(difluoromethyl)-4-fluoro-phenyl]-3-pyridyl]ethyl]-1,3-oxazinan-2-one

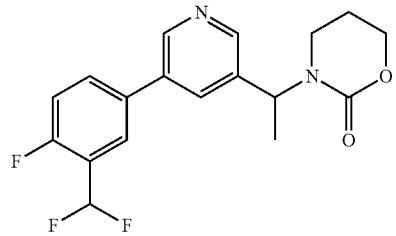 [SMILES: CC(c1cncc(-c2ccc(F)c(C(F)F)c2)c1)N1CCCOC1=O]

Prepared analogous to Example 22, using 3-bromo-5-(1-chloroethyl)pyridine (Intermediate 14) and 1,3-oxazinan-2-one in Step A. MS (ESI): mass calcd. for $C_{18}H_{17}F_3N_2O_2$, 350.1; m/z found, 351.0 [M+H]$^+$. $^1$H NMR (400 MHz, Methanol-d$_4$) δ 8.75 (d, J=2.1 Hz, 1H), 8.58 (d, J=1.9 Hz, 1H), 8.11-7.99 (m, 1H), 7.95-7.82 (m, 2H), 7.45-7.32 (m, 1H), 7.06 (t, J=54.5 Hz, 1H), 5.67 (q, J=7.2 Hz, 1H), 4.42-4.06 (m, 2H), 3.54-3.35 (m, 1H), 3.20-2.94 (m, 1H), 2.14-1.88 (m, 2H), 1.70 (d, J=7.2 Hz, 3H).

Example 62: 3-[[5-[3-(Difluoromethyl)phenyl]-2-methyl-3-pyridyl]methyl]-1,3-oxazinan-2-one

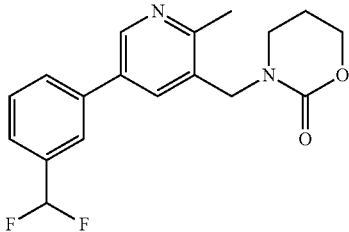 [SMILES: Cc1ncc(-c2cccc(C(F)F)c2)cc1CN1CCCOC1=O]

To a solution of 3-[(5-bromo-2-methyl-3-pyridyl)methyl]-1,3-oxazinan-2-one (Intermediate 37, 100 mg, 0.351 mmol) in degassed acetonitrile (2.46 mL) and water (386 μL) was added (3-(difluoromethyl)phenyl)boronic acid (66 mg, 0.384 mmol), [1,1'-bis(diphenylphosphino) ferrocene]dichloropalladium(II) (34 mg, 0.0465 mmol) and sodium carbonate (112 mg, 1.06 mmol). The reaction mixture was stirred at 80° C. for 1 h under argon, poured into water (5 mL) and extracted with ethyl acetate (3×5 mL). The combined organic layers were dried over sodium sulfate, filtered and evaporated. The residue was purified by preparative HPLC (Method D) to afford the title compound (99 mg, 0.298 mmol, 85%) as a light brown powder. MS (ESI): mass calcd. for $C_{18}H_{18}F_2N_2O_2$, 332.1; m/z found, 333.1 [M+H]$^+$. $^1$H NMR (500 MHz, DMSO-d$_6$) δ 8.71 (d, J=2.3 Hz, 1H), 7.92-7.84 (m, 2H), 7.78 (d, J=2.3 Hz, 1H), 7.70-7.59 (m, 2H), 7.11 (t, J=55.8 Hz, 1H), 4.59 (s, 2H), 4.27-4.21 (m, 2H), 3.24 (t, J=6.2 Hz, 2H), 2.54-2.47 (m, 3H), 2.02-1.94 (m, 2H).

Example 63: 3-[[5-[3-(Difluoromethoxy)phenyl]-2-methyl-3-pyridyl]methyl]-1,3-oxazinan-2-one

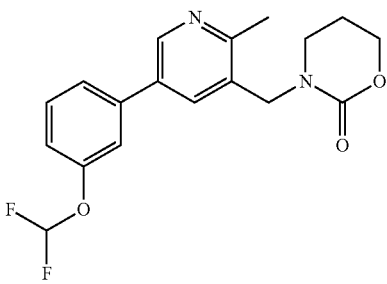 [SMILES: Cc1ncc(-c2cccc(OC(F)F)c2)cc1CN1CCCOC1=O]

Prepared analogous to Example 62, using (3-(difluoromethoxy)phenyl)boronic acid in Step B. MS (ESI): mass calcd. for $C_{17}H_{18}F_2N_2O_3$, 348.1; m/z found, 349.1 [M+H]$^+$. $^1$H NMR (500 MHz, DMSO-d$_6$) δ 8.70 (d, J=2.4 Hz, 1H), 7.76 (d, J=2.4 Hz, 1H), 7.60-7.53 (m, 2H), 7.52-7.47 (m, 1H), 7.34 (t, J=74.2 Hz, 1H), 7.26-7.21 (m, 1H), 4.57 (s, 2H), 4.27-4.20 (m, 2H), 3.25 (t, J=6.1 Hz, 2H), 2.55-2.47 (m, 3H), 2.02-1.94 (m, 2H).

Example 64: 3-[[5-(3-Chlorophenyl)-2-methyl-3-pyridyl]methyl]-1,3-oxazinan-2-one

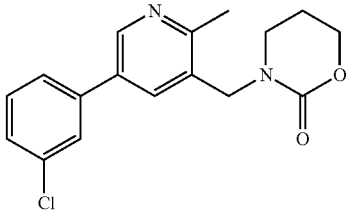 [SMILES: Cc1ncc(-c2cccc(Cl)c2)cc1CN1CCCOC1=O]

Prepared analogous to Example 62, using (3-chlorophenyl)boronic acid in Step B. MS (ESI): mass calcd. for $C_{17}H_{17}ClN_2O_2$, 316.1; m/z found, 317.1 [M+H]$^+$. $^1$H NMR (500 MHz, DMSO-d$_6$) δ 8.70 (d, J=2.4 Hz, 1H), 7.81-7.74 (m, 2H), 7.69-7.65 (m, 1H), 7.55-7.50 (m, 1H), 7.50-7.46 (m, 1H), 4.57 (s, 2H), 4.27-4.21 (m, 2H), 3.24 (t, J=6.2 Hz, 2H), 2.56-2.44 (m, 3H), 2.02-1.93 (m, 2H).

Example 65: 3-[[5-(3-Chloro-4-fluoro-phenyl)-2-methyl-3-pyridyl]methyl]-1,3-oxazinan-2-one

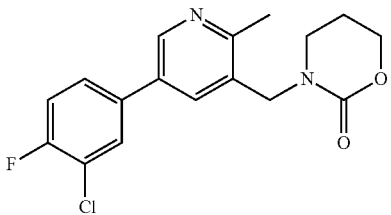 [SMILES: Cc1ncc(-c2ccc(F)c(Cl)c2)cc1CN1CCCOC1=O]

Prepared analogous to Example 62, using (3-chloro-4-fluorophenyl)boronic acid in Step B. MS (ESI): mass calcd. for $C_{17}H_{16}ClFN_2O_2$, 334.1; m/z found, 335.1 [M+H]$^+$. $^1$H NMR (500 MHz, DMSO-d$_6$) δ 8.72-8.67 (m, 1H), 7.99-7.92 (m, 1H), 7.80-7.75 (m, 1H), 7.75-7.68 (m, 1H), 7.58-7.51 (m, 1H), 4.57 (s, 2H), 4.29-4.20 (m, 2H), 3.23 (t, J=6.2 Hz, 2H), 2.54-2.46 (m, 3H), 2.03-1.93 (m, 2H).

Example 66: 3-[[5-(4-Fluoro-3-methyl-phenyl)-2-methyl-3-pyridyl]methyl]-1,3-oxazinan-2-one

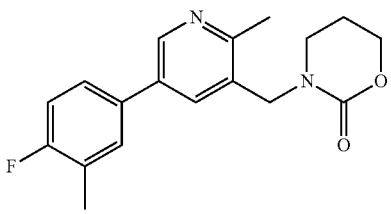 [SMILES: Cc1cc(-c2cnc(C)c(CN3CCCOC3=O)c2)ccc1F]

Prepared analogous to Example 62, using 4-fluoro-3-methylphenylboronic acid in Step B. MS (ESI): mass calcd. for $C_{18}H_{19}FN_2O_2$, 314.1; m/z found, 315.2 [M+H]$^+$. $^1$H NMR (500 MHz, DMSO-d$_6$) δ 8.64 (d, J=2.3 Hz, 1H), 7.70 (d, J=2.3 Hz, 1H), 7.62 (dd, J=7.6, 2.4 Hz, 1H), 7.55-7.50 (m, 1H), 7.29-7.23 (m, 1H), 4.56 (s, 2H), 4.26-4.22 (m, 2H), 3.23 (t, J=6.2 Hz, 2H), 2.48 (s, 3H), 2.33-2.31 (m, 3H), 2.01-1.94 (m, 2H).

Example 67: 3-[[5-(3,4-Difluorophenyl)-2-methyl-3-pyridyl]methyl]-1,3-oxazinan-2-one

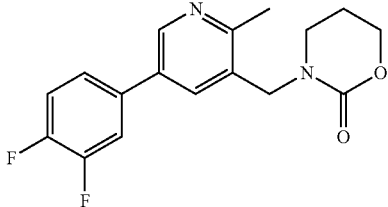 [SMILES: Cc1ncc(-c2ccc(F)c(F)c2)cc1CN1CCCOC1=O]

Prepared analogous to Example 62, using 3,4-difluorophenylboronic acid in Step B. MS (ESI): mass calcd. for $C_{17}H_{16}F_2N_2O_2$, 318.1; m/z found, 319.1 [M+H]$^+$. $^1$H NMR (500 MHz, DMSO-d$_6$) δ 8.69 (d, J=2.3 Hz, 1H), 7.88-7.81 (m, 1H), 7.75 (d, J=2.3 Hz, 1H), 7.60-7.52 (m, 2H), 4.56 (s, 2H), 4.28-4.21 (m, 2H), 3.24 (t, J=6.2 Hz, 2H), 2.56-2.43 (m, 3H), 2.04-1.93 (m, 2H).

Example 68: 3-[[5-(4-Fluorophenyl)-2-methyl-3-pyridyl]methyl]-1,3-oxazinan-2-one

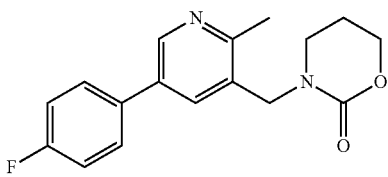 [SMILES: Cc1ncc(-c2ccc(F)cc2)cc1CN1CCCOC1=O]

Prepared analogous to Example 62, using 4-fluorophenylboronic acid in Step B. MS (ESI): mass calcd. for $C_{17}H_{17}FN_2O_2$, 300.1; m/z found, 301.2 [M+H]$^+$. $^1$H NMR (500 MHz, DMSO-d) 8.65 (d, J=2.3 Hz, 1H), 7.77-7.72 (m, 2H), 7.71 (d, J=2.3 Hz, 1H), 7.38-7.30 (m, 2H), 4.56 (s, 2H), 4.29-4.21 (m, 2H), 3.25 (t, J=6.2 Hz, 2H), 2.54-2.46 (m, 3H), 2.02-1.94 (m, 2H).

Example 69: 3-[[5-(3-Fluorophenyl)-2-methyl-3-pyridyl]methyl]-1,3-oxazinan-2-one

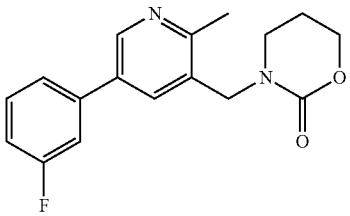 [SMILES: Cc1ncc(-c2cccc(F)c2)cc1CN1CCCOC1=O]

Prepared analogous to Example 62, using 3-fluorophenylboronic acid in Step B. MS (ESI): mass calcd. for $C_{17}H_{17}FN_2O_2$, 300.1; m/z found, 301.2 [M+H]$^+$. $^1$H NMR (300 MHz, DMSO-d$_6$) δ 8.71 (d, J=2.3 Hz, 1H), 7.77 (d, J=2.3 Hz, 1H), 7.64-7.49 (m, 3H), 7.31-7.19 (m, 1H), 4.57 (s, 2H), 4.29-4.19 (m, 2H), 3.25 (t, J=6.2 Hz, 2H), 2.60-2.40 (m, 3H), 2.04-1.92 (m, 2H).

Example 70: 3-[[5-(3,4-Difluoro-5-methyl-phenyl)-2-methyl-3-pyridyl]methyl]-1,3-oxazinan-2-one

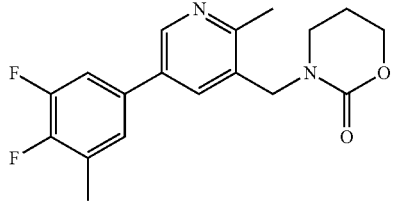 [SMILES: Cc1cc(-c2cnc(C)c(CN3CCCOC3=O)c2)cc(F)c1F]

Prepared analogous to Example 62, using 2-(3,4-difluoro-5-methylphenyl)-4,4,5,5-tetramethyl-1,3,2-dioxaborolane (Intermediate 8) in Step B. MS (ESI): mass calcd. for $C_{18}H_{18}F_2N_2O_2$, 332.1; m/z found, 333.1 [M+H]$^+$. $^1$H NMR (500 MHz, DMSO-d$_6$) δ 8.68 (d, J=2.4 Hz, 1H), 7.75 (d, J=2.3 Hz, 1H), 7.67-7.60 (m, 1H), 7.50-7.45 (m, 1H), 4.56 (s, 2H), 4.26-4.21 (m, 2H), 3.23 (t, J=6.2 Hz, 2H), 2.49 (s, 3H), 2.36 (d, J=2.1 Hz, 3H), 2.01-1.94 (m, 2H).

Example 71: 3-[[5-(2,4-Difluoro-3-methyl-phenyl)-2-methyl-3-pyridyl]methyl]-1,3-oxazinan-2-one

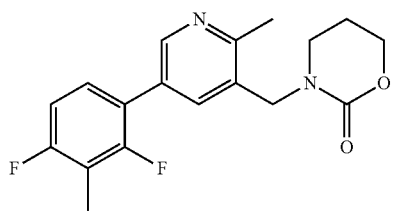 [SMILES: Cc1ncc(-c2ccc(F)c(C)c2F)cc1CN1CCCOC1=O]

Prepared analogous to Example 62, using 2,4-difluoro-3-methylphenylboronic acid pinacol ester in Step B. MS (ESI): mass calcd. for $C_{18}H_{18}F_2N_2O_2$, 332.1; m/z found, 333.1 [M+H]$^+$. $^1$H NMR (300 MHz, DMSO-d$_6$) δ 8.54-8.46 (m, 1H), 7.66-7.58 (m, 1H), 7.52-7.38 (m, 1H), 7.27-7.14 (m, 1H), 4.55 (s, 2H), 4.28-4.14 (m, 2H), 3.24 (t, J=6.2 Hz, 2H), 2.62-2.37 (m, 3H), 2.25-2.18 (m, 3H), 2.03-1.90 (m, 2H).

Example 72: 3-[[5-(2,4-Difluorophenyl)-2-methyl-3-pyridyl]methyl]-1,3-oxazinan-2-one

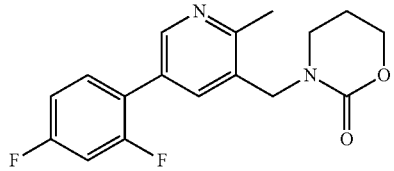 [SMILES: Cc1ncc(-c2ccc(F)cc2F)cc1CN1CCCOC1=O]

Prepared analogous to Example 62, using 2,4-difluorophenylboronic acid in Step B. MS (ESI): mass calcd. for $C_{17}H_{16}F_2N_2O_2$, 318.1; m/z found, 319.2 [M+H]$^+$. $^1$H NMR (300 MHz, DMSO-d$_6$) δ 8.55-8.48 (m, 1H), 7.70-7.58 (m, 2H), 7.48-7.36 (m, 1H), 7.24 (td, J=8.4, 2.5 Hz, 1H), 4.55 (s, 2H), 4.28-4.14 (m, 2H), 3.24 (t, J=6.2 Hz, 2H), 2.63-2.36 (m, 3H), 2.03-1.89 (m, 2H).

Example 73: 3-[[5-(3,4-Dichlorophenyl)-2-methyl-3-pyridyl]methyl]-1,3-oxazinan-2-one

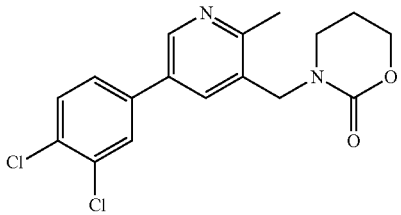 [SMILES: Cc1ncc(-c2ccc(Cl)c(Cl)c2)cc1CN1CCCOC1=O]

Prepared analogous to Example 62, using 3,4-dichlorophenylboronic acid in Step B. MS (ESI): mass calcd. for $C_{17}H_{16}Cl_2N_2O_2$, 350.1; m/z found, 351.1 [M+H]$^+$. $^1$H NMR (500 MHz, DMSO-d$_6$) δ 8.72 (d, J=2.3 Hz, 1H), 8.00 (d, J=2.1 Hz, 1H), 7.80 (d, J=2.4 Hz, 1H), 7.75 (d, J=8.4 Hz, 1H), 7.70 (dd, J=8.4, 2.2 Hz, 1H), 4.57 (s, 2H), 4.28-4.19 (m, 2H), 3.23 (t, J=6.2 Hz, 2H), 2.54-2.43 (m, 3H), 2.02-1.93 (m, 2H).

Example 74: 3-[[2-Methyl-5-[3-(Trifluoromethyl)phenyl]-3-pyridyl]methyl]-1,3-oxazinan-2-one

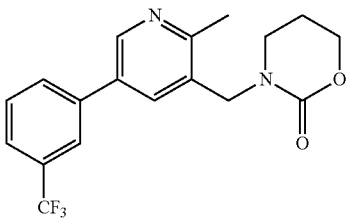 [SMILES: Cc1ncc(-c2cccc(C(F)(F)F)c2)cc1CN1CCCOC1=O]

Prepared analogous to Example 62, using 3-(trifluoromethyl)phenylboronic acid in Step B. MS (ESI): mass calcd. for $C_{18}H_{17}F_3N_2O_2$, 350.1; m/z found, 351.2 [M+H]$^+$. $^1$H NMR (500 MHz, DMSO-d$_6$) δ 8.76 (d, J=2.3 Hz, 1H), 8.04-7.98 (m, 2H), 7.84 (d, J=2.4 Hz, 1H), 7.81-7.71 (m, 2H), 4.59 (s, 2H), 4.27-4.19 (m, 2H), 3.24 (t, J=6.2 Hz, 2H), 2.51 (s, 3H), 2.01-1.93 (m, 2H).

Example 75: 3-[[5-[4-Fluoro-3-(trifluoromethyl)phenyl]-2-methyl-3-pyridyl]methyl]-1,3-oxazinan-2-one

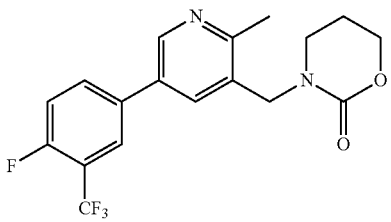 [SMILES: Cc1ncc(-c2ccc(F)c(C(F)(F)F)c2)cc1CN1CCCOC1=O]

Prepared analogous to Example 62, using 4-fluoro-3-(trifluoromethyl)phenylboronic acid in Step B. MS (ESI): mass calcd. for $C_{18}H_{16}F_4N_2O_2$, 368.1; m/z found, 369.1 [M+H]$^+$. $^1$H NMR (300 MHz, DMSO-d$_6$) δ 8.74 (d, J=2.3 Hz, 1H), 8.13-7.99 (m, 2H), 7.82 (d, J=2.3 Hz, 1H), 7.71- 7.60 (m, 1H), 4.58 (s, 2H), 4.29-4.16 (m, 2H), 3.24 (t, J=6.1 Hz, 2H), 2.62-2.36 (m, 3H), 2.03-1.91 (m, 2H).

Example 76: 3-[[5-(4-Fluoro-3-methyl-phenyl)-2-methyl-3-pyridyl]methyl]oxazolidin-2-one

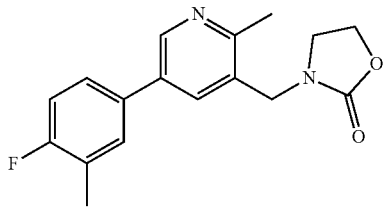 [SMILES: Cc1cc(-c2cnc(C)c(CN3CCOC3=O)c2)ccc1F]

Prepared analogous to Example 62, using 3-((5-bromo-2-methylpyridin-3-yl)methyl)oxazolidin-2-one (Intermediate 38) and 4-fluoro-3-methylphenylboronic acid in Step B. MS (ESI): mass calcd. for $C_{17}H_{17}FN_2O_2$, 300.1; m/z found, 301.2 [M+H]$^+$. $^1$H NMR (500 MHz, CDCl$_3$) δ 8.61 (d, J=2.3 Hz, 1H), 7.63 (d, J=2.2 Hz, 1H), 7.40-7.27 (m, 2H), 7.07 (t, J=8.9 Hz, 1H), 4.51 (s, 2H), 4.40-4.26 (m, 2H), 3.53-3.39 (m, 2H), 2.60 (s, 3H), 2.33 (d, J=1.9 Hz, 3H).

Example 77: 3-[[5-(2,4-Difluoro-3-methyl-phenyl)-2-methyl-3-pyridyl]methyl]oxazolidin-2-one

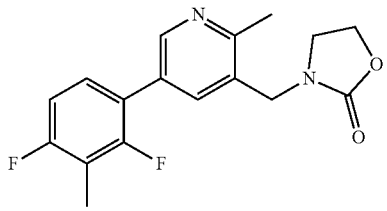 [SMILES: Cc1ncc(-c2ccc(F)c(C)c2F)cc1CN1CCOC1=O]

Prepared analogous to Example 76, using (2,4-difluoro-3-methylphenyl)boronic acid in Step B. MS (ESI): mass calcd. for $C_{17}H_{16}F_2N_2O_2$, 318.1; m/z found, 319.2 [M+H]$^+$. $^1$H NMR (500 MHz, CDCl$_3$) δ 8.62-8.46 (m, 1H), 7.69-7.54 (m, 1H), 7.25-7.11 (m, 1H), 6.94 (td, J=8.5, 1.4 Hz, 1H), 4.51 (s, 2H), 4.39-4.24 (m, 2H), 3.57-3.35 (m, 2H), 2.61 (s, 3H), 2.36-2.14 (m, 3H).

Example 78: 3-[[5-[3-(1,1-Difluoroethyl)-4-fluoro-phenyl]-2-methyl-3-pyridyl]methyl]oxazolidin-2-one

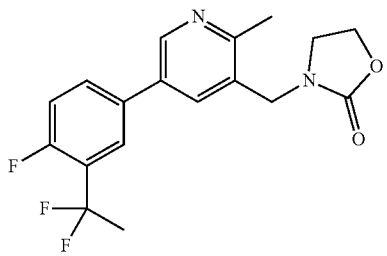 [SMILES: Cc1ncc(-c2ccc(F)c(C(C)(F)F)c2)cc1CN1CCOC1=O]

Prepared analogous to Example 76, using 2-(3-(1,1-difluoroethyl)-4-fluorophenyl)-4,4,5,5-tetramethyl-1,3,2-dioxaborolane (Intermediate 40) in Step B. MS (ESI): mass calcd. for $C_{18}H_{17}F_3N_2O_2$, 350.1; m/z found, 351.1 [M+H]+. 1H NMR (400 MHz, CDCl3) δ 8.63 (d, J=2.3 Hz, 1H), 7.69 (dd, J=7.0, 2.5 Hz, 1H), 7.66 (d, J=2.3 Hz, 1H), 7.62-7.54 (m, 1H), 7.26-7.18 (m, 1H), 4.53 (s, 2H), 4.38-4.31 (m, 2H), 3.50-3.43 (m, 2H), 2.62 (s, 3H), 2.04 (td, J=18.7, 1.2 Hz, 3H).

Example 79: 3-[[5-[3-(Difluoromethoxy)-4-fluoro-phenyl]-2-methyl-3-pyridyl]methyl] oxazolidin-2-one

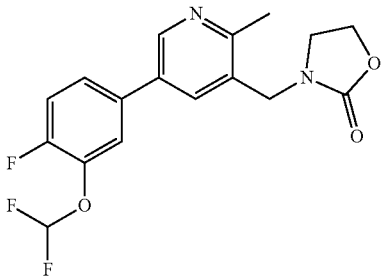 [SMILES: Cc1ncc(-c2ccc(F)c(OC(F)F)c2)cc1CN1CCOC1=O]

To a solution of 2-oxazolidinone (167 mg, 1.92 mmol) in DMF (6.3 mL) was added NaH (60% dispersion in mineral oil, 166 mg, 4.15 mmol), and the reaction mixture was stirred at 0° C. for 30 min. Then, 3-(chloromethyl)-5-(3-(difluoromethoxy)-4-fluorophenyl)-2-methylpyridine hydrochloride (Intermediate 17, 500 mg, 1.48 mmol) was added at 0° C. The reaction mixture was allowed to warm to room temperature and stirred for 2 h. Complete conversion was not observed and the reaction mixture was cooled to 0° C. An additional portion of NaH (60% dispersion in mineral oil, 30 mg, 0.75 mmol) was added, and the reaction was further stirred at room temperature for 1 h. Then, the reaction mixture was poured into water (15 mL) and extracted with EtOAc (3×15 mL). The organic layers were combined, concentrated and subjected to purification. Purification via silica gel column chromatography (0-2% methanol in DCM) gave the product. The product was triturated with Et2O (8 mL) to yield the title compound (405 mg, 1.15 mmol, 78%) as a white powder. MS (ESI): mass calcd. for $C_{17}H_{15}F_3N_2O_3$, 352.1; m/z found, 353.1 [M+H]+. 1H NMR (500 MHz, DMSO-d6) δ 8.72 (d, J=2.3 Hz, 1H), 7.89 (d, J=2.3 Hz, 1H), 7.73 (dd, J=7.6, 2.3 Hz, 1H), 7.68-7.63 (m, 1H), 7.54 (dd, J=10.5, 8.6 Hz, 1H), 7.35 (t, J=73.3 Hz, 1H), 4.46 (s, 2H), 4.33-4.26 (m, 2H), 3.48-3.41 (m, 2H), 2.51 (s, 3H).

Example 80: (R/S)-3-[[5-[3-(Difluoromethoxy)-4-fluoro-phenyl]-2-methyl-3-pyridyl]methyl]-5-methyl-oxazolidin-2-one

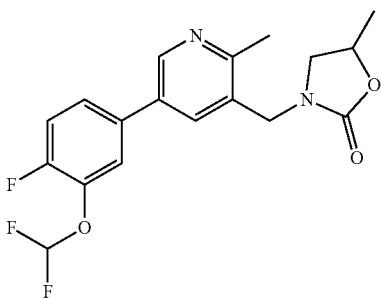 [SMILES: Cc1ncc(-c2ccc(F)c(OC(F)F)c2)cc1CN1CC(C)OC1=O]

Prepared analogous to Example 79, using racemic 5-methyl-1,3-oxazolidin-2-one. MS (ESI): mass calcd. for $C_{18}H_{17}F_3N_2O_3$, 366.1; m/z found, 367.1 [M+H]+. 1H NMR (500 MHz, Chloroform-d) δ 8.63 (s, 1H), 7.62 (d, J=2.1 Hz, 1H), 7.44-7.40 (m, 1H), 7.40-7.36 (m, 1H), 7.32-7.27 (m, 1H), 6.62 (t, J=73.3 Hz, 1H), 4.72-4.63 (m, 1H), 4.62-4.41 (m, 2H), 3.54 (t, J=8.3 Hz, 1H), 3.03 (dd, J=8.4, 6.9 Hz, 1H), 2.62 (s, 3H), 1.43 (d, J=6.2 Hz, 3H).

Example 81: (R/S)-3-[[5-[3-(Difluoromethoxy)-4-fluoro-phenyl]-2-methyl-3-pyridyl]methyl]-4-methyl-oxazolidin-2-one

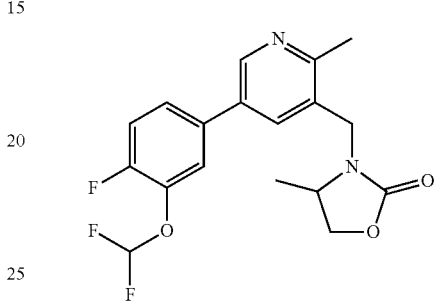

Prepared analogous to Example 79, using racemic 2-methyl-1,3-oxazolidin-2-one. MS (ESI): mass calcd. for $C_{18}H_{17}F_3N_2O_3$, 366.1; m/z found, 367.1 [M+H]+. 1H NMR (500 MHz, Chloroform-d) δ 8.57 (d, J=2.3 Hz, 1H), 7.61 (d, J=2.2 Hz, 1H), 7.40-7.36 (m, 1H), 7.36-7.32 (m, 1H), 7.28-7.20 (m, 1H), 6.59 (t, J=73.3 Hz, 1H), 4.69 (d, J=15.9 Hz, 1H), 4.44-4.39 (m, 1H), 4.31 (d, J=15.9 Hz, 1H), 3.90 (dd, J=8.7, 6.2 Hz, 1H), 3.77-3.69 (m, 1H), 2.59 (s, 3H), 1.22 (d, J=6.2 Hz, 3H).

Example 82: (R*)-3-[[5-[3-(Difluoromethoxy)-4-fluoro-phenyl]-2-methyl-3-pyridyl]methyl]-4-methyl-oxazolidin-2-one

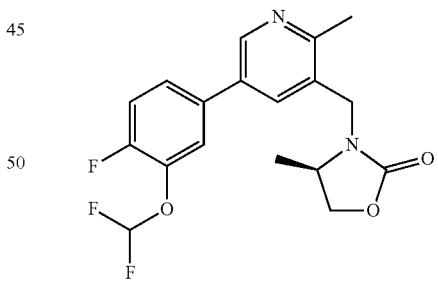

The title compound was obtained as a single enantiomer by Chiral SFC purification of Example 81 performed using SFC (Stationary phase: Chiralpak IE, 5 μm 250×21 mm, Mobile phase: 10% methanol, 90% CO2). The enantiomeric purity was confirmed by analytical SFC using a Chiralpak IE column (5 μm 250×4.6 mm), mobile phase of 10% MeOH, 90% CO2, and a flow rate of 2 mL/min over 35 minutes. Elution was monitored following absorbance at 254 nm, enantiopurity 81.7%, retention time of 22.98 min. MS (ESI): mass calcd. for $C_{18}H_{17}F_3N_2O_3$, 366.1; m/z found, 367.0 [M+H]+. 1HNMR is in agreement with Example 81.

Example 83: (S*)-3-[[5-[3-(Difluoromethoxy)-4-fluoro-phenyl]-2-methyl-3-pyridyl]methyl]-4-methyl-oxazolidin-2-one

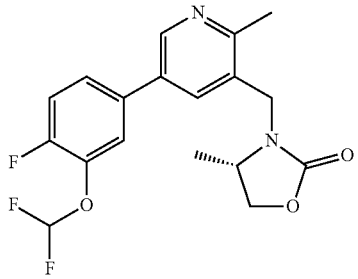 [SMILES: Cc1ncc(-c2ccc(F)c(OC(F)F)c2)cc1CN1C(=O)OC[C@@H]1C]

The title compound was obtained as a single enantiomer by Chiral SFC purification of Example 81 performed using SFC (Stationary phase: Chiralpak IE, 5 µm 250×21 mm, Mobile phase: 10% methanol, 90% $CO_2$). The enantiomeric purity was confirmed by analytical SFC using a Chiralpak IE column (5 µm 250×4.6 mm), mobile phase of 10% MeOH, 90% $CO_2$, and a flow rate of 2 mL/min over 35 minutes. Elution was monitored following absorbance at 254 nm, enantiopurity 81.2%, retention time of 23.42 min. MS (ESI): mass calcd. for $C_{18}H_{17}F_3N_2O_3$, 366.1; m/z found, 367.0 [M+H]$^+$. $^1$HNMR agrees with Example 81.

Example 84: 5-[[5-[3-(Difluoromethoxy)-4-fluoro-phenyl]-2-methyl-3-pyridyl]methyl]-7-oxa-5-azaspiro[2.4]heptan-6-one

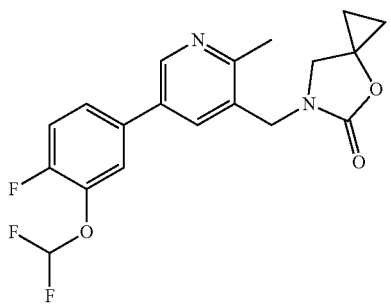 [SMILES: Cc1ncc(-c2ccc(F)c(OC(F)F)c2)cc1CN1CC2(CC2)OC1=O]

Prepared analogous to Example 79, using 4-oxa-6-azaspiro[2.4]heptan-5-one (Intermediate 2). MS (ESI): mass calcd. for $C_{19}H_{17}F_3N_2O_3$, 378.1; m/z found, 379.1 [M+H]$^+$. $^1$H NMR (500 MHz, Chloroform-d) δ 8.63 (s, 1H), 7.65 (d, J=2.3 Hz, 1H), 7.44-7.36 (m, 2H), 7.31-7.27 (m, 1H), 6.62 (t, J=73.3 Hz, 1H), 4.59 (s, 2H), 3.50 (s, 2H), 2.63 (s, 3H), 1.33-1.17 (m, 2H), 0.75-0.64 (m, 2H).

Example 85: 6-[[5-[3-(Difluoromethoxy)-4-fluoro-phenyl]-2-methyl-3-pyridyl]methyl]-8-oxa-6-azaspiro[3.4]octan-7-one

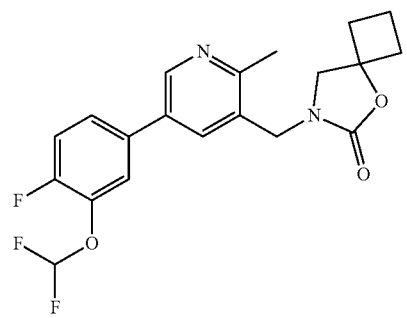 [SMILES: Cc1ncc(-c2ccc(F)c(OC(F)F)c2)cc1CN1CC2(CCC2)OC1=O]

Prepared analogous to Example 79, using 5-oxa-7-azaspiro[3.4]octane-6-one. MS (ESI): mass calcd. for $C_{20}H_{19}F_3N_2O_3$, 392.1; m/z found, 393.1 [M+H]$^+$. $^1$H NMR (500 MHz, Chloroform-d) δ 8.63 (d, J=2.3 Hz, 1H), 7.61 (d, J=2.3 Hz, 1H), 7.44-7.36 (m, 2H), 7.31-7.27 (m, 1H), 6.62 (t, J=73.2 Hz, 1H), 4.51 (s, 2H), 3.45 (s, 2H), 2.61 (s, 3H), 2.60-2.50 (m, 2H), 2.19-2.08 (m, 2H), 1.95-1.82 (m, 1H), 1.66-1.52 (m, 1H).

Example 86: (5R)-3-[[5-[3-(Difluoromethoxy)-4-fluoro-phenyl]-2-methyl-3-pyridyl]methyl]-5-methyl-oxazolidin-2-one

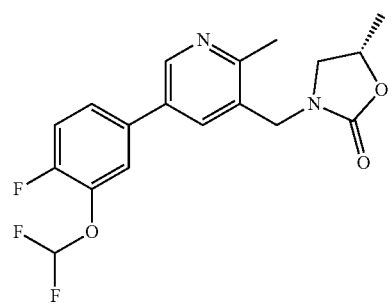 [SMILES: Cc1ncc(-c2ccc(F)c(OC(F)F)c2)cc1CN1C[C@H](C)OC1=O]

Prepared analogous to Example 79, using (R)-5-methyl-oxazolidin-2-one. MS (ESI): mass calcd. for $C_{18}H_{17}F_3N_2O_3$, 366.1; m/z found, 367.0 [M+H]$^+$. $^1$H NMR (500 MHz, Chloroform-d) δ 8.62 (d, J=2.3 Hz, 1H), 7.62 (d, J=2.3 Hz, 1H), 7.44-7.35 (m, 2H), 7.30-7.23 (m, 1H), 6.61 (t, J=73.3 Hz, 1H), 4.71-4.62 (m, 1H), 4.60-4.39 (m, 2H), 3.53 (t, J=8.3 Hz, 1H), 3.02 (dd, J=8.4, 6.9 Hz, 1H), 2.61 (s, 3H), 1.42 (d, J=6.3 Hz, 3H).

Example 87: 3-[[5-[3-(Difluoromethoxy)-4-fluorophenyl]-2-methyl-3-pyridyl]methyl]-5,5-dimethyl-oxazolidin-2-one

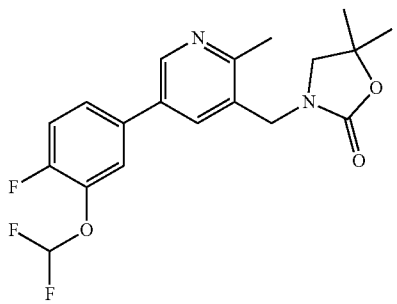 [SMILES: Cc1ncc(-c2ccc(F)c(OC(F)F)c2)cc1CN1CC(C)(C)OC1=O]

Prepared analogous to Example 79, using 5,5-dimethyl-1,3-oxazolidin-2-one. MS (ESI): mass calcd. for $C_{19}H_{19}F_3N_2O_3$, 380.1; m/z found, 381.1 [M+H]$^+$. $^1$H NMR (500 MHz, Chloroform-d) δ 8.63 (d, J=2.3 Hz, 1H), 7.62 (d, J=2.3 Hz, 1H), 7.44-7.35 (m, 2H), 7.28 (dd, J=10.0, 8.5 Hz, 1H), 6.61 (t, J=73.2 Hz, 1H), 4.53 (s, 2H), 3.18 (s, 2H), 2.62 (s, 3H), 1.45 (s, 6H).

Example 88: 3-[[5-[3-(Difluoromethoxy)-4-fluorophenyl]-2-methyl-3-pyridyl]methyl]-1,3-oxazinan-2-one

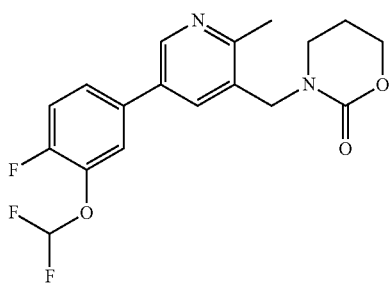 [SMILES: Cc1ncc(-c2ccc(F)c(OC(F)F)c2)cc1CN1CCCOC1=O]

Prepared analogous to Example 79, using 1,3-oxazinan-2-one. MS (ESI): mass calcd. for $C_{18}H_{17}F_3N_2O_3$, 366.1; m/z found, 367.1 [M+H]$^+$. $^1$H NMR (500 MHz, DMSO-d$_6$) δ 8.69 (d, J=2.4 Hz, 1H), 7.74 (d, J=2.3 Hz, 1H), 7.71-7.67 (m, 1H), 7.64-7.60 (m, 1H), 7.53 (dd, J=10.5, 8.6 Hz, 1H), 7.35 (t, J=73.3 Hz, 1H), 4.57 (s, 2H), 4.26-4.21 (m, 2H), 3.27-3.22 (m, 2H), 2.51 (s, 3H), 2.01-1.95 (m, 2H).

Example 89: 3-[[5-[4-Chloro-3-(difluoromethoxy)phenyl]-2-methyl-3-pyridyl]methyl]oxazolidin-2-one

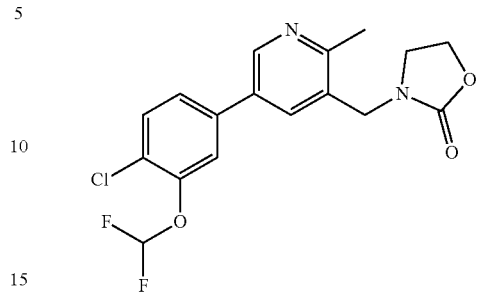

Prepared analogous to Example 79, using 5-(4-chloro-3-(difluoromethoxy)phenyl)-3-(chloromethyl)-2-methylpyridine hydrochloride (Intermediate 33). MS (ESI): mass calcd. for $C_{17}H_{15}ClF_2N_2O_3$, 368.1; m/z found, 369.1 [M+H]$^+$. $^1$H NMR (300 MHz, DMSO-d$_6$) δ 8.75 (d, J=2.3 Hz, 1H), 7.92 (d, J=2.4 Hz, 1H), 7.76-7.69 (m, 2H), 7.64 (dd, J=8.4, 2.1 Hz, 1H), 7.42 (t, J=73.3 Hz, 1H), 4.47 (s, 2H), 4.34-4.24 (m, 2H), 3.50-3.39 (m, 2H), 2.52 (s, 3H).

Example 90: 3-[[5-[3-(Difluoromethyl)-4-fluorophenyl]-2-methyl-3-pyridyl]methyl] oxazolidin-2-one

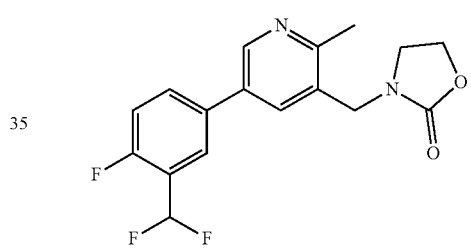

Prepared analogous to Example 79, using 3-(chloromethyl)-5-(3-(difluoromethyl)-4-fluorophenyl)-2-methylpyridine (Intermediate 34). MS (ESI): mass calcd. for $C_{17}H_{15}F_3N_2O_2$, 336.1; m/z found, 337.1 [M+H]$^+$. $^1$H NMR (300 MHz, DMSO-d$_6$) δ 8.73 (d, J=2.3 Hz, 1H), 8.01-7.93 (m, 2H), 7.92 (d, J=2.4 Hz, 1H), 7.57-7.47 (m, 1H), 7.26 (t, J=54.1 Hz, 1H), 4.47 (s, 2H), 4.36-4.23 (m, 2H), 3.51-3.38 (m, 2H), 2.62-2.39 (m, 3H).

Example 91: 6-[[5-[3-(Difluoromethyl)-4-fluorophenyl]-2-methyl-3-pyridyl]methyl]-8-oxa-6-azaspiro[3.4]octan-7-one

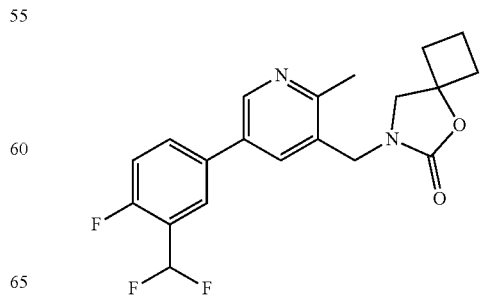

Prepared analogous to Example 79, using 3-(chloromethyl)-5-(3-(difluoromethyl)-4-fluorophenyl)-2-methylpyridine (Intermediate 34) and 5-oxa-7-azaspiro[3.4]octane-6-one. MS (ESI): mass calcd. for $C_{20}H_{19}F_3N_2O_2$, 376.1; m/z found, 377.1 [M+H]$^+$. $^1$H NMR (500 MHz, Chloroform-d) δ 8.65 (d, J=2.3 Hz, 1H), 7.84-7.72 (m, 1H), 7.71-7.56 (m, 2H), 7.25-7.21 (m, 1H), 6.94 (t, J=54.9 Hz, 1H), 4.51 (s, 2H), 3.45 (s, 2H), 2.60 (s, 3H), 2.59-2.50 (m, 2H), 2.17-2.08 (m, 2H), 1.93-1.83 (m, 1H), 1.64-1.52 (m, 1H).

Example 92: (5R)-3-[[5-[3-(Difluoromethyl)-4-fluoro-phenyl]-2-methyl-3-pyridyl]methyl]-5-methyl-oxazolidin-2-one

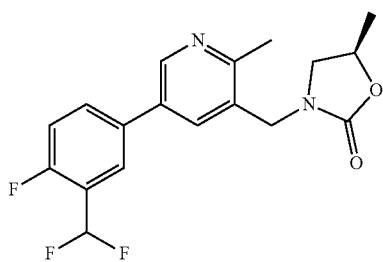

Prepared analogous to Example 79, using 3-(chloromethyl)-5-(3-(difluoromethyl)-4-fluorophenyl)-2-methylpyridine (Intermediate 34) and (R)-5-methyloxazolidine. MS (ESI): mass calcd. for $C_{18}H_{17}F_3N_2O_2$, 350.1; m/z found, 351.1 [M+H]$^+$. $^1$H NMR (500 MHz, Chloroform-d) δ 8.65 (d, J=2.3 Hz, 1H), 7.87-7.70 (m, 1H), 7.70-7.60 (m, 2H), 7.28-7.20 (m, 1H), 6.95 (t, J=54.9 Hz, 1H), 4.76-4.62 (m, 1H), 4.62-4.42 (m, 2H), 3.54 (t, J=8.3 Hz, 1H), 3.02 (dd, J=8.4, 6.9 Hz, 1H), 2.62 (s, 3H), 1.42 (d, J=6.2 Hz, 3H).

Example 93: 3-[[5-[3-(Difluoromethyl)-4-fluoro-phenyl]-2-methyl-3-pyridyl]methyl]-5,5-dimethyl-oxazolidin-2-one

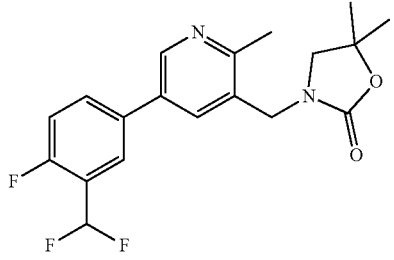 [SMILES: Cc1ncc(-c2ccc(F)c(C(F)F)c2)cc1CN1CC(C)(C)OC1=O]

Prepared analogous to Example 79, using 3-(chloromethyl)-5-(3-(difluoromethyl)-4-fluorophenyl)-2-methylpyridine (Intermediate 34) and 5-dimethyl-1,3-oxazolidin-2-one. MS (ESI): mass calcd. for $C_{19}H_{19}F_3N_2O_2$, 364.1; m/z found, 365.1 [M+H]$^+$. $^1$H NMR (500 MHz, Chloroform-d) δ 8.65 (d, J=2.3 Hz, 1H), 7.81-7.71 (m, 1H), 7.67-7.58 (m, 2H), 7.28-7.20 (m, 1H), 6.95 (t, J=54.9 Hz, 1H), 4.53 (s, 2H), 3.17 (s, 2H), 2.62 (s, 3H), 1.44 (s, 6H).

Example 94: (R/S)-3-[[5-[3-(Difluoromethyl)-4-fluoro-phenyl]-2-methyl-3-pyridyl]methyl]-5-methyl-oxazolidin-2-one

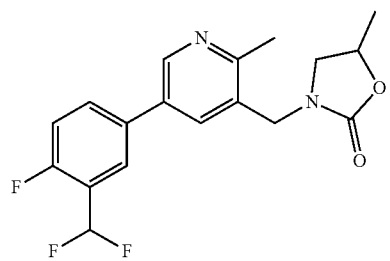 [SMILES: Cc1ncc(-c2ccc(F)c(C(F)F)c2)cc1CN1CC(C)OC1=O]

Prepared analogous to Example 79, using 3-(chloromethyl)-5-(3-(difluoromethyl)-4-fluorophenyl)-2-methylpyridine (Intermediate 34) and racemic 5-methyl-1,3-oxazolidin-2-one. MS (ESI): mass calcd. for $C_{18}H_{17}F_3N_2O_2$, 350.1; m/z found, 351.1 [M+H]$^+$. $^1$H NMR (500 MHz, Chloroform-d) δ 8.65 (d, J=2.3 Hz, 1H), 7.79-7.71 (m, 1H), 7.69-7.59 (m, 2H), 7.29-7.20 (m, 1H), 6.95 (t, J=54.9 Hz, 1H), 4.70-4.63 (m, 1H), 4.62-4.43 (m, 2H), 3.54 (t, J=8.3 Hz, 1H), 3.02 (dd, J=8.4, 7.0 Hz, 1H), 2.62 (s, 3H), 1.42 (d, J=6.3 Hz, 3H).

Example 95: (R/S)-3-[[5-[3-(difluoromethyl)-4-fluoro-phenyl]-2-methyl-3-pyridyl]methyl]-4-methyl-oxazolidin-2-one

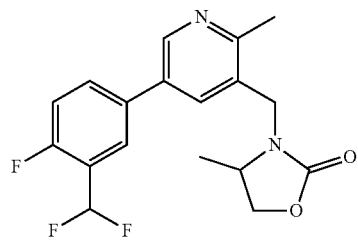

Prepared analogous to Example 79, using 3-(chloromethyl)-5-(3-(difluoromethyl)-4-fluorophenyl)-2-methylpyridine (Intermediate 34) and racemic 4-methyl-1,3-oxazolidin-2-one. MS (ESI): mass calcd. for $C_{18}H_{17}F_3N_2O_2$, 350.1; m/z found, 351.1 [M+H]$^+$. $^1$H NMR (500 MHz, Chloroform-d) δ 8.63 (d, J=2.3 Hz, 1H), 7.76-7.69 (m, 1H), 7.67 (d, J=2.3 Hz, 1H), 7.66-7.58 (m, 1H), 7.29-7.21 (m, 1H), 6.95 (t, J=54.9 Hz, 1H), 4.73 (d, J=15.9 Hz, 1H), 4.44 (t, J=8.5 Hz, 1H), 4.35 (d, J=15.9 Hz, 1H), 3.92 (dd, J=8.6, 6.3 Hz, 1H), 3.82-3.70 (m, 1H), 2.63 (s, 3H), 1.25 (d, J=6.2 Hz, 3H).

Example 96: 5-[[5-[3-(Difluoromethyl)-4-fluorophenyl]-2-methyl-3-pyridyl]methyl]-7-oxa-5-azaspiro[2.4]heptan-6-one

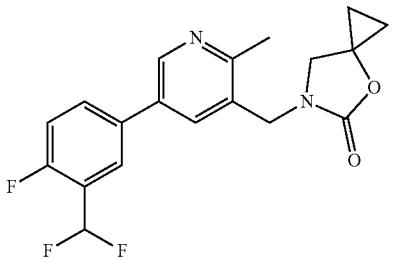 [SMILES: Cc1ncc(-c2ccc(F)c(C(F)F)c2)cc1CN1CC2(CC2)OC1=O]

Prepared analogous to Example 79, using 3-(chloromethyl)-5-(3-(difluoromethyl)-4-fluorophenyl)-2-methylpyridine (Intermediate 34) and 4-Oxa-6-azaspiro[2.4]heptan-5-one (Intermediate 2). MS (ESI): mass calcd. for $C_{19}H_{17}F_3N_2O_2$, 362.1; m/z found, 363.1 [M+H]$^+$. $^1$H NMR (500 MHz, Chloroform-d) δ 8.66 (d, J=2.3 Hz, 1H), 7.84-7.73 (m, 1H), 7.69 (d, J=2.3 Hz, 1H), 7.68-7.60 (m, 1H), 7.29-7.21 (m, 1H), 6.96 (t, J=54.9 Hz, 1H), 4.60 (s, 2H), 3.51 (s, 2H), 2.65 (s, 3H), 1.35-1.19 (m, 2H), 0.79-0.59 (m, 2H).

Example 97: 3-[[5-[3-(Difluoromethyl)-4-fluorophenyl]-2-methyl-3-pyridyl]methyl]-1,3-oxazinan-2-one

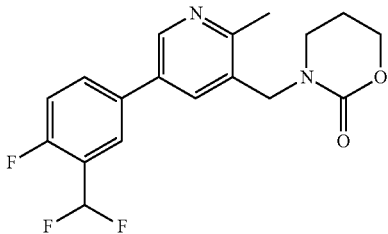 [SMILES: Cc1ncc(-c2ccc(F)c(C(F)F)c2)cc1CN1CCCOC1=O]

Prepared analogous to Example 79, using 3-(chloromethyl)-5-(3-(difluoromethyl)-4-fluorophenyl)-2-methylpyridine (Intermediate 34) and 1,3-oxazinan-2-one. MS (ESI): mass calcd. for $C_{18}H_{17}F_3N_2O_2$, 350.1; m/z found, 351.2 [M+H]$^+$. $^1$H NMR (500 MHz, DMSO-d$_6$) δ 8.71-8.63 (m, 1H), 7.96-7.87 (m, 2H), 7.79-7.70 (m, 1H), 7.53-7.44 (m, 1H), 7.23 (t, J=54.1 Hz, 1H), 4.55 (s, 2H), 4.26-4.16 (m, 2H), 3.25-3.16 (m, 2H), 2.54-2.39 (m, 3H), 1.99-1.88 (m, 2H).

Example 98: 3-[[5-(5-Chloro-2-thienyl)-2-methyl-3-pyridyl]methyl]oxazolidin-2-one

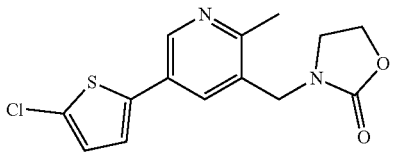 [SMILES: Cc1ncc(-c2ccc(Cl)s2)cc1CN1CCOC1=O]

Prepared analogous to Example 79 using 3-(chloromethyl)-5-(5-chlorothiophen-2-yl)-2-methylpyridine hydrochloride (Intermediate 27). MS (ESI): mass calcd. for $C_{14}H_{13}ClN_2O_2S$, 308.0; m/z found, 309.1 [M+H]$^+$. $^1$H NMR (300 MHz, DMSO-d$_6$) δ 8.65 (d, J=2.3 Hz, 1H), 7.79 (d, J=2.3 Hz, 1H), 7.51 (d, J=4.0 Hz, 1H), 7.21 (d, J=4.0 Hz, 1H), 4.43 (s, 2H), 4.36-4.24 (m, 2H), 3.50-3.38 (m, 2H), 2.48 (s, 3H)

Example 99: 3-[[2-Methyl-5-[5-(trifluoromethyl)-2-thienyl]-3-pyridyl]methyl]oxazolidin-2-one

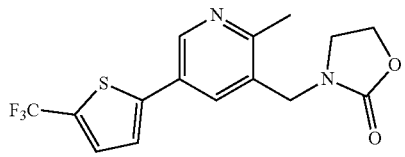 [SMILES: Cc1ncc(-c2ccc(C(F)(F)F)s2)cc1CN1CCOC1=O]

Prepared analogous to Example 79 using 3-(chloromethyl)-2-methyl-5-(5-(trifluoromethyl)thiophen-2-yl)pyridine hydrochloride (Intermediate 28). MS (ESI): mass calcd. for $C_{15}H_{13}F_3N_2O_2S$, 342.1; m/z found, 343.1 [M+H]$^+$. $^1$H NMR (300 MHz, DMSO-d$_6$) δ 8.79 (d, J=2.4 Hz, 1H), 7.93 (d, J=2.4 Hz, 1H), 7.84-7.76 (m, 1H), 7.76-7.69 (m, 1H), 4.45 (s, 2H), 4.37-4.25 (m, 2H), 3.52-3.38 (m, 2H), 2.60-2.40 (m, 3H).

Example 100: 3-[[5-[5-(Difluoromethyl)-2-thienyl]-2-methyl-3-pyridyl]methyl]oxazolidin-2-one

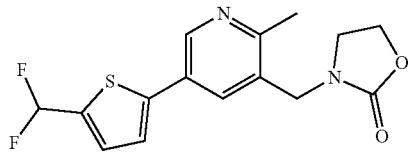 [SMILES: Cc1ncc(-c2ccc(C(F)F)s2)cc1CN1CCOC1=O]

Prepared analogous to Example 79, using 3-(chloromethyl)-5-(5-(difluoromethyl)thiophen-2-yl)-2-methylpyridine hydrochloride (Intermediate 20). MS (ESI): mass calcd. for $C_{15}H_{14}F_2N_2O_2S$, 324.1; m/z found, 325.1 [M+H]$^+$. $^1$H NMR (500 MHz, DMSO-d$_6$) δ 8.75 (d, J=2.3 Hz, 1H), 7.88 (d, J=2.3 Hz, 1H), 7.66-7.58 (m, 1H), 7.56-7.50 (m, 1H), 7.34 (t, J=55.2 Hz, 1H), 4.45 (s, 2H), 4.34-4.26 (m, 2H), 3.50-3.42 (m, 2H), 2.55-2.43 (m, 3H).

Example 101: 3-[[2-Methoxy-5-[3-(trifluoromethyl)phenyl]-3-pyridyl]methyl]oxazolidin-2-one

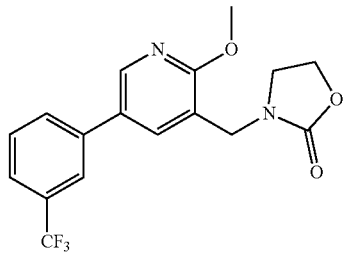 [SMILES: COc1ncc(-c2cccc(C(F)(F)F)c2)cc1CN1CCOC1=O]

Step A: 3-[(5-Bromo-2-methoxy-3-pyridyl)methyl]oxazolidin-2-one

To a solution of 2-oxazolidinone (2.21 g, 25.4 mmol) in dry N,N-dimethylformamide (700 µL) was added cesium carbonate (13.8 g, 42.3 mmol) under argon and the mixture was stirred at room temperature for 10 min. To the mixture was added 5-bromo-3-(chloromethyl)-2-methoxy-pyridine (Intermediate 13) (5.00 g, 21.1 mmol) and was stirred at room temperature for 18 h. To the reaction mixture was added water (250 mL) and the mixture was extracted with ethyl acetate (3×100 mL). The combined organic layers were dried over MgSO$_4$, filtered and evaporated. The residue was triturated with diisopropyl ether (4 mL) to afford the title compound (5.09 g, 17.7 mmol, 84%) as a pale yellow powder. MS (ESI): mass calcd. for $C_{10}H_{11}BrN_2O_3$, 286.0; m/z found, 287.0 [M+H]$^+$. $^1$H NMR (300 MHz, DMSO-d$_6$) δ 8.24 (d, J=2.5 Hz, 1H), 7.79 (d, J=2.5 Hz, 1H), 4.37-4.25 (m, 2H), 4.28 (s, 2H), 3.89 (s, 3H), 3.56-3.45 (m, 2H).

Step B: 3-[[2-Methoxy-5-[3-(trifluoromethyl)phenyl]-3-pyridyl]methyl]oxazolidin-2-one A mixture of 3-[(5-bromo-2-methoxy-3-pyridyl)methyl]oxazolidin-2-one (70 mg, 0.244 mmol), 3-trifluoromethylphenylboronic acid (56 mg, 0.295 mmol), tetrakis(triphenylphosphine)palladium(0) (28 mg, 0.0242 mmol) and potassium carbonate (67 mg, 0.485 mmol) in 1,4-dioxane (1 mL) and water (100 µL) was stirred at 80° C. for 4 h under argon. The reaction mixture was evaporated and the residue was purified by gradient silica gel column chromatography, eluting with n-hexane:ethyl acetate (2:1→1:1). The residue was taken up in diethyl ether (2 mL), filtered and the filtrate was evaporated to afford the title compound (60 mg, 0.170 mmol, 69%) as a pale yellow powder. MS (ESI): mass calcd. for $C_{17}H_{15}F_3N_2O_3$, 352.1; m/z found, 353.1 [M+H]$^+$. 1H NMR (300 MHz, DMSO-d$_6$) δ 8.52 (d, J=2.5 Hz, 1H), 8.06-7.92 (m, 3H), 7.78-7.66 (m, 2H), 4.38 (s, 2H), 4.33-4.20 (m, 2H), 3.96 (s, 3H), 3.58-3.45 (m, 2H).

Example 102: 3-[[2-Methoxy-5-(3,4,5-trifluorophenyl)-3-pyridyl]methyl]oxazolidin-2-one

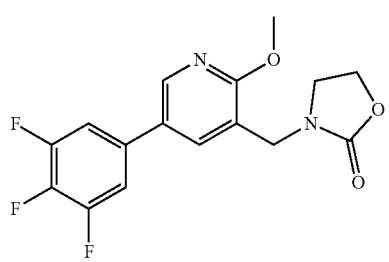 [SMILES: COc1ncc(-c2cc(F)c(F)c(F)c2)cc1CN1CCOC1=O]

Prepared analogous to Example 101, using 3,4,5-trifluorophenylboronic acid in Step B. MS (ESI): mass calcd. for $C_{16}H_{13}F_3N_2O_3$, 338.1; m/z found, 339.1 [M+H]$^+$. $^1$H NMR (300 MHz, DMSO-d$_6$) δ 8.50 (d, J=2.5 Hz, 1H), 7.94 (d, J=2.5 Hz, 1H), 7.81-7.67 (m, 2H), 4.36 (s, 2H), 4.35-4.24 (m, 2H), 3.95 (s, 3H), 3.59-3.45 (m, 2H).

Example 103: 3-[[5-(2,4-Difluoro-3-methyl-phenyl)-2-methoxy-3-pyridyl]methyl] oxazolidin-2-one

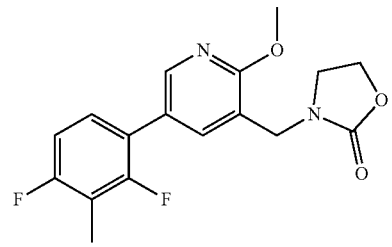 [SMILES: COc1ncc(-c2ccc(F)c(C)c2F)cc1CN1CCOC1=O]

Prepared analogous to Example 101, using 2,4-difluoro-3-methylphenylboronic acid in Step B. MS (ESI): mass calcd. for $C_{17}H_{16}F_2N_2O_3$, 334.1; m/z found, 335.1 [M+H]$^+$. $^1$H NMR (300 MHz, DMSO-d$_6$) δ 8.29-8.22 (m, 1H), 7.77-7.70 (m, 1H), 7.47-7.36 (m, 1H), 7.23-7.11 (m, 1H), 4.36 (s, 2H), 4.34-4.23 (m, 2H), 3.95 (s, 3H), 3.57-3.46 (m, 2H), 2.26-2.16 (m, 3H).

Example 104: 3-[[5-(3-Fluoro-5-methyl-phenyl)-2-methoxy-3-pyridyl]methyl]oxazolidin-2-one

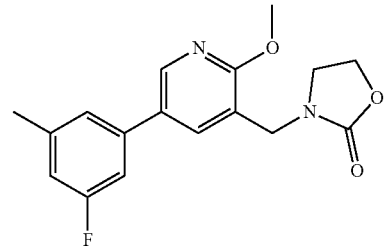 [SMILES: COc1ncc(-c2cc(C)cc(F)c2)cc1CN1CCOC1=O]

Prepared analogous to Example 101, using 3-fluoro-5-methylphenyl-boronic acid in Step B. MS (ESI): mass calcd. for $C_{17}H_{17}FN_2O_3$, 316.1; m/z found, 317.3 [M+H]$^+$. $^1$H NMR (300 MHz, DMSO-d$_6$) δ 8.46 (d, J=2.5 Hz, 1H), 7.90 (d, J=2.5 Hz, 1H), 7.41-7.28 (m, 2H), 7.15-6.95 (m, 1H), 4.36 (s, 2H), 4.33-4.24 (m, 2H), 3.95 (s, 3H), 3.59-3.42 (m, 2H), 2.39 (s, 3H).

Example 105: 3-[[2-Methoxy-5-(m-tolyl)-3-pyridyl]methyl]oxazolidin-2-one

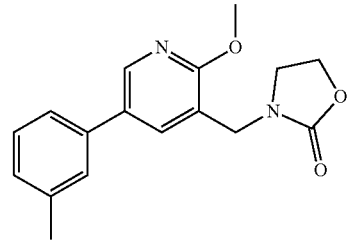 [SMILES: COc1ncc(-c2cccc(C)c2)cc1CN1CCOC1=O]

Prepared analogous to Example 101, using 3-methylphenylboronic acid in Step B. MS (ESI): mass calcd. for $C_{17}H_{13}N_2O_3$, 298.1; m/z found, 299.3 [M+H]$^+$. $^1$H NMR (300 MHz, DMSO-d$_6$) δ 8.41 (d, J=2.4 Hz, 1H), 7.85 (d, J=2.4 Hz, 1H), 7.52-7.40 (m, 2H), 7.40-7.31 (m, 1H), 7.23-7.14 (m, 1H), 4.37 (s, 2H), 4.34-4.21 (m, 2H), 3.94 (s, 3H), 3.60-3.42 (m, 2H), 2.38 (s, 3H).

Example 106: 3-[[5-(3,4-Dichlorophenyl)-2-methoxy-3-pyridyl]methyl]oxazolidin-2-one

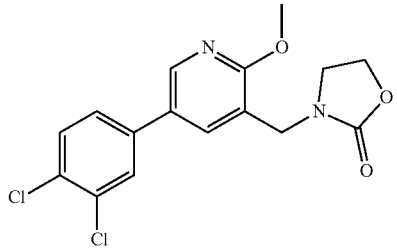 [SMILES: COc1ncc(-c2ccc(Cl)c(Cl)c2)cc1CN1CCOC1=O]

Prepared analogous to Example 101, using 3,4-dichlorophenylboronic acid in Step B. MS (ESI): mass calcd. for $C_{16}H_{14}Cl_2N_2O_3$, 352.0; m/z found, 353.2 [M+H]$^+$. $^1$H NMR (300 MHz, DMSO-d$_6$) δ 8.57-8.42 (m, 1H), 8.04-7.86 (m, 2H), 7.80-7.61 (m, 2H), 4.36 (s, 2H), 4.35-4.20 (m, 2H), 3.95 (s, 3H), 3.63-3.43 (m, 2H).

Example 107: 3-[[5-[4-Chloro-3-(difluoromethoxy)phenyl]-2-methoxy-3-pyridyl]methyl]oxazolidin-2-one

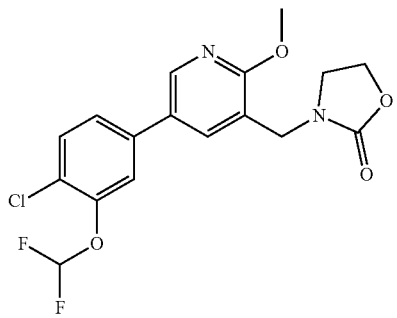 [SMILES: COc1ncc(-c2ccc(Cl)c(OC(F)F)c2)cc1CN1CCOC1=O]

Prepared analogous to Example 101, using 2-(4-chloro-3-(difluoromethoxy)phenyl)-4,4,5,5-tetramethyl-1,3,2-dioxaborolane (Intermediate 43) in Step B. MS (ESI): mass calcd. for $C_{17}H_{15}ClF_2N_2O_4$, 384.1; m/z found, 385.1 [M+H]$^+$. $^1$H NMR (300 MHz, DMSO-d$_6$) δ 8.49 (d, J=2.5 Hz, 1H), 7.92 (d, J=2.5 Hz, 1H), 7.69 (d, J=8.4 Hz, 1H), 7.67-7.63 (m, 1H), 7.59 (dd, J=8.3, 2.1 Hz, 1H), 7.41 (t, J=73.3 Hz, 1H), 4.37 (s, 2H), 4.34-4.22 (m, 2H), 3.96 (s, 3H), 3.58-3.46 (m, 2H).

Example 108: 3-[[5-(3-Chloro-4-fluoro-phenyl)-2-methoxy-3-pyridyl]methyl]oxazolidin-2-one

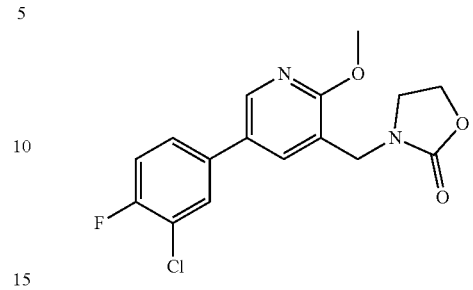

Prepared analogous to Example 101, using 3-chloro-4-fluorobenzeneboronic acid in Step B. MS (ESI): mass calcd. for $C_{16}H_{14}ClFN_2O_3$, 336.1; m/z found, 337.1 [M+H]$^+$. $^1$H NMR (300 MHz, DMSO-d$_6$) δ 8.46 (d, J=2.5 Hz, 1H), 7.98-7.86 (m, 2H), 7.74-7.64 (m, 1H), 7.52 (t, J=8.9 Hz, 1H), 4.36 (s, 2H), 4.35-4.24 (m, 2H), 3.94 (s, 3H), 3.58-3.46 (m, 2H).

Example 109: 3-[[5-(3-Chlorophenyl)-2-methoxy-3-pyridyl]methyl]oxazolidin-2-one

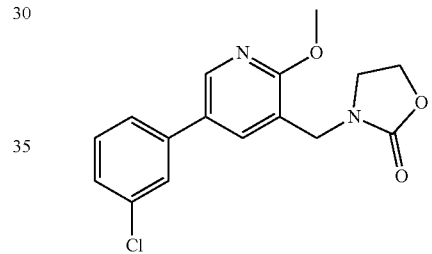

Prepared analogous to Example 101, using (3-chlorophenyl)boronic acid in Step B. MS (ESI): mass calcd. for $C_{16}H_{15}ClN_2O_3$, 318.1; m/z found, 319.1 [M+H]$^+$. $^1$H NMR (300 MHz, DMSO-d$_6$) δ 8.47 (d, J=2.5 Hz, 1H), 7.92 (d, J=2.5 Hz, 1H), 7.80-7.71 (m, 1H), 7.68-7.61 (m, 1H), 7.50 (t, J=7.8 Hz, 1H), 7.47-7.39 (m, 1H), 4.37 (s, 2H), 4.34-4.23 (m, 2H), 3.95 (s, 3H), 3.59-3.42 (m, 2H).

Example 110: 3-[[5-[3-(1,1-Difluoroethyl)-4-fluorophenyl]-2-methoxy-3-pyridyl]methyl]oxazolidin-2-one

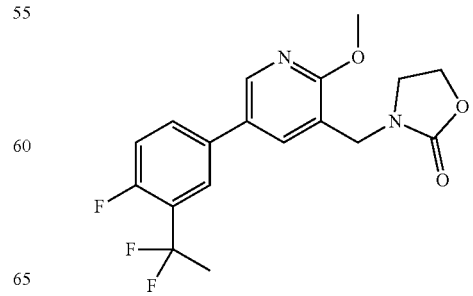

Prepared analogous to Example 101, using 2-(3-(1,1-difluoroethyl)-4-fluorophenyl)-4,4,5,5-tetramethyl-1,3,2-dioxaborolane (Intermediate 40) in Step B. MS (ESI): mass calcd. for $C_{18}H_{17}F_3N_2O_3$, 366.1; m/z found, 367.2 [M+H]$^+$. $^1$H NMR (300 MHz, DMSO-d$_6$) δ 8.45 (d, J=2.5 Hz, 1H), 7.91 (d, J=2.4 Hz, 1H), 7.89-7.80 (m, 1H), 7.80-7.70 (m, 1H), 7.47 (dd, J=11.1, 8.6 Hz, 1H), 4.37 (s, 2H), 4.33-4.22 (m, 2H), 3.95 (s, 3H), 3.59-3.42 (m, 2H), 2.07 (t, J=19.1 Hz, 3H).

Example 111: 3-[[5-[3-(1,1-Difluoroethyl)phenyl]-2-methoxy-3-pyridyl]methyl]oxazolidin-2-one

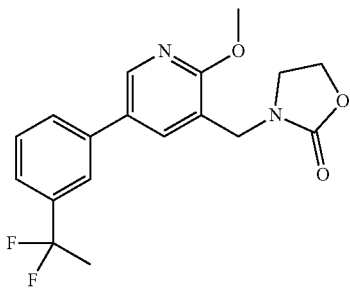 [SMILES: COc1ncc(-c2cccc(C(C)(F)F)c2)cc1CN1CCOC1=O]

Prepared analogous to Example 101, using 2-(3-(1,1-difluoroethyl)phenyl)-4,4,5,5-tetramethyl-1,3,2-dioxaborolane (Intermediate 41) in Step B. MS (ESI): mass calcd. for $C_{18}H_{18}F_2N_2O_3$, 348.1; m/z found, 349.3 [M+H]$^+$. $^1$H NMR (300 MHz, DMSO-d$_6$) δ 8.48 (d, J=2.4 Hz, 1H), 7.93 (d, J=2.5 Hz, 1H), 7.84-7.73 (m, 2H), 7.66-7.51 (m, 2H), 4.38 (s, 2H), 4.33-4.22 (m, 2H), 3.96 (s, 3H), 3.58-3.46 (m, 2H), 2.03 (t, J=18.9 Hz, 3H).

Example 112: 3-[[5-(3,4-Difluoro-5-methyl-phenyl)-2-methoxy-3-pyridyl]methyl] oxazolidin-2-one

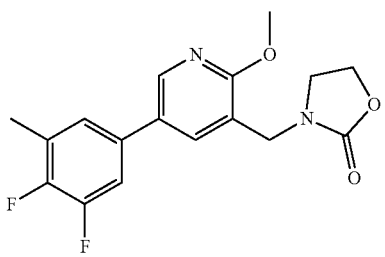

A mixture of 3-[[2-methoxy-5-(4,4,5,5-tetramethyl-1,3,2-dioxaborolan-2-yl)-3-pyridyl]methyl]oxazolidin-2-one (Intermediate 23, 80 mg, 0.239 mmol), 5-bromo-1,2-difluoro-3-methylbenzene (59 mg, 0.285 mmol), tetrakis(triphenylphosphine) palladium(0) (28 mg, 0.0242 mmol) and potassium carbonate (67 mg, 0.485 mmol) in 1,4-dioxane (1 mL) and water (100 μL) was stirred at 90° C. for 6 h under argon. The reaction mixture was evaporated and the residue was purified by silica gel column chromatography, eluting with n-hexane:ethyl acetate (2:1), to afford the title compound (56 mg, 0.168 mmol, 70%) as a white powder. MS (ESI): mass calcd. for $C_{17}H_{16}F_2N_2O_3$, 334.1; m/z found, 335.2 [M+H]$^+$. $^1$H NMR (300 MHz, DMSO-d$_6$) δ 8.49-8.38 (m, 1H), 7.93-7.81 (m, 1H), 7.70-7.54 (m, 1H), 7.44 (d, J=6.0 Hz, 1H), 4.35 (s, 2H), 4.34-4.23 (m, 2H), 3.94 (s, 3H), 3.59-3.43 (m, 2H), 2.35 (s, 3H).

Example 113: 3-[[5-[4-Fluoro-3-(trifluoromethoxy)phenyl]-2-methoxy-3-pyridyl]methyl]oxazolidin-2-one

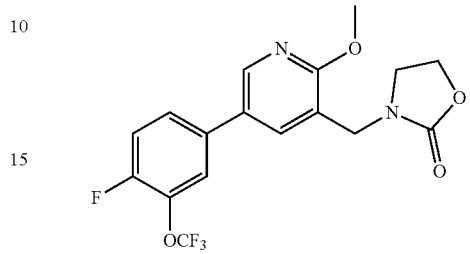

Prepared analogous to Example 112, using 4-bromo-1-fluoro-2-(trifluoromethoxy) benzene. MS (ESI): mass calcd. for $C_{17}H_{14}F_4N_2O_4$, 386.1; m/z found, 387.2 [M+H]$^+$. $^1$H NMR (300 MHz, DMSO-d$_6$) δ 8.47 (d, J=2.4 Hz, 1H), 7.97-7.85 (m, 2H), 7.83-7.73 (m, 1H), 7.62 (dd, J=10.2, 8.7 Hz, 1H), 4.37 (s, 2H), 4.34-4.22 (m, 2H), 3.95 (s, 3H), 3.59-3.43 (m, 2H).

Example 114: 3-[[5-(2,5-Difluoro-3-methyl-phenyl)-2-methoxy-3-pyridyl]methyl] oxazolidin-2-one

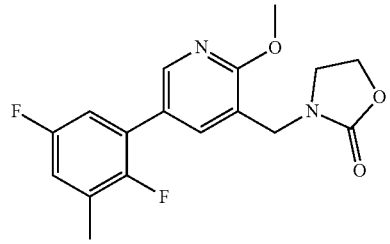 [SMILES: COc1ncc(-c2cc(F)cc(C)c2F)cc1CN1CCOC1=O]

Prepared analogous to Example 112, using 1-bromo-2,5-difluoro-3-methylbenzene. MS (ESI): mass calcd. for $C_{17}H_{16}F_2N_2O_3$, 334.1; m/z found, 335.3 [M+H]$^+$. $^1$H NMR (300 MHz, DMSO-d$_6$) δ 8.39-8.24 (m, 1H), 7.85-7.74 (m, 1H), 7.34-7.13 (m, 2H), 4.36 (s, 2H), 4.33-4.21 (m, 2H), 3.96 (s, 3H), 3.59-3.44 (m, 2H), 2.34-2.21 (m, 3H).

Example 115: 3-[[5-[4-Chloro-3-(difluoromethyl)phenyl]-2-methoxy-3-pyridyl]methyl]oxazolidin-2-one

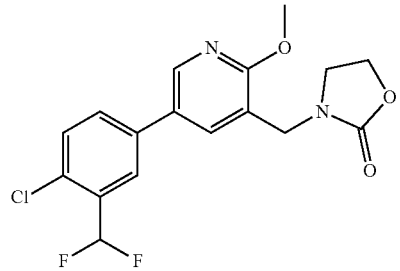 [SMILES: COc1ncc(-c2ccc(Cl)c(C(F)F)c2)cc1CN1CCOC1=O]

Prepared analogous to Example 112, using 4-bromo-1-chloro-2-(difluoromethyl) benzene. MS (ESI): mass calcd. for $C_{17}H_{15}ClF_2N_2O_3$, 368.1; m/z found, 369.2 [M+H]$^+$. $^1$H NMR (300 MHz, DMSO-d$_6$) δ 8.49 (d, J=2.5 Hz, 1H), 8.00-7.90 (m, 2H), 7.92-7.83 (m, 1H), 7.70 (d, J=8.4 Hz, 1H), 7.25 (t, J=54.1 Hz, 1H), 4.38 (s, 2H), 4.33-4.21 (m, 2H), 3.96 (s, 3H), 3.61-3.42 (m, 2H).

Example 116: 3-[[5-(4-Fluoro-3-methyl-phenyl)-2-methoxy-3-pyridyl]methyl]oxazolidin-2-one

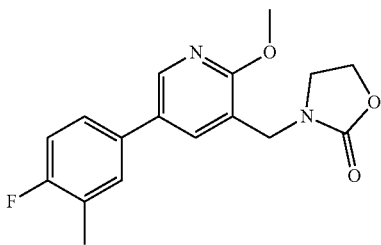 [SMILES: COc1ncc(-c2ccc(F)c(C)c2)cc1CN1CCOC1=O]

To a solution of 2-oxazolidinone (21 mg, 0.24 mmol) in dry N,N-dimethylformamide (400 μL) was added sodium hydride (60% in mineral oil, 17 mg, 0.43 mmol) at 0° C. and the reaction mixture was stirred at 0° C. for 30 min under argon. To the mixture was added a solution of 3-(chloromethyl)-5-(4-fluoro-3-methyl-phenyl)-2-methoxy-pyridine hydrochloride (Intermediate 18, 60 mg, 0.199 mmol) in dry N,N-dimethylformamide (400 μL) at 0° C. The reaction mixture was allowed to warm to room temperature and stirred for 18 h. To the reaction mixture was added water (1.5 mL) and the mixture was evaporated. The residue was purified by silica gel column chromatography, eluting with n-hexane:ethyl acetate (1:2), to afford the title compound (35 mg, 0.11 mmol, 55%) as a colorless oil. MS (ESI): mass calcd. for $C_{17}H_{17}FN_2O_3$, 316.1; m/z found, 317.1 [M+H]$^+$. $^1$H NMR (300 MHz, DMSO-d$_6$) δ 8.43-8.36 (m, 1H), 7.87-7.80 (m, 1H), 7.63-7.54 (m, 1H), 7.54-7.45 (m, 1H), 7.23 (t, J=9.1 Hz, 1H), 4.36 (s, 2H), 4.29 (t, J=8.0 Hz, 2H), 3.94 (s, 3H), 3.51 (t, J=8.0 Hz, 2H), 2.37-2.23 (m, 3H).

Example 117: (4S)-3-[[5-[3-(Difluoromethoxy)-4-fluoro-phenyl]-2-methoxy-3-pyridyl]methyl]-4-methyl-oxazolidin-2-one

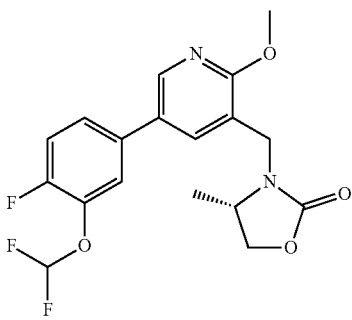 [SMILES: COc1ncc(-c2ccc(F)c(OC(F)F)c2)cc1CN1C(=O)OC[C@@H]1C]

Prepared analogous to Example 116, using 3-(chloromethyl)-5-(3-(difluoromethoxy)-4-fluorophenyl)-2-methoxy-pyridine hydrochloride (Intermediate 21) and (S)-4-methyl-oxazolidin-2-one. MS (ESI): mass calcd. for $C_{18}H_{17}F_3N_2O_4$, 382.1; m/z found, 383.2 [M+H]$^+$. $^1$H NMR (300 MHz, DMSO-d$_6$) δ 8.44 (d, J=2.5 Hz, 1H), 7.90 (d, J=2.5 Hz, 1H), 7.68-7.61 (m, 1H), 7.62-7.54 (m, 1H), 7.55-7.45 (m, 1H), 7.34 (t, J=73.3 Hz, 1H), 4.45 (d, J=15.9 Hz, 1H), 4.46-4.34 (m, 1H), 4.26 (d, J=16.0 Hz, 1H), 3.95 (s, 3H), 3.92-3.70 (m, 2H), 1.19 (d, J=5.6 Hz, 3H).

Example 118: (4R)-3-[[5-[3-(Difluoromethoxy)-4-fluoro-phenyl]-2-methoxy-3-pyridyl]methyl]-4-methyl-oxazolidin-2-one

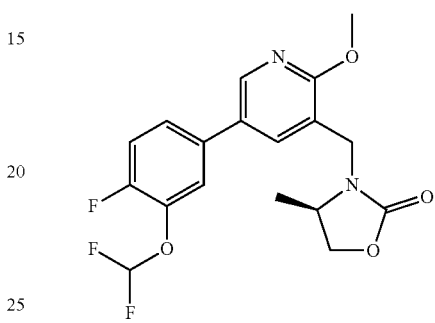

Prepared analogous to Example 116, using 3-(chloromethyl)-5-(3-(difluoromethoxy)-4-fluorophenyl)-2-methoxy-pyridine hydrochloride (Intermediate 21) and (R)-4-methyl-oxazolidin-2-one. MS (ESI): mass calcd. for $C_{18}H_{17}F_3N_2O_4$, 382.1; m/z found, 383.3 [M+H]$^+$. $^1$H NMR (300 MHz, DMSO-d$_6$) δ 8.44 (d, J=2.5 Hz, 1H), 7.90 (d, J=2.5 Hz, 1H), 7.68-7.61 (m, 1H), 7.62-7.54 (m, 1H), 7.56-7.46 (m, 1H), 7.34 (t, J=73.3 Hz, 1H), 4.45 (d, J=15.9 Hz, 1H), 4.45-4.35 (m, 1H), 4.27 (d, J=16.0 Hz, 1H), 3.95 (s, 3H), 3.92-3.71 (m, 2H), 1.19 (d, J=5.4 Hz, 3H).

Example 119: 3-[[5-[3-(Difluoromethoxy)-4-fluoro-phenyl]-2-methoxy-3-pyridyl]methyl]oxazolidin-2-one

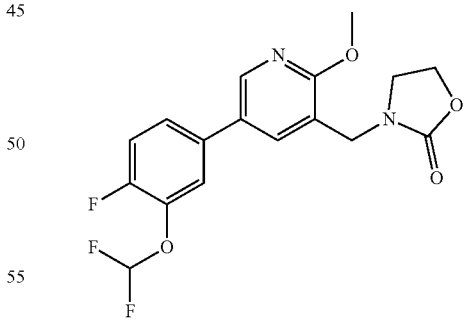

Prepared analogous to Example 116, using 3-(chloromethyl)-5-(3-(difluoromethoxy)-4-fluorophenyl)-2-methoxy-pyridine hydrochloride (Intermediate 21). MS (ESI): mass calcd. for $C_{17}H_{15}F_3N_2O_4$, 368.1; m/z found, 369.2 [M+H]$^+$. $^1$H NMR (500 MHz, DMSO-d$_6$) δ 8.45 (d, J=2.5 Hz, 1H), 7.89 (d, J=2.5 Hz, 1H), 7.67 (dd, J=7.6, 2.2 Hz, 1H), 7.63-7.58 (m, 1H), 7.53-7.48 (m, 1H), 7.35 (t, J=72.9 Hz, 1H), 4.36 (s, 2H), 4.32-4.24 (m, 2H), 3.95 (s, 3H), 3.54-3.48 (m, 2H).

Example 120: (4S)-3-[[5-[3-(Difluoromethyl)-4-fluoro-phenyl]-2-methoxy-3-pyridyl]methyl]-4-methyl-oxazolidin-2-one

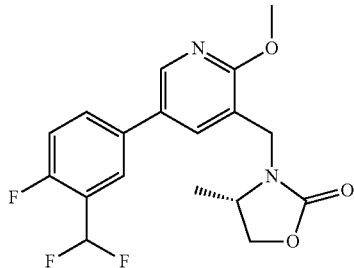 [SMILES: COc1ncc(-c2ccc(F)c(C(F)F)c2)cc1CN1C(=O)OC[C@@H]1C]

Prepared analogous to Example 116, using 3-(Chloromethyl)-5-(3-(difluoromethyl)-4-fluorophenyl)-2-methoxypyridine hydrochloride (Intermediate 35) and (S)-4-methyl-oxazolidin-2-one. MS (ESI): mass calcd. for $C_{18}H_{17}F_3N_2O_3$, 366.1; m/z found, 367.3 [M+H]$^+$. $^1$H NMR (300 MHz, DMSO-d$_6$) δ 8.44 (d, J=2.5 Hz, 1H), 7.92 (d, J=2.5 Hz, 1H), 7.91-7.80 (m, 2H), 7.56-7.44 (m, 1H), 7.25 (t, J=54.1 Hz, 1H), 4.45 (d, J=15.9 Hz, 1H), 4.44-4.34 (m, 1H), 4.27 (d, J=16.0 Hz, 1H), 3.95 (s, 3H), 3.91-3.71 (m, 2H), 1.19 (d, J=5.5 Hz, 3H).

Example 121: (4R)-3-[[5-[3-(Difluoromethyl)-4-fluoro-phenyl]-2-methoxy-3-pyridyl]methyl]-4-methyl-oxazolidin-2-one

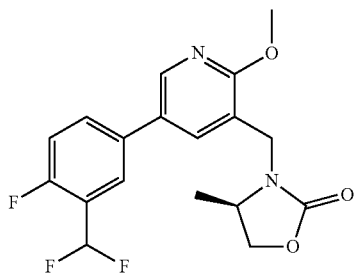 [SMILES: COc1ncc(-c2ccc(F)c(C(F)F)c2)cc1CN1C(=O)OC[C@H]1C]

Prepared analogous to Example 120, using (R)-4-methyloxazolidin-2-one in Step B. MS (ESI): mass calcd. for $C_{18}H_{17}F_3N_2O_3$, 366.1; m/z found, 367.3 [M+H]$^+$. $^1$H NMR (300 MHz, DMSO-d$_6$) δ 8.44 (d, J=2.5 Hz, 1H), 7.92 (d, J=2.5 Hz, 1H), 7.90-7.80 (m, 2H), 7.55-7.44 (m, 1H), 7.25 (t, J=54.1 Hz, 1H), 4.46 (d, J=16.0 Hz, 1H), 4.45-4.35 (m, 1H), 4.27 (d, J=16.0 Hz, 1H), 3.95 (s, 3H), 3.91-3.74 (m, 2H), 1.19 (d, J=5.6 Hz, 3H).

Example 122: 3-[[5-[3-(Difluoromethyl)-4-fluoro-phenyl]-2-methoxy-3-pyridyl]methyl]oxazolidin-2-one

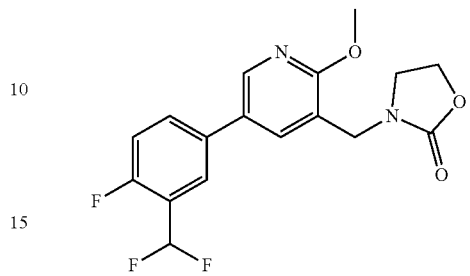

Prepared analogous to Example 120, using 2-oxazolidinone in Step B. MS (ESI): mass calcd. for $C_{17}H_{15}F_3N_2O_3$, 352.1; m/z found, 353.2 [M+H]$^+$. $^1$H NMR (500 MHz, DMSO-d$_6$) δ 8.45 (d, J=2.5 Hz, 1H), 7.91 (d, J=2.6 Hz, 1H), 7.95-7.85 (m, 2H), 7.52-7.45 (m, 1H), 7.24 (t, J=54.2 Hz, 1H), 4.37 (s, 2H), 4.31-4.25 (m, 2H), 3.96 (s, 3H), 3.56-3.48 (m, 2H).

Example 123: 3-[[2-(Difluoromethyl)-5-[3-(difluoromethyl)-4-fluoro-phenyl]-3-pyridyl]methyl]-1,3-oxazinan-2-one

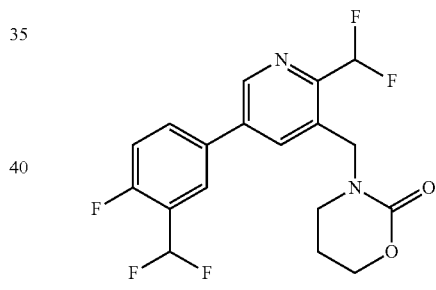

To a suspension of 3-(chloromethyl)-2-(difluoromethyl)-5-(3-(difluoromethyl)-4-fluorophenyl)pyridine hydrochloride salt (Intermediate 24, 65 mg, 0.181 mmol) in DMF (1 mL) at 0° C. was added NaH (60% dispersion in mineral oil, 25 mg, 0.625 mmol), and the reaction mixture was stirred for 30 min. Then, 1,3-oxazinan-2-one (22 mg, 0.218 mmol) was added and the reaction was stirred at room temperature for 2 h. The reaction mixture was quenched with water (5 mL) and extracted with EtOAc (3×5 mL). The combined organics were dried over Na$_2$SO$_4$, filtered and concentrated. The crude material was purified via silica gel chromatography (0-2% MeOH in DCM) to afford the title product (17 mg, 24%). MS (ESI): mass calcd. for $C_{18}H_{15}F_5N_2O_2$, 386.1; m/z found, 387.1 [M+H]$^+$. $^1$H NMR (500 MHz, DMSO-d$_6$) δ 8.94 (d, J=2.2 Hz, 1H), 8.04 (d, J=2.1 Hz, 1H), 8.04-7.99 (m, 2H), 7.62-7.54 (m, 1H), 7.28 (t, J=54.4 Hz, 1H), 7.20 (t, J=53.6 Hz, 1H), 4.75 (s, 2H), 4.28-4.21 (m, 2H), 3.34-3.25 (m, 2H), 2.03-1.93 (m, 2H).

Example 124: 3-[[2-(Difluoromethyl)-5-[3-(difluoromethyl)-4-fluoro-phenyl]-3-pyridyl]methyl]oxazolidin-2-one

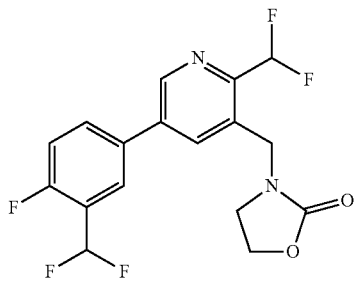 [SMILES: O=C1OCCN1Cc1cc(-c2ccc(F)c(C(F)F)c2)cnc1C(F)F]

Prepared analogous to Example 123, using 2-oxazolidinone. MS (ESI): mass calcd. for $C_{17}H_{13}F_5N_2O_2$, 372.1; m/z found, 373.1 [M+H]$^+$. $^1$H NMR (500 MHz, DMSO-d$_6$) δ 8.97 (d, J=2.1 Hz, 1H), 8.21-8.14 (m, 1H), 8.09-8.00 (m, 2H), 7.62-7.53 (m, 1H), 7.28 (t, J=54.3 Hz, 1H), 7.18 (t, J=53.4 Hz, 1H), 4.65 (s, 2H), 4.36-4.25 (m, 2H), 3.54-3.43 (m, 2H).

Example 125: 3-[[5-[3-(Difluoromethoxy)-4-fluorophenyl]-2-(difluoromethyl)-3-pyridyl]methyl]oxazolidin-2-one

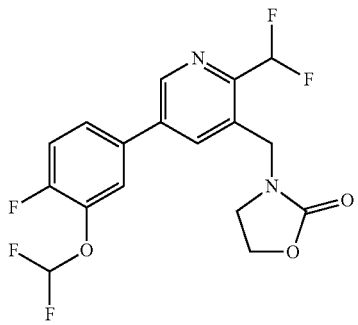 [SMILES: O=C1OCCN1Cc1cc(-c2ccc(F)c(OC(F)F)c2)cnc1C(F)F]

Prepared analogous to Example 123, using 2-oxazolidinone and 3-(chloromethyl)-5-(3-(difluoromethoxy)-4-fluorophenyl)-2-(difluoromethyl)pyridine hydrochloride (Intermediate 29). MS (ESI): mass calcd. for $C_{17}H_{13}F_5N_2O_3$, 388.1; m/z found, 389.1 [M+H]$^+$. $^1$H NMR (500 MHz, DMSO-d$_6$) δ 8.96 (d, J=2.2 Hz, 1H), 8.15 (d, J=2.1 Hz, 1H), 7.84 (dd, J=7.5, 2.3 Hz, 1H), 7.79-7.72 (m, 1H), 7.60 (dd, J=10.5, 8.6 Hz, 1H), 7.36 (t, J=73.3 Hz, 1H), 7.17 (t, J=53.6 Hz, 1H), 4.65 (s, 2H), 4.34-4.26 (m, 2H), 3.54-3.45 (m, 2H).

Example 126: 3-[[5-[3-(Difluoromethoxy)-4-fluorophenyl]-2-(difluoromethyl)-3-pyridyl]methyl]-1,3-oxazinan-2-one

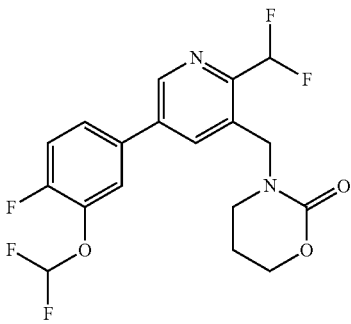 [SMILES: O=C1OCCCN1Cc1cc(-c2ccc(F)c(OC(F)F)c2)cnc1C(F)F]

Prepared analogous to Example 125, using 1,3-oxazinan-2-one in Step B. MS (ESI): mass calcd. for $C_{18}H_{15}F_5N_2O_3$, 402.1; m/z found, 403.1 [M+H]$^+$. $^1$H NMR (500 MHz, DMSO-d$_6$) δ 8.93 (d, J=2.2 Hz, 1H), 8.03-7.98 (m, 1H), 7.82-7.78 (m, 1H), 7.75-7.69 (m, 1H), 7.64-7.56 (m, 1H), 7.36 (t, J=73.4 Hz, 1H), 7.19 (t, J=53.7 Hz, 1H), 4.75 (s, 2H), 4.28-4.21 (m, 2H), 3.33-3.27 (m, 2H), 2.03-1.94 (m, 2H).

Example 127: 3-[[2-(Difluoromethyl)-5-(4-fluoro-3-methyl-phenyl)-3-pyridyl]methyl]-1,3-oxazinan-2-one

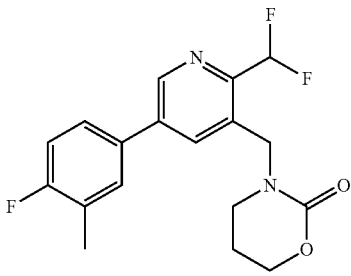 [SMILES: Cc1cc(-c2cnc(C(F)F)c(CN3CCCOC3=O)c2)ccc1F]

Prepared analogous to Example 126 using 3-(chloromethyl)-2-(difluoromethyl)-5-(4-fluoro-3-methylphenyl)pyridine hydrochloride (Intermediate 30). MS (ESI): mass calcd. for $C_{18}H_{17}F_3N_2O_2$, 350.1; m/z found, 351.1 [M+H]$^+$. $^1$H NMR (300 MHz, DMSO-d$_6$) δ 8.89 (d, J=2.1 Hz, 1H), 8.01-7.94 (m, 1H), 7.77-7.68 (m, 1H), 7.67-7.57 (m, 1H), 7.38-7.26 (m, 1H), 7.18 (t, J=53.2 Hz, 1H), 4.74 (s, 2H), 4.32-4.18 (m, 2H), 3.40-3.22 (m, 2H), 2.37-2.30 (m, 3H), 2.04-1.90 (m, 2H).

Example 128: 3-[[2-(Difluoromethyl)-5-(4-fluoro-3-methyl-phenyl)-3-pyridyl]methyl]oxazolidin-2-one

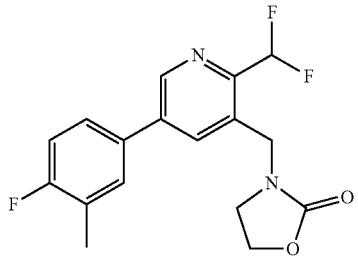 [SMILES: Cc1cc(-c2cnc(C(F)F)c(CN3CCOC3=O)c2)ccc1F]

Prepared analogous to Example 127, using 2-oxazolidinone in Step B. MS (ESI): mass calcd. for $C_{17}H_{15}F_3N_2O_2$, 336.1; m/z found, 337.1 [M+H]+. $^1$H NMR (500 MHz, DMSO-$d_6$) δ 8.92 (d, J=2.1 Hz, 1H), 8.10 (d, J=2.1 Hz, 1H), 7.75 (dd, J=7.3, 2.4 Hz, 1H), 7.69-7.62 (m, 1H), 7.35-7.28 (m, 1H), 7.16 (t, J=53.8 Hz, 1H), 4.64 (s, 2H), 4.35-4.26 (m, 2H), 3.53-3.44 (m, 2H), 2.33 (d, J=1.9 Hz, 3H).

Example 129: 3-[[5-[4-Chloro-3-(difluoromethoxy)phenyl]-2-(difluoromethyl)-3-pyridyl]methyl]-1,3-oxazinan-2-one

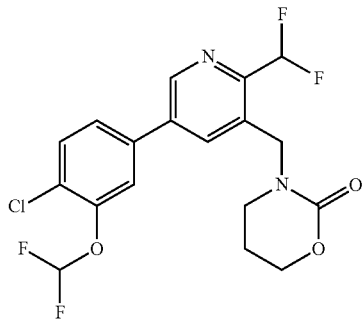 [SMILES: O=C1OCCCN1Cc1cc(-c2ccc(Cl)c(OC(F)F)c2)cnc1C(F)F]

Prepared analogous to Example 123, using 5-(4-chloro-3-(difluoromethoxy)phenyl)-3-(chloromethyl)-2-(difluoromethyl)pyridine hydrochloride (Intermediate 31). MS (ESI): mass calcd. for $C_{18}H_{15}ClF_4N_2O_3$, 418.1; m/z found, 419.1 [M+H]+. $^1$H NMR (300 MHz, DMSO-$d_6$) δ 8.96 (d, J=2.1 Hz, 1H), 8.07-7.97 (m, 1H), 7.83-7.74 (m, 2H), 7.69 (dd, J=8.4, 2.2 Hz, 1H), 7.42 (t, J=73.3 Hz, 1H), 7.20 (t, J=53.8 Hz, 1H), 4.75 (s, 2H), 4.32-4.18 (m, 2H), 3.44-3.21 (m, 2H), 2.06-1.91 (m, 2H).

Example 130: 3-[[5-[4-Chloro-3-(difluoromethoxy)phenyl]-2-(difluoromethyl)-3-pyridyl]methyl]oxazolidin-2-one

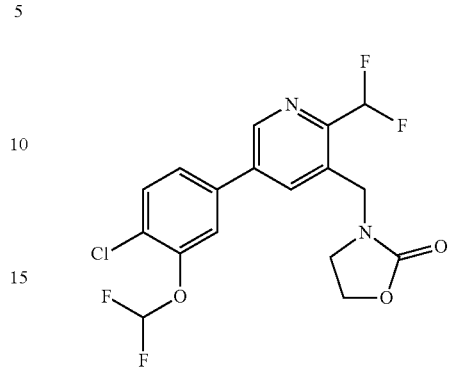

Prepared analogous to Example 129, using 2-oxazolidinone in Step B. MS (ESI): mass calcd. for $C_{17}H_{13}ClF_4N_2O_3$, 404.1; m/z found, 405.0 [M+H]+. $^1$H NMR (300 MHz, DMSO-$d_6$) δ 8.99 (d, J=2.1 Hz, 1H), 8.22-8.14 (m, 1H), 7.83-7.76 (m, 2H), 7.72 (dd, J=8.4, 1.9 Hz, 1H), 7.42 (t, J=72.9 Hz, 1H), 7.18 (t, J=53.1 Hz, 1H), 4.66 (s, 2H), 4.36-4.24 (m, 2H), 3.55-3.44 (m, 2H).

Example 131: 3-[[2-(Difluoromethoxy)-5-[3-(difluoromethyl)-4-fluoro-phenyl]-3-pyridyl]methyl]oxazolidin-2-one

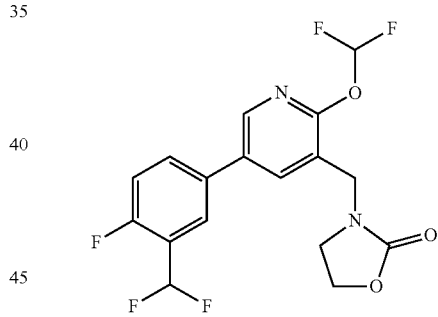

To a solution of 2-oxazolidinone (19 mg, 0.22 mmol) in dry N,N-dimethylformamide (350 μL) was added sodium hydride (60% in mineral oil, 16 mg, 0.4 mmol) at 0° C. and the reaction mixture was stirred at 0° C. for 30 min under argon. To the mixture was added a solution of 3-(chloromethyl)-2-(difluoromethoxy)-5-[3-(difluoromethyl)-4-fluorophenyl]pyridine hydrochloride salt (Intermediate 22, 68 mg, 0.20 mmol) in dry N,N-dimethylformamide (350 μL) at 0° C. The reaction mixture was allowed to warm to room temperature and stirred for 18 h. To the reaction mixture was added water (1 mL) and the mixture was concentrated. The residue was purified by silica gel column chromatography (0-50% EtOAc in hexanes) to afford the title compound (27 mg, 0.070 mmol, 34%) as a pale yellow powder. MS (ESI): mass calcd. for $C_{17}H_{13}FN_2O_3$, 388.1; m/z found, 389.0 [M+H]+. $^1$H NMR (500 MHz, DMSO-$d_6$) δ 8.54 (d, J=2.5 Hz, 1H), 8.14 (d, J=2.5 Hz, 1H), 8.00-7.93 (m, 2H), 7.77 (t, J=72.5 Hz, 1H), 7.56-7.49 (m, 1H), 7.26 (t, J=54.1 Hz, 1H), 4.44 (s, 2H), 4.33-4.26 (m, 2H), 3.59-3.51 (m, 2H).

Example 132: (4R)-3-[[2-(Difluoromethoxy)-5-[3-(difluoromethyl)-4-fluoro-phenyl]-3-pyridyl]methyl]-4-methyl-oxazolidin-2-one

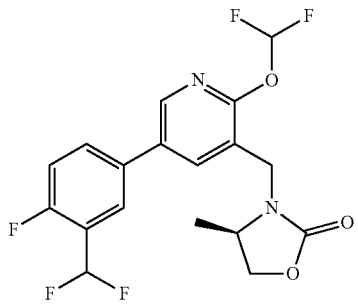 [SMILES: C[C@@H]1COC(=O)N1Cc1cc(-c2ccc(F)c(C(F)F)c2)cnc1OC(F)F]

Prepared analogous to Example 131, using (R)-4-methyloxazolidin-2-one. MS (ESI): mass calcd. for $C_{18}H_{15}F_5N_2O_3$, 402.1; m/z found, 403.1 [M+H]$^+$. $^1$H NMR (300 MHz, DMSO-d$_6$) δ 8.54 (d, J=2.4 Hz, 1H), 8.15 (d, J=2.4 Hz, 1H), 7.99-7.88 (m, 2H), 7.78 (t, J=72.5 Hz, 1H), 7.60-7.49 (m, 1H), 7.26 (t, J=54.1 Hz, 1H), 4.52 (d, J=16.0 Hz, 1H), 4.49-4.34 (m, 1H), 4.33 (d, J=16.0 Hz, 1H), 3.95-3.78 (m, 2H), 1.21 (d, J=5.4 Hz, 3H).

Example 133: 3-[[2-(Difluoromethoxy)-5-[3-(difluoromethoxy)-4-fluoro-phenyl]-3-pyridyl]methyl]oxazolidin-2-one

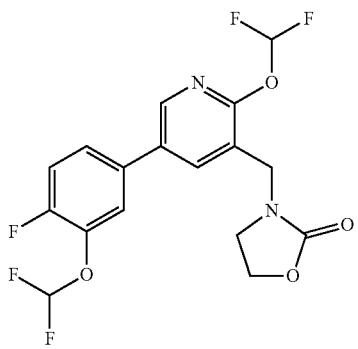 [SMILES: O=C1OCCN1Cc1cc(-c2ccc(F)c(OC(F)F)c2)cnc1OC(F)F]

Prepared analogous to Example 131 using 3-(chloromethyl)-2-(difluoromethoxy)-5-(3-(difluoromethoxy)-4-fluorophenyl)pyridine hydrochloride (Intermediate 32). MS (ESI): mass calcd. for $C_{17}H_{13}F_5N_2O_4$, 404.1; m/z found, 405.1 [M+H]$^+$. $^1$H NMR (300 MHz, DMSO-d$_6$) δ 8.54 (d, J=2.5 Hz, 1H), 8.12 (d, J=2.5 Hz, 1H), 7.77 (t, J=72.6 Hz, 1H), 7.76-7.71 (m, 1H), 7.70-7.62 (m, 1H), 7.61-7.49 (m, 1H), 7.35 (t, J=73.2 Hz, 1H), 4.43 (s, 2H), 4.35-4.23 (m, 2H), 3.61-3.49 (m, 2H).

Example 134: (4R)-3-[[2-(Difluoromethoxy)-5-[3-(difluoromethoxy)-4-fluoro-phenyl]-3-pyridyl]methyl]-4-methyl-oxazolidin-2-one

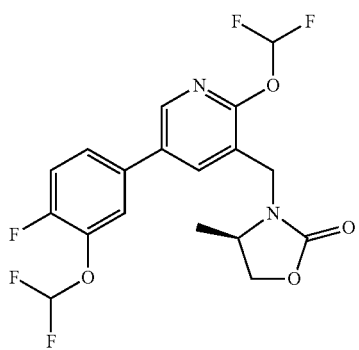 [SMILES: C[C@@H]1COC(=O)N1Cc1cc(-c2ccc(F)c(OC(F)F)c2)cnc1OC(F)F]

Prepared analogous to Example 133, using (R)-4-methyloxazolidin-2-one in Step B. MS (ESI): mass calcd. for $C_{18}H_{15}F_5N_2O_4$, 418.1; m/z found, 419.1 [M+H]$^+$. $^1$H NMR (300 MHz, DMSO-d$_6$) δ 8.53 (d, J=2.5 Hz, 1H), 8.13 (d, J=2.5 Hz, 1H), 7.78 (t, J=72.5 Hz, 1H), 7.75-7.67 (m, 1H), 7.68-7.60 (m, 1H), 7.60-7.51 (m, 1H), 7.35 (t, J=73.2 Hz, 1H), 4.51 (d, J=16.0 Hz, 1H), 4.46-4.37 (m, 1H), 4.32 (d, J=16.0 Hz, 1H), 3.96-3.75 (m, 2H), 1.21 (d, J=5.5 Hz, 3H).

Example 135: 3-[[2-(1,1-Difluoroethyl)-5-[3-(difluoromethyl)-4-fluoro-phenyl]-3-pyridyl]methyl]oxazolidin-2-one

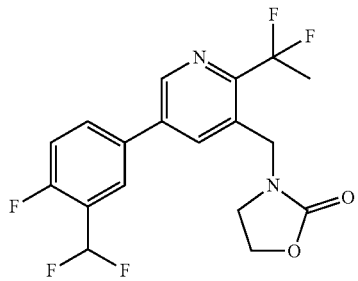 [SMILES: CC(F)(F)c1ncc(-c2ccc(F)c(C(F)F)c2)cc1CN1CCOC1=O]

Prepared analogous to Example 22, using 5-bromo-3-(bromomethyl)-2-(1,1-difluoroethyl)pyridine (Intermediate 16) in Step A. MS (ESI): mass calcd. for $C_{18}H_{15}F_5N_2O_2$, 386.1; m/z found, 387.1 [M+H]$^+$. $^1$H NMR (400 MHz, Methanol-d$_4$) δ 8.79 (d, J=2.2 Hz, 1H), 8.11 (d, J=2.2 Hz, 1H), 7.97-7.81 (m, 2H), 7.48-7.33 (m, 1H), 7.06 (t, J=54.5 Hz, 1H), 4.80 (s, 2H), 4.49-4.30 (m, 2H), 3.67-3.50 (m, 2H), 2.14 (t, J=19.5 Hz, 3H).

Example 136: 3-[[2-(1,1-Difluoroethyl)-5-[3-(difluoromethyl)-4-fluoro-phenyl]-3-pyridyl]methyl]-1,3-oxazinan-2-one

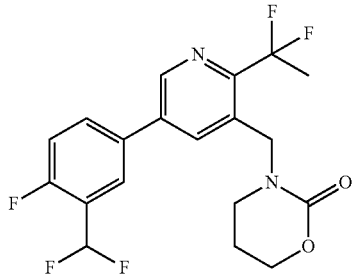 [SMILES: CC(F)(F)c1ncc(-c2ccc(F)c(C(F)F)c2)cc1CN1CCCOC1=O]

Prepared analogous to Example 22, using 5-bromo-3-(bromomethyl)-2-(1,1-difluoroethyl)pyridine (Intermediate 16) and 1,3-oxazinan-2-one in Step A. MS (ESI): mass calcd. for $C_{19}H_{17}F_5N_2O_2$, 400.1; m/z found, 401.1 [M+H]$^+$. $^1$H NMR (400 MHz, Methanol-d$_4$) δ 8.76 (d, J=2.1 Hz, 1H), 7.96 (d, J=2.2 Hz, 1H), 7.92-7.81 (m, 2H), 7.47-7.34 (m, 1H), 7.06 (t, J=54.6 Hz, 1H), 4.92 (s, 2H), 4.43-4.29 (m, 2H), 3.39 (t, J=6.2 Hz, 2H), 2.21-2.02 (m, 5H).

Example 137: 3-[[2-(1,1-Difluoroethyl)-5-[3-(difluoromethoxy)-4-fluoro-phenyl]-3-pyridyl]methyl]-1,3-oxazinan-2-one

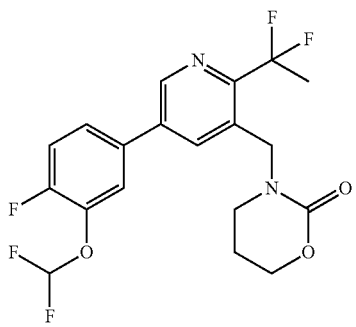 [SMILES: CC(F)(F)c1ncc(-c2ccc(F)c(OC(F)F)c2)cc1CN1CCCOC1=O]

Prepared analogous to Example 1, using 5-bromo-3-(bromomethyl)-2-(1,1-difluoroethyl)pyridine (Intermediate 16) in Step A. MS (ESI): mass calcd. for $C_{19}H_{17}F_5N_2O_3$, 416.1; m/z found, 417.1 [M+H]$^+$. $^1$H NMR (500 MHz, DMSO-d$_6$) δ 8.85 (d, J=2.1 Hz, 1H), 7.86 (d, J=2.1 Hz, 1H), 7.76 (dd, J=7.5, 2.2 Hz, 1H), 7.71-7.65 (m, 1H), 7.59 (dd, J=10.5, 8.6 Hz, 1H), 7.36 (t, J=73.1 Hz, 1H), 4.78 (s, 2H), 4.31-4.26 (m, 2H), 3.38-3.33 (m, 2H), 2.12 (t, J=19.7 Hz, 3H), 2.06-1.99 (m, 2H).

Example 138: 6-[[2-(1,1-Difluoroethyl)-5-[3-(difluoromethyl)-4-fluoro-phenyl]-3-pyridyl]methyl]-8-oxa-6-azaspiro[3.4]octan-7-one

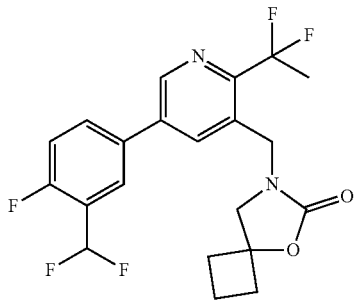 [SMILES: CC(F)(F)c1ncc(-c2ccc(F)c(C(F)F)c2)cc1CN1CC2(CCC2)OC1=O]

Prepared analogous to Example 79, using 3-(chloromethyl)-2-(1,1-difluoroethyl)-5-(3-(difluoromethyl)-4-fluorophenyl)pyridine hydrochloride (Intermediate 25) and 5-oxa-7-azaspiro[3.4] octan-6-one. MS (ESI): mass calcd. for $C_{21}H_{19}F_5N_2O_2$, 426.1; m/z found, 427.3 [M+H]$^+$. $^1$H NMR (300 MHz, DMSO-d$_6$) δ 9.03-8.80 (m, 1H), 8.13-7.88 (m, 3H), 7.68-7.51 (m, 1H), 7.28 (t, J=54.1 Hz, 1H), 4.68 (s, 2H), 3.63 (s, 2H), 2.62-2.30 (m, 2H), 2.25-1.99 (m, 2H), 2.11 (t, J=19.7 Hz, 3H), 1.85-1.65 (m, 1H), 1.65-1.47 (m, 1H).

Example 139: (5R)-3-[[2-(1,1-Difluoroethyl)-5-[3-(difluoromethyl)-4-fluoro-phenyl]-3-pyridyl]methyl]-5-methyl-oxazolidin-2-one

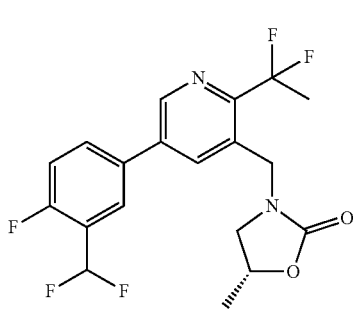 [SMILES: C[C@@H]1CN(Cc2cc(-c3ccc(F)c(C(F)F)c3)cnc2C(C)(F)F)C(=O)O1]

Prepared analogous to Example 79, using 3-(chloromethyl)-2-(1,1-difluoroethyl)-5-(3-(difluoromethyl)-4-fluorophenyl)pyridine hydrochloride (Intermediate 25) and (R)-5-methyloxazolidin-2-one. MS (ESI): mass calcd. for $C_{19}H_{17}F_5N_2O_2$, 400.1; m/z found, 401.2 [M+H]$^+$. $^1$H NMR (500 MHz, DMSO-d$_6$) δ 8.90 (d, J=2.1 Hz, 1H), 8.08 (d, J=2.2 Hz, 1H), 8.05-7.98 (m, 2H), 7.61-7.54 (m, 1H), 7.28 (t, J=54.1 Hz, 1H), 4.75-4.71 (m, 1H), 4.71-4.66 (m, 1H), 4.66-4.60 (m, 1H), 3.63 (t, J=8.4 Hz, 1H), 3.11 (dd, J=8.6, 6.9 Hz, 1H), 2.12 (t, J=19.7 Hz, 3H), 1.32 (d, J=6.2 Hz, 3H).

Example 140: (5S)-3-[[2-(1,1-Difluoroethyl)-5-[3-(difluoromethyl)-4-fluoro-phenyl]-3-pyridyl]methyl]-5-methyl-oxazolidin-2-one

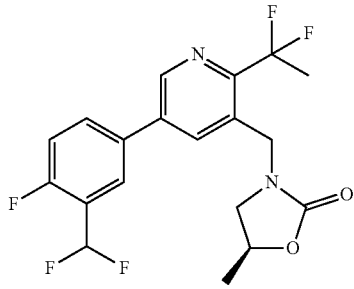 [SMILES: C[C@H]1CN(Cc2cc(-c3ccc(F)c(C(F)F)c3)cnc2C(C)(F)F)C(=O)O1]

Prepared analogous to Example 79, using 3-(chloromethyl)-2-(1,1-difluoroethyl)-5-(3-(difluoromethyl)-4-fluorophenyl)pyridine hydrochloride (Intermediate 25) and (S)-5-methyloxazolidin-2-one. MS (ESI): mass calcd. for $C_{21}H_{19}F_5N_2O_2$, 426.1; m/z found, 427.3 [M+H]$^+$. $^1$H NMR (300 MHz, DMSO-d$_6$) δ 9.03-8.80 (m, 1H), 8.13-7.88 (m, 3H), 7.68-7.51 (m, 1H), 7.28 (t, J=54.1 Hz, 1H), 4.68 (s, 2H), 3.63 (s, 2H), 2.62-2.30 (m, 2H), 2.25-1.99 (m, 2H), 2.11 (t, J=19.7 Hz, 3H), 1.85-1.65 (m, 1H), 1.65-1.47 (m, 1H).

Example 141: 5-[[2-(1,1-Difluoroethyl)-5-[3-(difluoromethyl)-4-fluoro-phenyl]-3-pyridyl]methyl]-7-oxa-5-azaspiro[2.4]heptan-6-one

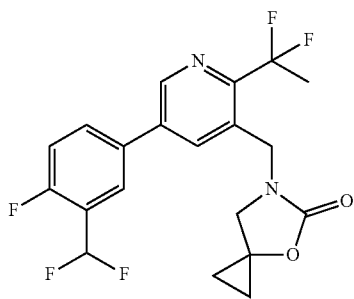 [SMILES: CC(F)(F)c1ncc(-c2ccc(F)c(C(F)F)c2)cc1CN1CC2(CC2)OC1=O]

Prepared analogous to Example 79, using 3-(chloromethyl)-2-(1,1-difluoroethyl)-5-(3-(difluoromethyl)-4-fluorophenyl)pyridine hydrochloride (Intermediate 25) and 4-oxa-6-azaspiro[2.4]heptan-5-one (Intermediate 2). MS (ESI): mass calcd. for $C_2H_{17}F_5N_2O_2$, 412.1; m/z found, 413.3 [M+H]$^+$. $^1$H NMR (300 MHz, DMSO-d$_6$) δ 9.00-8.85 (m, 1H), 8.16-8.06 (m, 1H), 8.09-7.95 (m, 2H), 7.68-7.52 (m, 1H), 7.29 (t, J=54.1 Hz, 1H), 4.76 (s, 2H), 3.63 (s, 2H), 2.12 (t, J=19.6 Hz, 3H), 1.15-0.98 (m, 2H), 0.87-0.68 (m, 2H).

Example 142: (4S)-3-[[2-(1,1-Difluoroethyl)-5-[3-(difluoromethyl)-4-fluoro-phenyl]-3-pyridyl]methyl]-4-methyl-oxazolidin-2-one

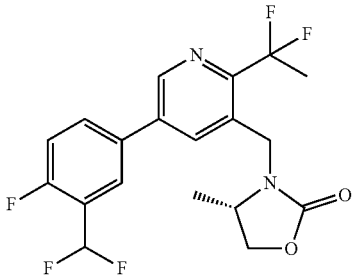 [SMILES: C[C@H]1COC(=O)N1Cc1cc(-c2ccc(F)c(C(F)F)c2)cnc1C(C)(F)F]

Prepared analogous to Example 79, using 3-(chloromethyl)-2-(1,1-difluoroethyl)-5-(3-(difluoromethyl)-4-fluorophenyl)pyridine hydrochloride (Intermediate 25) and (S)-4-methyloxazolidin-2-one. MS (ESI): mass calcd. for $C_{19}H_{17}F_5N_2O_2$, 400.1; m/z found, 401.1 [M+H]$^+$. $^1$H NMR (500 MHz, DMSO-d$_6$) δ 8.87 (d, J=2.1 Hz, 1H), 8.08 (d, J=2.1 Hz, 1H), 8.02-7.94 (m, 2H), 7.60-7.53 (m, 1H), 7.27 (t, J=54.0 Hz, 1H), 4.71 (d, J=16.9 Hz, 1H), 4.65 (d, J=16.9 Hz, 1H), 4.50-4.42 (m, 1H), 3.97-3.88 (m, 2H), 2.13 (t, J=19.8 Hz, 3H), 1.13 (d, J=5.8 Hz, 3H).

Example 143: (4R)-3-[[2-(1,1-Difluoroethyl)-5-[3-(difluoromethyl)-4-fluoro-phenyl]-3-pyridyl]methyl]-4-methyl-oxazolidin-2-one

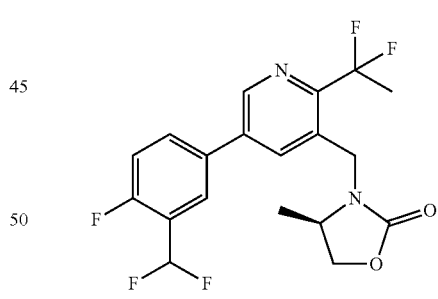

Prepared analogous to Example 79, using 3-(chloromethyl)-2-(1,1-difluoroethyl)-5-(3-(difluoromethyl)-4-fluorophenyl)pyridine hydrochloride (Intermediate 25) and (R)-4-methyloxazolidin-2-one. MS (ESI): mass calcd. for $C_{19}H_{17}F_5N_2O_2$, 400.1; m/z found, 401.2 [M+H]$^+$. $^1$H NMR (500 MHz, DMSO-d$_6$) δ 8.85 (d, J=2.0 Hz, 1H), 8.06 (d, J=2.1 Hz, 1H), 8.00-7.94 (m, 2H), 7.58-7.51 (m, 1H), 7.25 (t, J=54.0 Hz, 1H), 4.68 (d, J=16.9 Hz, 1H), 4.63 (d, J=17.0 Hz, 1H), 4.48-4.38 (m, 1H), 3.94-3.85 (m, 2H), 2.11 (t, J=19.8 Hz, 3H), 1.10 (d, J=5.7 Hz, 3H).

Example 144: (4R)-3-[[2-(1,1-Difluoroethyl)-5-[3-(difluoromethoxy)-4-fluoro-phenyl]-3-pyridyl]methyl]-4-methyl-oxazolidin-2-one

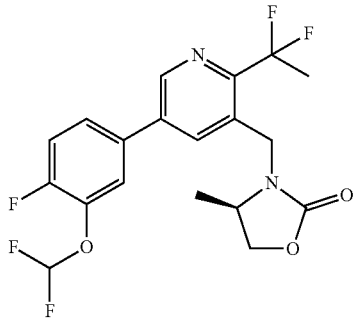 [SMILES: C[C@@H]1COC(=O)N1Cc1cc(-c2ccc(F)c(OC(F)F)c2)cnc1C(C)(F)F]

Prepared analogous to Example 79, using 3-(chloromethyl)-2-(1,1-difluoroethyl)-5-[3-(difluoromethoxy)-4-fluoro-phenyl]pyridine hydrochloride (Intermediate 26) and (R)-4-methyloxazolidin-2-one. MS (ESI): mass calcd. for $C_{19}H_{17}F_5N_2O_3$, 416.1; m/z found, 417.3 $[M+H]^+$. $^1H$ NMR (500 MHz, DMSO-$d_6$) δ 8.87 (d, J=2.0 Hz, 1H), 8.06 (d, J=2.1 Hz, 1H), 7.77 (dd, J=7.6, 2.2 Hz, 1H), 7.72-7.67 (m, 1H), 7.59 (dd, J=10.5, 8.6 Hz, 1H), 7.36 (t, J=73.1 Hz, 1H), 4.70 (d, J=17.0 Hz, 1H), 4.64 (d, J=17.0 Hz, 1H), 4.51-4.41 (m, 1H), 3.98-3.89 (m, 2H), 2.13 (t, J=19.8 Hz, 3H), 1.13 (d, J=5.8 Hz, 3H).

Example 145: (4S)-3-[[2-(1,1-Difluoroethyl)-5-[3-(difluoromethoxy)-4-fluoro-phenyl]-3-pyridyl]methyl]-4-methyl-oxazolidin-2-one

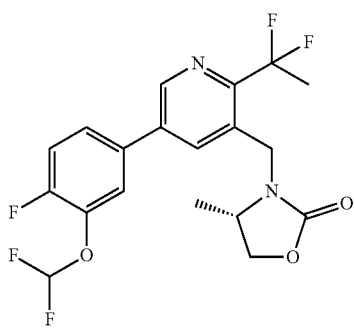 [SMILES: C[C@H]1COC(=O)N1Cc1cc(-c2ccc(F)c(OC(F)F)c2)cnc1C(C)(F)F]

Prepared analogous to Example 79, using 3-(chloromethyl)-2-(1,1-difluoroethyl)-5-[3-(difluoromethoxy)-4-fluoro-phenyl]pyridine hydrochloride (Intermediate 26) and (S)-4-methyloxazolidin-2-one. MS (ESI): mass calcd. for $C_{19}H_{17}F_5N_2O_3$, 416.1; m/z found, 417.3 $[M+H]^+$. $^1H$ NMR (500 MHz, DMSO-$d_6$) δ 8.87 (d, J=2.0 Hz, 1H), 8.06 (d, J=2.1 Hz, 1H), 7.77 (dd, J=7.6, 2.2 Hz, 1H), 7.72-7.67 (m, 1H), 7.59 (dd, J=10.5, 8.6 Hz, 1H), 7.36 (t, J=73.1 Hz, 1H), 4.70 (d, J=17.0 Hz, 1H), 4.64 (d, J=16.9 Hz, 1H), 4.51-4.42 (m, 1H), 3.98-3.89 (m, 2H), 2.13 (t, J=19.8 Hz, 3H), 1.13 (d, J=5.8 Hz, 3H).

Example 146: 5-[[2-(1,1-Difluoroethyl)-5-[3-(difluoromethoxy)-4-fluoro-phenyl]-3-pyridyl]methyl]-7-oxa-5-azaspiro[2.4]heptan-6-one

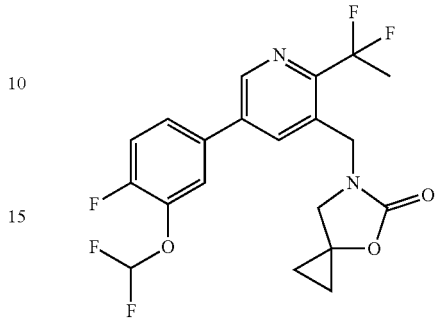

Prepared analogous to Example 79, using 3-(chloromethyl)-2-(1,1-difluoroethyl)-5-[3-(difluoromethoxy)-4-fluoro-phenyl]pyridine hydrochloride (Intermediate 26) and 4-oxa-6-azaspiro[2.4]heptan-5-one (Intermediate 2). MS (ESI): mass calcd. for $C_{20}H_{17}F_5N_2O_3$, 428.1; m/z found, 429.2 $[M+H]^+$. $^1H$ NMR (500 MHz, DMSO-$d_6$) δ 8.91 (d, J=2.0 Hz, 1H), 8.08 (d, J=2.1 Hz, 1H), 7.80 (dd, J=7.5, 2.2 Hz, 1H), 7.74-7.68 (m, 1H), 7.61 (dd, J=10.5, 8.6 Hz, 1H), 7.36 (t, J=73.1 Hz, 1H), 4.75 (s, 2H), 3.63 (s, 2H), 2.12 (t, J=19.7 Hz, 3H), 1.09-1.05 (m, 2H), 0.81-0.75 (m, 2H).

Example 147: 6-[[2-(1,1-Difluoroethyl)-5-[3-(difluoromethoxy)-4-fluoro-phenyl]-3-pyridyl]methyl]-8-oxa-6-azaspiro[3.4]octan-7-one

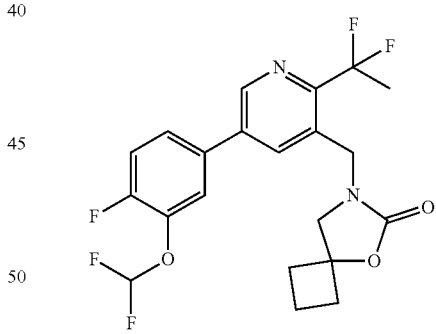

Prepared analogous to Example 79, using 3-(chloromethyl)-2-(1,1-difluoroethyl)-5-[3-(difluoromethoxy)-4-fluoro-phenyl]pyridine hydrochloride (Intermediate 26) and 5-oxa-7-azaspiro[3.4]octan-6-one. MS (ESI): mass calcd. for $C_{21}H_{19}F_5N_2O_3$, 442.1; m/z found, 443.3 $[M+H]^+$. $^1H$ NMR (500 MHz, DMSO-$d_6$) δ 8.90 (d, J=2.1 Hz, 1H), 8.00 (d, J=2.2 Hz, 1H), 7.78 (dd, J=7.5, 2.3 Hz, 1H), 7.73-7.69 (m, 1H), 7.61 (dd, J=10.5, 8.6 Hz, 1H), 7.35 (t, J=73.0 Hz, 1H), 4.67 (s, 2H), 3.63 (s, 2H), 2.42-2.33 (m, 2H), 2.21-2.14 (m, 2H), 2.12 (t, J=19.8 Hz, 3H), 1.78-1.69 (m, 1H), 1.63-1.52 (m, 1H).

Example 148: (5S)-3-[[2-(1,1-Difluoroethyl)-5-[3-(difluoromethoxy)-4-fluoro-phenyl]-3-pyridyl]methyl]-5-methyl-oxazolidin-2-one

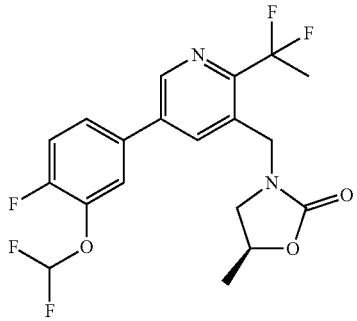 [SMILES: C[C@H]1CN(Cc2cc(-c3ccc(F)c(OC(F)F)c3)cnc2C(C)(F)F)C(=O)O1]

Prepared analogous to Example 79, using 3-(chloromethyl)-2-(1,1-difluoroethyl)-5-[3-(difluoromethoxy)-4-fluoro-phenyl]pyridine hydrochloride (Intermediate 26) and (S)-5-methyloxazolidin-2-one. MS (ESI): mass calcd. for $C_{19}H_{17}F_5N_2O_3$, 416.1; m/z found, 417.2 [M+H]$^+$. $^1$H NMR (500 MHz, DMSO-d$_6$) δ 8.89 (d, J=2.0 Hz, 1H), 8.06 (d, J=2.1 Hz, 1H), 7.80 (dd, J=7.5, 2.2 Hz, 1H), 7.75-7.69 (m, 1H), 7.60 (dd, J=10.5, 8.6 Hz, 1H), 7.35 (t, J=73.1 Hz, 1H), 4.72 (d, J=16.2 Hz, 1H), 4.71-4.66 (m, 1H), 4.63 (d, J=16.2 Hz, 1H), 3.64 (t, J=8.4 Hz, 1H), 3.12 (dd, J=8.6, 6.9 Hz, 1H), 2.12 (t, J=19.7 Hz, 3H), 1.33 (d, J=6.2 Hz, 3H).

Example 149: (5R)-3-[[2-(1,1-Difluoroethyl)-5-[3-(difluoromethoxy)-4-fluoro-phenyl]-3-pyridyl]methyl]-5-methyl-oxazolidin-2-one

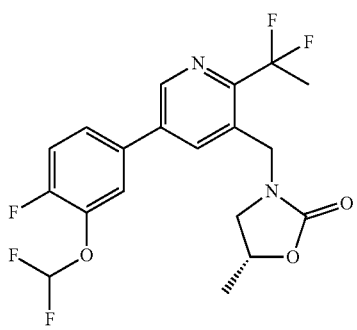 [SMILES: C[C@@H]1CN(Cc2cc(-c3ccc(F)c(OC(F)F)c3)cnc2C(C)(F)F)C(=O)O1]

Prepared analogous to Example 79, using 3-(chloromethyl)-2-(1,1-difluoroethyl)-5-[3-(difluoromethoxy)-4-fluoro-phenyl]pyridine hydrochloride (Intermediate 26) and (R)-5-methyloxazolidin-2-one. MS (ESI): mass calcd. for $C_{19}H_{17}F_5N_2O_3$, 416.1; m/z found, 417.2 [M+H]$^+$. $^1$H NMR (500 MHz, DMSO-d$_6$) δ 8.89 (d, J=2.1 Hz, 1H), 8.06 (d, J=2.2 Hz, 1H), 7.80 (dd, J=7.6, 2.3 Hz, 1H), 7.75-7.69 (m, 1H), 7.59 (dd, J=10.5, 8.6 Hz, 1H), 7.35 (t, J=73.1 Hz, 1H), 4.70 (d, J=16.2 Hz, 1H), 4.71-4.66 (m, 1H), 4.63 (d, J=16.2 Hz, 1H), 3.64 (t, J=8.4 Hz, 1H), 3.12 (dd, J=8.6, 6.9 Hz, 1H), 2.12 (t, J=19.7 Hz, 3H), 1.33 (d, J=6.2 Hz, 3H).

Example 150: 3-((5-(3-(Difluoromethoxy)-4-fluorophenyl)-2-fluoropyridin-3-yl)methyl)oxazolidin-2-one

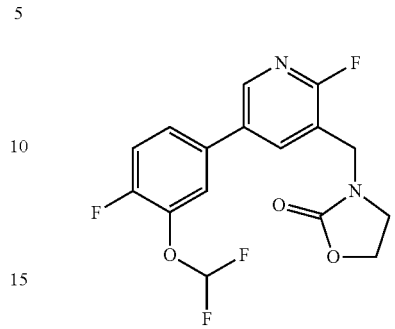

A mixture of 3-(chloromethyl)-5-(3-(difluoromethoxy)-4-fluorophenyl)-2-fluoropyridine (Intermediate 44, 30 mg, 0.1 mmol), oxazolidin-2-one (9.4 mg, 0.1 mmol) and cesium carbonate (96.0 mg, 0.3 mmol) in DMF (2.8 mL) was stirred at room temperature. After 16 h, solids were filtered off and the filtrate was evaporated. Purification (METHOD G) afforded the title compound (14 mg, 41%). MS (ESI): mass calcd. for $C_{16}H_{12}F_4N_2O_3$, 356.1; m/z found, 357.0 [M+H]$^+$. $^1$H NMR (500 MHz, DMSO-d$_6$) δ 8.54-8.50 (m, 1H), 8.22 (dd, J=9.2, 2.6 Hz, 1H), 7.76 (dd, J=7.5, 2.3 Hz, 1H), 7.70-7.65 (m, 1H), 7.56 (dd, J=10.5, 8.6 Hz, 1H), 7.35 (t, J=73.2 Hz, 1H), 4.47 (s, 2H), 4.31-4.27 (m, 2H), 3.56-3.50 (m, 2H).

Example 151: 3-((5-(3-(Difluoromethoxy)-4-fluorophenyl)-2-fluoropyridin-3-yl)methyl)-1,3-oxazinan-2-one

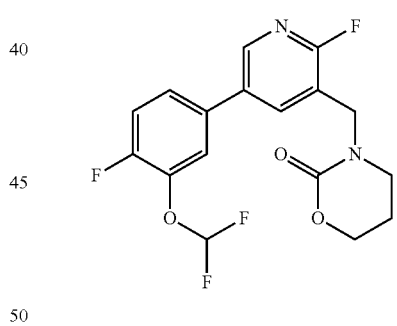

Prepared analogous to Example 150, using 1,3-oxazinan-2-one instead of oxazolidin-2-one. MS (ESI): mass calcd. for $C_{17}H_{14}F_4N_2O_3$, 370.1; m/z found, 371.0 [M+H]$^+$. $^1$H NMR (600 MHz, DMSO-d$_6$) δ 8.49-8.47 (m, 1H), 8.09 (dd, J=9.2, 2.5 Hz, 1H), 7.73 (dd, J=7.5, 2.3 Hz, 1H), 7.66-7.62 (m, 1H), 7.56 (dd, J=10.5, 8.6 Hz, 1H), 7.35 (t, J=73.2 Hz, 1H), 4.54 (s, 2H), 4.24-4.20 (m, 2H), 3.37 (t, J=6.2 Hz, 2H), 2.01-1.96 (m, 2H).

5.3. Biological Assays: Effect of Compounds of Formula (I) on Cloned Human GluN1/GluN2B Ion Channels Expressed in Mammalian Cells NMDA receptors are ion channels that are highly permeable to $Ca^{2+}$ ions, rendering it possible to monitor NMDA receptor function using cell-based calcium flux assay. In this assay, co-agonists glutamate and glycine are added to cells heterologously expressing human GluN1/GluN2B NMDA receptors to initiate cellular Ca$^{2+}$ influx. The time course of the changes in intracellular calcium is measured using a fluorescent dye and a FLIPR (Fluorometric Imaging Plate Reader) device.

Twenty four hours before measurements, the expression of the NMDA receptors in the stable cell line is induced with Tet-On inducible system in the presence of a non-selective NMDA receptor blocker. On the day of the experiment, cell culture media is carefully washed and the cells are loaded with Calcium 5 Dye Kit (Molecular Devices) in dye loading buffer containing 137 mM NaCl, 4 mM KCl, 2 mM CaCl$_2$, 0.5 mM MgCl$_2$ (standard assay) or 1.5 mM MgCl$_2$ (HTS assay), 10 mM HEPES and 5 mM D-glucose; pH 7.4. After 1 h incubation at the room temperature, the dye is washed away with the assay buffer (137 mM NaCl (standard assay) or 150 mM (HTS assay), 4 mM KCl (standard assay) or 3 mM (HTS assay), 2 mM CaCl$_2$, 0.01 mM EDTA, 10 mM HEPES and 5 mM D-glucose; pH 7.4) In the FLIPR TETRA reader, various concentrations of the test compounds are added to the cells for 5 min while fluorescence is monitored to detect potential agonist activity. Next, co-agonists, glutamate and glycine are added for another 5 minutes. The concentration of glutamate corresponding to ~EC$_{40}$ (standard assay) or EC$_{40}$ (HTS assay) is used to maximize the assay's signal window and ability to detect NMDA receptor antagonists and negative allosteric modulators. A saturating concentration (10 µM) of glycine is also present in the assay. A non-selective NMDA receptor antagonist, (+)MK-801 is used as a positive control for antagonist activity. The fluorescent signal in the presence of test compounds is quantified and normalized to the signal defined by the appropriate control wells.

Results of the assay performed on the compounds of Examples 1 to 151 are shown in Table 4.

TABLE 4

| Example # | Compound Name | GluN2B IC$_{50}$ (nM) standard assay |
|---|---|---|
| 1 | 3-[[5-[3-(Difluoromethoxy)-4-fluoro-phenyl]-3-pyridyl]methyl]-1,3-oxazinan-2-one; | 10 |
| 2 | 3-[[5-[3-(Difluoromethoxy)-4-fluoro-phenyl]-3-pyridyl]methyl]oxazolidin-2-one; | 12 |
| 3 | (4S)-3-[[5-[3-(Difluoromethoxy)-4-fluoro-phenyl]-3-pyridyl]methyl]-4-isopropyl-oxazolidin-2-one; | 3010 |
| 4 | 1-[[5-[3-(Difluoromethoxy)-4-fluoro-phenyl]-3-pyridyl]methyl]-4H-3,1-benzoxazin-2-one; | 123 |
| 5 | (R/S)-3-[[5-[3-(Difluoromethoxy)-4-fluoro-phenyl]-3-pyridyl]methyl]-4-methyl-oxazolidin-2-one; | 20 |
| 6 | (R/S)-3-[[5-[3-(Difluoromethoxy)-4-fluoro-phenyl]-3-pyridyl]methyl]-5-methyl-oxazolidin-2-one; | 15 |
| 7 | (S*)-3-[[5-[3-(Difluoromethoxy)-4-fluoro-phenyl]-3-pyridyl]methyl]-5-methyl-oxazolidin-2-one; | 17 |
| 8 | (R*)-3-[[5-[3-(Difluoromethoxy)-4-fluoro-phenyl]-3-pyridyl]methyl]-5-methyl-oxazolidin-2-one; | 11 |
| 9 | 5-[[5-[3-(Difluoromethoxy)-4-fluoro-phenyl]-3-pyridyl]methyl]-7-oxa-5-azaspiro[2.4]heptan-6-one; | 12 |
| 10 | 3-[[5-[3-(Difluoromethoxy)-4-fluoro-phenyl]-3-pyridyl]methyl]-6,6-dimethyl-1,3-oxazinan-2-one; | 521 |
| 11 | (4R)-3-[[5-[3-(Difluoromethoxy)-4-fluoro-phenyl]-3-pyridyl]methyl]-4-isopropyl-oxazolidin-2-one; | >2999 |
| 12 | 6-[[5-[3-(Difluoromethoxy)-4-fluoro-phenyl]-3-pyridyl]methyl]-8-oxa-6-azaspiro[3.4]octan-7-one; | 59 |
| 13 | 6-[[5-[3-(Difluoromethoxy)-4-fluoro-phenyl]-3-pyridyl]methyl]-2,8-dioxa-6-azaspiro[3.4]octan-7-one; | 39 |
| 14 | (R/S)-3-[[5-[3-(Difluoromethoxy)-4-fluoro-phenyl]-3-pyridyl]methyl]-5-isopropyl-oxazolidin-2-one; | 97 |
| 15 | (R*)-3-[[5-[3-(Difluoromethoxy)-4-fluoro-phenyl]-3-pyridyl]methyl]-5-isopropyl-oxazolidin-2-one; | 45 |
| 16 | (S*)-3-[[5-[3-(Difluoromethoxy)-4-fluoro-phenyl]-3-pyridyl]methyl]-5-isopropyl-oxazolidin-2-one; | 52 |
| 17 | (R/S)-3-[[5-[3-(Difluoromethoxy)-4-fluoro-phenyl]-3-pyridyl]methyl]-5-(morpholinomethyl)oxazolidin-2-one; | not tested |
| 18 | (R*)-3-[[5-[3-(Difluoromethoxy)-4-fluoro-phenyl]-3-pyridyl]methyl]-5-(morpholinomethyl)oxazolidin-2-one; | 751 |
| 19 | (S*)-3-[[5-[3-(Difluoromethoxy)-4-fluoro-phenyl]-3-pyridyl]methyl]-5-(morpholinomethyl)oxazolidin-2-one; | 1350 |
| 20 | 2-[[5-[3-(Difluoromethoxy)-4-fluoro-phenyl]-3-pyridyl]methyl]-4,8-dioxa-2-azaspiro[4.5]decan-3-one; | 267 |
| 21 | 6-[[5-[3-(Difluoromethyl)-4-fluoro-phenyl]-3-pyridyl]methyl]-8-oxa-2,6-diazaspiro[3.4]octan-7-one; | 806 |
| 22 | 3-[[5-[3-(Difluoromethyl)-4-fluoro-phenyl]-3-pyridyl]methyl]oxazolidin-2-one; | 11 |
| 23 | (4S)-3-[[5-[3-(Difluoromethyl)-4-fluoro-phenyl]-3-pyridyl]methyl]-4-isopropyl-oxazolidin-2-one; | 2600 |
| 24 | 1-[[5-[3-(Difluoromethyl)-4-fluoro-phenyl]-3-pyridyl]methyl]-4H-3,1-benzoxazin-2-one; | 73 |
| 25 | (R/S)-3-[[5-[3-(Difluoromethyl)-4-fluoro-phenyl]-3-pyridyl]methyl]-4-methyl-oxazolidin-2-one; | 31 |
| 26 | (R/S)-3-[[5-[3-(Difluoromethyl)-4-fluoro-phenyl]-3-pyridyl]methyl]-5-methyl-oxazolidin-2-one; | 28 |
| 27 | (S*)-3-[[5-[3-(Difluoromethyl)-4-fluoro-phenyl]-3-pyridyl]methyl]-5-methyl-oxazolidin-2-one; | 14 |
| 28 | (R*)-3-[[5-[3-(Difluoromethyl)-4-fluoro-phenyl]-3-pyridyl]methyl]-5-methyl-oxazolidin-2-one; | 14 |
| 29 | 5-[[5-[3-(Difluoromethyl)-4-fluoro-phenyl]-3-pyridyl]methyl]-7-oxa-5-azaspiro[2.4]heptan-6-one; | 12 |
| 30 | 3-[[5-[3-(Difluoromethyl)-4-fluoro-phenyl]-3-pyridyl]methyl]-6,6-dimethyl-1,3-oxazinan-2-one; | 603 |
| 31 | (4R)-3-[[5-[3-(Difluoromethyl)-4-fluoro-phenyl]-3-pyridyl]methyl]-4-isopropyl-oxazolidin-2-one; | >2999 |
| 32 | 6-[[5-[3-(Difluoromethyl)-4-fluoro-phenyl]-3-pyridyl]methyl]-8-oxa-6-azaspiro[3.4]octan-7-one; | 26 |
| 33 | (5R)-3-[[5-[3-(Difluoromethyl)-4-fluoro-phenyl]-3-pyridyl]methyl]-5-methyl-oxazolidin-2-one; | 16 |
| 34 | 6-[[5-[3-(Difluoromethyl)-4-fluoro-phenyl]-3-pyridyl]methyl]-2,8-dioxa-6-azaspiro[3.4]octan-7-one; | 30 |
| 35 | (R/S)-3-[[5-[3-(Difluoromethyl)-4-fluoro-phenyl]-3-pyridyl]methyl]-5-isopropyl-oxazolidin-2-one; | 29 |
| 36 | (R*)-3-[[5-[3-(Difluoromethyl)-4-fluoro-phenyl]-3-pyridyl]methyl]-5-isopropyl-oxazolidin-2-one; | 31 |
| 37 | (S*)-3-[[5-[3-(Difluoromethyl)-4-fluoro-phenyl]-3-pyridyl]methyl]-5-isopropyl-oxazolidin-2-one; | 50 |
| 38 | 3-[[5-[3-(Difluoromethyl)-4-fluoro-phenyl]-3-pyridyl]methyl]-1,3-oxazinan-2-one; | 9 |
| 39 | (R/S)-3-[[5-[3-(Difluoromethyl)-4-fluoro-phenyl]-3-pyridyl]methyl]-5-(morpholinomethyl)oxazolidin-2-one; | not tested |
| 40 | (R*)-3-[[5-[3-(Difluoromethyl)-4-fluoro-phenyl]-3-pyridyl]methyl]-5-(morpholinomethyl)oxazolidin-2-one; | 205 |
| 41 | (S*)-3-[[5-[3-(Difluoromethyl)-4-fluoro-phenyl]-3-pyridyl]methyl]-5-(morpholinomethyl)oxazolidin-2-one; | 751 |
| 42 | 2-[[5-[3-(Difluoromethyl)-4-fluoro-phenyl]-3-pyridyl]methyl]-4,8-dioxa-2-azaspiro[4.5]decan-3-one; | 108 |
| 43 | 6-[[5-[3-(Difluoromethyl)-4-fluoro-phenyl]-3-pyridyl]methyl]-8-oxa-2,6-diazaspiro[3.4]octan-7-one; | 2620 |
| 44 | 3-[[5-(4-Fluoro-3-methyl-phenyl)-3-pyridyl]methyl]oxazolidin-2-one; | 12 |
| 45 | 3-[[5-(2,4-Difluoro-3-methyl-phenyl)-3-pyridyl]methyl]oxazolidin-2-one; | 9 |
| 46 | 3-[[5-[3-(Trifluoromethyl)phenyl]-3-pyridyl]methyl]oxazolidin-2-one; | 26 |
| 47 | 3-[[5-[4-Chloro-3-(difluoromethoxy)phenyl]-3-pyridyl]methyl]oxazolidin-2-one; | 11 |
| 48 | 3-[[5-[3-Fluoro-4-(trifluoromethoxy)phenyl]-3-pyridyl]methyl]oxazolidin-2-one; | 912 |
| 49 | 3-[[5-[3-(1,1-Difluoroethyl)-4-fluoro-phenyl]-3-pyridyl]methyl]oxazolidin-2-one; | 30 |
| 50 | 3-[[5-[6-(Trifluoromethyl)-2-pyridyl]-3-pyridyl]methyl]oxazolidin-2-one; | 786 |
| 51 | 3-[[5-[2-(Trifluoromethyl)-4-pyridyl]-3-pyridyl]methyl]oxazolidin-2-one; | 1000 |

TABLE 4-continued

| Example # | Compound Name | GluN2B IC$_{50}$ (nM) standard assay |
|---|---|---|
| 52 | 3-[[5-[4-Fluoro-3-(trifluoromethyl)phenyl]-3-pyridyl]methyl]-1,3-oxazinan-2-one; | 27 |
| 53 | 3-[[5-[4-chloro-3-(difluoromethoxy)phenyl]-3-pyridyl]methyl]-1,3-oxazinan-2-one; | |
| 54 | 3-[Dideuterio-[5-[3-(difluoromethyl)-4-fluoro-phenyl]-3-pyridyl]methyl]oxazolidin-2-one; | 13 |
| 55 | 3-[Dideuterio-[5-[3-(difluoromethoxy)-4-fluoro-phenyl]-3-pyridyl]methyl]-1,3-oxazinan-2-one; | 12 |
| 56 | 3-[Dideuterio-[5-[3-(difluoromethoxy)-4-fluoro-phenyl]-2-methyl-3-pyridyl]methyl]-1,3-oxazinan-2-one; | 9 |
| 57 | 3-[Dideuterio-[5-(4-fluoro-3-methyl-phenyl)-2-methyl-3-pyridyl]methyl]-1,3-oxazinan-2-one; | 23 |
| 58 | 3-[Dideuterio-[5-[3-(difluoromethyl)-4-fluoro-phenyl]-2-methyl-3-pyridyl]methyl]-1,3-oxazinan-2-one; | 25 |
| 59 | 3-[Dideuterio-[5-[3-(Difluoromethyl)-4-fluoro-phenyl]-2-methyl-3-pyridyl]methyl]oxazolidin-2-one; | 13 |
| 60 | (R/S)-3-[1-[5-[3-(difluoromethyl)-4-fluoro-phenyl]-3-pyridyl]ethyl]oxazolidin-2-one; | 785 |
| 61 | (R/S)-3-[1-[5-[3-(difluoromethyl)-4-fluoro-phenyl]-3-pyridyl]ethyl]-1,3-oxazinan-2-one; | 323 |
| 62 | 3-[[5-[3-(Difluoromethyl)phenyl]-2-methyl-3-pyridyl]methyl]-1,3-oxazinan-2-one; | 128 |
| 63 | 3-[[5-[3-(Difluoromethoxy)phenyl]-2-methyl-3-pyridyl]methyl]-1,3-oxazinan-2-one; | 174 |
| 64 | 3-[[5-(3-Chlorophenyl)-2-methyl-3-pyridyl]methyl]-1,3-oxazinan-2-one; | 406 |
| 65 | 3-[[5-(3-Chloro-4-fluoro-phenyl)-2-methyl-3-pyridyl]methyl]-1,3-oxazinan-2-one; | 30 |
| 66 | 3-[[5-(4-Fluoro-3-methyl-phenyl)-2-methyl-3-pyridyl]methyl]-1,3-oxazinan-2-one; | 23 |
| 67 | 3-[[5-(3,4-Difluorophenyl)-2-methyl-3-pyridyl]methyl]-1,3-oxazinan-2-one; | 344 |
| 68 | 3-[[5-(4-Fluorophenyl)-2-methyl-3-pyridyl]methyl]-1,3-oxazinan-2-one; | >2999 |
| 69 | 3-[[5-(3-Fluorophenyl)-2-methyl-3-pyridyl]methyl]-1,3-oxazinan-2-one; | 3020 |
| 70 | 3-[[5-(3,4-Difluoro-5-methyl-phenyl)-2-methyl-3-pyridyl]methyl]-1,3-oxazinan-2-one; | 13 |
| 71 | 3-[[5-(2,4-Difluoro-3-methyl-phenyl)-2-methyl-3-pyridyl]methyl]-1,3-oxazinan-2-one; | 22 |
| 72 | 3-[[5-(2,4-Difluorophenyl)-2-methyl-3-pyridyl]methyl]-1,3-oxazinan-2-one; | 2240 |
| 73 | 3-[[5-(3,4-Dichlorophenyl)-2-methyl-3-pyridyl]methyl]-1,3-oxazinan-2-one; | 19 |
| 74 | 3-[[2-Methyl-5-[3-(Trifluoromethyl)phenyl]-3-pyridyl]methyl]-1,3-oxazinan-2-one; | 50 |
| 75 | 3-[[5-[4-Fluoro-3-(trifluoromethyl)phenyl]-2-methyl-3-pyridyl]methyl]-1,3-oxazinan-2-one; | 39 |
| 76 | 3-[[5-(4-Fluoro-3-methyl-phenyl)-2-methyl-3-pyridyl]methyl]oxazolidin-2-one; | 19 |
| 77 | 3-[[5-(2,4-Difluoro-3-methyl-phenyl)-2-methyl-3-pyridyl]methyl]oxazolidin-2-one; | 13 |
| 78 | 3-[[5-[3-(1,1-Difluoroethyl)-4-fluoro-phenyl]-2-methyl-3-pyridyl]methyl]oxazolidin-2-one; | 32 |
| 79 | 3-[[5-[3-(Difluoromethoxy)-4-fluoro-phenyl]-2-methyl-3-pyridyl]methyl]oxazolidin-2-one; | 10 |
| 80 | (R/S)-3-[[5-[3-(Difluoromethoxy)-4-fluoro-phenyl]-2-methyl-3-pyridyl]methyl]-5-methyl-oxazolidin-2-one; | 22 |
| 81 | (R/S)-3-[[5-[3-(Difluoromethoxy)-4-fluoro-phenyl]-2-methyl-3-pyridyl]methyl]-4-methyl-oxazolidin-2-one; | 79 |
| 82 | (R*)-3-[[5-[3-(Difluoromethoxy)-4-fluoro-phenyl]-2-methyl-3-pyridyl]methyl]-4-methyl-oxazolidin-2-one; | 66 |
| 83 | (S*)-3-[[5-[3-(Difluoromethoxy)-4-fluoro-phenyl]-2-methyl-3-pyridyl]methyl]-4-methyl-oxazolidin-2-one; | 30 |
| 84 | 5-[[5-[3-(Difluoromethoxy)-4-fluoro-phenyl]-3-pyridyl]methyl]-7-oxa-5-azaspiro[2.4]heptan-6-one; | 52 |
| 85 | 6-[[5-[3-(Difluoromethoxy)-4-fluoro-phenyl]-3-pyridyl]methyl]-8-oxa-6-azaspiro[3.4]octan-7-one; | 107 |
| 86 | (5R)-3-[[5-[3-(Difluoromethoxy)-4-fluoro-phenyl]-3-pyridyl]methyl]-5-methyl-oxazolidin-2-one; | 20 |
| 87 | 3-[[5-[3-(Difluoromethoxy)-4-fluoro-phenyl]-3-pyridyl]methyl]-5,5-dimethyl-oxazolidin-2-one; | 373 |
| 88 | 3-[[5-[3-(Difluoromethoxy)-4-fluoro-phenyl]-2-methyl-3-pyridyl]methyl]-1,3-oxazinan-2-one; | 22 |
| 89 | 3-[[5-[4-Chloro-3-(difluoromethoxy)phenyl]-2-methyl-3-pyridyl]methyl]oxazolidin-2-one; | 14 |
| 90 | 3-[[5-[3-(Difluoromethyl)-4-fluoro-phenyl]-2-methyl-3-pyridyl]methyl]oxazolidin-2-one; | 13 |
| 91 | 6-[[5-[3-(Difluoromethyl)-4-fluoro-phenyl]-2-methyl-3-pyridyl]methyl]-8-oxa-6-azaspiro[3.4]octan-7-one; | 84 |
| 92 | (5R)-3-[[5-[3-(Difluoromethyl)-4-fluoro-phenyl]-2-methyl-3-pyridyl]methyl]-5-methyl-oxazolidin-2-one; | 63 |
| 93 | 3-[[5-[3-(Difluoromethyl)-4-fluoro-phenyl]-2-methyl-3-pyridyl]methyl]-5,5-dimethyl-oxazolidin-2-one; | 526 |
| 94 | (R/S)-3-[[5-[3-(Difluoromethyl)-4-fluoro-phenyl]-2-methyl-3-pyridyl]methyl]-5-methyl-oxazolidin-2-one; | 21 |
| 95 | (R/S)-3-[[5-[3-(difluoromethyl)-4-fluoro-phenyl]-2-methyl-3-pyridyl]methyl]-4-methyl-oxazolidin-2-one; | 113 |
| 96 | 5-[[5-[3-(Difluoromethyl)-4-fluoro-phenyl]-2-methyl-3-pyridyl]methyl]-7-oxa-5-azaspiro[2.4]heptan-6-one; | 31 |
| 97 | 3-[[5-[3-(Difluoromethyl)-4-fluoro-phenyl]-2-methyl-3-pyridyl]methyl]-1,3-oxazinan-2-one; | 27 |
| 98 | 3-[[5-(5-Chloro-2-thienyl)-2-methyl-3-pyridyl]methyl]oxazolidin-2-one; | 187 |
| 99 | 3-[[2-Methyl-5-[5-(trifluoromethyl)-2-thienyl]-3-pyridyl]methyl]oxazolidin-2-one; | 16 |
| 100 | 3-[[5-[5-(Difluoromethyl)-2-thienyl]-2-methyl-3-pyridyl]methyl]oxazolidin-2-one; | 42 |
| 101 | 3-[[2-Methoxy-5-[3-(trifluoromethyl)phenyl]-3-pyridyl]methyl]oxazolidin-2-one; | 53 |
| 102 | 3-[[2-Methoxy-5-(3,4,5-trifluorophenyl)-3-pyridyl]methyl]oxazolidin-2-one; | 172 |
| 103 | 3-[[5-(2,4-Difluoro-3-methyl-phenyl)-2-methoxy-3-pyridyl]methyl]oxazolidin-2-one; | 46 |
| 104 | 3-[[5-(3-Fluoro-5-methyl-phenyl)-2-methoxy-3-pyridyl]methyl]oxazolidin-2-one; | 159 |
| 105 | 3-[[2-Methoxy-5-(m-tolyl)-3-pyridyl]methyl]oxazolidin-2-one; | 434 |
| 106 | 3-[[5-(3,4-Dichlorophenyl)-2-methoxy-3-pyridyl]methyl]oxazolidin-2-one; | 33 |
| 107 | 3-[[5-[4-Chloro-3-(difluoromethoxy)phenyl]-2-methoxy-3-pyridyl]methyl]oxazolidin-2-one; | 11 |
| 108 | 3-[[5-(3-Chloro-4-fluoro-phenyl)-2-methoxy-3-pyridyl]methyl]oxazolidin-2-one; | 32 |
| 109 | 3-[[5-(3-Chlorophenyl)-2-methoxy-3-pyridyl]methyl]oxazolidin-2-one; | 477 |
| 110 | 3-[[5-[3-(1,1-Difluoroethyl)-4-fluoro-phenyl]-2-methoxy-3-pyridyl]methyl]oxazolidin-2-one; | 37 |
| 111 | 3-[[5-[3-(1,1-Difluoroethyl)phenyl]-2-methoxy-3-pyridyl]methyl]oxazolidin-2-one; | 47 |
| 112 | 3-[[5-(3,4-Difluoro-5-methyl-phenyl)-2-methoxy-3-pyridyl]methyl]oxazolidin-2-one; | 18 |
| 113 | 3-[[5-[4-Fluoro-3-(triuoromethyl)phenyl]-2-methoxy-3-pyridyl]methyl]oxazolidin-2-one; | 13 |
| 114 | 3-[[5-(2,5-Difluoro-3-methyl-phenyl)-2-methoxy-3-pyridyl]methyl]oxazolidin-2-one; | 542 |
| 115 | 3-[[5-[4-Chloro-3-(difluoromethyl)phenyl]-2-methoxy-3-pyridyl]methyl]oxazolidin-2-one; | 10 |
| 116 | 3-[[5-(4-Fluoro-3-methyl-phenyl)-2-methoxy-3-pyridyl]methyl]oxazolidin-2-one; | 18 |
| 117 | (4S)-3-[[5-[3-(Difluoromethoxy)-4-fluoro-phenyl]-2-methoxy-3-pyridyl]methyl]-4-methyl-oxazolidin-2-one; | 60 |
| 118 | (4R)-3-[[5-[3-(Difluoromethoxy)-4-fluoro-phenyl]-2-methoxy-3-pyridyl]methyl]-4-methyl-oxazolidin-2-one; | 26 |
| 119 | 3-[[5-[3-(Difluoromethoxy)-4-fluoro-phenyl]-2-methoxy-3-pyridyl]methyl]oxazolidin-2-one; | 12 |
| 120 | (4S)-3-[[5[3-(Difluoromethyl)-4-fluoro-phenyl]-2-methoxy-3-pyridyl]methyl]-4-methyl-oxazolidin-2-one; | 121 |
| 121 | (4R)-3-[[5-[3-(Difluoromethyl)-4-fluoro-phenyl]-2-methoxy-3-pyridyl]methyl]-4-methyl-oxazolidin-2-one; | 21 |
| 122 | 3-[[5-[3-(Difluoromethyl)-4-fluoro-phenyl]-2-methoxy-3-pyridyl]methyl]oxazolidin-2-one; | 15 |
| 123 | 3-[[2-(Difluoromethyl)-5-[3-(difluoromethyl)-4-fluoro-phenyl]-3-pyridyl]methyl]-1,3-oxazinan-2-one; | 63 |
| 124 | 3-[[2-(Difluoromethyl)-5-[3-(difluoromethyl)-4-fluoro-phenyl]-3-pyridyl]methyl]oxazolidin-2-one; | 56 |
| 125 | 3-[[5-[3-(Difluoromethoxy)-4-fluoro-phenyl]-2-(difluoromethyl)-3-pyridyl]methyl]oxazolidin-2-one; | 39 |

TABLE 4-continued

| Example # | Compound Name | GluN2B IC$_{50}$ (nM) standard assay |
|---|---|---|
| 126 | 3-[[5-[3-(Difluoromethoxy)-4-fluoro-phenyl]-2-(difluoromethyl)-3-pyridyl]methyl]-1,3-oxazinan-2-one; | 19 |
| 127 | 3-[[2-(Difluoromethyl)-5-(4-fluoro-3-methyl-phenyl)-3-pyridyl]methyl]-1,3-oxazinan-2-one; | 276 |
| 128 | 3-[[2-(Difluoromethyl)-5-(4-fluoro-3-methyl-phenyl)-3-pyridyl]methyl]oxazolidin-2-one; | 204 |
| 129 | 3-[[5-[4-Chloro-3-(difluoromethoxy)phenyl]-2-(difluoromethyl)-3-pyridyl]methyl]-1,3-oxazinan-2-one; | 59 |
| 130 | 3-[[5-[4-Chloro-3-(difluoromethoxy)phenyl]-2-(difluoromethyl)-3-pyridyl]methyl]oxazolidin-2-one; | 30 |
| 131 | 3-[[2-(Difluoromethoxy)-5-[3-(difluoromethyl)-4-fluoro-phenyl]-3-pyridyl]methyl]oxazolidin-2-one; | 153 |
| 132 | (4R)-3-[[2-(Difluoromethoxy)-5-[3-(difluoromethyl)-4-fluoro-phenyl]-3-pyridyl]methyl]-4-methyl-oxazolidin-2-one; | 176 |
| 133 | 3-[[2-(Difluoromethoxy)-5-[3-(difluoromethoxy)-4-fluoro-phenyl]-3-pyridyl]methyl]oxazolidin-2-one; | 76 |
| 134 | (4R)-3-[[2-(Difluoromethoxy)-5-[3-(difluoromethoxy)-4-fluoro-phenyl]-3-pyridyl]methyl]-4-methyl-oxazolidin-2-one; | 61 |
| 135 | 3-[[2-(1,1-Difluoroethyl)-5-[3-(difluoromethyl)-4-fluoro-phenyl]-3-pyridyl]methyl]oxazolidin-2-one; | 47 |
| 136 | 3-[[2-(1,1-Difluoroethyl)-5-[3-(difluoromethyl)-4-fluoro-phenyl]-3-pyridyl]methyl]-1,3-oxazinan-2-one; | 99 |
| 137 | 3-[[2-(1,1-Difluoroethyl)-5-[3-(difluoromethoxy)-4-fluoro-phenyl]-3-pyridyl]methyl]-1,3-oxazinan-2-one; | 76 |
| 138 | 6-[[2-(1,1-Difluoroethyl)-5-[3-(difluoromethyl)-4-fluoro-phenyl]-3-pyridyl]methyl]-8-oxa-6-azaspiro[3.4]octan-7-one; | 549 |
| 139 | (5R)-3-[[2-(1,1-Difluoroethyl)-5-[3-(difluoromethyl)-4-fluoro-phenyl]-3-pyridyl]methyl]-5-methyl-oxazolidin-2-one; | 134 |
| 140 | (5S)-3-[[2-(1,1-Difluoroethyl)-5-[3-(difluoromethyl)-4-fluoro-phenyl]-3-pyridyl]methyl]-5-methyl-oxazolidin-2-one; | 111 |
| 141 | 5-[[2-(1,1-Difluoroethyl)-5-[3-(difluoromethyl)-4-fluoro-phenyl]-3-pyridyl]methyl]-7-oxa-5-azaspiro[2.4]heptan-6-one; | 245 |
| 142 | (4S)-3-[[2-(1,1-Difluoroethyl)-5-[3-(difluoromethyl)-4-fluoro-phenyl]-3-pyridyl]methyl]-4-methyl-oxazolidin-2-one; | 2000 |
| 143 | (4R)-3-[[2-(1,1-Difluoroethyl)-5-[3-(difluoromethyl)-4-fluoro-phenyl]-3-pyridyl]methyl]-4-methyl-oxazolidin-2-one; | 180 |
| 144 | (4R)-3-[[2-(1,1-Difluoroethyl)-5-[3-(difluoromethoxy)-4-fluoro-phenyl]-3-pyridyl]methyl]-4-methyl-oxazolidin-2-one; | 157 |
| 145 | (4S)-3-[[2-(1,1-Difluoroethyl)-5-[3-(difluoromethoxy)-4-fluoro-phenyl]-3-pyridyl]methyl]-4-methyl-oxazolidin-2-one; | 492 |
| 146 | 5-[[2-(1,1-Difluoroethyl)-5-[3-(difluoromethoxy)-4-fluoro-phenyl]-3-pyridyl]methyl]-7-oxa-5-azaspiro[2.4]heptan-6-one; | 212 |
| 147 | 6-[[2-(1,1-Difluoroethyl)-5-[3-(difluoromethoxy)-4-fluoro-phenyl]-3-pyridyl]methyl]-8-oxa-6-azaspiro[3.4]octan-7-one; | 392 |
| 148 | (5S)-3-[[2-(1,1-Difluoroethyl)-5-[3-(difluoromethoxy)-4-fluoro-phenyl]-3-pyridyl]methyl]-5-methyl-oxazolidin-2-one; | 147 |
| 149 | (5R)-3-[[2-(1,1-Difluoroethyl)-5-[3-(difluoromethoxy)-4-fluoro-phenyl]-3-pyridyl]methyl]-5-methyl-oxazolidin-2-one; | 127 |
| 150 | 3-((5-(3-(Difluoromethoxy)-4-fluorophenyl)-2-fluoropyridin-3-yl)methyl)oxazolidin-2-one; and | 11 |
| 151 | 3-((5-(3-(Difluoromethoxy)-4-fluorophenyl)-2-fluoropyridin-3-yl)methyl)-1,3-oxazinan-2-one. | 11 |

5.4. Liver Microsomal Stability Assay (Extraction Ratio)

Microsomal stability studies (see, Chrovian et al, "H-Pyrrolo[3,2-b]pyridine GluN2B-Selective Negative Allosteric Modulators". ACS Med Chem Lett. 2019 Jan. 10; 10(3): 261-266) were conducted on a Biomek® FX Robotic Liquid Handling Workstation (Beckman Coulter, Brea, Calif.), which consists of a 96-channel pipette head, a 12-position workstation deck, and a plate incubator. Test compounds (1 μM) were spiked in a reaction mix consisting of 100 mM potassium phosphate buffer (pH 7.4), 3 mM MgCl$_2$, and 0.5 mg/mL liver microsomes from mouse, rat, and human (BD Gentest). The reaction was brought to 37° C. and initiated by adding NADPH to a final concentration of 1 mM. After mixing on the platedeck, 50 μL aliquots were excised from the reaction plate at 0, 5, 10, 20, 40, and 60 min and quenched with four volumes of acetonitrile spiked with 500 μg/nL of the internal standard phenytoin. Quenched plates were centrifuged at 5700 rpm for 10 min at 4° C., and supernatant was diluted 1:3 in water before LC/MS/MS analysis. The compound half-lives were derived from plots of the ln of percent remaining compound over time to determine the intrinsic clearance. The predicted hepatic clearance was derived from the intrinsic clearance value using equations from the well-stirred model (Current Drug Metabolism, 2008, 9, 940-951), where no correction was made plasma protein binding and the blood to plasma concentration ratio was assumed to be one. The extraction ratio (ER) was calculated by dividing the predicted hepatic clearance by species blood flow (Q), where Q is 90, 55, and 21.7 mL/min/kg for mouse, rat and human, respectively.

Results of the assay performed on several compounds of the Examples are shown in Table 5.

TABLE 5

| Example # | Extraction Ratio @ 1 μM |
|---|---|
| 1 | 0.49 |
| 22 | 0.63 |
| 27 | 0.42 |
| 38 | <0.298 |
| 53 | 0.61 |
| 54 | 0.61 |
| 60 | 0.42 |
| 90 | 0.60 |
| 97 | 0.55 |

6. SPECIFIC EMBODIMENTS

The present disclosure is exemplified by the specific embodiments below.

1. A compound of Formula (I):

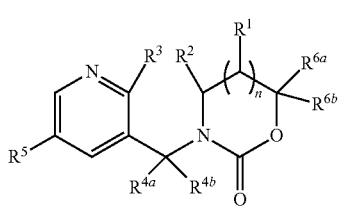

(I)

or a pharmaceutically acceptable salt, solvate, isotopic variant, or N-oxide thereof, wherein:

n is 0 or 1;

R$^1$, when present, is H; or R$^1$, together with R$^2$ and the carbon atoms to which they are attached, forms a phenyl ring;

R², when not forming a phenyl ring with R¹ and the carbon atoms to which they are attached, is H or alkyl;

R³ is H, halogen, alkyl, haloalkyl, O-alkyl, or O-haloalkyl;

$R^{4a}$ and $R^{4b}$ are, each independent from the other, H or alkyl;

R⁵ is aryl which is optionally substituted with one, two, or three substituents each of which is independently halogen, alkyl, haloalkyl, or O-haloalkyl; pyridinyl which is optionally substituted with one substituent which is haloalkyl; or thienyl which is optionally substituted with one substituent which is halogen or haloalkyl; and $R^{6a}$ and $R^{6b}$ are, each independent from the other, H or alkyl which is optionally substituted with one substituent which is heterocycloalkyl; or $R^{6a}$ and $R^{6b}$ together with the carbon atom to which they are attached form a cycloalkyl ring or a heterocycloalkyl ring.

2. The compound of embodiment 1, or a pharmaceutically acceptable salt, solvate, isotopic variant, or N-oxide thereof, having the structure of Formula (Ia):

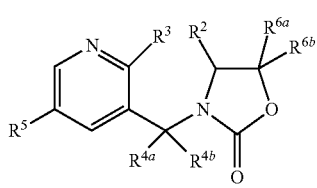

(Ia)

3. The compound of embodiment 1, or a pharmaceutically acceptable salt, solvate, isotopic variant, or N-oxide thereof, having the structure of Formula (Ib):

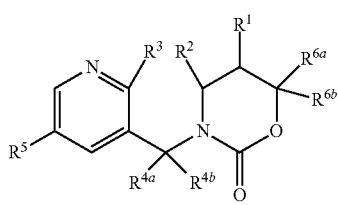

(Ib)

4. The compound of embodiment 1 or embodiment 3, or a pharmaceutically acceptable salt, solvate, isotopic variant, or N-oxide thereof, wherein R¹ when present, together with R² and the atoms to which they are attached, forms a phenyl ring.

5. The compound of embodiment 1 or embodiment 3, or a pharmaceutically acceptable salt, solvate, isotopic variant, or N-oxide thereof, wherein R¹ when present, is H.

6. The compound of any one of embodiments 1 to 3, or a pharmaceutically acceptable salt, solvate, isotopic variant, or N-oxide thereof, wherein R² is H or alkyl.

7. The compound of embodiment 6, or a pharmaceutically acceptable salt, solvate, isotopic variant, or N-oxide thereof, wherein R² is H.

8. The compound of embodiment 6, or a pharmaceutically acceptable salt, solvate, isotopic variant, or N-oxide thereof, wherein R² is alkyl.

9. The compound of embodiment 6, or a pharmaceutically acceptable salt, solvate, isotopic variant, or N-oxide thereof, wherein R² is $C_1$-$C_6$alkyl.

10. The compound of embodiment 6, or a pharmaceutically acceptable salt, solvate, isotopic variant, or N-oxide thereof, wherein R² is $C_1$-$C_3$alkyl.

11. The compound of embodiment 6, or a pharmaceutically acceptable salt, solvate, isotopic variant, or N-oxide thereof, wherein R² is —CH₃.

12. The compound of embodiment 6, or a pharmaceutically acceptable salt, solvate, isotopic variant, or N-oxide thereof, wherein R² is —CH(CH₃)₂.

13. The compound of any one of embodiments 8 to 12, or a pharmaceutically acceptable salt, solvate, isotopic variant, or N-oxide thereof, wherein the stereochemistry at the carbon to which R² is attached is (R).

14. The compound of any one of embodiments 8 to 12, or a pharmaceutically acceptable salt, solvate, isotopic variant, or N-oxide thereof, wherein the stereochemistry at the carbon to which R² is attached is (S).

15. The compound of any one of embodiments 1 to 14, or a pharmaceutically acceptable salt, solvate, isotopic variant, or N-oxide thereof, wherein R³ is H, alkyl, haloalkyl, O-alkyl, or O-haloalkyl.

16. The compound of any one of embodiments 1 to 14, or a pharmaceutically acceptable salt, solvate, isotopic variant, or N-oxide thereof, wherein R³ is H, halogen, $C_1$-$C_6$alkyl, $C_1$-$C_6$haloalkyl, O—$C_1$-$C_6$alkyl, or O—$C_1$-$C_6$haloalkyl.

17. The compound of any one of embodiments 1 to 14, or a pharmaceutically acceptable salt, solvate, isotopic variant, or N-oxide thereof, wherein R³ is H, halogen, $C_1$-$C_3$alkyl, $C_1$-$C_3$haloalkyl, O—$C_1$-$C_3$alkyl, or O—$C_1$-$C_3$haloalkyl.

18. The compound of any one of embodiments 1 to 14, or a pharmaceutically acceptable salt, solvate, isotopic variant, or N-oxide thereof, wherein R³ is H.

19. The compound of any one of embodiments 1 to 14, or a pharmaceutically acceptable salt, solvate, isotopic variant, or N-oxide thereof, wherein R³ is F.

20. The compound of any one of embodiments 1 to 14, or a pharmaceutically acceptable salt, solvate, isotopic variant, or N-oxide thereof, wherein R³ is alkyl.

21. The compound of embodiment 20, or a pharmaceutically acceptable salt, solvate, isotopic variant, or N-oxide thereof, wherein R³ is $C_1$-$C_6$alkyl.

22. The compound of embodiment 21, or a pharmaceutically acceptable salt, solvate, isotopic variant, or N-oxide thereof, wherein R³ is $C_1$-$C_3$alkyl.

23. The compound of embodiment 22, or a pharmaceutically acceptable salt, solvate, isotopic variant, or N-oxide thereof, wherein R³ is $C_1$-$C_2$alkyl.

24. The compound of embodiment 23, or a pharmaceutically acceptable salt, solvate, isotopic variant, or N-oxide thereof, wherein R³ is —CH₃.

25. The compound of any one of embodiments 1 to 14, or a pharmaceutically acceptable salt, solvate, isotopic variant, or N-oxide thereof, wherein R³ is haloalkyl.

26. The compound of embodiment 25, or a pharmaceutically acceptable salt, solvate, isotopic variant, or N-oxide thereof, wherein R³ comprises one or more F atoms.

27. The compound of embodiment 25 or embodiment 26, or a pharmaceutically acceptable salt, solvate, isotopic variant, or N-oxide thereof, wherein R³ is $C_1$-$C_6$haloalkyl.

28. The compound of embodiment 27, or a pharmaceutically acceptable salt, solvate, isotopic variant, or N-oxide thereof, wherein R³ is $C_1$-$C_3$haloalkyl.

29. The compound of embodiment 28, or a pharmaceutically acceptable salt, solvate, isotopic variant, or N-oxide thereof, wherein R³ is $C_1$-$C_2$haloalkyl.

30. The compound of embodiment 29, or a pharmaceutically acceptable salt, solvate, isotopic variant, or N-oxide thereof, wherein $R^3$ is —CHF$_2$.

31. The compound of embodiment 29, or a pharmaceutically acceptable salt, solvate, isotopic variant, or N-oxide thereof, wherein $R^3$ is —CF$_2$CH$_3$.

32. The compound of any one of embodiments 1 to 14, or a pharmaceutically acceptable salt, solvate, isotopic variant, or N-oxide thereof, wherein $R^3$ is O-alkyl.

33. The compound of embodiment 32, or a pharmaceutically acceptable salt, solvate, isotopic variant, or N-oxide thereof, wherein $R^3$ is —OC$_1$-C$_6$alkyl.

34. The compound of embodiment 33, or a pharmaceutically acceptable salt, solvate, isotopic variant, or N-oxide thereof, wherein $R^3$ is —OC$_1$-C$_3$alkyl.

35. The compound of embodiment 34, or a pharmaceutically acceptable salt, solvate, isotopic variant, or N-oxide thereof, wherein $R^3$ is —OC$_1$-C$_2$alkyl.

36. The compound of embodiment 35, or a pharmaceutically acceptable salt, solvate, isotopic variant, or N-oxide thereof, wherein $R^3$ is —OCH$_3$.

37. The compound of any one of embodiments 1 to 14, or a pharmaceutically acceptable salt, solvate, isotopic variant, or N-oxide thereof, wherein $R^3$ is O-haloalkyl.

38. The compound of embodiment 37, or a pharmaceutically acceptable salt, solvate, isotopic variant, or N-oxide thereof, wherein $R^3$ comprises one or more F atoms.

39. The compound of embodiment 37 or embodiment 38, or a pharmaceutically acceptable salt, solvate, isotopic variant, or N-oxide thereof, wherein $R^3$ is O—C$_1$-C$_6$haloalkyl.

40. The compound of embodiment 39, or a pharmaceutically acceptable salt, solvate, isotopic variant, or N-oxide thereof, wherein $R^3$ is O—C$_1$-C$_6$haloalkyl.

41. The compound of embodiment 40, or a pharmaceutically acceptable salt, solvate, isotopic variant, or N-oxide thereof, wherein $R^3$ is O—C$_1$-C$_2$haloalkyl.

42. The compound of embodiment 41, or a pharmaceutically acceptable salt, solvate, isotopic variant, or N-oxide thereof, wherein $R^3$ is —OCHF$_2$.

43. The compound of any one of embodiments 1 to 42, or a pharmaceutically acceptable salt, solvate, isotopic variant, or N-oxide thereof, wherein $R^{4a}$ and $R^{4b}$ are both H.

44. The compound of embodiment 43, or a pharmaceutically acceptable salt, solvate, isotopic variant, or N-oxide thereof, wherein both $R^{4a}$ and $R^{4b}$ are $^1$H.

45. The compound of embodiment 43, or a pharmaceutically acceptable salt, solvate, isotopic variant, or N-oxide thereof, wherein one of $R^{4a}$ and $R^{4b}$ is $^1$H and the other is $^2$H.

46. The compound of embodiment 43, or a pharmaceutically acceptable salt, solvate, isotopic variant, or N-oxide thereof, wherein $R^{4a}$ and $R^{4b}$ are both $^2$H.

47. The compound of any one of embodiments 1 to 42, or a pharmaceutically acceptable salt, solvate, isotopic variant, or N-oxide thereof, wherein $R^{4a}$ is H and $R^{4b}$ is alkyl.

48. The compound of embodiment 47, or a pharmaceutically acceptable salt, solvate, isotopic variant, or N-oxide thereof, wherein $R^{4a}$ is $^1$H.

49. The compound of embodiment 47, or a pharmaceutically acceptable salt, solvate, isotopic variant, or N-oxide thereof, wherein $R^{4a}$ is $^2$H.

50. The compound of embodiments 47 to 49, or a pharmaceutically acceptable salt, solvate, isotopic variant, or N-oxide thereof, wherein $R^{4b}$ is C$_1$-C$_6$alkyl.

51. The compound of embodiment 50, or a pharmaceutically acceptable salt, solvate, isotopic variant, or N-oxide thereof, wherein $R^{4b}$ is C$_1$-C$_3$alkyl.

52. The compound of embodiment 51, or a pharmaceutically acceptable salt, solvate, isotopic variant, or N-oxide thereof, wherein $R^{4b}$ is C$_1$-C$_2$alkyl.

53. The compound of embodiment 52, or a pharmaceutically acceptable salt, solvate, isotopic variant, or N-oxide thereof, wherein $R^{4b}$ is —CH$_3$.

54. The compound of any one of embodiments 1 to 53, or a pharmaceutically acceptable salt, solvate, isotopic variant, or N-oxide thereof, wherein $R^5$ is

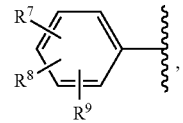

and wherein:
each of $R^7$, $R^8$, and $R^9$ is, independent from the others, H, halogen, alkyl, haloalkyl, or O-haloalkyl.

55. The compound of embodiment 2, or a pharmaceutically acceptable salt, solvate, isotopic variant, or N-oxide thereof, having the structure of Formula (Ic):

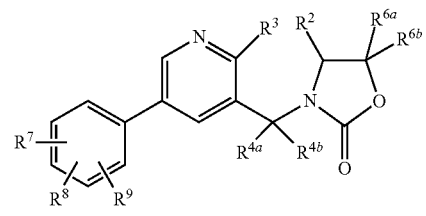

(Ic)

wherein each of $R^7$, $R^8$, and $R^9$ is, independent from the others, H, halogen, alkyl, haloalkyl, or O-haloalkyl.

56. The compound of embodiment 3, or a pharmaceutically acceptable salt, solvate, isotopic variant, or N-oxide thereof, having the structure of Formula (Id):

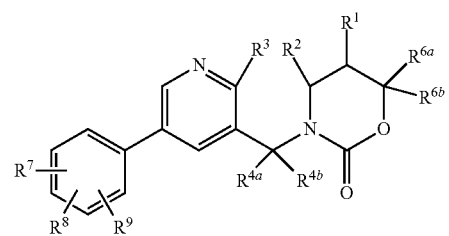

(Id)

wherein each of $R^7$, $R^8$, and $R^9$ is, independent from the others, H, halogen, alkyl, haloalkyl, or O-haloalkyl.

57. The compound of any one of embodiments 54 to 56, or a pharmaceutically acceptable salt, solvate, isotopic variant, or N-oxide thereof, wherein each of $R^7$, $R^8$, and $R^9$ is, independent from the others, H, halogen, C$_1$-C$_6$alkyl, C$_1$-C$_6$haloalkyl, or O—C$_1$-C$_6$haloalkyl.

58. The compound of any one of embodiments 54 to 56, or a pharmaceutically acceptable salt, solvate, isotopic variant, or N-oxide thereof, wherein each of $R^7$, $R^8$, and $R^9$ is, independent from the others, H, halogen, C$_1$-C$_6$alkyl, C$_1$-C$_6$haloalkyl, or O—C$_1$-C$_6$haloalkyl.

59. The compound of any one of embodiments 54 to 58, or a pharmaceutically acceptable salt, solvate, isotopic variant, or N-oxide thereof, wherein $R^7$ is H.

60. The compound of any one of embodiments 54 to 58, or a pharmaceutically acceptable salt, solvate, isotopic variant, or N-oxide thereof, wherein $R^7$ is halogen.

61. The compound of embodiment 60, or a pharmaceutically acceptable salt, solvate, isotopic variant, or N-oxide thereof, wherein $R^7$ is F or Cl.

62. The compound of embodiment 61, or a pharmaceutically acceptable salt, solvate, isotopic variant, or N-oxide thereof, wherein $R^7$ is F.

63. The compound of embodiment 61, or a pharmaceutically acceptable salt, solvate, isotopic variant, or N-oxide thereof, wherein $R^7$ is Cl.

64. The compound of any one of embodiments 54 to 56, or a pharmaceutically acceptable salt, solvate, isotopic variant, or N-oxide thereof, wherein $R^7$ is alkyl.

65. The compound of embodiment 64, or a pharmaceutically acceptable salt, solvate, isotopic variant, or N-oxide thereof, wherein $R^7$ is $C_1$-$C_6$alkyl.

66. The compound of embodiment 65, or a pharmaceutically acceptable salt, solvate, isotopic variant, or N-oxide thereof, wherein $R^7$ is $C_1$-$C_6$alkyl.

67. The compound of embodiment 66, or a pharmaceutically acceptable salt, solvate, isotopic variant, or N-oxide thereof, wherein $R^7$ is $C_1$-$C_2$alkyl.

68. The compound of embodiment 67, or a pharmaceutically acceptable salt, solvate, isotopic variant, or N-oxide thereof, wherein $R^7$ is —$CH_3$.

69. The compound of any one of embodiments 54 to 56, or a pharmaceutically acceptable salt, solvate, isotopic variant, or N-oxide thereof, wherein $R^7$ is haloalkyl.

70. The compound of embodiment 69, or a pharmaceutically acceptable salt, solvate, isotopic variant, or N-oxide thereof, wherein $R^7$ is $C_1$-$C_6$haloalkyl.

71. The compound of embodiment 70, or a pharmaceutically acceptable salt, solvate, isotopic variant, or N-oxide thereof, wherein $R^7$ is $C_1$-$C_6$haloalkyl.

72. The compound of embodiment 71, or a pharmaceutically acceptable salt, solvate, isotopic variant, or N-oxide thereof, wherein $R^7$ is $C_1$-$C_2$haloalkyl.

73. The compound of embodiment 72, or a pharmaceutically acceptable salt, solvate, isotopic variant, or N-oxide thereof, wherein $R^7$ is —$CHF_2$.

74. The compound of embodiment 72, or a pharmaceutically acceptable salt, solvate, isotopic variant, or N-oxide thereof, wherein $R^7$ is —$CF_2CH_3$.

75. The compound of embodiment 72, or a pharmaceutically acceptable salt, solvate, isotopic variant, or N-oxide thereof, wherein $R^7$ is —$CF_3$.

76. The compound of any one of embodiments 54 to 56, or a pharmaceutically acceptable salt, solvate, isotopic variant, or N-oxide thereof, wherein $R^7$ is O-haloalkyl.

77. The compound of embodiment 76, or a pharmaceutically acceptable salt, solvate, isotopic variant, or N-oxide thereof, wherein $R^7$ is O—$C_1$-$C_6$haloalkyl.

78. The compound of embodiment 77, or a pharmaceutically acceptable salt, solvate, isotopic variant, or N-oxide thereof, wherein $R^7$ is O—$C_1$-$C_6$haloalkyl.

79. The compound of embodiment 78, or a pharmaceutically acceptable salt, solvate, isotopic variant, or N-oxide thereof, wherein $R^7$ is O—$C_1$-C2haloalkyl.

80. The compound of embodiment 79, or a pharmaceutically acceptable salt, solvate, isotopic variant, or N-oxide thereof, wherein $R^7$ is —$OCHF_2$.

81. The compound of embodiment 79, or a pharmaceutically acceptable salt, solvate, isotopic variant, or N-oxide thereof, wherein $R^7$ is —$OCF_3$.

82. The compound of any one of embodiments 54 to 81, or a pharmaceutically acceptable salt, solvate, isotopic variant, or N-oxide thereof, wherein $R^8$ is H.

83. The compound of any one of embodiments 54 to 81, or a pharmaceutically acceptable salt, solvate, isotopic variant, or N-oxide thereof, wherein $R^8$ is halogen.

84. The compound of embodiment 83, or a pharmaceutically acceptable salt, solvate, isotopic variant, or N-oxide thereof, wherein $R^8$ is F or Cl.

85. The compound of embodiment 84, or a pharmaceutically acceptable salt, solvate, isotopic variant, or N-oxide thereof, wherein $R^8$ is F.

86. The compound of embodiment 84, or a pharmaceutically acceptable salt, solvate, isotopic variant, or N-oxide thereof, wherein $R^8$ is Cl.

87. The compound of any one of embodiments 54 to 81, or a pharmaceutically acceptable salt, solvate, isotopic variant, or N-oxide thereof, wherein $R^8$ is alkyl.

88. The compound of embodiment 87, or a pharmaceutically acceptable salt, solvate, isotopic variant, or N-oxide thereof, wherein $R^8$ is $C_1$-$C_6$alkyl.

89. The compound of embodiment 88, or a pharmaceutically acceptable salt, solvate, isotopic variant, or N-oxide thereof, wherein $R^8$ is $C_1$-$C_3$alkyl.

90. The compound of embodiment 89, or a pharmaceutically acceptable salt, solvate, isotopic variant, or N-oxide thereof, wherein $R^8$ is $C_1$-$C_2$alkyl.

91. The compound of embodiment 90, or a pharmaceutically acceptable salt, solvate, isotopic variant, or N-oxide thereof, wherein $R^8$ is —$CH_3$.

92. The compound of any one of embodiments 54 to 81, or a pharmaceutically acceptable salt, solvate, isotopic variant, or N-oxide thereof, wherein $R^8$ is haloalkyl.

93. The compound of embodiment 92, or a pharmaceutically acceptable salt, solvate, isotopic variant, or N-oxide thereof, wherein $R^8$ is $C_1$-$C_6$haloalkyl.

94. The compound of embodiment 93, or a pharmaceutically acceptable salt, solvate, isotopic variant, or N-oxide thereof, wherein $R^8$ is $C_1$-$C_6$haloalkyl.

95. The compound of embodiment 94, or a pharmaceutically acceptable salt, solvate, isotopic variant, or N-oxide thereof, wherein $R^8$ is $C_1$-$C_2$haloalkyl.

96. The compound of embodiment 95, or a pharmaceutically acceptable salt, solvate, isotopic variant, or N-oxide thereof, wherein $R^8$ is —$CHF_2$.

97. The compound of embodiment 95, or a pharmaceutically acceptable salt, solvate, isotopic variant, or N-oxide thereof, wherein $R^8$ is —$CF_2CH_3$.

98. The compound of embodiment 95, or a pharmaceutically acceptable salt, solvate, isotopic variant, or N-oxide thereof, wherein $R^8$ is —$CF_3$.

99. The compound of any one of embodiments 54 to 81, or a pharmaceutically acceptable salt, solvate, isotopic variant, or N-oxide thereof, wherein $R^8$ is O-haloalkyl.

100. The compound of embodiment 99, or a pharmaceutically acceptable salt, solvate, isotopic variant, or N-oxide thereof, wherein $R^8$ is O—$C_1$-$C_6$haloalkyl.

101. The compound of embodiment 100, or a pharmaceutically acceptable salt, solvate, isotopic variant, or N-oxide thereof, wherein $R^8$ is O—$C_1$-$C_3$haloalkyl.

102. The compound of embodiment 101, or a pharmaceutically acceptable salt, solvate, isotopic variant, or N-oxide thereof, wherein $R^8$ is O—$C_1$-$C_2$haloalkyl.

103. The compound of embodiment 102, or a pharmaceutically acceptable salt, solvate, isotopic variant, or N-oxide thereof, wherein $R^8$ is —$OCHF_2$.

104. The compound of embodiment 102, or a pharmaceutically acceptable salt, solvate, isotopic variant, or N-oxide thereof, wherein $R^8$ is —$OCF_3$.

105. The compound of any one of embodiments 54 to 104, or a pharmaceutically acceptable salt, solvate, isotopic variant, or N-oxide thereof, wherein $R^9$ is H.

106. The compound of any one of embodiments 54 to 104, or a pharmaceutically acceptable salt, solvate, isotopic variant, or N-oxide thereof, wherein $R^9$ is halogen.

107. The compound of embodiment 106, or a pharmaceutically acceptable salt, solvate, isotopic variant, or N-oxide thereof, wherein $R^9$ is F or Cl.

108. The compound of embodiment 107, or a pharmaceutically acceptable salt, solvate, isotopic variant, or N-oxide thereof, wherein $R^9$ is F.

109. The compound of embodiment 107, or a pharmaceutically acceptable salt, solvate, isotopic variant, or N-oxide thereof, wherein $R^9$ is Cl.

110. The compound of any one of embodiments 54 to 104, or a pharmaceutically acceptable salt, solvate, isotopic variant, or N-oxide thereof, wherein $R^9$ is alkyl.

111. The compound of embodiment 110, or a pharmaceutically acceptable salt, solvate, isotopic variant, or N-oxide thereof, wherein $R^9$ is $C_1$-$C_6$alkyl.

112. The compound of embodiment 111, or a pharmaceutically acceptable salt, solvate, isotopic variant, or N-oxide thereof, wherein $R^9$ is $C_1$-$C_9$alkyl.

113. The compound of embodiment 112, or a pharmaceutically acceptable salt, solvate, isotopic variant, or N-oxide thereof, wherein $R^9$ is $C_1$-$C_2$alkyl.

114. The compound of embodiment 113, or a pharmaceutically acceptable salt, solvate, isotopic variant, or N-oxide thereof, wherein $R^9$ is —$CH_3$.

115. The compound of any one of embodiments 54 to 104, or a pharmaceutically acceptable salt, solvate, isotopic variant, or N-oxide thereof, wherein $R^9$ is haloalkyl.

116. The compound of embodiment 115, or a pharmaceutically acceptable salt, solvate, isotopic variant, or N-oxide thereof, wherein $R^9$ is $C_1$-$C_6$haloalkyl.

117. The compound of embodiment 116, or a pharmaceutically acceptable salt, solvate, isotopic variant, or N-oxide thereof, wherein $R^9$ is $C_1$-$C_6$haloalkyl.

118. The compound of embodiment 117, or a pharmaceutically acceptable salt, solvate, isotopic variant, or N-oxide thereof, wherein $R^9$ is $C_1$-$C_2$haloalkyl.

119. The compound of embodiment 118, or a pharmaceutically acceptable salt, solvate, isotopic variant, or N-oxide thereof, wherein $R^9$ is —$CHF_2$.

120. The compound of embodiment 118, or a pharmaceutically acceptable salt, solvate, isotopic variant, or N-oxide thereof, wherein $R^9$ is —$CF_2CH_3$.

121. The compound of embodiment 118, or a pharmaceutically acceptable salt, solvate, isotopic variant, or N-oxide thereof, wherein $R^9$ is —$CF_3$.

122. The compound of any one of embodiments 54 to 104, or a pharmaceutically acceptable salt, solvate, isotopic variant, or N-oxide thereof, wherein $R^9$ is O-haloalkyl.

123. The compound of embodiment 122, or a pharmaceutically acceptable salt, solvate, isotopic variant, or N-oxide thereof, wherein $R^9$ is O—$C_1$-$C_6$haloalkyl.

124. The compound of embodiment 123, or a pharmaceutically acceptable salt, solvate, isotopic variant, or N-oxide thereof, wherein $R^9$ is O—$C_1$-$C_3$haloalkyl.

125. The compound of embodiment 124, or a pharmaceutically acceptable salt, solvate, isotopic variant, or N-oxide thereof, wherein $R^9$ is O—$C_1$-$C_2$haloalkyl.

126. The compound of embodiment 125, or a pharmaceutically acceptable salt, solvate, isotopic variant, or N-oxide thereof, wherein $R^9$ is —$OCHF_2$.

127. The compound of embodiment 125, or a pharmaceutically acceptable salt, solvate, isotopic variant, or N-oxide thereof, wherein $R^9$ is —$OCF_3$.

128. The compound of any one of embodiments 54 to 127, wherein $R^7$ is in the ortho position, $R^8$ is in the ortho position, and $R^9$ in the meta position.

129. The compound of any one of embodiments 54 to 127, wherein $R^7$ is in the ortho position, $R^8$ is in the ortho position, and $R^9$ in the para position.

130. The compound of any one of embodiments 54 to 127, wherein $R^7$ is in the ortho position, $R^8$ is in the meta position, and $R^9$ in the para position.

131. The compound of any one of embodiments 54 to 127, wherein $R^7$ is in the ortho position, $R^8$ is in the meta position, and $R^9$ in the meta position.

132. The compound of any one of embodiments 54 to 127, wherein $R^7$ is in the meta position, $R^3$ is in the meta position, and $R^9$ in the para position.

133. The compound of any one of embodiments 1 to 53, or a pharmaceutically acceptable salt, solvate, isotopic variant, or N-oxide thereof, wherein $R^5$ is aryl which is optionally substituted with one, two, or three substituents each of which is independently halogen, alkyl, haloalkyl, or O-haloalkyl.

134. The compound of embodiment 133, or a pharmaceutically acceptable salt, solvate, isotopic variant, or N-oxide thereof, wherein $R^5$ is aryl which is optionally substituted with one, two, or three substituents each of which is independently halogen, $C_1$-$C_6$alkyl, $C_1$-$C_6$haloalkyl, or O—$C_1$-$C_6$haloalkyl.

135. The compound of embodiment 133, or a pharmaceutically acceptable salt, solvate, isotopic variant, or N-oxide thereof, wherein $R^5$ is aryl which is optionally substituted with one, two, or three substituents each of which is independently halogen, $C_1$-$C_3$alkyl, $C_1$-$C_3$haloalkyl, or O—$C_1$-$C_3$haloalkyl.

136. The compound of any one of embodiments 1 to 53, or a pharmaceutically acceptable salt, solvate, isotopic variant, or N-oxide thereof, wherein $R^5$ is aryl substituted with one substituent which is halogen, alkyl, haloalkyl, or O-haloalkyl.

137. The compound of embodiment 136, or a pharmaceutically acceptable salt, solvate, isotopic variant, or N-oxide thereof, wherein $R^5$ is aryl substituted with one substituent which is halogen, $C_1$-$C_6$alkyl, $C_1$-$C_6$haloalkyl, or O—$C_1$-$C_6$haloalkyl.

138. The compound of embodiment 136, or a pharmaceutically acceptable salt, solvate, isotopic variant, or N-oxide thereof, wherein $R^5$ is aryl substituted with one substituent which is halogen, $C_1$-$C_3$alkyl, $C_1$-$C_3$haloalkyl, or O—$C_1$-$C_3$haloalkyl.

139. The compound of any one of embodiments 136 to 138, or a pharmaceutically acceptable salt, solvate, isotopic variant, or N-oxide thereof, wherein $R^5$ is:

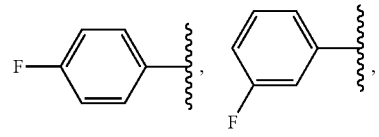

-continued

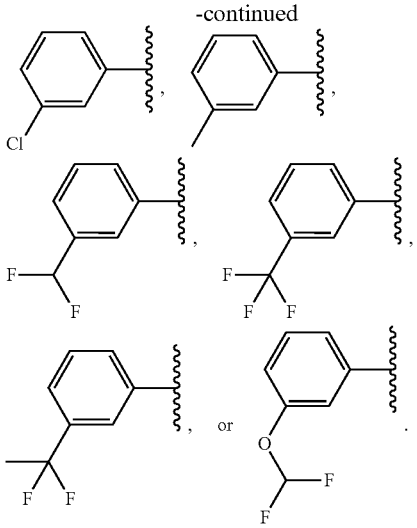

140. The compound of embodiment 139, or a pharmaceutically acceptable salt, solvate, isotopic variant, or N-oxide thereof, wherein $R^5$ is

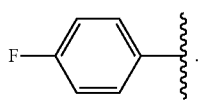

141. The compound of embodiment 139, or a pharmaceutically acceptable salt, solvate, isotopic variant, or N-oxide thereof, wherein $R^5$ is

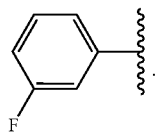

142. The compound of embodiment 139, or a pharmaceutically acceptable salt, solvate, isotopic variant, or N-oxide thereof, wherein $R^5$ is

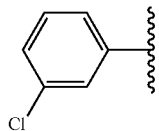

143. The compound of embodiment 139, or a pharmaceutically acceptable salt, solvate, isotopic variant, or N-oxide thereof, wherein $R^5$ is

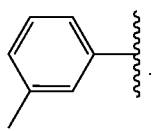

144. The compound of embodiment 139, or a pharmaceutically acceptable salt, solvate, isotopic variant, or N-oxide thereof, wherein $R^5$ is

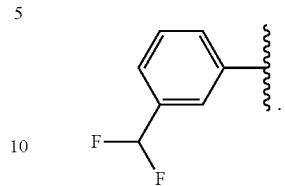

145. The compound of embodiment 139, or a pharmaceutically acceptable salt, solvate, isotopic variant, or N-oxide thereof, wherein $R^5$ is

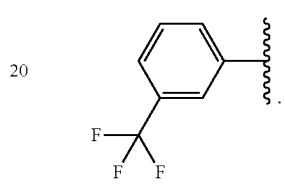

146. The compound of embodiment 139, or a pharmaceutically acceptable salt, solvate, isotopic variant, or N-oxide thereof, wherein $R^5$ is

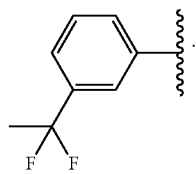 [SMILES: *c1cccc(C(C)(F)F)c1]

147. The compound of embodiment 139, or a pharmaceutically acceptable salt, solvate, isotopic variant, or N-oxide thereof, wherein $R^5$ is

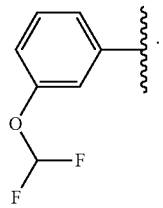

148. The compound of any one of embodiments 1 to 53, or a pharmaceutically acceptable salt, solvate, isotopic variant, or N-oxide thereof, wherein $R^5$ is aryl substituted with two substituents each of which is independently halogen, alkyl, haloalkyl, or O-haloalkyl.

149. The compound of embodiment 148, or a pharmaceutically acceptable salt, solvate, isotopic variant, or N-oxide thereof, wherein $R^5$ is aryl substituted with two substituents each of which is independently halogen, $C_1$-$C_6$alkyl, $C_1$-$C_6$haloalkyl, or O—$C_1$-$C_6$haloalkyl.

150. The compound of embodiment 148, or a pharmaceutically acceptable salt, solvate, isotopic variant, or N-oxide thereof, wherein $R^5$ is aryl substituted with two substituents each of which is independently halogen, $C_1$-$C_6$alkyl, $C_1$-$C_6$haloalkyl, or O—$C_1$-$C_6$haloalkyl.

151. The compound of any one of embodiments 148 to 150, or a pharmaceutically acceptable salt, solvate, isotopic variant, or N-oxide thereof, wherein R⁵ is:

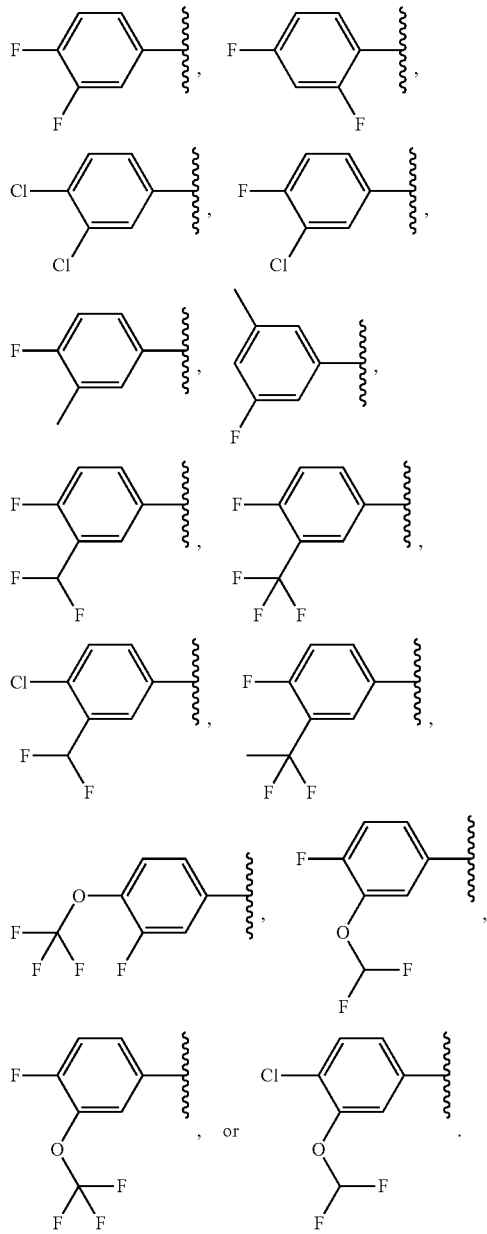

152. The compound of embodiment 151, or a pharmaceutically acceptable salt, solvate, isotopic variant, or N-oxide thereof, wherein R⁵ is

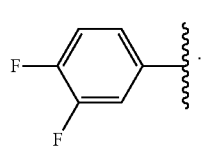

153. The compound of embodiment 151, or a pharmaceutically acceptable salt, solvate, isotopic variant, or N-oxide thereof, wherein R⁵ is

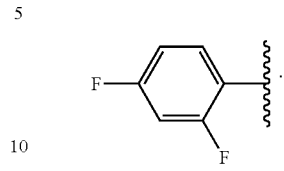

154. The compound of embodiment 151, or a pharmaceutically acceptable salt, solvate, isotopic variant, or N-oxide thereof, wherein R⁵ is

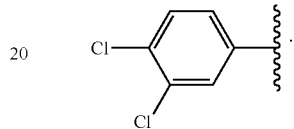

155. The compound of embodiment 151, or a pharmaceutically acceptable salt, solvate, isotopic variant, or N-oxide thereof, wherein R⁵ is

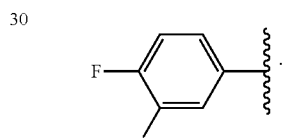

156. The compound of embodiment 151, or a pharmaceutically acceptable salt, solvate, isotopic variant, or N-oxide thereof, wherein R⁵ is

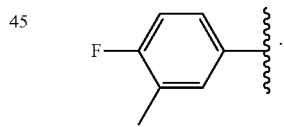

157. The compound of embodiment 151, or a pharmaceutically acceptable salt, solvate, isotopic variant, or N-oxide thereof, wherein R⁵ is

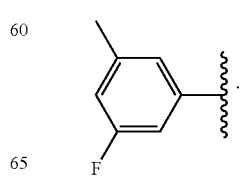

158. The compound of embodiment 151, or a pharmaceutically acceptable salt, solvate, isotopic variant, or N-oxide thereof, wherein $R^5$ is

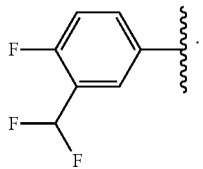

159. The compound of embodiment 151, or a pharmaceutically acceptable salt, solvate, isotopic variant, or N-oxide thereof, wherein $R^5$ is

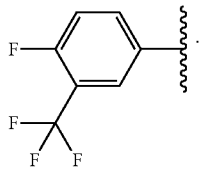

160. The compound of embodiment 151, or a pharmaceutically acceptable salt, solvate, isotopic variant, or N-oxide thereof, wherein $R^5$ is

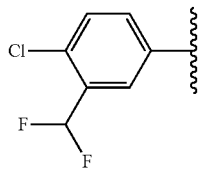

161. The compound of embodiment 151, or a pharmaceutically acceptable salt, solvate, isotopic variant, or N-oxide thereof, wherein $R^5$ is

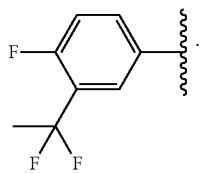

162. The compound of embodiment 151, or a pharmaceutically acceptable salt, solvate, isotopic variant, or N-oxide thereof, wherein $R^5$ is

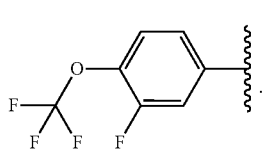

163. The compound of embodiment 151, or a pharmaceutically acceptable salt, solvate, isotopic variant, or N-oxide thereof, wherein $R^5$ is

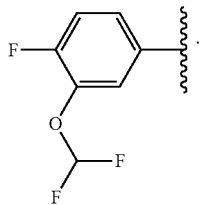

164. The compound of embodiment 151, or a pharmaceutically acceptable salt, solvate, isotopic variant, or N-oxide thereof, wherein $R^5$ is

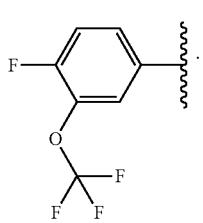

165. The compound of embodiment 151, or a pharmaceutically acceptable salt, solvate, isotopic variant, or N-oxide thereof, wherein $R^5$ is

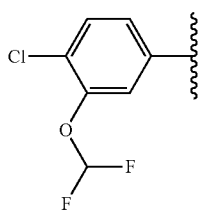

166. The compound of any one of embodiments 1 to 53, or a pharmaceutically acceptable salt, solvate, isotopic variant, or N-oxide thereof, wherein $R^5$ is aryl substituted with three substituents each of which is independently halogen or alkyl.

167. The compound of embodiment 166, or a pharmaceutically acceptable salt, solvate, isotopic variant, or N-oxide thereof, wherein $R^5$ is aryl substituted with three substituents each of which is independently halogen or $C_1$-$C_8$alkyl.

168. The compound of embodiment 166, or a pharmaceutically acceptable salt, solvate, isotopic variant, or N-oxide thereof, wherein $R^5$ is aryl substituted with three substituents each of which is independently halogen or $C_1$-$C_3$alkyl.

169. The compound of any one of embodiments 166 to 168, or a pharmaceutically acceptable salt, solvate, isotopic variant, or N-oxide thereof, wherein $R^5$ is:

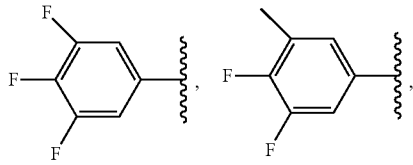

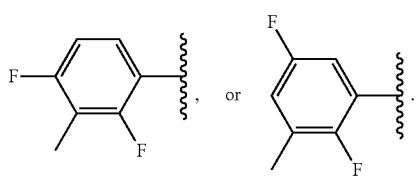

170. The compound of embodiment 169, or a pharmaceutically acceptable salt, solvate, isotopic variant, or N-oxide thereof, wherein $R^5$ is

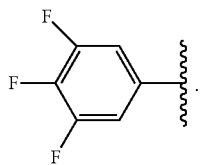

171. The compound of embodiment 169 or a pharmaceutically acceptable salt, solvate, isotopic variant, or N-oxide thereof, wherein $R^5$ is

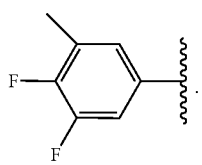

172. The compound of embodiment 169, or a pharmaceutically acceptable salt, solvate, isotopic variant, or N-oxide thereof, wherein $R^5$ is

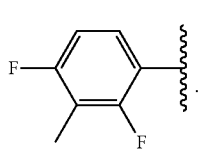

173. The compound of embodiment 169, or a pharmaceutically acceptable salt, solvate, isotopic variant, or N-oxide thereof, wherein $R^5$ is

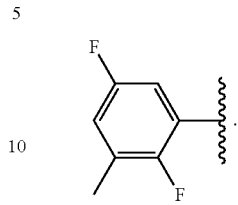

174. The compound of any one of embodiments 1 to 53 or a pharmaceutically acceptable salt, solvate, isotopic variant, or N-oxide thereof, wherein $R^5$ is pyridinyl which is optionally substituted with one substituent which is $C_1$-$C_6$haloalkyl.

175. The compound of embodiment 174 or a pharmaceutically acceptable salt, solvate, isotopic variant, or N-oxide thereof, wherein $R^5$ is pyridinyl substituted with one substituent which is $C_1$-$C_6$haloalkyl.

176. The compound of embodiment 175 or a pharmaceutically acceptable salt, solvate, isotopic variant, or N-oxide thereof, wherein $R^5$ is pyridinyl substituted with —$CF_3$.

177. The compound of embodiment 176 or a pharmaceutically acceptable salt, solvate, isotopic variant, or N-oxide thereof, wherein $R^5$ is

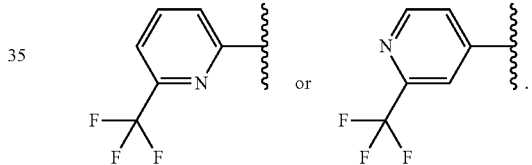

178. The compound of embodiment 177 or a pharmaceutically acceptable salt, solvate, isotopic variant, or N-oxide thereof, wherein $R^5$ is

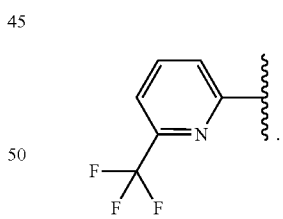

179. The compound of embodiment 177 or a pharmaceutically acceptable salt, solvate, isotopic variant, or N-oxide thereof, wherein $R^5$ is

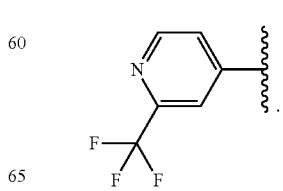

180. The compound of embodiment 2, or a pharmaceutically acceptable salt, solvate, isotopic variant, or N-oxide thereof, having the structure of Formula (Ie):

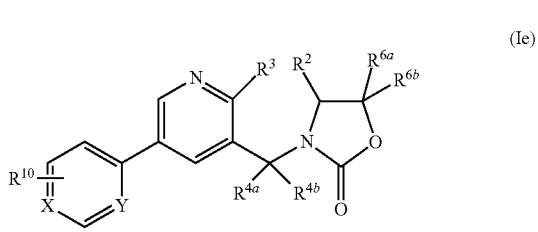

wherein one of X and Y is N and the other is H, and wherein $R^{10}$ is $C_1$-$C_6$haloalkyl.

181. The compound of any one of embodiments 1 to 53, or a pharmaceutically acceptable salt, solvate, isotopic variant, or N-oxide thereof, wherein $R^5$ is thienyl which is optionally substituted with one substituent which is halogen or haloalkyl.

182. The compound of embodiment 181, or a pharmaceutically acceptable salt, solvate, isotopic variant, or N-oxide thereof, wherein $R^5$ is thienyl which is optionally substituted with one substituent which is halogen or $C_1$-$C_6$haloalkyl.

183. The compound of embodiment 182, or a pharmaceutically acceptable salt, solvate, isotopic variant, or N-oxide thereof, wherein $R^5$ is thienyl substituted with one substituent which is halogen.

184. The compound of embodiment 183, or a pharmaceutically acceptable salt, solvate, isotopic variant, or N-oxide thereof, wherein $R^5$ is thienyl substituted with —Cl.

185. The compound of embodiment 184, wherein $R^5$ is

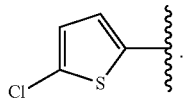

186. The compound of embodiment 182, or a pharmaceutically acceptable salt, solvate, isotopic variant, or N-oxide thereof, wherein $R^5$ is thienyl substituted with —$CHF_2$ or —$CF_3$.

187. The compound of embodiment 186, or a pharmaceutically acceptable salt, solvate, isotopic variant, or N-oxide thereof, wherein $R^5$ is thienyl substituted with —$CHF_2$.

188. The compound of embodiment 187, or a pharmaceutically acceptable salt, solvate, isotopic variant, or N-oxide thereof, wherein $R^5$ is

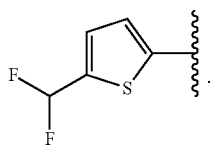

189. The compound of embodiment 186, or a pharmaceutically acceptable salt, solvate, isotopic variant, or N-oxide thereof, wherein $R^5$ is thienyl substituted with —$CF_3$.

190. The compound of embodiment 189, or a pharmaceutically acceptable salt, solvate, isotopic variant, or N-oxide thereof, wherein $R^5$ is

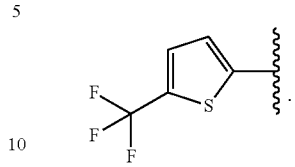

191. The compound of embodiment 2, or a pharmaceutically acceptable salt, solvate, isotopic variant, or N-oxide thereof, having the structure of Formula (If):

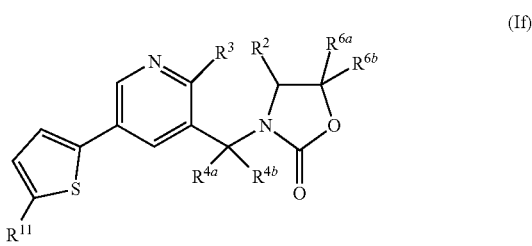

wherein $R^{11}$ is halo or $C_1$-$C_6$haloalkyl.

192. The compound of any one of embodiments 1 to 191, or a pharmaceutically acceptable salt, solvate, isotopic variant, or N-oxide thereof, wherein $R^{6a}$ and $R^{6b}$ are, each independent from the other, H or $C_1$-$C_6$alkyl which is optionally substituted with one substituent which is 4 to 6 membered heterocycloalkyl; or $R^{6a}$ and $R^{6b}$ together with the carbon atom to which they are attached form a $C_3$-$C_6$cycloalkyl ring or a 4 to 6 membered heterocycloalkyl ring.

193. The compound of any one of embodiments 1 to 191, or a pharmaceutically acceptable salt, solvate, isotopic variant, or N-oxide thereof, wherein $R^{6a}$ and $R^{6b}$ are both H.

194. The compound of any one of embodiments 1 to 191, or a pharmaceutically acceptable salt, solvate, isotopic variant, or N-oxide thereof, wherein one of $R^{6a}$ and $R^{6b}$ is H and the other is alkyl which is optionally substituted with one substituent which is heterocycloalkyl.

195. The compound of embodiment 194, or a pharmaceutically acceptable salt, solvate, isotopic variant, or N-oxide thereof, wherein one of $R^{6a}$ and $R^{6b}$ is H and the other is $C_1$-$C_6$alkyl which is optionally substituted with one substituent which is a 4 to 6 membered heterocycloalkyl.

196. The compound of embodiment 195, or a pharmaceutically acceptable salt, solvate, isotopic variant, or N-oxide thereof, wherein one of $R^{6a}$ and $R^{6b}$ is H and the other is $C_1$-$C_3$alkyl which is optionally substituted with one substituent which is 4 to 6 membered heterocycloalkyl.

197. The compound of embodiment 196, or a pharmaceutically acceptable salt, solvate, isotopic variant, or N-oxide thereof, wherein one of $R^{6a}$ and $R^{6b}$ is H and the other is —$CH_3$.

198. The compound of embodiment 196, or a pharmaceutically acceptable salt, solvate, isotopic variant, or N-oxide thereof, wherein one of $R^{6a}$ and $R^{6b}$ is H and the other is —$CH(CH_3)_2$.

199. The compound of embodiment 196, or a pharmaceutically acceptable salt, solvate, isotopic variant, or N-oxide thereof, wherein one of $R^{6a}$ and $R^{6b}$ is H and the other is —$CH_2R^{12}$, where $R^{12}$ is 4 to 6 membered heterocycloalkyl.

200. The compound of embodiment 199, or a pharmaceutically acceptable salt, solvate, isotopic variant, or N-oxide thereof, wherein $R^{12}$ is

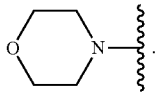

201. The compound of any one of embodiments 194 to 200, or a pharmaceutically acceptable salt, solvate, isotopic variant, or N-oxide thereof, wherein the stereochemistry at the carbon to which $R^{6a}$ and $R^{6b}$ are attached is (R).

202. The compound of any one of embodiments 194 to 200, or a pharmaceutically acceptable salt, solvate, isotopic variant, or N-oxide thereof, wherein the stereochemistry at the carbon to which $R^{6a}$ and $R^{6b}$ are attached is (S).

203. The compound of any one of embodiments 1 to 191, or a pharmaceutically acceptable salt, solvate, isotopic variant, or N-oxide thereof, wherein $R^{6a}$ and $R^{6b}$ are both alkyl.

204. The compound of embodiment 203, or a pharmaceutically acceptable salt, solvate, isotopic variant, or N-oxide thereof, wherein $R^{6a}$ and $R^{6b}$ are both $C_1$-$C_6$alkyl.

205. The compound of embodiment 204, or a pharmaceutically acceptable salt, solvate, isotopic variant, or N-oxide thereof, wherein $R^{6a}$ and $R^{6b}$ are both $C_1$-$C_2$alkyl.

206. The compound of embodiment 205, or a pharmaceutically acceptable salt, solvate, isotopic variant, or N-oxide thereof, wherein $R^{6a}$ and $R^{6b}$ are both —$CH_3$.

207. The compound of any one of embodiments 1 to 191, or a pharmaceutically acceptable salt, solvate, isotopic variant, or N-oxide thereof, wherein $R^{6a}$ and $R^{6b}$ together with the carbon atom to which they are attached form a cycloalkyl ring or a heterocycloalkyl ring.

208. The compound of embodiment 207, or a pharmaceutically acceptable salt, solvate, isotopic variant, or N-oxide thereof, wherein $R^{6a}$ and $R^{6b}$ together with the carbon atom to which they are attached form a $C_3$-$C_6$cycloalkyl ring or a 4 to 6 membered heterocycloalkyl ring.

209. The compound of embodiment 208, or a pharmaceutically acceptable salt, solvate, isotopic variant, or N-oxide thereof, wherein $R^{6a}$ and $R^{6b}$ together with the carbon atom to which they are attached form a $C_3$-$C_6$cycloalkyl ring.

210. The compound of embodiment 209, or a pharmaceutically acceptable salt, solvate, isotopic variant, or N-oxide thereof, wherein $R^{6a}$ and $R^{6b}$ together with the carbon atom to which they are attached form a cyclopropyl or cyclobutyl ring.

211. The compound of embodiment 210, or a pharmaceutically acceptable salt, solvate, isotopic variant, or N-oxide thereof, wherein $R^{6a}$ and $R^{6b}$ together with the carbon atom to which they are attached form a cyclopropyl ring.

212. The compound of embodiment 210, or a pharmaceutically acceptable salt, solvate, isotopic variant, or N-oxide thereof, wherein $R^{6a}$ and $R^{6b}$ together with the carbon atom to which they are attached form a cyclobutyl ring.

213. The compound of embodiment 207, or a pharmaceutically acceptable salt, solvate, isotopic variant, or N-oxide thereof, wherein $R^{6a}$ and $R^{6b}$ together with the carbon atom to which they are attached form a heterocycloalkyl ring.

214. The compound of embodiment 213, or a pharmaceutically acceptable salt, solvate, isotopic variant, or N-oxide thereof, wherein $R^{6a}$ and $R^{6b}$ together with the carbon atom to which they are attached form a 4 to 6 membered heterocycloalkyl ring.

215. The compound of embodiment 214, or a pharmaceutically acceptable salt, solvate, isotopic variant, or N-oxide thereof, wherein $R^{6a}$ and $R^{6b}$ together with the carbon atom to which they are attached is:

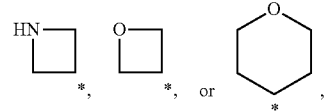

wherein * denotes the point of attachment of the ring to the remainder of the molecule.

216. The compound of embodiment 215, or a pharmaceutically acceptable salt, solvate, isotopic variant, or N-oxide thereof, wherein $R^{6a}$ and $R^{6b}$ together with the carbon atom to which they are attached is

217. The compound of embodiment 215, or a pharmaceutically acceptable salt, solvate, isotopic variant, or N-oxide thereof, wherein $R^{6a}$ and $R^{6b}$ together with the carbon atom to which they are attached is

218. The compound of embodiment 215, or a pharmaceutically acceptable salt, solvate, isotopic variant, or N-oxide thereof, wherein $R^{6a}$ and $R^{6b}$ together with the carbon atom to which they are attached is

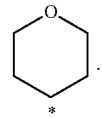

219. A compound, or a pharmaceutically acceptable salt, solvate, isotopic variant, or N-oxide thereof, wherein the compound is 3-[[5-[3-(Difluoromethoxy)-4-fluoro-phenyl]-3-pyridyl]methyl]-1,3-oxazinan-2-one;
3-[[5-[3-(Difluoromethoxy)-4-fluoro-phenyl]-3-pyridyl]methyl]oxazolidin-2-one;
(4S)-3-[[5-[3-(Difluoromethoxy)-4-fluoro-phenyl]-3-pyridyl]methyl]-4-isopropyl-oxazolidin-2-one;
1-[[5-[3-(Difluoromethoxy)-4-fluoro-phenyl]-3-pyridyl]methyl]-4H-3,1-benzoxazin-2-one;
(R/S)-3-[[5-[3-(Difluoromethoxy)-4-fluoro-phenyl]-3-pyridyl]methyl]-4-methyl-oxazolidin-2-one;
(R/S)-3-[[5-[3-(Difluoromethoxy)-4-fluoro-phenyl]-3-pyridyl]methyl]-5-methyl-oxazolidin-2-one;

(S*)-3-[[5-[3-(Difluoromethoxy)-4-fluoro-phenyl]-3-pyridyl]methyl]-5-methyl-oxazolidin-2-one;
(R*)-3-[[5-[3-(Difluoromethoxy)-4-fluoro-phenyl]-3-pyridyl]methyl]-5-methyl-oxazolidin-2-one;
5-[[5-[3-(Difluoromethoxy)-4-fluoro-phenyl]-3-pyridyl]methyl]-7-oxa-5-azaspiro[2.4]heptan-6-one;
3-[[5-[3-(Difluoromethoxy)-4-fluoro-phenyl]-3-pyridyl]methyl]-6,6-dimethyl-1,3-oxazinan-2-one;
(4R)-3-[[5-[3-(Difluoromethoxy)-4-fluoro-phenyl]-3-pyridyl]methyl]-4-isopropyl-oxazolidin-2-one;
6-[[5-[3-(Difluoromethoxy)-4-fluoro-phenyl]-3-pyridyl]methyl]-8-oxa-6-azaspiro[3.4]octan-7-one;
6-[[5-[3-(Difluoromethoxy)-4-fluoro-phenyl]-3-pyridyl]methyl]-2,8-dioxa-6-azaspiro[3.4]octan-7-one;
(R/S)-3-[[5-[3-(Difluoromethoxy)-4-fluoro-phenyl]-3-pyridyl]methyl]-5-isopropyl-oxazolidin-2-one;
(R*)-3-[[5-[3-(Difluoromethoxy)-4-fluoro-phenyl]-3-pyridyl]methyl]-5-isopropyl-oxazolidin-2-one;
(S*)-3-[[5-[3-(Difluoromethoxy)-4-fluoro-phenyl]-3-pyridyl]methyl]-5-isopropyl-oxazolidin-2-one;
(R/S)-3-[[5-[3-(Difluoromethoxy)-4-fluoro-phenyl]-3-pyridyl]methyl]-5-(morpholinomethyl)oxazolidin-2-one;
(R*)-3-[[5-[3-(Difluoromethoxy)-4-fluoro-phenyl]-3-pyridyl]methyl]-5-(morpholinomethyl)oxazolidin-2-one;
(S*)-3-[[5-[3-(Difluoromethoxy)-4-fluoro-phenyl]-3-pyridyl]methyl]-5-(morpholinomethyl)oxazolidin-2-one;
2-[[5-[3-(Difluoromethoxy)-4-fluoro-phenyl]-3-pyridyl]methyl]-4,8-dioxa-2-azaspiro[4.5]decan-3-one;
6-[[5-[3-(Difluoromethyl)-4-fluoro-phenyl]-3-pyridyl]methyl]-8-oxa-2,6-diazaspiro[3.4]octan-7-one;
3-[[5-[3-(Difluoromethyl)-4-fluoro-phenyl]-3-pyridyl]methyl]oxazolidin-2-one;
(4S)-3-[[5-[3-(Difluoromethyl)-4-fluoro-phenyl]-3-pyridyl]methyl]-4-isopropyl-oxazolidin-2-one;
1-[[5-[3-(Difluoromethyl)-4-fluoro-phenyl]-3-pyridyl]methyl]-4H-3,1-benzoxazin-2-one
(R/S)-3-[[5-[3-(Difluoromethyl)-4-fluoro-phenyl]-3-pyridyl]methyl]-4-methyl-oxazolidin-2-one;
(R/S)-3-[[5-[3-(Difluoromethyl)-4-fluoro-phenyl]-3-pyridyl]methyl]-5-methyl-oxazolidin-2-one;
(S*)-3-[[5-[3-(Difluoromethyl)-4-fluoro-phenyl]-3-pyridyl]methyl]-5-methyl-oxazolidin-2-one
(R*)-3-[[5-[3-(Difluoromethyl)-4-fluoro-phenyl]-3-pyridyl]methyl]-5-methyl-oxazolidin-2-one;
5-[[5-[3-(Difluoromethyl)-4-fluoro-phenyl]-3-pyridyl]methyl]-7-oxa-5-azaspiro[2.4]heptan-6-one;
3-[[5-[3-(Difluoromethyl)-4-fluoro-phenyl]-3-pyridyl]methyl]-6,6-dimethyl-1,3-oxazinan-2-one;
(4R)-3-[[5-[3-(Difluoromethyl)-4-fluoro-phenyl]-3-pyridyl]methyl]-4-isopropyl-oxazolidin-2-one;
6-[[5-[3-(Difluoromethyl)-4-fluoro-phenyl]-3-pyridyl]methyl]-8-oxa-6-azaspiro[3.4]octan-7-one;
(5R)-3-[[5-[3-(Difluoromethyl)-4-fluoro-phenyl]-3-pyridyl]methyl]-5-methyl-oxazolidin-2-one;
6-[[5-[3-(Difluoromethyl)-4-fluoro-phenyl]-3-pyridyl]methyl]-2,8-dioxa-6-azaspiro[3.4]octan-7-one;
(R/S)-3-[[5-[3-(Difluoromethyl)-4-fluoro-phenyl]-3-pyridyl]methyl]-5-isopropyl-oxazolidin-2-one;
(R*)-3-[[5-[3-(Difluoromethyl)-4-fluoro-phenyl]-3-pyridyl]methyl]-5-isopropyl-oxazolidin-2-one
(S*)-3-[[5-[3-(Difluoromethyl)-4-fluoro-phenyl]-3-pyridyl]methyl]-5-isopropyl-oxazolidin-2-one;
3-[[5-[3-(Difluoromethyl)-4-fluoro-phenyl]-3-pyridyl]methyl]-1,3-oxazinan-2-one;
(R/S)-3-[[5-[3-(Difluoromethyl)-4-fluoro-phenyl]-3-pyridyl]methyl]-5-(morpholinomethyl)oxazolidin-2-one;
(R*)-3-[[5-[3-(Difluoromethyl)-4-fluoro-phenyl]-3-pyridyl]methyl]-5-(morpholinomethyl)oxazolidin-2-one;
(S*)-3-[[5-[3-(Difluoromethyl)-4-fluoro-phenyl]-3-pyridyl]methyl]-5-(morpholinomethyl)oxazolidin-2-one;
2-[[5-[3-(Difluoromethyl)-4-fluoro-phenyl]-3-pyridyl]methyl]-4,8-dioxa-2-azaspiro[4.5]decan-3-one;
6-[[5-[3-(Difluoromethoxy)-4-fluoro-phenyl]-3-pyridyl]methyl]-8-oxa-2,6-diazaspiro[3.4]octan-7-one;
3-[[5-(4-Fluoro-3-methyl-phenyl)-3-pyridyl]methyl]oxazolidin-2-one;
3-[[5-(2,4-Difluoro-3-methyl-phenyl)-3-pyridyl]methyl]oxazolidin-2-one;
3-[[5-[3-(Trifluoromethyl)phenyl]-3-pyridyl]methyl]oxazolidin-2-one;
3-[[5-[4-Chloro-3-(difluoromethoxy)phenyl]-3-pyridyl]methyl]oxazolidin-2-one;
3-[[5-[3-Fluoro-4-(trifluoromethoxy)phenyl]-3-pyridyl]methyl]oxazolidin-2-one;
3-[[5-[3-(1,1-Difluoroethyl)-4-fluoro-phenyl]-3-pyridyl]methyl]oxazolidin-2-one;
3-[[5-[6-(Trifluoromethyl)-2-pyridyl]-3-pyridyl]methyl]oxazolidin-2-one;
3-[[5-[2-(Trifluoromethyl)-4-pyridyl]-3-pyridyl]methyl]oxazolidin-2-one;
3-[[5-[4-Fluoro-3-(trifluoromethyl)phenyl]-3-pyridyl]methyl]-1,3-oxazinan-2-one;
3-[[5-[4-chloro-3-(difluoromethoxy)phenyl]-3-pyridyl]methyl]-1,3-oxazinan-2-one;
3-[Dideuterio-[5-[3-(difluoromethyl)-4-fluoro-phenyl]-3-pyridyl]methyl] oxazolidin-2-one;
3-[Dideuterio-[5-[3-(difluoromethoxy)-4-fluoro-phenyl]-3-pyridyl]methyl]-1,3-oxazinan-2-one;
3-[Dideuterio-[5-[3-(difluoromethoxy)-4-fluoro-phenyl]-2-methyl-3-pyridyl]methyl]-1,3-oxazinan-2-one;
3-[Dideuterio-[5-(4-fluoro-3-methyl-phenyl)-2-methyl-3-pyridyl]methyl]-1,3-oxazinan-2-one;
3-[Dideuterio-[5-[3-(difluoromethyl)-4-fluoro-phenyl]-2-methyl-3-pyridyl]methyl]-1,3-oxazinan-2-one;
3-[Dideuterio-[5-[3-(difluoromethyl)-4-fluoro-phenyl]-2-methyl-3-pyridyl]methyl]oxazolidin-2-one;
(R/S)-3-[1-[5-[3-(difluoromethyl)-4-fluoro-phenyl]-3-pyridyl]ethyl]oxazolidin-2-one;
(R/S)-3-[1-[5-[3-(difluoromethyl)-4-fluoro-phenyl]-3-pyridyl]ethyl]-1,3-oxazinan-2-one;
3-[[5-[3-(Difluoromethyl)phenyl]-2-methyl-3-pyridyl]methyl]-1,3-oxazinan-2-one;
3-[[5-[3-(Difluoromethoxy)phenyl]-2-methyl-3-pyridyl]methyl]-1,3-oxazinan-2-one;
3-[[5-(3-Chlorophenyl)-2-methyl-3-pyridyl]methyl]-1,3-oxazinan-2-one;
3-[[5-(3-Chloro-4-fluoro-phenyl)-2-methyl-3-pyridyl]methyl]-1,3-oxazinan-2-one;
3-[[5-(4-Fluoro-3-methyl-phenyl)-2-methyl-3-pyridyl]methyl]-1,3-oxazinan-2-one;
3-[[5-(3,4-Difluorophenyl)-2-methyl-3-pyridyl]methyl]-1,3-oxazinan-2-one;
3-[[5-(4-Fluorophenyl)-2-methyl-3-pyridyl]methyl]-1,3-oxazinan-2-one;
3-[[5-(3-Fluorophenyl)-2-methyl-3-pyridyl]methyl]-1,3-oxazinan-2-one;
3-[[5-(3,4-Difluoro-5-methyl-phenyl)-2-methyl-3-pyridyl]methyl]-1,3-oxazinan-2-one;
3-[[5-(2,4-Difluoro-3-methyl-phenyl)-2-methyl-3-pyridyl]methyl]-1,3-oxazinan-2-one;
3-[[5-(2,4-Difluorophenyl)-2-methyl-3-pyridyl]methyl]-1,3-oxazinan-2-one;

3-[[5-(3,4-Dichlorophenyl)-2-methyl-3-pyridyl]methyl]-1,3-oxazinan-2-one;
3-[[2-Methyl-5-[3-(Trifluoromethyl)phenyl]-3-pyridyl]methyl]-1,3-oxazinan-2-one
3-[[5-[4-Fluoro-3-(trifluoromethyl)phenyl]-2-methyl-3-pyridyl]methyl]-1,3-oxazinan-2-one;
3-[[5-(4-Fluoro-3-methyl-phenyl)-2-methyl-3-pyridyl]methyl]oxazolidin-2-one;
3-[[5-(2,4-Difluoro-3-methyl-phenyl)-2-methyl-3-pyridyl]methyl]oxazolidin-2-one;
3-[[5-[3-(1,1-Difluoroethyl)-4-fluoro-phenyl]-2-methyl-3-pyridyl]methyl]oxazolidin-2-one;
3-[[5-[3-(Difluoromethoxy)-4-fluoro-phenyl]-2-methyl-3-pyridyl]methyl] oxazolidin-2-one;
(R/S)-3-[[5-[3-(Difluoromethoxy)-4-fluoro-phenyl]-2-methyl-3-pyridyl]methyl]-5-methyl-oxazolidin-2-one;
(R/S)-3-[[5-[3-(Difluoromethoxy)-4-fluoro-phenyl]-2-methyl-3-pyridyl]methyl]-4-methyl-oxazolidin-2-one;
(R*)-3-[[5-[3-(Difluoromethoxy)-4-fluoro-phenyl]-2-methyl-3-pyridyl]methyl]-4-methyl-oxazolidin-2-one;
(S*)-3-[[5-[3-(Difluoromethoxy)-4-fluoro-phenyl]-2-methyl-3-pyridyl]methyl]-4-methyl-oxazolidin-2-one;
5-[[5-[3-(Difluoromethoxy)-4-fluoro-phenyl]-2-methyl-3-pyridyl]methyl]-7-oxa-5-azaspiro[2.4]heptan-6-one;
6-[[5-[3-(Difluoromethoxy)-4-fluoro-phenyl]-2-methyl-3-pyridyl]methyl]-8-oxa-6-azaspiro[3.4]octan-7-one;
(5R)-3-[[5-[3-(Difluoromethoxy)-4-fluoro-phenyl]-2-methyl-3-pyridyl]methyl]-5-methyl-oxazolidin-2-one;
3-[[5-[3-(Difluoromethoxy)-4-fluoro-phenyl]-2-methyl-3-pyridyl]methyl]-5,5-dimethyl-oxazolidin-2-one;
3-[[5-[3-(Difluoromethoxy)-4-fluoro-phenyl]-2-methyl-3-pyridyl]methyl]-1,3-oxazinan-2-one;
3-[[5-[4-Chloro-3-(difluoromethoxy)phenyl]-2-methyl-3-pyridyl]methyl] oxazolidin-2-one;
3-[[5-[3-(Difluoromethyl)-4-fluoro-phenyl]-2-methyl-3-pyridyl]methyl] oxazolidin-2-one;
6-[[5-[3-(Difluoromethyl)-4-fluoro-phenyl]-2-methyl-3-pyridyl]methyl]-8-oxa-6-azaspiro[3.4]octan-7-one;
(5R)-3-[[5-[3-(Difluoromethyl)-4-fluoro-phenyl]-2-methyl-3-pyridyl]methyl]-5-methyl-oxazolidin-2-one;
3-[[5-[3-(Difluoromethyl)-4-fluoro-phenyl]-2-methyl-3-pyridyl]methyl]-5,5-dimethyl-oxazolidin-2-one;
(R/S)-3-[[5-[3-(Difluoromethyl)-4-fluoro-phenyl]-2-methyl-3-pyridyl]methyl]-5-methyl-oxazolidin-2-one;
(R/S)-3-[[5-[3-(difluoromethyl)-4-fluoro-phenyl]-2-methyl-3-pyridyl]methyl]-4-methyl-oxazolidin-2-one;
5-[[5-[3-(Difluoromethyl)-4-fluoro-phenyl]-2-methyl-3-pyridyl]methyl]-7-oxa-5-azaspiro[2.4]heptan-6-one;
3-[[5-[3-(Difluoromethyl)-4-fluoro-phenyl]-2-methyl-3-pyridyl]methyl]-1,3-oxazinan-2-one
3-[[5-(5-Chloro-2-thienyl)-2-methyl-3-pyridyl]methyl]oxazolidin-2-one;
3-[[2-Methyl-5-[5-(trifluoromethyl)-2-thienyl]-3-pyridyl]methyl]oxazolidin-2-one;
3-[[5-[5-(Difluoromethyl)-2-thienyl]-2-methyl-3-pyridyl]methyl]oxazolidin-2-one;
3-[[2-Methoxy-5-[3-(trifluoromethyl)phenyl]-3-pyridyl]methyl]oxazolidin-2-one;
3-[[2-Methoxy-5-(3,4,5-trifluorophenyl)-3-pyridyl]methyl]oxazolidin-2-one;
3-[[5-(2,4-Difluoro-3-methyl-phenyl)-2-methoxy-3-pyridyl]methyl] oxazolidin-2-one;
3-[[5-(3-Fluoro-5-methyl-phenyl)-2-methoxy-3-pyridyl]methyl]oxazolidin-2-one;
3-[[2-Methoxy-5-(m-tolyl)-3-pyridyl]methyl]oxazolidin-2-one;
3-[[5-(3,4-Dichlorophenyl)-2-methoxy-3-pyridyl]methyl]oxazolidin-2-one;
3-[[5-[4-Chloro-3-(difluoromethoxy)phenyl]-2-methoxy-3-pyridyl]methyl]oxazolidin-2-one
3-[[5-(3-Chloro-4-fluoro-phenyl)-2-methoxy-3-pyridyl]methyl]oxazolidin-2-one;
3-[[5-(3-Chlorophenyl)-2-methoxy-3-pyridyl]methyl]oxazolidin-2-one;
3-[[5-[3-(1,1-Difluoroethyl)-4-fluoro-phenyl]-2-methoxy-3-pyridyl]methyl]oxazolidin-2-one
3-[[5-[3-(1,1-Difluoroethyl)phenyl]-2-methoxy-3-pyridyl]methyl]oxazolidin-2-one;
3-[[5-(3,4-Difluoro-5-methyl-phenyl)-2-methoxy-3-pyridyl]methyl] oxazolidin-2-one;
3-[[5-[4-Fluoro-3-(trifluoromethoxy)phenyl]-2-methoxy-3-pyridyl]methyl]oxazolidin-2-one;
3-[[5-(2,5-Difluoro-3-methyl-phenyl)-2-methoxy-3-pyridyl]methyl] oxazolidin-2-one;
3-[[5-[4-Chloro-3-(difluoromethyl)phenyl]-2-methoxy-3-pyridyl]methyl]oxazolidin-2-one;
3-[[5-(4-Fluoro-3-methyl-phenyl)-2-methoxy-3-pyridyl]methyl]oxazolidin-2-one;
(4S)-3-[[5-[3-(Difluoromethoxy)-4-fluoro-phenyl]-2-methoxy-3-pyridyl]methyl]-4-methyl-oxazolidin-2-one;
(4R)-3-[[5-[3-(Difluoromethoxy)-4-fluoro-phenyl]-2-methoxy-3-pyridyl]methyl]-4-methyl-oxazolidin-2-one;
3-[[5-[3-(Difluoromethoxy)-4-fluoro-phenyl]-2-methoxy-3-pyridyl]methyl] oxazolidin-2-one;
(4S)-3-[[5-[3-(Difluoromethyl)-4-fluoro-phenyl]-2-methoxy-3-pyridyl]methyl]-4-methyl-oxazolidin-2-one;
(4R)-3-[[5-[3-(Difluoromethyl)-4-fluoro-phenyl]-2-methoxy-3-pyridyl]methyl]-4-methyl-oxazolidin-2-one;
3-[[5-[3-(Difluoromethyl)-4-fluoro-phenyl]-2-methoxy-3-pyridyl]methyl]oxazolidin-2-one;
3-[[2-(Difluoromethyl)-5-[3-(difluoromethyl)-4-fluoro-phenyl]-3-pyridyl]methyl]-1,3-oxazinan-2-one;
3-[[2-(Difluoromethyl)-5-[3-(difluoromethyl)-4-fluoro-phenyl]-3-pyridyl]methyl]oxazolidin-2-one;
3-[[5-[3-(Difluoromethoxy)-4-fluoro-phenyl]-2-(difluoromethyl)-3-pyridyl]methyl]oxazolidin-2-one;
3-[[5-[3-(Difluoromethoxy)-4-fluoro-phenyl]-2-(difluoromethyl)-3-pyridyl]methyl]-1,3-oxazinan-2-one;
3-[[2-(Difluoromethyl)-5-(4-fluoro-3-methyl-phenyl)-3-pyridyl]methyl]-1,3-oxazinan-2-one;
3-[[2-(Difluoromethyl)-5-(4-fluoro-3-methyl-phenyl)-3-pyridyl]methyl]oxazolidin-2-one;
3-[[5-[4-Chloro-3-(difluoromethoxy)phenyl]-2-(difluoromethyl)-3-pyridyl]methyl]-1,3-oxazinan-2-one;
3-[[5-[4-Chloro-3-(difluoromethoxy)phenyl]-2-(difluoromethyl)-3-pyridyl]methyl]oxazolidin-2-one;
3-[[2-(Difluoromethoxy)-5-[3-(difluoromethyl)-4-fluoro-phenyl]-3-pyridyl]methyl]oxazolidin-2-one;
(4R)-3-[[2-(Difluoromethoxy)-5-[3-(difluoromethyl)-4-fluoro-phenyl]-3-pyridyl]methyl]-4-methyl-oxazolidin-2-one;
3-[[2-(Difluoromethoxy)-5-[3-(difluoromethoxy)-4-fluoro-phenyl]-3-pyridyl]methyl]oxazolidin-2-one;
(4R)-3-[[2-(Difluoromethoxy)-5-[3-(difluoromethoxy)-4-fluoro-phenyl]-3-pyridyl]methyl]-4-methyl-oxazolidin-2-one;
3-[[2-(1,1-Difluoroethyl)-5-[3-(difluoromethyl)-4-fluoro-phenyl]-3-pyridyl]methyl]oxazolidin-2-one;
3-[[2-(1,1-Difluoroethyl)-5-[3-(difluoromethyl)-4-fluoro-phenyl]-3-pyridyl]methyl]-1,3-oxazinan-2-one;
3-[[2-(1,1-Difluoroethyl)-5-[3-(difluoromethoxy)-4-fluoro-phenyl]-3-pyridyl]methyl]-1,3-oxazinan-2-one;

6-[[2-(1,1-Difluoroethyl)-5-[3-(difluoromethyl)-4-fluoro-phenyl]-3-pyridyl]methyl]-8-oxa-6-azaspiro[3.4]octan-7-one;
(5R)-3-[[2-(1,1-Difluoroethyl)-5-[3-(difluoromethyl)-4-fluoro-phenyl]-3-pyridyl]methyl]-5-methyl-oxazolidin-2-one;
(5S)-3-[[2-(1,1-Difluoroethyl)-5-[3-(difluoromethyl)-4-fluoro-phenyl]-3-pyridyl]methyl]-5-methyl-oxazolidin-2-one;
5-[[2-(1,1-Difluoroethyl)-5-[3-(difluoromethyl)-4-fluoro-phenyl]-3-pyridyl]methyl]-7-oxa-5-azaspiro[2.4]heptan-6-one;
(4S)-3-[[2-(1,1-Difluoroethyl)-5-[3-(difluoromethyl)-4-fluoro-phenyl]-3-pyridyl]methyl]-4-methyl-oxazolidin-2-one;
(4R)-3-[[2-(1,1-Difluoroethyl)-5-[3-(difluoromethyl)-4-fluoro-phenyl]-3-pyridyl]methyl]-4-methyl-oxazolidin-2-one;
(4R)-3-[[2-(1,1-Difluoroethyl)-5-[3-(difluoromethoxy)-4-fluoro-phenyl]-3-pyridyl]methyl]-4-methyl-oxazolidin-2-one;
(4S)-3-[[2-(1,1-Difluoroethyl)-5-[3-(difluoromethoxy)-4-fluoro-phenyl]-3-pyridyl]methyl]-4-methyl-oxazolidin-2-one;
5-[[2-(1,1-Difluoroethyl)-5-[3-(difluoromethoxy)-4-fluoro-phenyl]-3-pyridyl]methyl]-7-oxa-5-azaspiro[2.4]heptan-6-one;
6-[[2-(1,1-Difluoroethyl)-5-[3-(difluoromethoxy)-4-fluoro-phenyl]-3-pyridyl]methyl]-8-oxa-6-azaspiro[3.4]octan-7-one;
(5S)-3-[[2-(1,1-Difluoroethyl)-5-[3-(difluoromethoxy)-4-fluoro-phenyl]-3-pyridyl]methyl]-5-methyl-oxazolidin-2-one; or
(5R)-3-[[2-(1,1-Difluoroethyl)-5-[3-(difluoromethoxy)-4-fluoro-phenyl]-3-pyridyl]methyl]-5-methyl-oxazolidin-2-one.

220. A compound, or a pharmaceutically acceptable salt, solvate, isotopic variant, or N-oxide thereof, wherein the compound is
3-[[5-[3-(Difluoromethoxy)-4-fluoro-phenyl]-3-pyridyl]methyl]-1,3-oxazinan-2-one;
3-[[5-[3-(Difluoromethyl)-4-fluoro-phenyl]-3-pyridyl]methyl]oxazolidin-2-one;
(S*)-3-[[5-[3-(Difluoromethyl)-4-fluoro-phenyl]-3-pyridyl]methyl]-5-methyl-oxazolidin-2-one;
3-[[5-[3-(Difluoromethyl)-4-fluoro-phenyl]-3-pyridyl]methyl]-1,3-oxazinan-2-one;
3-[[5-[4-chloro-3-(difluoromethoxy)phenyl]-3-pyridyl]methyl]-1,3-oxazinan-2-one;
3-[Dideuterio-[5-[3-(difluoromethyl)-4-fluoro-phenyl]-3-pyridyl]methyl] oxazolidin-2-one;
(R/S)-3-[1-[5-[3-(difluoromethyl)-4-fluoro-phenyl]-3-pyridyl]ethyl]oxazolidin-2-one trifluoroacetate salt;
3-[[5-[3-(Difluoromethyl)-4-fluoro-phenyl]-2-methyl-3-pyridyl]methyl] oxazolidin-2-one; or
3-[[5-[3-(Difluoromethyl)-4-fluoro-phenyl]-2-methyl-3-pyridyl]methyl]-1,3-oxazinan-2-one.

221. A compound, or a pharmaceutically acceptable salt, solvate, isotopic variant, or N-oxide thereof, wherein the compound is
3-((5-(3-(Difluoromethoxy)-4-fluorophenyl)-2-fluoropyridin-3-yl)methyl)oxazolidin-2-one; or
3-((5-(3-(Difluoromethoxy)-4-fluorophenyl)-2-fluoropyridin-3-yl)methyl)-1,3-oxazinan-2-one.

222. The compound of any one of embodiments 1 to 221, or a pharmaceutically acceptable salt or solvate thereof.

223. The compound of any one of embodiments 1 to 221, or a pharmaceutically acceptable salt or N-oxide thereof.

224. The compound of any one of embodiments 1 to 221, or a pharmaceutically acceptable salt thereof.

225. The compound of any one of embodiments 1 to 221.

226. A pharmaceutically acceptable salt of the compound of any one of embodiments 1 to 221.

227. A pharmaceutical composition comprising the compound of any one of embodiments 1 to 221, or a pharmaceutically acceptable salt, solvate, isotopic variant, or N-oxide thereof, and a pharmaceutically acceptable excipient.

228. A pharmaceutical composition comprising the compound of any one of embodiments 1 to 221, or a pharmaceutically acceptable salt or solvate thereof, and a pharmaceutically acceptable excipient.

229. A pharmaceutical composition comprising the compound of any one of embodiments 1 to 221, or a pharmaceutically acceptable salt or N-oxide thereof, and a pharmaceutically acceptable excipient.

230. A pharmaceutical composition comprising the compound of any one of embodiments 1 to 221, or a pharmaceutically acceptable salt thereof, and a pharmaceutically acceptable excipient.

231. A pharmaceutical composition comprising the compound of any one of embodiments 1 to 221 and a pharmaceutically acceptable excipient.

232. A pharmaceutical composition comprising a pharmaceutically acceptable salt of the compound of any one of embodiments 1 to 221, and a pharmaceutically acceptable excipient.

233. A unit dosage form comprising a therapeutically effective amount of the pharmaceutical composition of any one of embodiments 227 to 232.

234. A method of treating a subject suffering from or diagnosed with a disease, disorder, or medical condition mediated by GluN2B receptor activity, comprising administering to the subject a therapeutically effective amount of the compound of any one of embodiments 1 to 221, or a pharmaceutically acceptable salt, solvate, isotopic variant, or N-oxide thereof.

235. A method of treating a subject suffering from or diagnosed with a disease, disorder, or medical condition mediated by GluN2B receptor activity, comprising administering to the subject a therapeutically effective amount of the compound of any one of embodiments 1 to 221, or a pharmaceutically acceptable salt, or solvate thereof.

236. A method of treating a subject suffering from or diagnosed with a disease, disorder, or medical condition mediated by GluN2B receptor activity, comprising administering to the subject a therapeutically effective amount of the compound of any one of embodiments 1 to 221, or a pharmaceutically acceptable salt or N-oxide thereof.

237. A method of treating a subject suffering from or diagnosed with a disease, disorder, or medical condition mediated by GluN2B receptor activity, comprising administering to the subject a therapeutically effective amount of the compound of any one of embodiments 1 to 221, or a pharmaceutically acceptable salt thereof.

238. A method of treating a subject suffering from or diagnosed with a disease, disorder, or medical condition mediated by GluN2B receptor activity, comprising administering to the subject a therapeutically effective amount of the pharmaceutical composition of any one of embodiments 227 to 232 or the unit dosage form of embodiment 233.

239. The method of any one of embodiments 233 to 238, wherein the disease, disorder or medical condition mediated by GluN2B receptor activity comprises bipolar disorder, major depressive disorder, treatment-resistant depression, a mood disorder, post-partum depression, seasonal affective disorder, Alzheimer's disease, Parkinson's disease, Huntington's chorea, multiple sclerosis, cognitive impairment, head injury, spinal cord injury, stroke, epilepsy, dyskinesias, amyotrophic lateral sclerosis, neurodegeneration associated with a bacterial or chronic infection, pain, diabetic neuropathy, migraine, cerebral ischemia, schizophrenia, encephalitis, autism or an autism spectrum disorder, a memory disorder, a learning disorder, obsessive compulsive disorder, attention deficit hyperactivity disorder (ADHD) or an addictive illness.

240. The method of embodiment 239, wherein the disease, disorder or medical condition mediated by GluN2B receptor activity comprises bipolar disorder, a mood disorder, treatment resistant depression, major depressive disorder, or epilepsy.

241. The method of embodiment 240, wherein the disease, disorder or medical condition mediated by GluN2B receptor activity comprises bipolar disorder.

242. The method of embodiment 240, wherein the disease, disorder or medical condition mediated by GluN2B receptor activity comprises a mood disorder.

243. The method of embodiment 240, wherein the disease, disorder or medical condition mediated by GluN2B receptor activity comprises treatment resistant depression.

244. The method of embodiment 240, wherein the disease, disorder or medical condition mediated by GluN2B receptor activity comprises major depressive disorder.

245. The method of embodiment 240, wherein the disease, disorder or medical condition mediated by GluN2B receptor activity comprises epilepsy.

7. CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

What is claimed is:
1. A compound of Formula (I):

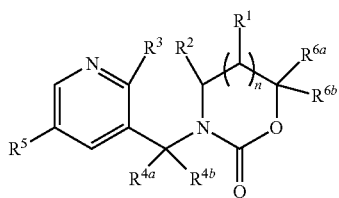

or a pharmaceutically acceptable salt, solvate, isotopic variant, or N-oxide thereof, wherein:
n is 0 or 1;
$R^1$, when present, is H; or $R^1$, together with $R^2$ and the carbon atoms to which they are attached, forms a phenyl ring;

$R^2$, when not forming a phenyl ring with $R^1$ and the carbon atoms to which they are attached, is H or $C_1$-$C_6$alkyl;
$R^3$ is H, halogen, $C_1$-$C_6$alkyl, $C_1$-$C_6$haloalkyl, O—$C_1$-$C_6$alkyl, or O—$C_1$-$C_6$haloalkyl;
$R^{4a}$ and $R^{4b}$ are, each independent from the other, H or $C_1$-$C_6$alkyl;
$R^5$ is aryl which is optionally substituted with one, two, or three substituents each of which is independently halogen, $C_1$-$C_6$alkyl, $C_1$-$C_6$haloalkyl, or O—$C_1$-$C_6$haloalkyl; pyridinyl which is optionally substituted with one substituent which is $C_1$-$C_6$haloalkyl; or thienyl which is optionally substituted with one substituent which is halogen or $C_1$-$C_6$alkyl; and
$R^{6a}$ and $R^{6b}$ are, each independent from the other, H or $C_1$-$C_6$alkyl which is optionally substituted with one substituent which is a 4 to 6 membered heterocycloalkyl; or $R^{6a}$ and $R^{6b}$ together with the carbon atom to which they are attached form a $C_3$-$C_6$cycloalkyl ring or a 4 to 6 membered heterocycloalkyl ring.

2. The compound of claim 1, or a pharmaceutically acceptable salt, solvate, isotopic variant, or N-oxide thereof, having the structure of Formula (Ia):

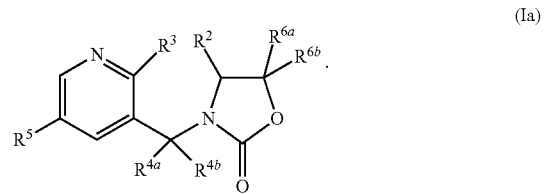

3. The compound of claim 1, or a pharmaceutically acceptable salt, solvate, isotopic variant, or N-oxide thereof, having the structure of Formula (Ib):

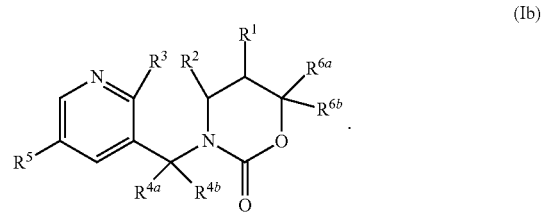

4. The compound of claim 3, or a pharmaceutically acceptable salt, solvate, isotopic variant, or N-oxide thereof, wherein $R^1$ is H.

5. The compound of claim 3, or a pharmaceutically acceptable salt, solvate, isotopic variant, or N-oxide thereof, wherein $R^1$ together with $R^2$ and the atoms to which they are attached forms a phenyl ring.

6. The compound of claim 1, or a pharmaceutically acceptable salt, solvate, isotopic variant, or N-oxide thereof, wherein $R^2$ is H or $C_1$-$C_6$alkyl.

7. The compound of claim 6, or a pharmaceutically acceptable salt, solvate, isotopic variant, or N-oxide thereof, wherein $R^2$ is —$CH_3$ or —$CH(CH_3)_2$.

8. The compound of claim 1, or a pharmaceutically acceptable salt, solvate, isotopic variant, or N-oxide thereof, wherein $R^3$ is H, F, —$CH_3$, —$CH_2CH_3$, —$CHF_2$, —$CF_2CH_3$, —$OCH_3$, or —$OCHF_2$.

9. The compound of claim 1, or a pharmaceutically acceptable salt, solvate, isotopic variant, or N-oxide thereof, wherein $R^{4a}$ and $R^{4b}$ are both H; or $R^{4a}$ is H and $R^{4b}$ is $C_1$-$C_6$alkyl.

10. The compound of claim 9, or a pharmaceutically acceptable salt, solvate, isotopic variant, or N-oxide thereof, wherein $R^{4a}$ is H and $R^{4b}$ is —$CH_3$.

11. The compound of claim 1, or a pharmaceutically acceptable salt, solvate, isotopic variant, or N-oxide thereof, wherein $R^5$ is

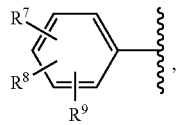

and wherein:
each of $R^7$, $R^8$, and $R^9$ is, independent from the others, H, halogen, $C_1$-$C_6$alkyl, $C_1$-$C_6$haloalkyl, or O—$C_1$-$C_6$haloalkyl.

12. The compound of claim 11, or a pharmaceutically acceptable salt, solvate, isotopic variant, or N-oxide thereof, wherein each of $R^7$, $R^8$, and $R^9$ is, independent from the others H, F, Cl, —$CH_3$, —$CHF_2$, —$CF_2CH_3$, —$CF_3$, —$OCHF_2$, or —$OCF_3$.

13. The compound of claim 11, or a pharmaceutically acceptable salt, solvate, isotopic variant, or N-oxide thereof, wherein $R^5$ is:

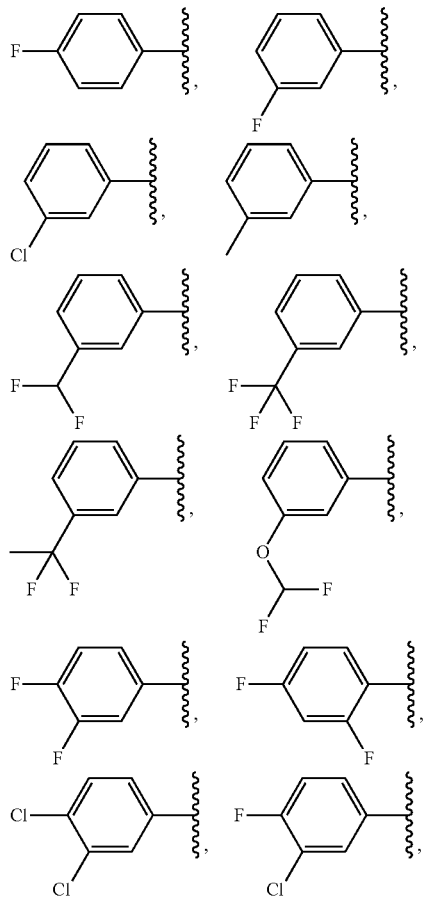

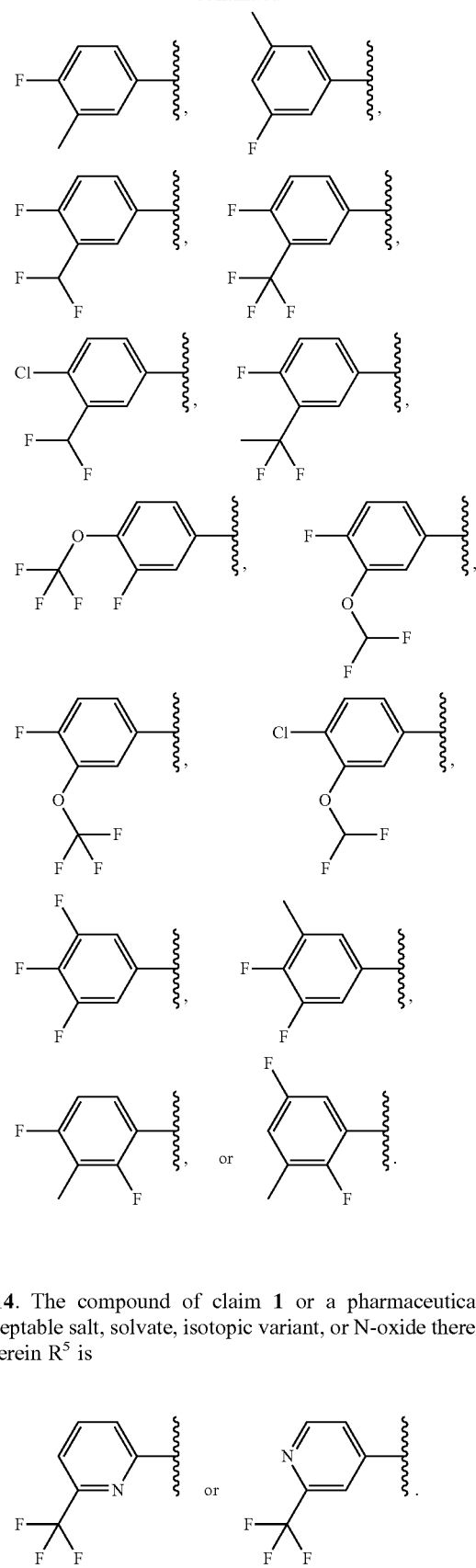

14. The compound of claim 1 or a pharmaceutically acceptable salt, solvate, isotopic variant, or N-oxide thereof, wherein $R^5$ is

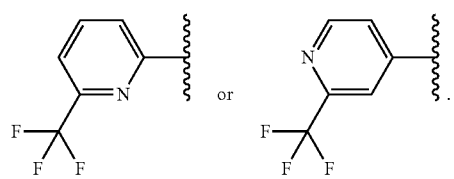

15. The compound of claim 1, or a pharmaceutically acceptable salt, solvate, isotopic variant, or N-oxide thereof, wherein $R^5$ is

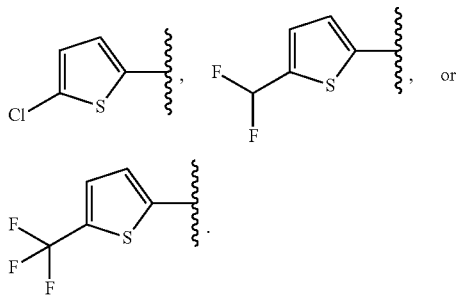

16. The compound of claim 1, or a pharmaceutically acceptable salt, solvate, isotopic variant, or N-oxide thereof, wherein $R^{6a}$ and $R^{6b}$ are both H.

17. The compound of claim 1, or a pharmaceutically acceptable salt, solvate, isotopic variant, or N-oxide thereof, wherein one of $R^{6a}$ and $R^{6b}$ is H and the other is $C_1$-$C_6$alkyl which is optionally substituted with one substituent which is a 4 to 6 membered heterocycloalkyl.

18. The compound of claim 1, or a pharmaceutically acceptable salt, solvate, isotopic variant, or N-oxide thereof, wherein one of $R^{6a}$ and $R^{6b}$ is H and the other is —$CH_3$, —$CH(CH_3)_2$, or —$CH_2R^{12}$, where $R^{12}$ is 4 to 6 membered heterocycloalkyl.

19. The compound of claim 18, or a pharmaceutically acceptable salt, solvate, isotopic variant, or N-oxide thereof, wherein $R^{12}$ is

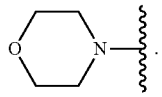

20. The compound of claim 1, or a pharmaceutically acceptable salt, solvate, isotopic variant, or N-oxide thereof, wherein $R^{6a}$ and $R^{6b}$ are both $C_1$-$C_6$alkyl.

21. The compound of claim 1, or a pharmaceutically acceptable salt, solvate, isotopic variant, or N-oxide thereof, wherein $R^{6a}$ and $R^{6b}$ together with the carbon atom to which they are attached form a cyclobutyl ring or a cyclopropyl ring.

22. The compound of claim 1, or a pharmaceutically acceptable salt, solvate, isotopic variant, or N-oxide thereof, wherein $R^{6a}$ and $R^{6b}$ together with the carbon atom to which they are attached is:

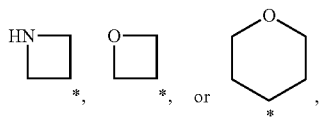

wherein * denotes the point of attachment of the ring to the remainder of the molecule.

23. The compound of claim 2, or a pharmaceutically acceptable salt, solvate, isotopic variant, or N-oxide thereof, wherein:
$R^2$ is H or —$CH_3$;
$R^3$ is —$CH_3$, —$OCH_3$, or —$OCHF_2$;
$R^{4a}$ and $R^{4b}$ both H;
$R^5$ is

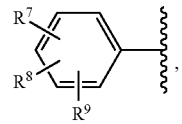

wherein each of $R^7$, $R^8$, and $R^9$ is, independent from the others, H, halogen, $C_1$-$C_6$alkyl, $C_1$-$C_6$haloalkyl, or O—$C_1$-$C_6$haloalkyl; and
$R^{6a}$ and $R^{6b}$ are both H.

24. The compound of claim 23, or a pharmaceutically acceptable salt, solvate, isotopic variant, or N-oxide thereof, wherein $R^5$ is

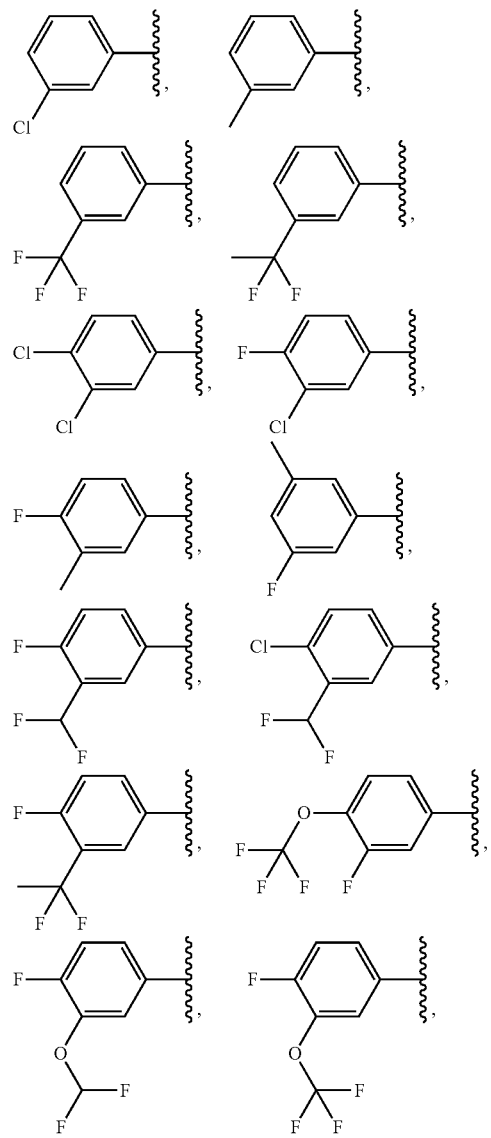

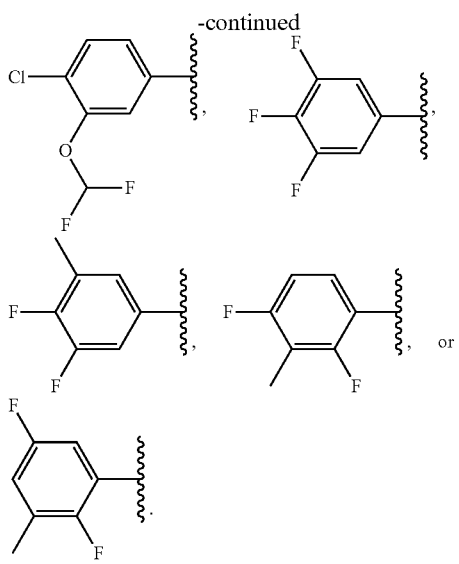

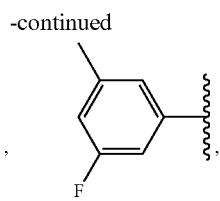

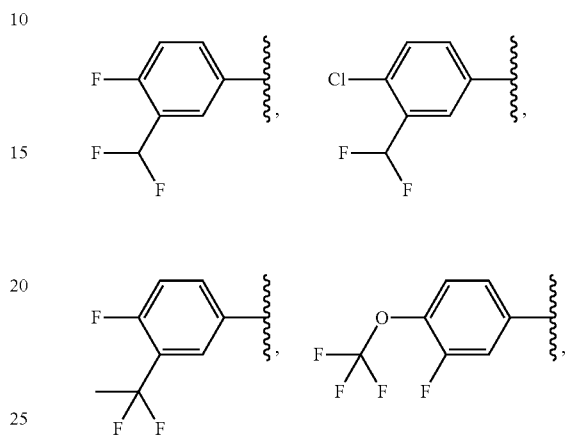

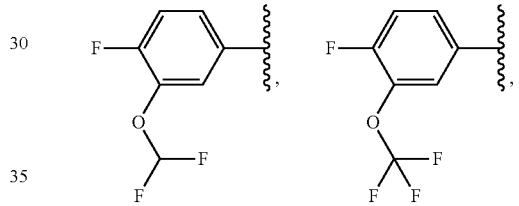

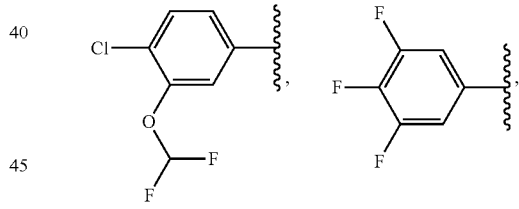

25. The compound of claim 3, or a pharmaceutically acceptable salt, solvate, isotopic variant, or N-oxide thereof, wherein:

$R^1$ is H;

$R^2$ is H;

$R^3$ is H, F, or —CH$_3$;

$R^{4a}$ and $R^{4b}$ are both H;

$R^5$ is

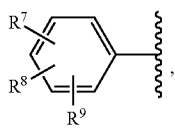

wherein each of $R^7$, $R^8$, and $R^9$ is, independent from the others, H, halogen, C$_1$-C$_6$alkyl, C$_1$-C$_6$haloalkyl, or O—C$_1$-C$_6$haloalkyl; and $R^{6a}$ and $R^{6b}$ are both H.

26. The compound of claim 25, or a pharmaceutically acceptable salt, solvate, isotopic variant, or N-oxide thereof, wherein $R^5$ is

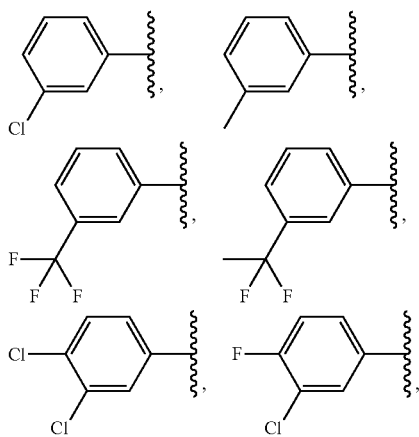

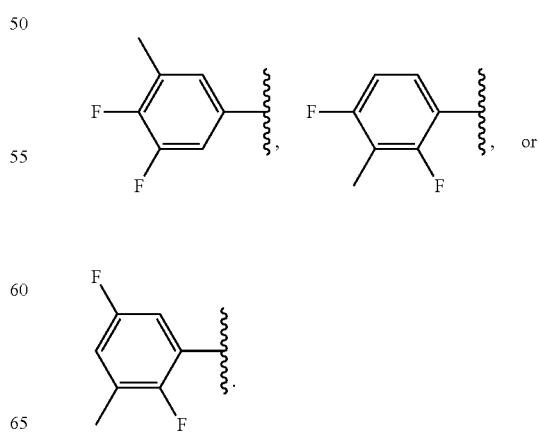

27. The compound of claim 1, or a pharmaceutically acceptable salt, solvate, isotopic variant, or N-oxide thereof, wherein $R^1$, when present, is H;
$R^2$ is H;
$R^3$ is H or $C_1$-$C_3$alkyl;
$R^{4a}$ and $R^{4b}$ are both H; or $R^{4a}$ is H and $R^{4b}$ is $C_1$-$C_3$alkyl;
$R^5$ is

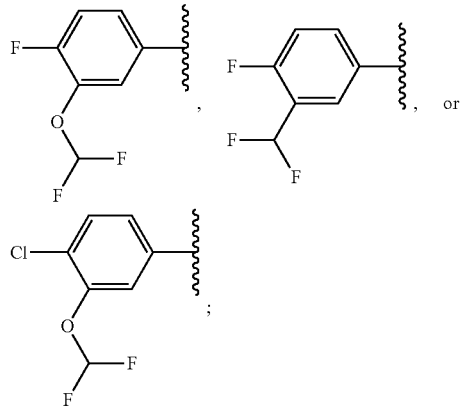

and
$R^{6a}$ and $R^{6b}$ are both H; or one of $R^{6a}$ and $R^{6b}$ is H and the other is $C_1$-$C_3$alkyl.

28. A compound, or a pharmaceutically acceptable salt, solvate, isotopic variant, or N-oxide thereof, wherein the compound is 3-[[5-[3-(Difluoromethoxy)-4-fluoro-phenyl]-3-pyridyl]methyl]-1,3-oxazinan-2-one;
3-[[5-[3-(Difluoromethoxy)-4-fluoro-phenyl]-3-pyridyl]methyl]oxazolidin-2-one;
(4S)-3-[[5-[3-(Difluoromethoxy)-4-fluoro-phenyl]-3-pyridyl]methyl]-4-isopropyl-oxazolidin-2-one;
1-[[5-[3-(Difluoromethoxy)-4-fluoro-phenyl]-3-pyridyl]methyl]-4H-3,1-benzoxazin-2-one;
(R/S)-3-[[5-[3-(Difluoromethoxy)-4-fluoro-phenyl]-3-pyridyl]methyl]-4-methyl-oxazolidin-2-one;
(R/S)-3-[[5-[3-(Difluoromethoxy)-4-fluoro-phenyl]-3-pyridyl]methyl]-5-methyl-oxazolidin-2-one;
(S*)-3-[[5-[3-(Difluoromethoxy)-4-fluoro-phenyl]-3-pyridyl]methyl]-5-methyl-oxazolidin-2-one;
(R*)-3-[[5-[3-(Difluoromethoxy)-4-fluoro-phenyl]-3-pyridyl]methyl]-5-methyl-oxazolidin-2-one;
5-[[5-[3-(Difluoromethoxy)-4-fluoro-phenyl]-3-pyridyl]methyl]-7-oxa-5-azaspiro[2.4]heptan-6-one;
3-[[5-[3-(Difluoromethoxy)-4-fluoro-phenyl]-3-pyridyl]methyl]-6,6-dimethyl-1,3-oxazinan-2-one;
(4R)-3-[[5-[3-(Difluoromethoxy)-4-fluoro-phenyl]-3-pyridyl]methyl]-4-isopropyl-oxazolidin-2-one;
6-[[5-[3-(Difluoromethoxy)-4-fluoro-phenyl]-3-pyridyl]methyl]-8-oxa-6-azaspiro[3.4]octan-7-one;
6-[[5-[3-(Difluoromethoxy)-4-fluoro-phenyl]-3-pyridyl]methyl]-2,8-dioxa-6-azaspiro[3.4]octan-7-one;
(R/S)-3-[[5-[3-(Difluoromethoxy)-4-fluoro-phenyl]-3-pyridyl]methyl]-5-isopropyl-oxazolidin-2-one;
(R*)-3-[[5-[3-(Difluoromethoxy)-4-fluoro-phenyl]-3-pyridyl]methyl]-5-isopropyl-oxazolidin-2-one;
(S*)-3-[[5-[3-(Difluoromethoxy)-4-fluoro-phenyl]-3-pyridyl]methyl]-5-isopropyl-oxazolidin-2-one;
(R/S)-3-[[5-[3-(Difluoromethoxy)-4-fluoro-phenyl]-3-pyridyl]methyl]-5-(morpholinomethyl)oxazolidin-2-one;
(R*)-3-[[5-[3-(Difluoromethoxy)-4-fluoro-phenyl]-3-pyridyl]methyl]-5-(morpholinomethyl)oxazolidin-2-one;
(S*)-3-[[5-[3-(Difluoromethoxy)-4-fluoro-phenyl]-3-pyridyl]methyl]-5-(morpholinomethyl)oxazolidin-2-one;
2-[[5-[3-(Difluoromethoxy)-4-fluoro-phenyl]-3-pyridyl]methyl]-4,8-dioxa-2-azaspiro[4.5]decan-3-one;
6-[[5-[3-(Difluoromethyl)-4-fluoro-phenyl]-3-pyridyl]methyl]-8-oxa-2,6-diazaspiro[3.4]octan-7-one;
3-[[5-[3-(Difluoromethyl)-4-fluoro-phenyl]-3-pyridyl]methyl]oxazolidin-2-one;
(4S)-3-[[5-[3-(Difluoromethyl)-4-fluoro-phenyl]-3-pyridyl]methyl]-4-isopropyl-oxazolidin-2-one;
1-[[5-[3-(Difluoromethyl)-4-fluoro-phenyl]-3-pyridyl]methyl]-4H-3,1-benzoxazin-2-one
(R/S)-3-[[5-[3-(Difluoromethyl)-4-fluoro-phenyl]-3-pyridyl]methyl]-4-methyl-oxazolidin-2-one;
(R/S)-3-[[5-[3-(Difluoromethyl)-4-fluoro-phenyl]-3-pyridyl]methyl]-5-methyl-oxazolidin-2-one;
(S*)-3-[[5-[3-(Difluoromethyl)-4-fluoro-phenyl]-3-pyridyl]methyl]-5-methyl-oxazolidin-2-one
(R*)-3-[[5-[3-(Difluoromethyl)-4-fluoro-phenyl]-3-pyridyl]methyl]-5-methyl-oxazolidin-2-one;
5-[[5-[3-(Difluoromethyl)-4-fluoro-phenyl]-3-pyridyl]methyl]-7-oxa-5-azaspiro[2.4]heptan-6-one;
3-[[5-[3-(Difluoromethyl)-4-fluoro-phenyl]-3-pyridyl]methyl]-6,6-dimethyl-1,3-oxazinan-2-one;
(4R)-3-[[5-[3-(Difluoromethyl)-4-fluoro-phenyl]-3-pyridyl]methyl]-4-isopropyl-oxazolidin-2-one;
6-[[5-[3-(Difluoromethyl)-4-fluoro-phenyl]-3-pyridyl]methyl]-8-oxa-6-azaspiro[3.4]octan-7-one;
(5R)-3-[[5-[3-(Difluoromethyl)-4-fluoro-phenyl]-3-pyridyl]methyl]-5-methyl-oxazolidin-2-one;
6-[[5-[3-(Difluoromethyl)-4-fluoro-phenyl]-3-pyridyl]methyl]-2,8-dioxa-6-azaspiro[3.4]octan-7-one;
(R/S)-3-[[5-[3-(Difluoromethyl)-4-fluoro-phenyl]-3-pyridyl]methyl]-5-isopropyl-oxazolidin-2-one;
(R*)-3-[[5-[3-(Difluoromethyl)-4-fluoro-phenyl]-3-pyridyl]methyl]-5-isopropyl-oxazolidin-2-one
(S*)-3-[[5-[3-(Difluoromethyl)-4-fluoro-phenyl]-3-pyridyl]methyl]-5-isopropyl-oxazolidin-2-one;
3-[[5-[3-(Difluoromethyl)-4-fluoro-phenyl]-3-pyridyl]methyl]-1,3-oxazinan-2-one;
(R/S)-3-[[5-[3-(Difluoromethyl)-4-fluoro-phenyl]-3-pyridyl]methyl]-5-(morpholinomethyl)oxazolidin-2-one;
(R*)-3-[[5-[3-(Difluoromethyl)-4-fluoro-phenyl]-3-pyridyl]methyl]-5-(morpholinomethyl)oxazolidin-2-one;
(S*)-3-[[5-[3-(Difluoromethyl)-4-fluoro-phenyl]-3-pyridyl]methyl]-5-(morpholinomethyl)oxazolidin-2-one;
2-[[5-[3-(Difluoromethyl)-4-fluoro-phenyl]-3-pyridyl]methyl]-4,8-dioxa-2-azaspiro[4.5]decan-3-one;
6-[[5-[3-(Difluoromethoxy)-4-fluoro-phenyl]-3-pyridyl]methyl]-8-oxa-2,6-diazaspiro[3.4]octan-7-one;
3-[[5-(4-Fluoro-3-methyl-phenyl)-3-pyridyl]methyl]oxazolidin-2-one;
3-[[5-(2,4-Difluoro-3-methyl-phenyl)-3-pyridyl]methyl]oxazolidin-2-one;
3-[[5-[3-(Trifluoromethyl)phenyl]-3-pyridyl]methyl]oxazolidin-2-one;

3-[[5-[4-Chloro-3-(difluoromethoxy)phenyl]-3-pyridyl]methyl]oxazolidin-2-one;
3-[[5-[3-Fluoro-4-(trifluoromethoxy)phenyl]-3-pyridyl]methyl]oxazolidin-2-one;
3-[[5-[3-(1,1-Difluoroethyl)-4-fluoro-phenyl]-3-pyridyl]methyl]oxazolidin-2-one;
3-[[5-[6-(Trifluoromethyl)-2-pyridyl]-3-pyridyl]methyl]oxazolidin-2-one;
3-[[5-[2-(Trifluoromethyl)-4-pyridyl]-3-pyridyl]methyl]oxazolidin-2-one;
3-[[5-[4-Fluoro-3-(trifluoromethyl)phenyl]-3-pyridyl]methyl]-1,3-oxazinan-2-one;
3-[[5-[4-chloro-3-(difluoromethoxy)phenyl]-3-pyridyl]methyl]-1,3-oxazinan-2-one;
3-[Dideuterio-[5-[3-(difluoromethyl)-4-fluoro-phenyl]-3-pyridyl]methyl] oxazolidin-2-one;
3-[Dideuterio-[5-[3-(difluoromethoxy)-4-fluoro-phenyl]-3-pyridyl]methyl]-1,3-oxazinan-2-one;
3-[Dideuterio-[5-[3-(difluoromethoxy)-4-fluoro-phenyl]-2-methyl-3-pyridyl]methyl]-1,3-oxazinan-2-one;
3-[Dideuterio-[5-(4-fluoro-3-methyl-phenyl)-2-methyl-3-pyridyl]methyl]-1,3-oxazinan-2-one;
3-[Dideuterio-[5-[3-(difluoromethyl)-4-fluoro-phenyl]-2-methyl-3-pyridyl]methyl]-1,3-oxazinan-2-one;
3-[Dideuterio-[5-[3-(difluoromethyl)-4-fluoro-phenyl]-2-methyl-3-pyridyl]methyl]oxazolidin-2-one;
(R/S)-3-[1-[5-[3-(difluoromethyl)-4-fluoro-phenyl]-3-pyridyl]ethyl]oxazolidin-2-one;
(R/S)-3-[1-[5-[3-(difluoromethyl)-4-fluoro-phenyl]-3-pyridyl]ethyl]-1,3-oxazinan-2-one;
3-[[5-[3-(Difluoromethyl)phenyl]-2-methyl-3-pyridyl]methyl]-1,3-oxazinan-2-one;
3-[[5-[3-(Difluoromethoxy)phenyl]-2-methyl-3-pyridyl]methyl]-1,3-oxazinan-2-one;
3-[[5-(3-Chlorophenyl)-2-methyl-3-pyridyl]methyl]-1,3-oxazinan-2-one;
3-[[5-(3-Chloro-4-fluoro-phenyl)-2-methyl-3-pyridyl]methyl]-1,3-oxazinan-2-one;
3-[[5-(4-Fluoro-3-methyl-phenyl)-2-methyl-3-pyridyl]methyl]-1,3-oxazinan-2-one;
3-[[5-(3,4-Difluorophenyl)-2-methyl-3-pyridyl]methyl]-1,3-oxazinan-2-one;
3-[[5-(4-Fluorophenyl)-2-methyl-3-pyridyl]methyl]-1,3-oxazinan-2-one;
3-[[5-(3-Fluorophenyl)-2-methyl-3-pyridyl]methyl]-1,3-oxazinan-2-one;
3-[[5-(3,4-Difluoro-5-methyl-phenyl)-2-methyl-3-pyridyl]methyl]-1,3-oxazinan-2-one;
3-[[5-(2,4-Difluoro-3-methyl-phenyl)-2-methyl-3-pyridyl]methyl]-1,3-oxazinan-2-one;
3-[[5-(2,4-Difluorophenyl)-2-methyl-3-pyridyl]methyl]-1,3-oxazinan-2-one;
3-[[5-(3,4-Dichlorophenyl)-2-methyl-3-pyridyl]methyl]-1,3-oxazinan-2-one;
3-[[2-Methyl-5-[3-(Trifluoromethyl)phenyl]-3-pyridyl]methyl]-1,3-oxazinan-2-one
3-[[5-[4-Fluoro-3-(trifluoromethyl)phenyl]-2-methyl-3-pyridyl]methyl]-1,3-oxazinan-2-one
3-[[5-(4-Fluoro-3-methyl-phenyl)-2-methyl-3-pyridyl]methyl]oxazolidin-2-one;
3-[[5-(2,4-Difluoro-3-methyl-phenyl)-2-methyl-3-pyridyl]methyl]oxazolidin-2-one;
3-[[5-[3-(1,1-Difluoroethyl)-4-fluoro-phenyl]-2-methyl-3-pyridyl]methyl]oxazolidin-2-one;
3-[[5-[3-(Difluoromethoxy)-4-fluoro-phenyl]-2-methyl-3-pyridyl]methyl] oxazolidin-2-one;
(R/S)-3-[[5-[3-(Difluoromethoxy)-4-fluoro-phenyl]-2-methyl-3-pyridyl]methyl]-5-methyl-oxazolidin-2-one;
(R/S)-3-[[5-[3-(Difluoromethoxy)-4-fluoro-phenyl]-2-methyl-3-pyridyl]methyl]-4-methyl-oxazolidin-2-one;
(R*)-3-[[5-[3-(Difluoromethoxy)-4-fluoro-phenyl]-2-methyl-3-pyridyl]methyl]-4-methyl-oxazolidin-2-one;
(S*)-3-[[5-[3-(Difluoromethoxy)-4-fluoro-phenyl]-2-methyl-3-pyridyl]methyl]-4-methyl-oxazolidin-2-one;
5-[[5-[3-(Difluoromethoxy)-4-fluoro-phenyl]-2-methyl-3-pyridyl]methyl]-7-oxa-5-azaspiro[2.4]heptan-6-one;
6-[[5-[3-(Difluoromethoxy)-4-fluoro-phenyl]-2-methyl-3-pyridyl]methyl]-8-oxa-6-azaspiro[3.4]octan-7-one;
(5R)-3-[[5-[3-(Difluoromethoxy)-4-fluoro-phenyl]-2-methyl-3-pyridyl]methyl]-5-methyl-oxazolidin-2-one;
3-[[5-[3-(Difluoromethoxy)-4-fluoro-phenyl]-2-methyl-3-pyridyl]methyl]-5,5-dimethyl-oxazolidin-2-one;
3-[[5-[3-(Difluoromethoxy)-4-fluoro-phenyl]-2-methyl-3-pyridyl]methyl]-1,3-oxazinan-2-one;
3-[[5-[4-Chloro-3-(difluoromethoxy)phenyl]-2-methyl-3-pyridyl]methyl] oxazolidin-2-one;
3-[[5-[3-(Difluoromethyl)-4-fluoro-phenyl]-2-methyl-3-pyridyl]methyl] oxazolidin-2-one;
6-[[5-[3-(Difluoromethyl)-4-fluoro-phenyl]-2-methyl-3-pyridyl]methyl]-8-oxa-6-azaspiro[3.4]octan-7-one;
(5R)-3-[[5-[3-(Difluoromethyl)-4-fluoro-phenyl]-2-methyl-3-pyridyl]methyl]-5-methyl-oxazolidin-2-one;
3-[[5-[3-(Difluoromethyl)-4-fluoro-phenyl]-2-methyl-3-pyridyl]methyl]-5,5-dimethyl-oxazolidin-2-one;
(R/S)-3-[[5-[3-(Difluoromethyl)-4-fluoro-phenyl]-2-methyl-3-pyridyl]methyl]-5-methyl-oxazolidin-2-one;
(R/S)-3-[[5-[3-(difluoromethyl)-4-fluoro-phenyl]-2-methyl-3-pyridyl]methyl]-4-methyl-oxazolidin-2-one;
5-[[5-[3-(Difluoromethyl)-4-fluoro-phenyl]-2-methyl-3-pyridyl]methyl]-7-oxa-5-azaspiro[2.4]heptan-6-one;
3-[[5-[3-(Difluoromethyl)-4-fluoro-phenyl]-2-methyl-3-pyridyl]methyl]-1,3-oxazinan-2-one;
3-[[5-(5-Chloro-2-thienyl)-2-methyl-3-pyridyl]methyl]oxazolidin-2-one;
3-[[2-Methyl-5-[5-(trifluoromethyl)-2-thienyl]-3-pyridyl]methyl]oxazolidin-2-one;
3-[[5-[5-(Difluoromethyl)-2-thienyl]-2-methyl-3-pyridyl]methyl]oxazolidin-2-one;
3-[[2-Methoxy-5-[3-(trifluoromethyl)phenyl]-3-pyridyl]methyl]oxazolidin-2-one;
3-[[2-Methoxy-5-(3,4,5-trifluorophenyl)-3-pyridyl]methyl]oxazolidin-2-one;
3-[[5-(2,4-Difluoro-3-methyl-phenyl)-2-methoxy-3-pyridyl]methyl] oxazolidin-2-one;
3-[[5-(3-Fluoro-5-methyl-phenyl)-2-methoxy-3-pyridyl]methyl]oxazolidin-2-one;
3-[[2-Methoxy-5-(m-tolyl)-3-pyridyl]methyl]oxazolidin-2-one;
3-[[5-(3,4-Dichlorophenyl)-2-methoxy-3-pyridyl]methyl]oxazolidin-2-one;
3-[[5-[4-Chloro-3-(difluoromethoxy)phenyl]-2-methoxy-3-pyridyl]methyl]oxazolidin-2-one;
3-[[5-(3-Chloro-4-fluoro-phenyl)-2-methoxy-3-pyridyl]methyl]oxazolidin-2-one;
3-[[5-(3-Chlorophenyl)-2-methoxy-3-pyridyl]methyl]oxazolidin-2-one;
3-[[5-[3-(1,1-Difluoroethyl)-4-fluoro-phenyl]-2-methoxy-3-pyridyl]methyl]oxazolidin-2-one;
3-[[5-[3-(1,1-Difluoroethyl)phenyl]-2-methoxy-3-pyridyl]methyl]oxazolidin-2-one;
3-[[5-(3,4-Difluoro-5-methyl-phenyl)-2-methoxy-3-pyridyl]methyl] oxazolidin-2-one;

3-[[5-[4-Fluoro-3-(trifluoromethoxy)phenyl]-2-methoxy-3-pyridyl]methyl]oxazolidin-2-one;
3-[[5-(2,5-Difluoro-3-methyl-phenyl)-2-methoxy-3-pyridyl]methyl] oxazolidin-2-one;
3-[[5-[4-Chloro-3-(difluoromethyl)phenyl]-2-methoxy-3-pyridyl]methyl]oxazolidin-2-one;
3-[[5-(4-Fluoro-3-methyl-phenyl)-2-methoxy-3-pyridyl]methyl]oxazolidin-2-one;
(4S)-3-[[5-[3-(Difluoromethoxy)-4-fluoro-phenyl]-2-methoxy-3-pyridyl]methyl]-4-methyl-oxazolidin-2-one;
(4R)-3-[[5-[3-(Difluoromethoxy)-4-fluoro-phenyl]-2-methoxy-3-pyridyl]methyl]-4-methyl-oxazolidin-2-one;
3-[[5-[3-(Difluoromethoxy)-4-fluoro-phenyl]-2-methoxy-3-pyridyl]methyl] oxazolidin-2-one;
(4S)-3-[[5-[3-(Difluoromethyl)-4-fluoro-phenyl]-2-methoxy-3-pyridyl]methyl]-4-methyl-oxazolidin-2-one;
(4R)-3-[[5-[3-(Difluoromethyl)-4-fluoro-phenyl]-2-methoxy-3-pyridyl]methyl]-4-methyl-oxazolidin-2-one;
3-[[5-[3-(Difluoromethyl)-4-fluoro-phenyl]-2-methoxy-3-pyridyl]methyl]oxazolidin-2-one;
3-[[2-(Difluoromethyl)-5-[3-(difluoromethyl)-4-fluoro-phenyl]-3-pyridyl]methyl]-1,3-oxazinan-2-one;
3-[[2-(Difluoromethyl)-5-[3-(difluoromethyl)-4-fluoro-phenyl]-3-pyridyl]methyl]oxazolidin-2-one;
3-[[5-[3-(Difluoromethoxy)-4-fluoro-phenyl]-2-(difluoromethyl)-3-pyridyl]methyl]oxazolidin-2-one;
3-[[5-[3-(Difluoromethoxy)-4-fluoro-phenyl]-2-(difluoromethyl)-3-pyridyl]methyl]-1,3-oxazinan-2-one;
3-[[2-(Difluoromethyl)-5-(4-fluoro-3-methyl-phenyl)-3-pyridyl]methyl]-1,3-oxazinan-2-one;
3-[[2-(Difluoromethyl)-5-(4-fluoro-3-methyl-phenyl)-3-pyridyl]methyl]oxazolidin-2-one;
3-[[5-[4-Chloro-3-(difluoromethoxy)phenyl]-2-(difluoromethyl)-3-pyridyl]methyl]-1,3-oxazinan-2-one;
3-[[5-[4-Chloro-3-(difluoromethoxy)phenyl]-2-(difluoromethyl)-3-pyridyl]methyl]oxazolidin-2-one;
3-[[2-(Difluoromethoxy)-5-[3-(difluoromethyl)-4-fluoro-phenyl]-3-pyridyl]methyl]oxazolidin-2-one;
(4R)-3-[[2-(Difluoromethoxy)-5-[3-(difluoromethyl)-4-fluoro-phenyl]-3-pyridyl]methyl]-4-methyl-oxazolidin-2-one;
3-[[2-(Difluoromethoxy)-5-[3-(difluoromethoxy)-4-fluoro-phenyl]-3-pyridyl]methyl]oxazolidin-2-one;
(4R)-3-[[2-(Difluoromethoxy)-5-[3-(difluoromethoxy)-4-fluoro-phenyl]-3-pyridyl]methyl]-4-methyl-oxazolidin-2-one;
3-[[2-(1,1-Difluoroethyl)-5-[3-(difluoromethyl)-4-fluoro-phenyl]-3-pyridyl]methyl]oxazolidin-2-one;
3-[[2-(1,1-Difluoroethyl)-5-[3-(difluoromethyl)-4-fluoro-phenyl]-3-pyridyl]methyl]-1,3-oxazinan-2-one;
3-[[2-(1,1-Difluoroethyl)-5-[3-(difluoromethoxy)-4-fluoro-phenyl]-3-pyridyl]methyl]-1,3-oxazinan-2-one;
6-[[2-(1,1-Difluoroethyl)-5-[3-(difluoromethyl)-4-fluoro-phenyl]-3-pyridyl]methyl]-8-oxa-6-azaspiro[3.4]octan-7-one;
(5R)-3-[[2-(1,1-Difluoroethyl)-5-[3-(difluoromethyl)-4-fluoro-phenyl]-3-pyridyl]methyl]-5-methyl-oxazolidin-2-one;
(5S)-3-[[2-(1,1-Difluoroethyl)-5-[3-(difluoromethyl)-4-fluoro-phenyl]-3-pyridyl]methyl]-5-methyl-oxazolidin-2-one;
5-[[2-(1,1-Difluoroethyl)-5-[3-(difluoromethyl)-4-fluoro-phenyl]-3-pyridyl]methyl]-7-oxa-5-azaspiro[2.4]heptan-6-one;
(4S)-3-[[2-(1,1-Difluoroethyl)-5-[3-(difluoromethyl)-4-fluoro-phenyl]-3-pyridyl]methyl]-4-methyl-oxazolidin-2-one;
(4R)-3-[[2-(1,1-Difluoroethyl)-5-[3-(difluoromethyl)-4-fluoro-phenyl]-3-pyridyl]methyl]-4-methyl-oxazolidin-2-one;
(4R)-3-[[2-(1,1-Difluoroethyl)-5-[3-(difluoromethoxy)-4-fluoro-phenyl]-3-pyridyl]methyl]-4-methyl-oxazolidin-2-one;
(4S)-3-[[2-(1,1-Difluoroethyl)-5-[3-(difluoromethoxy)-4-fluoro-phenyl]-3-pyridyl]methyl]-4-methyl-oxazolidin-2-one;
5-[[2-(1,1-Difluoroethyl)-5-[3-(difluoromethoxy)-4-fluoro-phenyl]-3-pyridyl]methyl]-7-oxa-5-azaspiro[2.4]heptan-6-one;
6-[[2-(1,1-Difluoroethyl)-5-[3-(difluoromethoxy)-4-fluoro-phenyl]-3-pyridyl]methyl]-8-oxa-6-azaspiro[3.4]octan-7-one;
(5S)-3-[[2-(1,1-Difluoroethyl)-5-[3-(difluoromethoxy)-4-fluoro-phenyl]-3-pyridyl]methyl]-5-methyl-oxazolidin-2-one;
(5R)-3-[[2-(1,1-Difluoroethyl)-5-[3-(difluoromethoxy)-4-fluoro-phenyl]-3-pyridyl]methyl]-5-methyl-oxazolidin-2-one;
3-((5-(3-(Difluoromethoxy)-4-fluorophenyl)-2-fluoropyridin-3-yl)methyl)oxazolidin-2-one; or
3-((5-(3-(Difluoromethoxy)-4-fluorophenyl)-2-fluoropyridin-3-yl)methyl)-1,3-oxazinan-2-one.

29. A compound, or a pharmaceutically acceptable salt, solvate, isotopic variant, or N-oxide thereof, wherein the compound is 3-[[5-[3-(Difluoromethoxy)-4-fluoro-phenyl]-3-pyridyl]methyl]-1,3-oxazinan-2-one;
3-[[5-[3-(Difluoromethyl)-4-fluoro-phenyl]-3-pyridyl]methyl]oxazolidin-2-one;
(S*)-3-[[5-[3-(Difluoromethyl)-4-fluoro-phenyl]-3-pyridyl]methyl]-5-methyl-oxazolidin-2-one;
3-[[5-[3-(Difluoromethyl)-4-fluoro-phenyl]-3-pyridyl]methyl]-1,3-oxazinan-2-one;
3-[[5-[4-chloro-3-(difluoromethoxy)phenyl]-3-pyridyl]methyl]-1,3-oxazinan-2-one;
3-[Dideuterio-[5-[3-(difluoromethyl)-4-fluoro-phenyl]-3-pyridyl]methyl] oxazolidin-2-one;
(R/S)-3-[1-[5-[3-(difluoromethyl)-4-fluoro-phenyl]-3-pyridyl]ethyl]oxazolidin-2-one trifluoroacetate salt;
3-[[5-[3-(Difluoromethyl)-4-fluoro-phenyl]-2-methyl-3-pyridyl]methyl] oxazolidin-2-one; or
3-[[5-[3-(Difluoromethyl)-4-fluoro-phenyl]-2-methyl-3-pyridyl]methyl]-1,3-oxazinan-2-one.

30. A pharmaceutical composition comprising: (A) the compound of claim 1, or a pharmaceutically acceptable salt, solvate, isotopic variant, or N-oxide thereof, and (B) at least one pharmaceutically acceptable excipient.

31. A method of treating a subject suffering from or diagnosed with a disease, disorder, or medical condition mediated by GluN2B receptor activity, comprising administering to the subject a therapeutically effective amount of the compound of claim 1, or a pharmaceutically acceptable salt, solvate, isotopic variant, or N-oxide thereof.

32. The method of claim 31, wherein the disease, disorder or medical condition mediated by GluN2B receptor activity comprises bipolar disorder, major depressive disorder, treatment-resistant depression, a mood disorder, post-partum depression, seasonal affective disorder, Alzheimer's disease, Parkinson's disease, Huntington's chorea, multiple sclerosis, cognitive impairment, head injury, spinal cord injury, stroke, epilepsy, dyskinesias, amyotrophic lateral sclerosis, neurodegeneration associated with a bacterial or chronic infection, pain, diabetic neuropathy, migraine, cerebral ischemia, schizophrenia, encephalitis, autism or an autism spectrum disorder, a memory disorder, a learning disorder, obsessive compulsive disorder, attention deficit hyperactivity disorder (ADHD) or an addictive illness.

33. The method of claim 32, wherein the disease, disorder or medical condition mediated by GluN2B receptor activity comprises bipolar disorder, a mood disorder, treatment resistant depression, major depressive disorder, or epilepsy.

\* \* \* \* \*